US009523094B2

(12) United States Patent
Hung

(10) Patent No.: US 9,523,094 B2
(45) Date of Patent: Dec. 20, 2016

(54) METHODS OF TREATING KENNEDY'S DISEASE

(71) Applicant: Ionis Pharmaceuticals, Inc., Carlsbad, CA (US)

(72) Inventor: Gene Hung, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/434,693

(22) PCT Filed: Oct. 11, 2013

(86) PCT No.: PCT/US2013/064680
§ 371 (c)(1),
(2) Date: Apr. 9, 2015

(87) PCT Pub. No.: WO2014/059364
PCT Pub. Date: Apr. 17, 2014

(65) Prior Publication Data
US 2015/0284725 A1 Oct. 8, 2015

Related U.S. Application Data

(60) Provisional application No. 61/712,745, filed on Oct. 11, 2012.

(51) Int. Cl.
*A61K 31/70* (2006.01)
*C07H 21/02* (2006.01)
*C07H 21/04* (2006.01)
*C12N 15/113* (2010.01)
*A61K 31/713* (2006.01)
*C12N 5/00* (2006.01)

(52) U.S. Cl.
CPC ......... *C12N 15/1138* (2013.01); *A61K 31/713* (2013.01); *C12N 2310/11* (2013.01); *C12N 2310/315* (2013.01); *C12N 2310/321* (2013.01); *C12N 2310/3341* (2013.01); *C12N 2320/30* (2013.01)

(58) Field of Classification Search
None
See application file for complete search history.

(56) References Cited

U.S. PATENT DOCUMENTS

| 4,981,957 | A | 1/1991 | Lebleu et al. |
| 5,034,506 | A | 7/1991 | Summerton et al. |
| 5,118,800 | A | 6/1992 | Smith et al. |
| 5,166,315 | A | 11/1992 | Summerton et al. |
| 5,185,444 | A | 2/1993 | Summerton et al. |
| 5,319,080 | A | 6/1994 | Leumann |
| 5,359,044 | A | 10/1994 | Cook et al. |
| 5,393,878 | A | 2/1995 | Leumann |
| 5,446,137 | A | 8/1995 | Maag et al. |
| 5,466,786 | A | 11/1995 | Buhr et al. |
| 5,514,785 | A | 5/1996 | Van Ness et al. |
| 5,519,134 | A | 5/1996 | Acevedo et al. |
| 5,567,811 | A | 10/1996 | Misiura et al. |
| 5,576,427 | A | 11/1996 | Cook et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,670,633 | A | 9/1997 | Cook et al. |
| 5,698,685 | A | 12/1997 | Summerton et al. |
| 5,700,920 | A | 12/1997 | Altmann et al. |
| 5,792,847 | A | 8/1998 | Buhr et al. |
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,670,461 | B1 | 12/2003 | Nielsen et al. |
| 6,673,661 | B1 | 1/2004 | Liu et al. |
| 6,770,748 | B2 | 8/2004 | Imanishi et al. |
| 6,794,499 | B2 | 9/2004 | Wengel et al. |

(Continued)

FOREIGN PATENT DOCUMENTS

| WO | WO 98/39352 | 9/1998 |
| WO | WO 99/14226 | 3/1999 |
| WO | WO 00/63364 | 10/2000 |
| WO | WO 01/49687 | 7/2001 |
| WO | WO 03/004602 | 1/2003 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |

(Continued)

OTHER PUBLICATIONS

Fishbeck, Medizinische Genetik, vol. 3, Abstract S7-01, pp. 357-452, see p. 420, 2009.*

(Continued)

*Primary Examiner* — Sean McGarry
(74) *Attorney, Agent, or Firm* — Ionis Pharmaceuticals, Inc. Patent Dept.

(57) ABSTRACT

Certain embodiments are directed to methods of ameliorating, treating, or preventing Kennedy's Disease in a subject carrying a mutation in the Androgen Receptor (AR) gene, such as expansion of a CAG trinucleotide repeat, which is associated with Kennedy's Disease, by administering an antisense compound targeted to AR. Several embodiments provided herein relate to the discovery that antisense compounds targeting Androgen Receptor can ameliorate, treat, or prevent Kennedy's Disease in a subject carrying a mutation in the Androgen Receptor gene, such as expansion of a CAG trinucleotide repeat, which is associated with Kennedy's Disease.

14 Claims, No Drawings

(56) References Cited

U.S. PATENT DOCUMENTS

| | | | |
|---|---|---|---|
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 7,737,125 | B2 | 6/2010 | Worm |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2005/0130923 | A1 | 6/2005 | Bhat et al. |
| 2006/0003959 | A1 | 1/2006 | Burden et al. |
| 2007/0031844 | A1 | 2/2007 | Khvorova et al. |
| 2008/0039618 | A1 | 2/2008 | Allerson et al. |
| 2009/0012281 | A1 | 1/2009 | Swayze et al. |
| 2011/0152348 | A1* | 6/2011 | Worm ............ C12N 15/1137 514/44 A |
| 2011/0319471 | A1 | 12/2011 | Worm |
| 2014/0031409 | A1* | 1/2014 | Worm ............ C12N 15/1137 514/44 A |

FOREIGN PATENT DOCUMENTS

| | | |
|---|---|---|
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2012/065051 | 5/2012 |

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allshire, "RNAi and Heterochromatin—a Hushed-Up Affair" Science (2002) 297: 1818-1819.

Altmann et al., "Second Generation Antisense Oligonucleotides Inhibitionof PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Branch et al., "A good antisense molecule is hard to find," TIBS (1998) 23:45-50.

Caplen et al., "Rescue of polyglutamine-mediated cytotoxicity by double-stranded RNA-mediated RNA interference" Hum. Mol. Genet. (2002) 11(2):175-184.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2): 923-937.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

Gu et al., "Base pairing properties of D- and L-cyclohexene nucleic acids (CeNA)" Oligonucleotides (2003) 13(6):479-489.

Gu et al., "Enzymatic resolution and base pairing properties of D- and L-cyclohexenyl nucleic acids (CeNA)" Nucleosides Nucleotides Nucleic Acids (2005) 24(5-7):993-998.

Gu et al., "Synthesis of enantiomeric-pure cyclohexenyl nucleoside building blocks for oligonucleotide synthesis" Tetrahedron (2004) 60(9):2111-2123.

Hall et al., "Establishment and Maintenance of a Heterochromatin Domain" Science (2002) 297: 2232-2237.

Horvath et al., "Stereoselective synthesis of (-)-ara-cyclohexenyl-adenine" Tetrahedron Letters (2007) 48:3621-3623.

Jenuwein "An RNA-Guided Pathway for the Epigenome" Science (2002) 5590: 2215-2218.

Kabanov et al., "A new class of antivirals: antisense oligonucleotides combined with a hydrophobic substituent effectively inhibit influenza virus reproduction and synthesis of virus-specific proteins in MOCK cells" FEBS Lett., (1990) 259: 327-330.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Letsinger et al., "Cholesteryl-conjugated oligonucleotides: Synthesis, properties, and activity as inhibitors of replication of human immunodeficiency virus in cell culture" PNAS (1989) 86: 6553-6556.

Leumann et al., "DNA Analogues: From Supramolecular Principles to Biological Properties" Bioorganic & Medicinal Chemistry (2002) 10:841-854.

Maher et al., "Comparative bybrid arrest by tandem antisense oligodeoxyribonucleotides or oligodeoxyribonucleoside methylphosphonates in a cell-free system" Nuc. Acid. Res. (1988) 16(8):3341-3358.

Manoharan et al., "Chemical Modifications to Improve Uptake and Bioavailability of Antisense Oligonucleotides" Arm. N.Y. Acad. Sci. (1992) 660: 306-309.

Manoharan et al., "Cholic Acid-Oligonucleotide Conjugates for Antisense Applications" Bioorg. Med. Chem. Let. (1994) 4(8): 1053-1060.

Manoharan et al., "Inoduction of a lipophilic thioether tether in the minor groove of nucleic acids for antisense applications" Bioorg. Med. Chem. Let. (1993) 3(12): 2765-2770.

Manoharan et al., "Lipidic Nucleic Acids" Tetrahedron Lett. (1995) 36(21): 3651-3654.

Manoharan et al., "Oligonucleotide Conjugates: Alteration of the Pharmacokinetic Properties of Antisense Agents" Nucleosides & Nucleotides (1995) 14(3-5): 969-973.

Martin, "New acces to 2'-O-alkylated ribonucleosides and properties of 2'-O-alkylated oligoribonucleotides" Hely. Chim. Acta. (1995) 78:486-504.

(56) References Cited

OTHER PUBLICATIONS

Mishra et al., "Improved leishmanicidal effect of phosphorotioate antisense oligonucleotides by LDL-mediated delivery" Biochim. Biophys. Acta (1995) 1264: 229-237.

Nauwelaerts et al., "Cyclohexenyl nucleic acids: conformationally flexible oligonucleotides" Nucleic Acids Res. (2005) 33(8):2452-2463.

Nauwelaerts et al., "Structural characterization and biological evaluation of small interfering RNAs containing cyclohexenyl nucleosides" J. Am. Chem. Soc. (2007) 129(30):9340-9348.

New England Biolabs 1998/99 Catalog (cover page and pp. 121 and 284).

Oberhauser et al., "Effective incorporation of 2'-O-methyl-oligoribonucleotides into liposomes and enhanced cell association through modification with thiocholesterol" Nucl. Acids Res. (1992) 20(3): 533-538.

Orum et al., "Locked nucleic acids: A promising molecular family for gene-function analysis and antisense drug development" Curr. Opinion Mol. Ther. (2001) 3:239-243.

Pal-Bhadra et al., "Heterochromatic Silencing and HP1 Localization in *Drosophila* are Dependent on the RNAi Machinery" Science (2004) 303: 669-672.

Reynolds et al., "Rational siRNA design for RNA interference" Nature Biotechnology (2004) 22(3):326-330.

Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.

Robeyns et al., "Structure of the fully modified left-handed cyclohexene nucleic acid sequence GTGTACAC" J. Am. Chem. Soc. (2008) 130(6):1979-1984.

Saison-Behmoaras et al., "Short modified antisense oligonucleotides directed against Ha-ras point mutation induce selective cleavage of the mRNA and inhibit T24 cells proliferation" EMBO J. (1991) 10: 1111-1118.

Sanghvi et al., "Heterocyclic Base Modifications in Nucleic Acids and Their Applications in Antisense Oligonucleotides" Antisense Research and Applications (1993) pp. 273-288.

Shea et al., "Synthesis, hybridization properties and antiviral activity of lipid-oligodeoxynucleotide conjugates" Nucl. Acids Res. (1990) 18: 3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Smith et al., "Comparison of biosequences" Adv. Appl. Math. (1981) 2(4):482-489.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75: 49-54.

Thalmann et al., "Androgen-independent cancer progression and bone metastasis in the LNCaP model of human prostate cancer." Cancer Res. (1994) 54(10): 2577-2581.

Verbeure et al., "RNase H mediated cleavage of RNA by cyclohexene nucleic acid (CeNA)" Nucleic Acids Res. (2001) 29(24):4941-4947.

Verdel et al., "RNAi-Mediated Targeting of Heterochromatin by the RITS Complex" Science (2004) 303: 672-676.

Volpe et al., "Regulation of heterochromatic silencing and histone H3 lysine-9 methylation by RNAi." Science (2002) 297(5588): 1833-1837.

Wahlestedt et al., "Potent and nontoxic antisense oligonucleotide containing locked nucleic acids" Proc. Natl. Acad. Sci. USA (2000) 97: 5633-5638.

Wang et al., "A straightforward stereoselective synthesis of D- and L-5-hydroxy-4-hydroxymethyl-2- cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Woolf et al. "Specificity of antisense oligonucleotides in vivo"PNAS (1992) 89:7305-7309.

Zhang et al., "PowerBLAST: A New Network Blast Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Greenland et al., "Kennedy's disease: pathogenesis and clinical approaches" Internal Medicine Journal (2004) 34:279-289.

Maclean et al., "Spinal and bulbar muscular atrophy: androgen receptor dysfunction caused by a trinucleotide repeat expansion" Journal of Neurological Sciences (1996) 135: 149-157.

\* cited by examiner

SEQUENCE LISTING

<160> NUMBER OF SEQ ID NOS: 231

<210> SEQ ID NO 1
<211> LENGTH: 191001
<212> TYPE: DNA
<213> ORGANISM: Homo sapiens

<400> SEQUENCE: 1
ctgacagaaa gcagatcatt ggttgcctga ggaggaggag tataggagag gtggagggaa     60
aatgtacaaa gtggcacaat aaaaactttt ggaatcatag atatattcac tatcttgatt    120

```
gagtgatgat ttcatgagtg cacgcgtgtg tcaaaaatga tcaatttatg caactttaaa    180
tatgtgcagt ttattgtata tatcaattat acctcagtac ggctattaaa aagaaaccct    240
ctggctgcac aatgcagaac tgattctagg aaagagtgga gggaggatga ccatttacag    300
tgctccaggt ggaagagaac ggtgccttct ggaagtgaac taggttggca acaacagaga    360
tgaaataaat gggcagatgt gtgagatact taggaaataa aacccgatgg tcaccatttt    420
ccaaaggtca gctcatcctg gctttccaga gcaaagagct agggaagact ttattaataa    480
atccctcttg aagttgcaga ggaagcttat agcagaaact tactctcaac ctgactaatc    540
tgagagaaca cctctggttc catttgatta ctaaaaaact gcaaagaaca ggaggagaaa    600
gaagaagaaa gctggtacaa acagtgaact tatataatat taatcaataa ttgtctcttg    660
ttcttaaaag caatgggaag aaaatgagat ttgagctgga agatcagagt tcaaaatcca    720
aataaagtat atggccctaa tatgcttata gtagttaacc tttcctgata atgatataat    780
tgttgacagc accatcttta aaaataaaaa taacatagta atccttcaga tttgtagaat    840
gctttcctgt ttacaagttt gttctataca cattatgtct tttaaatgac acactagcct    900
tctgagggta acttatattg gcaacagttt tcagatgtgg aaactgtgaa gacaatgttg    960
gtgatgtgga agcaacataa actttggagt cttttcagacc caggtttgaa tgtcagactg   1020
cttttttattc agagtaactt cagagcatta tttctcacct taatttttttt tcaggcctct   1080
ttgtgtctat gtgtcctctt cactcctgtc cattgttcat tcagtgattt ttgcaccttc   1140
cttcactgtt agtgtgtaga cacatagttc tcctggctct gagacctatg ttaattccat   1200
tctaccatcc tgccagccca ctcaattcct attgagcaat gctagttgaa agttgtggtg   1260
ggattaaatg ttgcaatgag tattcaaatg aggttgaagt atctacgcat tctacttaca   1320
tatggtgagg tatattcaag gaaggctgta gccattaaaa tctcaggaaa taattttttca   1380
cctcctcagg tgaaagggtc ttcaggcctt tgtgttctgg aaggttcatt tatagccatt   1440
tcccaaatga caatgcgatt gatgagtcta gagtctagct caaatagcaa tggactggaa   1500
gactagttta ggttttacta atgtggaaca tagaacaaat tatgtccttg tttcagcctg   1560
ttcatctgtg aaatagagcc tatcatatcc agtcttcctt gcctttaggt ttgagttacc   1620
ttctttggtc aaggtaagta aatgcctatg atgtttggct gtgcacaaga taaagctaca   1680
acaaagctac aacccatctt ttctctgtag aagactgcaa aaagcaaaag agacccaggc   1740
aaaaatctcg gaatgacttt tggaacagag agcctcccca gaatcagaag tcaaaggaat   1800
ttaaaacata gggaggccca gggtctctac tgacataaag gaaagatgtt ttccttatag   1860
gtttacgttt acatttttctc tctctttcca ttcccacttg catctccacc tttacacagg   1920
gcttatggga cctcctccac aaaagagcag ttgcagtaac ccacatcatc ctctacgcct   1980
ggctgtccat caagaggcga aaagcagccc tatataggtt ctatccttgg atagttccag   2040
ttgtaaagtt taaatatgc gaaggcaact tggaaaagca agcggctgca tacaaagcaa   2100
acgtttacag agctctggac aaaattgagc gcctatgtgt acatggcaag tgtttttagt   2160
gtttgtgtgt ttacctgctt gtctgggtga ttttgccttt gagagtctgg atgagaaatg   2220
catggttaaa ggcaattcca gacaggaaga aaggcagaga agagggtaga aatgacctct   2280
gattcttggg gctgagggtt cctagagcaa atggcacaat gccacgaggc ccgatctatc   2340
cctatgacgg aatctaaggt ttcagcaagt atctgctggc ttggtcatgg cttgctcctc   2400
agtttgtagg agactctccc actctcccat ctgcgcgctc ttatcagtcc tgaaaagaac   2460
ccctggcagc caggagcagg tattcctatc gtccttttcc tccctccctc gcctccaccc   2520
```

-continued

```
tgttggtttt ttagattggg ctttggaacc aaatttggtg agtgctggcc tccaggaaat    2580
ctggagccct ggcgcctaaa ccttggttta ggaaagcagg agctattcag gaagcagggg    2640
tcctccaggg ctagagctag cctctcctgc cctcgcccac gctgcgccag cacttgtttc    2700
tccaaagcca ctaggcaggc gttagcgcgc ggtgagggga ggggagaaaa ggaaagggga    2760
ggggagggaa aaggaggtgg gaaggcaagg aggccggccc ggtgggggcg ggacccgact    2820
cgcaaactgt tgcatttgct ctccacctcc cagcgccccc tccgagatcc cggggagcca    2880
gcttgctggg agagcgggac ggtccggagc aagcccagag gcagaggagg cgacagaggg    2940
aaaaagggcc gagctagccg ctccagtgct gtacaggagc cgaagggacg caccacgcca    3000
gccccagccc ggctccagcg acagccaacg cctcttgcag cgcggcggct tcgaagccgc    3060
cgccccgagc tgcccctttcc tcttcggtga agttttttaaa agctgctaaa gactcggagg    3120
aagcaaggaa agtgcctggt aggactgacg gctgcctttg tcctcctcct ctccaccccg    3180 cctccccca ccctgccttc ccccctccc ccgtcttctc tcccgcagct gcctcagtcg    3240
gctactctca gccaaccccc ctcaccaccc ttctccccac ccgcccccc gccccgtcg    3300 gcccagcgct gccagcccga gtttgcagag aggtaactcc ctttggctgc gagcgggcga    3360
gctagctgca cattgcaaag aaggctctta ggagccaggc gactggggag cggcttcagc    3420
actgcagcca cgacccgcct ggttaggctg cacgcggaga gaaccctctg ttttccccca    3480
ctctctctcc acctcctcct gccttcccca ccccgagtgc ggagccagag atcaaaagat    3540
gaaaaggcag tcaggtcttc agtagccaaa aacaaaaca aacaaaaaca aaaagccga    3600 aataaaagaa aaagataata actcagttct tatttgcacc tacttcagtg gacactgaat    3660
ttggaaggtg gaggattttg tttttttctt ttaagatctg ggcatctttt gaatctaccc    3720
ttcaagtatt aagagacaga ctgtgagcct agcaggcag atcttgtcca ccgtgtgtct    3780
tcttctgcac gagactttga ggctgtcaga gcgctttttg cgtggttgct cccgcaagtt    3840
tccttctctg gagcttcccg caggtgggca gctagctgca gcgactaccg catcatcaca    3900
gcctgttgaa ctcttctgag caagagaagg ggaggcgggg taagggaagt aggtggaaga    3960
ttcagccaag ctcaaggatg gaagtgcagt tagggctggg aagggtctac cctcggccgc    4020
cgtccaagac ctaccgagga gctttccaga atctgttcca gagcgtgcgc gaagtgatcc    4080
agaacccggg ccccaggcac ccagaggccg cgagcgcagc acctcccggc gccagtttgc    4140
tgctgctgca gcagcagcag cagcagcagc agcagcagca gcagcagcag cagcagcagc    4200
agcagcagca gcagcaagag actagcccca ggcagcagca gcagcagcag ggtgaggatg    4260
gttctcccca agcccatcgt agaggcccca caggctacct ggtcctggat gaggaacagc    4320
aaccttcaca gccgcagtcg gccctggagt gccacccga gagaggttgc gtcccagagc    4380
ctggagccgc cgtggccgcc agcaagggc tgccgcagca gctgccagca cctccggacg    4440
aggatgactc agctgcccca tccacgttgt ccctgctggg ccccactttc cccggcttaa    4500
gcagctgctc cgctgacctt aaagacatcc tgagcgaggc cagcaccatg caactccttc    4560
agcaacagca gcaggaagca gtatccgaag gcagcagcag cgggagagcg agggaggcct    4620
cgggggctcc cacttcctcc aaggacaatt acttaggggg cacttcgacc atttctgaca    4680
acgccaagga gttgtgtaag gcagtgtcgg tgtccatggg cctgggtgtg gaggcgttgg    4740
agcatctgag tccaggggaa cagcttcggg gggattgcat gtacgcccca cttttgggag    4800
ttccaccccg tgtgcgtccc actccttgtg ccccattggc cgaatgcaaa ggttctctgc    4860
tagacgacag cgcaggcaag agcactgaag atactgctga gtattcccct ttcaagggag    4920
```

```
gttacaccaa agggctagaa ggcgagagcc taggctgctc tggcagcgct gcagcaggga    4980
gctccgggac acttgaactg ccgtctaccc tgtctctcta caagtccgga gcactggacg    5040
aggcagctgc gtaccagagt cgcgactact acaactttcc actggctctg gccggaccgc    5100
cgcccctcc gccgcctccc catccccacg ctcgcatcaa gctggagaac ccgctggact    5160
acggcagcgc ctgggcggct gcggcggcgc agtgccgcta tggggacctg gcgagcctgc    5220
atggcgcggg tgcagcggga cccggttctg ggtcaccctc agccgccgct tcctcatcct    5280
ggcacactct cttcacagcc gaagaaggcc agttgtatgg accgtgtggt ggtggtgggg    5340
gtggtggcgg cggcggcggc ggcggcggcg cggcggcgg cggcggcggc ggcggcgagg    5400
cgggagctgt agcccctac ggctacactc ggccccctca ggggctggcg ggccaggaaa    5460
gcgacttcac cgcacctgat gtgtggtacc ctggcggcat ggtgagcaga gtgccctatc    5520
ccagtcccac ttgtgtcaaa agcgaaatgg gcccctggat ggatagctac tccggacctt    5580
acggggacat gcgtaagtt tttccttcca gaaatgtcgc ctttcggccc agggcagagt    5640
cactctgtgt tctggggtat ctagcggctc ctacctgcgc gaacactcag attgcccctg    5700
ggagagctca gcagggtaaa cctagagctc tcccgtggac tcccggcctg ccagaggttt    5760
aacctgagct ctcctaattt ctgctgcgtg ccctgggtgc tgattcctgc cctcccagat    5820
tcttcaactc ccccaaccgc cccaaattct cactacctcc tggtactcga ggtcccaaac    5880
agaaatccta ttgcacgggc caccttcaga gataaagctc ccaagccctc cactcttcct    5940
ttcctcctgt cctcaaagtc tgagaacctc aacaggaatt tgggcaattt ctcctcttca    6000
ggtctgttag gatttcactt tcagcctgcg cagattagag tcaaaaagac cggcccaata    6060
gcttctcagc gggtatcctc cagagaggta aagtgaaatt ctcggttagg gaaagaaagt    6120
ggtctctggg tgctgaggtc tgctgtgtga aagggtgaac ttctttctcc tgaagcaact    6180
ggggacttgc tccagggctg gaggtcagta gagataatcc aaaccgtcat gtttagagta    6240
ggcagagggg caactttctt ggtaaagact tcacaggatt tgcactcaca gtttctcaac    6300
gttggttgac tatgttgaaa gtagttgctt gggtcggttt tctcttgtaa agtgtttatt    6360
ttctctgtgg attataacag atccacagcc ccctacttca ggtttgcatc agatctataa    6420
agaggagaat attcttttaa tgtacaattt aattaggctt gactctgact tacaaaactg    6480
ttggaaaaca tttttttgta aagcattttcc tgctatttca gtgtgctcca aaatctccac    6540
tggggagggt ggagtgaggt tttttattat attccttat ttttaggaca tgtttgcatt    6600
ttagaatatg tgcagttagc tctaacaaat tgagtaagaa ctcttaatga cctatgagcc    6660
gtaatcttac cccaaagttt taattagcat atgagaaaag tggcaggcaa ttgcatcgtg    6720
cttattaaaa attattcctc accgcagttg ttgagcttct tggagaccat gctgaagatt    6780
ttctccccca gcaaattaag atattagttt atctgctgag ggaggacaga ctgaattggg    6840
gaattaactc ctcaggtagg ccaggtgctg atgtccctgt ggacttttgt cttattcttt    6900
gtttctatgg ctgttttctt ttacctgtga cttctccgaa atttctttgt tagccttaac    6960
atctttgttt ggggacttaa atccagcaat tgccttcttt tcactgatgc tttccttctt    7020
acaaggtaga tagcacagtg ttagtaaaga aagaaagagg agggtaggat ttcatattat    7080
ttcgtgggct gttgaagaaa cagcttctta ccaggcttta cattccatta ggtttttaat    7140
gtttgactta caagattttc agaggggttca tttgatattg tcaaagtctt ttccagttaa    7200
tttagactct tcatttttgt aatgggttta tgctatggga caaaaaaagt attcttcatt    7260
```

-continued

```
ttataagaac aaatttactt ggtagggtta attttttttc tagggctgtc actagacggt    7320
ggagcccctc ttctactgta aacttttctt gggggaaaat gtctaaggtg cattttgacc    7380
tgccatgata ctaaacccag acactggaac cttccatctt ctgcatgcct ccccacaac     7440
ttacttactt aacagggaaa aaactgatgg ttccacatat ttgctaaaaa atgtgtgcct    7500
tcaaagacaa aaccaaaatt tttagggaat aactatagag agcaaaagtt actcccatca    7560
agtagacaac gagcttggtg attttatttc aggtcttaat gaaaaaagct tctttatgag    7620
gaaggttatc atatcttggt gcctccttga cagtccgctt aaattaatga cataaactaa    7680
tgagaattta gcagttcctg cagaaagtac aagtttattt ttttttttctg gtttgtgatt   7740
gctgcactga atatgaggag tctagttaaa gggacaactg gtgttcctgt cttgtgagtt    7800
gacgaagact ttccatttct aggatataga aaatccttaa gccggtttat tgaaaattaa    7860
tcaatttaat cagaatgcaa tcaattccaa tacaaaagtt agtattttct ttcttttat     7920
tgaaaattaa tttaatcaga atacaatcaa ttccaatcca aaagttgata ttttcttact    7980
ttctcttttt ttccctcatt ttgtagggat acaatttggt gaaaggcaag agatttctta    8040
agccaaagca agagtgtctt ccctctctgt gttgcatgca ttatgtgcca tgtttgagct    8100
aaaaatctca aaatttgggca ggcttccaat gacctgttgg gtccctccct ttaccattca   8160
tgtgtgtgtt tatgtacata attttgtgga ggggttttttt taaaccttag taacatctgc   8220
actcactctg tgttcttata catttacagt gtttctgctg agaggaggga agatgcaaag    8280
gtggtctctt ttacttaatt tagcatgtgg tttgaacaga aggaaaaata aaaagtgatg    8340
gggcttgtgt gcaaccctga tgatatttta tggagctgtc tgtcttctct ctgagatcaa    8400
acaggactac aactttgtta attgaccact ggctcccttg gcaaaagtag ggcttcttat    8460
attccagcaa gcagcacaat aatatgacaa aaatttattc ttgggagttg ggttctaaga    8520
gagtgcatgc cagaattaga gtttggggtt tagagaaatt atccagatgc caaaagaaca    8580
ttttaatttt tctcttggta atttgttctg gtctccatag taggtagtat tttagtagtg    8640
ctttgatatt gacaagtctt gctccctttc tctattagat ttttcaaaat aaggcatttt    8700
attaattcct ctttccttct cctctctcct ctcagttatc aagcattttt atgactatct    8760
tacaagcaac agtttgtctt gtaaagcaga attttccttt gaaaccaaga cagattattt    8820
ctgcccatag gcttcaggaa ccaatatttt ggcaagaagc atcttttctt tgtggtcagc    8880
aaataggtgg tgagttctgt ctggatccca acaatcaaca cctgaggacc aaatagccac    8940
actgggtggc accccattcg gaagtataca caggaagtag ccctcttgct tgttcacagc    9000
tcaagtcagc caaagattaa cactggtgag agatattttc aaagaagttt gcaggcttcc    9060
aattgcaggg tcattttggg gtgctttctt gcctgtacta attttatctc atcaagcttc    9120
cattctttga gctgtaaact ttgaaataat atactggatt tgctggtacg tttaattttc    9180
tttgttaagt gttttcattc ccatagtaat ttttcatcta gtgtacatat atgcatttaa    9240
aacaaaaatt ctttggtctc cttatgcgta tatgcactgc ggcttgtaca cgtacaagct    9300
acttggtggg attatgtgaa ctggagttag aaatgtggac aattttatta tgattatttt    9360
taatggtgat atcaagatca ccagtttcat tcggaacctt gcataagcag ggagcagaat    9420
gcggactggg tgtggcaaag caagggctta ttttatagcc aaacctgaaa tcacaactct    9480
gaaaaataaa aaaaaaaaa accaaacaaa aaaatcaagt tttgtgagct tggtcagaga    9540
aggaaaagga aatctctccc taccccccac ctccaccatt ttctctttgt ctgcagcttc    9600
ctcaagtgct gcctgtcccc gattttcttt tattccactc ctttcatgtt tttgacattg    9660
```

```
aaatacagac tcttctttcc acttctcagg gtattttttct tattcaccct gtggcatgct   9720
cctaaagaat ttcttttta aaaaaaatct gtagagtagt agattagatt aaccccagta    9780 tctctcccctt aagactagat gacatgaggg gattgcaaaa tgaatagctg gttttttttt   9840
tttttttttt ttttaccctt gaggttaaag cctggttcaa cagttgctga gagagttaac   9900
tagattgctt gaggacttgg caatttcata aagtattttg tcttatgctg tctctgtctc   9960
tgtcttgatc tctgtctctc tctgtctact gtaatgttgg ctactttctc tcagagcctg  10020
agagacagct ctgagacact tcccaggtct gttcggttca gaccctcagta gctggatcac  10080 aagcagtacc caatatgcat atgagggtgc gtgctgcaag tgtccggctg ggctaatctg  10140
cttaagcttc ataaaaatta atcatttgaa acaaagaaa gatattaaag aaattattct   10200
atctccgact tcccctatca gcattccatc aagttctggg atgttaaatt cagagaaagt  10260
taaccttatc ttaaacacaa agttgacttt taaacaaaat tgcttataaa gttctgtaca  10320
gttaccagca ttggttgccc tttgtcgtac ggaagagaat tatgaaatct catatttaca  10380
tagcattctt ccaaaaaaag agacggtgtt ttccagttta ttcactgcat tcgtgtaagt  10440
gtgagtaggc caggaggggt gcttagtgat tacccttttg ctaggtaaca aagtagaaag  10500
ttagattttc tatgatattt gtttaccacg taggggaacc tctctagagc aatactccca  10560
agctttttct tcttgaaatt tcccacctga cagataatac tttagattgt tgctcttaag  10620
gacttctctc agtagctgct acatagagat gattgtccgt gaattattgc ttgcacactc  10680
atgggtgatg ctactccctc tctctcatgg caattcttgc tgccaacctg caggccacac  10740
caggattgag ggcagctcat ctcgataaat ttatagcatt aaagtgctgg gtcatttgag  10800
aatgttgtca atttaggtta cttagtacct aagttttatt ctttaaataa cagctttatt  10860
gagacgtaat ttacaatcca tacaattcac tcatctaaag tgtacagttt catgcttttt  10920
agaatattca gagttgtgca accattattg caatcaattt tagaacattt taatcacccc  10980
caaaggaaac cctatgcacc tttgtgttca tcccctata ttccctcagt ccttagcaac  11040
caataatcta cttctatcta tggatgtgct tattctaaca ttttgtatga atgaaatcat  11100
gtaatatgtg gtcttttgtg actagcttct ttcacataaa atatgttttc aaggtcatcc  11160
atgttgaagc acatatcagt acttcactat ttttatagc ctaataatgt tccactatat   11220
ggatatacca cattctatct atccatttat caggtgatga gcattacggt tgtttccacc  11280
ttttggctat tatgaataat actgctgtga acattcacgt gcaagtttat tgtggacata  11340
ttcagtccac atattttgga cattttcagt tcttttggat acatacatag gattgaaatc  11400
tctgagtcat atgatacctc tgtgtttatc cttttgaaga actgtcaaac tgttttctaa  11460
agtgtctgca ctgttttaca atcccatcag caacctatgg gggtccatttt cttccacatc  11520 cttgccaaca cttgttattc tctgtctttt tcattatagc tatattagtg ggtgtgaagt  11580
ggtacctcat tgtggctttt atttccattt ccctaataac aaataatgtt cagtatccat  11640
gttcttattg gccatttgta tatcttcttt tttgagaaat atctatttgg atcctttgct  11700 cagttttag ttgggttttt tattattgag tttaagatt tttaaaaaat atattctgga  11760
tacatgtcct ttaatagatt gtgatttgta gatatttttt cacattctgt gagttgtctt  11820 ttttacttc cttttttttc ttttttacgtt cttaatggta tctagattga agcacaaaaa  11880 tgttttaag tttgatgaag tccaattcat ctatttattt tctgtttgg cttatgattt  11940 tggcgtcgta tctaagaagt ctttgcctaa tccaagatca caaagattta catatgtttc  12000
```

-continued

```
cttctaagag ttttatagtt ttcgctattt acatttaggt ctttcatcag tttttgatgta    12060 atgtttatat atgactgagg tagggtcca acttcattct tttgcatgta gatattcagt      12120
tctcacaata ttgttgttga atctttcctc acttaactgt cttggcaccc tttgtgtaaa     12180
atcagttgac cgtaaatgtg agggtttaat tgtggactct caactatatt cagttgatct     12240
atatgtttat tcctatgccg gtaccacgtt atcttgatta ttgtaggttt ttagtgagtt     12300
ttgaaattag gaattttgaa ctcttcaact ttggtcttct ttttcaagat tgctttggct     12360
cttgtgggtc ccttgaattt tcaaatgaat tgggataagc ttgtcaattt ctacgaagaa     12420
gtcagctagg attctcacag gaactatatt aaatctgtaa accaatttgg ggagcattgt     12480
catctcaaca acgttaagtt attttcatcc ataaatatgc gatgtcttcc catttattta     12540
ggtcttcctt ttgtcaacaa ttttattgt tttcagatta taagttttgc agttcttttt      12600
aaaatttatt cctaagtgat ttatttttg atactataaa ttgaactgtc ttattgattt      12660
tattttcaga ttattcgctg ccaatgtatg gaaatataat tgttttgtat attgatcttg     12720
tatcctgcaa ccttgctgaa aatacctgag ttttgaatgc ttctgggact tatggggaag     12780
agggcttctg ctgctgcact gaaagttaaa gcttacttca tttcatcctg tatgaaggct     12840
gcatggggac attcttctca gttttactca gctataaatt cgaactggta atcccatccc     12900
ctttcgggat gaataggaga gtgttttaa atgttcatct ctttagagaa cagcaggaaa      12960 gaagccagt aaggtttggg tagtttataa tccctttttt agaatttgga tttgggaact     13020
attagcaagg cagtgagtaa taataataat ttctatatag aaaactaaca tgtagaggtg     13080
acaaatgaaa tcactagcta tattaggctt atgtttaggt tatcgtaagc agctaaaatc     13140
ataattttat gttttatat gttgtccttt ggacaaagta aattccagta ctccttctga     13200
tgtgcatttc tagatgggga aaggattcat ttactctcat ataatttaag cttcttttta     13260
gggatgtact ccatagccat gaagcaaaga taaaattcat ctatacacag actgaacttt     13320
gtcttcatta acactctagg ctaagggtca tagctaatca gctacaactg taatgtcctg     13380
ataattgtga attaactgca gggcacccag caaaaggttt agttataatc taatagctgt     13440
ctgtagagat tagcctaata aagggatttt ttaaaaaaga atctggccgg gcatggtggc     13500
tcaatcctgt aatcccagca ctttgggagg ccgaggtggg tggatcacct gagatcggga     13560
gtccaagacc agcctggcca acatggtgaa acccccatgtc tactaaaaat acaaaaatta     13620
tccaggcgtt ttggtgagca cccacaatcc cagctacttg tgaggctgag gcaggaggat     13680
cacttaagcc taagaggcag aggttgcagt gagccgagat catgccactg cactccaggc     13740
tccgtcaaaa aaaaaaaaaa aaaagaatct atcaatcaac cacttttcat taagcacctg     13800
ctatgtgccc agcatgtgct aggaagagat aaggtgaaag gggacacaat tcagacagaa     13860
tcttcttgag gtaactgctt acgaggagct tatagccact aaaaacaaaa acaaacaaaa     13920
accaaacaac caaaaaccaa acagaaatgc agtatcatca tgccatgatg cctgtatgag     13980
atcctggatt gtacggtatg gatttcttaa aatgtagata ttttaaaaaa aaagaggaat    14040
gaatcaatag aggctgaagt ggtcagcaat gttacctgtg gctgctttta atccttcgtg    14100
gaagtaagta ggagcatgtc taaactcaag caatagatta aagatcttga tgtatatttt    14160
aaataacaga agttagtacc actggaaaga atgaactgga ggaatgggtt gaaatctatt    14220
tctgcttatt caatagtgca ccccagtcaa gttagttgcc aatttcttct tcagtttctt    14280
tggctatatc attgcacttg gtgggtacat gtttatgatg tctttatctg aacaagtcag    14340
caataatatg agtaataaat taaaattgaa ggtgattaat ggctctgaat ttgacataag    14400
```

```
agttgttttc ctgccttcta agtttccatt gatcctgatg aattgcacaa accaaacaat    14460
tcggggagta aggggggcaca tgatgatctt ataagagctt tgctgtatta gacaacgtaa    14520
cattctgaaa tggcctacca cctaacatgg gctctgttct ctgcaggttg agtaggttcc    14580
ttgcttgtgg aactgtagtc ccgctatttg gccgctaggg ggactgcaag tgccccgtgg    14640
caggatttcc ctgggaatgg tgagcctcca ttgatggttt caacacacag ccaaggccct    14700
atcgcaggat aacttgaacc agaactgcct agcaccagac aataaataag ctactatggt    14760
acttactgtt tcatttggga tgttgtttct cgaagtggca agcatttttt agtaatattt    14820 tgactttta ataccttct ttgcatatgg agcagaaaac agtgacactg gatatattca    14880
agtagcactg tccagtttat agagaagttt catattccat tattgcattt cattcttgtt    14940
tctacctttt acaagtaact agagtttgga gtattataat agtattcata ctattacagt    15000
actattattc ccattataaa aattgtgcaa agagtggtta agttacatgt ttacaatcaa    15060
acagcttcaa agtgactgat ctggaatttc agtcccattc tttcttctcc agatcatgtg    15120
ttccctgctt ttatctcaca gctctttta ccttatagat gggaaacatg agagtcagag    15180
aggcaaaaga accacaagtg gtatcaatac tagaaattta tgaatttctt aaggcttcta    15240
ggtttgttac ccatccacca gactgatgga tttggttgtg tgagagttct gggtgccaat    15300
aaccttgcca ttctacttta cagactgcat atattcaata aatgcttatt aagcatctac    15360
tatatgccaa attctgtact aggcaccaat gatgtagtgg tgaacagaac agacaaaaat    15420
ctcttcgtgg agcagacagt ttaatgagag gagacatgta gtgtacatct gagcatgaaa    15480
agtgccatgc agaataactt cacagagtgt agggtataga gattgatggt gagagggaat    15540
attttatatt tgctggccag ggaaaaacctt actggaaaag taaattttga gtagtgacct    15600
gaaggaaatt aggaaatgag ctgctatttg gacatctgga gttagaatat tccaggccca    15660
gggaaccaca ggcgcaaagg gcctgaggca ggagcacact tgctgtgatg gaggacaaag    15720
aggcccatat ggctggttta aataagtgaa ggatggtaga caatgagatc agagttaatg    15780
aggttgcatg gtaggtcttc cttaggactt tgaattttac tcctaagcag gttgtattgg    15840
acggttttga gcagggtaac atgacctgac ttacatttta acaggctccc tcctcttcat    15900
aacatctgtc actctgatat attatacgtt tgtttgttta cttactgtat gtgggggggaa    15960 gagactgtgg gagcaagggg ggaagcaggg aaacaagtac actgcagtga tctgggtgag    16020
aggtgaccgt gtctcagact aaggtggtat tggtggagaa ggtaggaagt ggctgaattc    16080
tggatgagtt ttgatggtat agccaacagc atttactgac agattggata ttcactgtga    16140
aaaaaataga gatgaggatg attgccaagt ttttggtctg agtaactgga aaaatgagat    16200
tgccatttac tgaaatggtg aagactgtat gtagagcagg tgcatgggca gggtagaaat    16260
caagagtttg atttttgact tataaagttt gaattatctg atgaacatcc tgatggcttc    16320
ttctcagtta gttctcatgc agtgccttca gctttgctgt tcttcaagaa aattaaaaag    16380
gaacttagag atcgcctagg ctgtaggtac cctctcccct ctttccttt actttataga    16440 ggtctataga agggtaggga cttatccaag gtgaaacagt gagctggcga cagaactagg    16500
gcacaaaccc agttctcttg aattctgaat cagtagattt tctttttta gtgtgattct    16560 gaggactcat ttgggcaaga gtgagttttt tgttattgtt ttttgtttgt ttctttgccc    16620
aaacctaaaa ccaggtaatt aaactaaata gtgaataaaa ctgggaaact atacaaattg    16680
gttgctctcc ccaatcacac tgaaatatta ttattttac tgaaccacat accaaaatat    16740
```

```
ttttcctgta aaaacacagt aagtgaactt ttaaaggcaa ttgagctttt aacaaagcta    16800
gaatctacag aggacctgga cagaaatggc cttaaatcct aggaaattag agttcatgga    16860
acctgggaga ccatcttgtc cagctagctc attttatggg tgaggtgcct gaggcaccaa    16920
gatggaaagg gacctggcta agctcataca gcaagctagt gcctgagcct agtcagagcc    16980
tgttttaagg gttagtcgta tgttgttttc ttgaaaaaag ttacattgga aaagtgaaaa    17040
ttctttggtc catactgaga acaaagaatt atacataatc atatataata ataatgatag    17100
cacttcctga atgtttgctg tgtaaacttt ggcaccttgc atgaattgat tcatttaatt    17160
ctcatgtcaa ctttaggaag caggcctaga gaggttaagg aacatgtcca agggtcacac    17220
agctaggaag tagcagaact tgtgtgcact cccaggaagt ctggcttcta accacaaggt    17280
tctaactact gtgcaatacc aggagcttct cagattaccc ttcacctttta ccaacccaaa    17340 tgactggtga cgtaggtgac ttcattatgc tctgcccta ttatagtcca ctgatcctca    17400 ccaataggt gggtggccta gaggttaaag tagaggcaga gtgatggaaa ggggtggtta    17460
gaagaagttg atgactcatg atagggattg gaaaacagga ctacaggaat tattgaaaag    17520
ggcctagaga tcccaaggag gttgatctcc gactgctaca aacctgggca attcaatgcc    17580
tgcttaaata ggagagttaa gataagaaaa ataaaattgc caattttttac agtcagacat    17640 tgttttattt attttacatg tattaattca tttaatcctc aaaatactcc atgaggtagc    17700
tacaattatc atttctatgt tgtagatgaa gaaacaggca cagagcaatt aaataacatg    17760
cacaagatta gagaacaagt aagtggaagt gccaatatta gaatctaggt agttcagctc    17820
cacaacttat gttattttcc actatattta tggaatgagg taattttctt ataacagaaa    17880
gtttttaaaa tgcaaaaaca ttgtgcctga acttcaaaca ctgaacaact catatcctta    17940
atatgcacca gtttctttta agcactctta gaaggaagga tacttaacct aatgtcacat    18000
ggtgagtaag tagcagaacc ggaacttgaa tttgagactc cggactgcca gacctctttc    18060
cactctatca cttgggctcc cttctaacat tgacttgtct ccctccattc ctcctccgta    18120
ttgttctgcc cttcaccttt taattacctg tctccatcaa caagattgga cagagaattg    18180
ggagagtgag cagagtccat ttccttccag agactggaca aaaggaacaa aatgttagga    18240
aaaaatgtca gcatgtggga tttgtgggat ttacactaaa taagaaggga cacttcccag    18300
gactgacaag atgctacctc cgtccctcta ggccccaatg tgttgtgcag gatcccatag    18360
gaagtcatga atgtggttgt cagataacct ttttgttact gtggaaatgg aagcaggcta    18420
ctgcaaaaat ctgtctctcc aggttttctt ttaaagaagg tagtcttgct aaatgataac    18480
tatttcagca tttatttgaa aatgggcagt gcaggagaga aagaattttt ccaagcttgt    18540
cacattgggc cacctctctg aagcattgtc caacttctaa ttagatgagg agactgcata    18600
aaccaagagt tgagagtaaa gatggaaaca cttgatgttt ggtgtttggg tgcagaaagg    18660
attccagaac atgttttggg tctctttact ctgtccatcc ctccttccct ttcatctttg    18720
tttaaaaacc acagttagca aatgtgtagt ctgtttgcaa ttgttcatct gaaaaatttg    18780
tttgatcagc cttttgaata aaaagacca aattagactg agatatttca gtcaccaact    18840
atctaataat agaccaaaaa ttttaaccat gctcatactt tcatatggta tgtagtttgc    18900
tttagacatt ttctgggctt cagtgaggtg ctagattgac tcaaaatatg gcaggtcaga    18960
tgtgggattg agcagggtgg actcttctct acccttccca attcagagtt ccccatcaaa    19020
gatgatctca tagtgtttga aaaaccaagc tgaaggcttt gggaattagg gtgctgaagg    19080
gatatgctgt ttcccaaagc cttctcagtc attccttctc cccccagttc agattcttaa    19140
```

```
cacctctttc caggattagt gcagtgatcc cacgtccttt ctctctagct ctctctgcta   19200
ctctctaatt cctattgtat ttgtgccacc agatctttcc aaagtttagc tccaatcttg   19260
tctgtatact gctttaaatg tctattagtc tttaagctcc ttaagggtgg gagtcctgtc   19320 ttatttttc cctattcttc gtgcttaatg caaaggaagc cttgctgtat agttgtgtaa   19380
tgcatgatta caatttcagc ttctccccat tggcttatgg gttaaagtcc aaattattta   19440
aatctggtgt tcaagtcctt ttatgatctg cttatttttc cagcctgaat tcctggagtt   19500
cccttacaaa actcttaaaa cccagccaaa aggatctagt cactgtcact ttaaaccatc   19560
ctcactctct tgttttttga acatgttatt tttcttataa tcccttttgac cttgaaggct   19620 atcccaattt caatactatc cattcttcta tgacagcccc ctacaaaatg aatattctca   19680
acctcccaac ccaaggagaa gtgatctata tgacacaata tggttgaaag aatgttggct   19740
tcacttcttt atctgtaaac caggggctag aaatctctag tttataagat tttgtggaga   19800
ggggatcata tgtgattatg gatgttaggc acaagtcaag agtgcataag acctttgga   19860 tttatccctt ttttctttct ccatcaatat ggtacttagt cccttaaatc agaagtactt   19920
gtgttaatgt ctgataacgt ccttctaaat atacctctaa acatctgtct ctctttaggg   19980
caaaggttgg atatatctgc aaagattctc tttggatata agatatccac agcacataac   20040
ttaacagtgg tgtacacagt aggtattcca taagtatttc tttatgaaat gattcagagt   20100
caatagtagt aagtaactgc caaaacaac tgatggattg taagttccat taacataaat   20160
acagtcagcc ctccatatcc atggattcca tatccacaga tttaagcaac tgcagatgga   20220
aaatatattt tagagacaca gtaaaaataa caattcgaca gtaaaaaaat acaaataaaa   20280
ttatgtaaaa caactattta cataacattg tattagctat tacaagtaat ctagatataa   20340
atgaaatata tgggggatgt ataggttaa aatacaaata tgacaccatt ttatatgttt   20400
tagttaagga acatgaatat ttttggattt tggtattcat gggagtgggg aatggaacc   20460 atgccccttc aaataccaag ggactattat atgggacaca gaataaagga gttgattgtc   20520
ttgctctgtt aaattctggt cagacacatt tgcaatgtat tgttcagccc cagtattcat   20580
ggagcatctc cttttgtaaa gcatggagga gctgtgagag agacatggag cagtgaacat   20640
aactattgtt tcaacgtacc tgaaggatta tcatggaata aagaagttag atgttttct   20700 gtagtacccc aaagggcaaa agcaatgagg acagattaca gttcagtaaa cgaaagaggt   20760 ttttttttt tttttttttt tttttgaga tgggagtctt cactcttgtc gcccaggctg   20820
gagtgcaatg gcgcaatctt ggctcactgc aacctcgcct cccgggttca agtgattctc   20880
ctgccttagc ctctggagta gctgggatta caggtgtata ccaccactcc tgggtaattt   20940
tatttattat ttatttattt ctttatttat tttagtagag acggagattt catcatgttg   21000
gccaagctgg tctcaaactc ctgactgcag gtgatccgcc tgcctcggcc tcccaaattg   21060
ttgagattac aggcgtgaat caatgtgccc agcctgaaag atattttctt agaatagctt   21120 ctttcacccct tcatcagaag ttgtcaacat ggaccatatg agttttgttt ggtctatatg   21180
gtgtatatgt gtgtgtgtgt gtgtgtgtgt gtgtgtgt gtgtgtatgt gtgtgtgttt   21240
attgaattac ttgctaacat tttacttcaa aattcagatt tccaccatag ggaatgaaga   21300
tctggcaata caggactttc attcctacat ggtaatgacc agctgtaggt gaaaagcagc   21360
tgatcctctg gatgggccat gcactttgca gtttgcccag gcagcactga tccgcttat   21420 tcatttaagt tacctgcttg actcttctag tcattcgagt atgtcatccc catcagatca   21480
```

```
gagacctaag caaatcttgg gtcccttgct tactccaagg gctttcactc ctcgtatagg    21540
aggagctaaa gaaatgtaca agcagcacca caataggatc agacctggct ttcaattcta    21600
gcacggccac ataacatagt tggatgacct caggacagta acataacccc tctgagcctc    21660
tagatcttca ttatctgtag agcactcttc ttatagagtt attataagaa tgaaataaaa    21720
caactaggat aaagggcatg gcacttagta ggtgctgaaa tattagttcc cttcttctaa    21780
ttcaccacac catatctgtc tatctattgg ctgaatcaca taaatagtaa attcacattc    21840
actgaagaca ttcaagaaga gtctggaccc tttgggaacc atgtataggg caaaggtttg    21900
aactcatagt agatgatttt tacagtcact ttttaacaat ttaaaagcct atagatgact    21960
ccaaaatgcc catttggatg atatgaggca tactttgtgt agttaaggat tttaaataca    22020
taacagagag gctgaagggc cttcgggaaa gaagctgggg taagagtcaa agtgtagtat    22080
gttgaccgat gttcaggaat aggctttggc atctgacaga ttttgtttta aatactggct    22140
ctgggtctta ctagcttcca gttctgggct gcttcacctc tcttgagttt cagtttcttc    22200
atttctaaaa tgaagatact aatgcttcct ttgtttgggtt tttgtgaata taagtgagat    22260
aataaatgta aatatctagc ccagggcctg gtgcatagta caagcttcat aaattgtacc    22320
tattattatt agtagtagta gtagtccaga caaacagagg ttgggaaaac gctagactct    22380
ggctgacata catgggcttt tccccaggcc actgctgcct ggcttcccct tccacaaagc    22440
tttgagtctc caaaatgctt tggctggaat gtaagcgtga ggtcattgca gataacaggg    22500
gagcatgatt tgcttcggta atgcaagtta ttaagttact tccctcagcc cagctgaaat    22560
ctcttattgg ttgatgtgtg cttcaaagtg tgagacagag ctagtctgag gagagaggga    22620
gagtgagaag attcctcttc ttggccagag gtcatggtct tccacaagga acagaatgac    22680
tcaatgcaaa ttatgggacc tcttttgagtt tggggcccct acatttaaac tagtaactcc    22740
gttgcacata ttggcaccct tcccccaaca aaattactgg gcaggaattt tcttgaatcc    22800
ttccgtggcc tggaatgatc tcccttctca tccttgtgat ccacacagct ggcaaatggc    22860
aggcagcaga acaaaaacaa gcctcttagc atatagggag agaaagagtc acagcagtac    22920
tgaatttgct tgggaaccta atgttaacaa aggaccttcc tctcaacacc ccaaacagat    22980
taaaacattt ttttaacagc aagttgtgtc tcggagcagc tctttgcttg ggtatattta    23040
aagatctgct gagtcattta agagcaggct ggcatatcct aagaggcaag gactataccc    23100
cagtctatgg gggagtaagt tgagaggtga aatctgtttg gctttctccc atggaaacaa    23160
acaaggtgat ccacttccat ctcccacgac tctggagagc atctactaag ccttcttatt    23220
ctatcaactt tgaactcctc agtgtataat agagtaaggg tgagagggaa ggagcagtcg    23280
taccagtgtc attattggta tgttcaggag ttcaatttct tcctgattca gtcttggcgg    23340
gatgtatttg tttgggaatt tatccatttt ttctagattt ttctagtttg tgtgcataga    23400
ggtgttcata ataccttctg atagttattt ttatttctgt ggtgtcagtg gtaataaccc    23460
ctgctgtctg aaattgtaat ggccctgcta ttggtagctg agagtagcat ggaagtgtca    23520
ggttgatggg ttcatttaat tctttttcttt tcagtttcag tcacatgcat tgttaccatg    23580
gcatatgaca gttgctagaa agtgaaataa ttttttttct actttattct ccactgcact    23640
tctaaattta ttagtggaga aattagcagt taccaactgt tcattatagg tacacattgg    23700
ggtttcctta gagccaattt tcccctggt tttcatcttg taaatctgta atcctaaaaa    23760
ttagcaaaac ctagagcttc tctttggtcc tggcctgttt gaaccctgtt ccacagaccc    23820
caatcttctt tcttgtttga ggcaactatc cttctctttg cccaccgcca ttttccttca    23880
```

```
tctactttc  ccttctctag  cacctcagac  tgtcttccca  cagtggcaca  gcctcccact   23940
ccactttcac  tgtgccatct  ccttgccatc  aaaaccatcc  tcacagaccc  ttctgaaacc   24000
acttctagga  agggaaatca  caatggatcc  atgaaggatg  ctttctggat  gactttaaaa   24060
gattggtatt  aagatatttt  atcagtggta  gcaacactga  cttattcagg  cagccatgcc   24120
ccggatctat  aagaaatcag  gtaagctaaa  agttgcttga  gctggcagga  gacctagttc   24180
tcttttttcc  tttccctctt  gcattttgtt  tatcgatggt  tttcaaagga  cttagaggct   24240
ggctttgtta  tagttagttg  gtaagagaaa  tggtggagga  ccggaaaatg  ggagtggaac   24300
gaatgagcat  gtttgagact  aagttattac  aattcctagg  atgtataaat  tgcttgaaat   24360
ctaccaagta  ctttcagaca  cattatcttt  tttactcttc  aaaatcaact  tggaggtagg   24420
cacaacaggg  atcaaatcct  tagttcacag  atgagtaaac  tgagactgga  ggaaattaaa   24480
ggagattcca  aggtaactca  gacaataagc  aacagaacca  ggatttggtg  aattttttgg   24540
ggggtgggag  gtacagagtc  tcactcaggc  tggagtgcag  tggcaaggtc  tcgtctcact   24600
gcaacctctg  cctcctgagt  tcaagtgatt  ctcgtgcctc  aacctcctga  gtagctggga   24660
ttacagacat  gtgctacaat  gcctggctaa  ttttttgtatt  tttagtagag  atgaggtttt   24720
gtcatgttgc  ccaggccggt  cctgaattct  tggtctcaag  tgatccacct  ccattggcct   24780
tccaaagtgc  agggattata  agcatgagcc  actgctccca  gccccagacc  attaattttt   24840
gacagtaagt  ccaactttt  tcaagttcac  agctcagatt  tgctattgaa  tgaatgagta   24900
tatatgtcat  ttgggaacat  tctttccaac  ttttggttga  agatttgttt  tatcacttgt   24960 gaaaatttt  tttcattctt  agcaatgtca  gtttagttaa  atgagcattt  catttgcgaa   25020
ttcactaatt  aattatttta  ttcatcaata  catttcctga  gtaccaactt  tctatcaaac   25080
cctgtgctgg  attctgaggc  tacaaagaga  aataagatac  catctcaggc  ctctaaaatc   25140
tcacagactg  gggactgaca  tctcagtagt  aaacatatga  acagcaactt  gtgaaacgcc   25200
attagcaaaa  tctcaagtta  tattcttcag  tgactatggc  catcctaaaa  atgggtgtc   25260 ttttatttgg  ggtaaatgaa  gatgaagcct  tatgagaaat  tgcattttaa  tctaatcttg   25320
tcttgctaag  aacagaagtg  gaatgtttca  gcctctgtgt  gtgtatttgt  gtgtgtgaag   25380
gttgagtgtg  tgatgatgga  tggggctgcg  agattgttaa  gtaggatcta  tgggggggcct  25440 taaatggtcc  tggtgagtcc  caactttctg  gttatgtatt  tgagtagagt  atgggggtga   25500
caaagattgt  tgtttaagag  ttgattttag  atttttttcca  agtaaatggt  cagctgactt   25560
ggagcatcat  cattccactt  gctttgaaaa  cctgccactt  aaggctcctt  ccagtcatag   25620
gttaactctt  tctggtcaag  tattactctt  tttgagcatt  tacctgtcag  tgacaggtac   25680
aatgttagat  gttgtctctc  tgttttcttg  tttaatcttt  actttgatcc  taggtagctc   25740
ttattagttc  cactttatag  gtaagaaact  gaatttcaga  gacttgaatg  acttgttcaa   25800
gatcacatag  tatagtaact  tggtagtttg  ggacttgaat  tttgattgtt  cagttttttg   25860
tttgtttgtt  tcctggcctc  cctgctgttt  tcactattcc  acaccacttc  agctttattt   25920
ttcatagagg  ccattaaatg  taccctccat  cagccaaagc  ctcttgcctc  ccttcaacgt   25980
aactcttctc  tagcgtcctc  ttaataatct  tctgaaaagg  tttacagcc  tttctgggta   26040 ctgggaccca  gagtcttaat  ccaggctctt  aagtgcctta  tttaactgta  atatggaaaa   26100
tcaaagtcac  agctaattca  ggaaaaatga  gtttgggatg  tgaatttcct  aggcaacttg   26160
tcatctcttt  tttacttcct  tagcttcata  aacttaccca  caatgttccc  tgaggactaa   26220
```

| | | | | |
|---|---|---|---|---|
| gagtaatgga | gggtgatgag | gaaaggcttt | cctcccttcc | tttccgagag tcctttagcc | 26280 |
| aaatgccaca | cctcctcctg | tttccctagt | ctccgtgcag | agatggaagt gggagataga | 26340 |
| catgggttcc | tttcagccct | gagttcatgc | cagggttttc | tttccctcta gctggactga | 26400 |
| ggtaggagga | gaggttgaag | tccaccaata | agaccatgag | tgaagaagac taaagtactt | 26460 |
| gaaagagcag | cagacctacg | cttaaaatac | tagggtttgt | gtccagactt tgtgggttac | 26520 |
| tatctgtata | attttgggca | agtcaacagt | tctgagtcag | agttccctta tcagcagatt | 26580 |
| ggaagataaa | ttctaattat | atagatgaaa | cattaagtct | agaagtaatt tgtaaattca | 26640 |
| gaaagggctt | atagatttaa | agtgtagccg | ttttgattac | cacaaactaa atcctatact | 26700 |
| tcagggataa | aatcttctcc | tgttttttct | aaaagcctgt | gcatgtgtgg tgtaaggggt | 26760 |
| gggttttccc | ttgtaccagc | aacttagcaa | ttgtagtaac | ggggctgagg gcagtggcat | 26820 |
| gcttcttcat | tgagcaagtg | tgaaaagagg | gttatgcatt | cagggggtcag cagatggcag | 26880 |
| gcagagtagc | ccctccaaat | ctccctccca | taccacaaag | ccctcttatt tattcaaact | 26940 |
| taacattaga | agctcatttc | aagtaggcac | gtctgtgtct | gggcgtctat tttccttctt | 27000 |
| tgtatatagc | aggcatttgt | caacttggtg | aaaagcatta | ctcttctttc catttctgag | 27060 |
| gactaattgt | gcttcttcgc | tagacacgag | ttcaaaacag | tgggttgaaa gagggcaagt | 27120 |
| ttatgccaaa | gaatcagaaa | tagtcataat | ttagagagaa | ttctagaggt cagttccctt | 27180 |
| tcgtatggac | tgggcaactg | aaacccagac | agggaaggga | attagaccaa gttcacaagc | 27240 |
| acaaacactt | tactggcaca | ttcagattgg | aaatcgaggg | cttctgctcc caggtcagaa | 27300 |
| ctaaatgccc | tttctagcta | gggtgttctt | tgatctcagt | gattttgact ctttctactg | 27360 |
| cactctgggg | acagtgggtt | ctgcggtacc | aactccaatt | aaagtgggaa tatgtaccag | 27420 |
| cccctcccct | tggtttttat | ttttcagagg | cctggcagtc | agaggggattc tgatctctat | 27480 |
| atgcaatatt | ttcacactac | tgtacttatt | gaaatcacat | ttgaatcttg gcaattaaca | 27540 |
| aggcagtaat | tggcatcagg | agggtatgtt | agtttgctta | tctgcgccgt ccctcctctt | 27600 |
| cccaacccac | tgtgtattgc | agaatgtttt | atcagctctg | atttgccaag ttgctctctt | 27660 |
| ctccagtagg | tgctgcgagc | agagagggat | tcctcggagg | tcatctgttc catcttcttg | 27720 |
| cctatgcaaa | tgcctgcctg | aagctgctgg | aggctggctt | tgtaccggac tttgtacagg | 27780 |
| gaaccaggga | aacgaatgca | gagtgctcct | gacattgcct | gtcactttt cccatgatac | 27840 |
| tctggcttca | caggtgggag | gttcttcaat | tgaaaactta | gaactcagtt tctagggtag | 27900 |
| tgagtgttgt | aaggtttgga | ctgtgaccta | atattacgca | gccatgacat tatctattag | 27960 |
| gcatctagac | tagcttgctt | gaatatctta | gcatgttgac | taatttgggg cagaatatag | 28020 |
| tgtgggtggg | ggattttgtg | tgtgggggg | ggttgggggt | tgagcaattc attattatta | 28080 |
| aaatgcaaaa | agcacttaat | tcgctatgat | aagattgcct | ttttcatgca tactggccta | 28140 |
| cctgcaagac | ccctagagac | agtaagcagc | atacatggtg | tcttccagtt ttcagccttt | 28200 |
| gtgcaaggaa | caactgtggg | tttctgcaca | tgtgttgtgg | tttgatgttt gtatgtgatt | 28260 |
| gtgtaccagg | gtatgtgtgt | ctgttattgt | gagttcattt | ctgagcagtt gtgacacaca | 28320 |
| gagatccaga | aacagtgtct | taccctgtgt | gctttgctag | tgggaacgtg tcttttcttt | 28380 |
| tgtgctcgta | tctctgtgta | atcgagtgtc | ttgctaagtc | aatgtgcctc tgtctctttt | 28440 |
| taccagttct | gtctttgtgt | ctctgtgcct | tcatgtattt | ttcccctga gtttgcacgt | 28500 |
| ctctgtctat | gtggatatct | ctcactccag | gccactgtat | cactgtgtct gtattacagc | 28560 |
| tgtttatttc | tgtcggtgtg | tggatttcta | tgtctgtttt | catcttaatt tgtgtgtcta | 28620 |

```
agcaagactg tttggggtg actatttcag tttatgtcat agccattctt tgtgtgactg    28680
cttctaggta tgtcttttc tatgcccta ttgtccccat ctccatgtgt ctctgtgtgt    28740
atatgttcta atgtatctgc ctacttatct tagtttgtat ttctctgggt gtatatccct    28800
ctcttgcagt tctgggcctt tgcagtttt ggcttatgtt tttgtatata tccactagaa    28860
ttggcttctt atctttttg tgcatgtttt agtttgtatg agtgagcata tccaactctg    28920
tctttgagaa gcagaactgt ctgtgtttgc agtcagttgt gttggctgtc cctgtgtttg    28980
tccctgtgtg tgcatttcat tgtatgtgta cgcatccatg tatctttctg cttctctgtg    29040
accagatatt tctgtgtagc tgtctatgta tattggcttc tgtctgtgtc tgtgttgttg    29100
gctctacgtc tgtgcatatg cacccaccgg gttcataaaa agctcacctg ctctccaagg    29160
aatctaccag attattttgt gaaataactc acgtttcgtt tttttacttg ccagctgcta    29220
tggtacttaa aagtgtgttg gtacgtaggt gtgcataatt tattcatgta ggatgtcaaa    29280
agagtcagtt aaaaattatg cacagtgtgt ctttattaac aggacacttg tgtgtagaga    29340
atccttgaga aatgagtggt tagatgataa atcttttcat attaattcca tgatgtcagt    29400
gaagtaaatt tgcaagatat gggctgcata agaactatgt tctttttaaa actcagcata    29460
ttgatggtgg agaaagcatt tatttgtact gcaaagtctt atttctgata agacatcaca    29520
aataagaatt attgtgatga gacttatcac aaataagaat tattgtgata attcttattt    29580
gtgataagaa ttactgggtt agaaggtgtt acttttctgg ttttgtttgg gtttttgttt    29640
tgaagtgtta ctacagatgg tgtcttaggg acaaagagct ctgaggttga cttagaacac    29700
atggagtaca gataaaaagg agaatgaaaa gtaacagaga gatgggcata ttccttgttt    29760
gaatggagtc atccaggggc tcaggatgga gtgcacagga aatggagagg tgaaggtcat    29820
agagagaagt ttagcaggac cagatctttc cttgtcctgg gctgctgtga ccatataagg    29880
aaggcagtaa ggggagggt agggatgagg aagagaccag ctctcctctt tctttctgat    29940
ggaaggttac cacctctatt taaaacttct gttctttgg tttctctttc tttctttgat    30000
tatattattt tctggacttg ttctgccaaa gcaagaagga aattccacat gtggctcact    30060
catttattat acttgtttct ttgcacgata ttaaagacag cttgttaagt gtcactgcaa    30120
acatcataca cactgatcca ctgatatggg caggggttc tttatgccag ttctgctctc    30180
ttcccagtgt atctgtggtg cttaatgggc gcaaccatga tttttctgat gtcagtctgt    30240
gatgtcagtt gtccagtgtg tatgcaggct gcttaagagt acatacagtt ccttcacaat    30300
tatggtagtc cctgagaagg aagtggtcat taataaaaga ctaggttcag tagaaacatg    30360
taagttgtct aggtgttgga aattaataca gtactgtgct aagggaacat atatctagaa    30420
gttaactgaa ttatgctcaa taaaaagagt acaaatgttt cataaatatt ttgacctaat    30480
cctcctgtaa gattaggaga gggatatttc cgatattcaa ataattttt taattggcaa    30540
acaccttaga catactattt acataaaatt gacatgacaa aattaagtca ttgtgtctgt    30600
tttatgataa aacaggctct tttgatttag ttagaattat tgaatgtaaa ataatgaaaa    30660
ttaaaaaaaa aacaaggagg aggaatctat cctattttat aattcagacc gttgaattga    30720
gttttctttt tgttgtattg atttaaatgc agagaagtct atgatgctgg attccagtca    30780
gaagataaac atttgtatgt gggctctaca ttgcagccaa ccttgataat ttcaaacctc    30840
gattttctca tctgtataat ggtaataata aagcctgtct cagtagctac caaatgattg    30900
catatgacaa acttctcact tatttaaggg aaaaaataag aaaagaagg acaataggt    30960
```

```
ggattttttca tatagtaaaa tttattcagt tagggtaata ttctgagatt gtcttctgaa    31020
gcaaaccctg caaaccctgg ccattctgtt ttgtttagga aagaattcat cagttctgat    31080
tctgcctttt ctggggaggg aggctgagta ttggattgaa gaggagtcac tacttttctg    31140
agatgatata tccgtggtaa aaattattaa tgctttgcac atgcaacata gagtgttcaa    31200
ttttgttagt caacaaatat ttaagtggca gctgttatga cctcaggggt gtagtgactt    31260
ccttattgtc cttttaattat taaaaaagaa atctatatca gaatatcagg taaactctta    31320
ttacatcaaa tattataata aagatacttt ttatattctc taaacaaagt agagatctca    31380
gatgttggtt catttatcaa tataatatta gatttgaaaa ttccagtata caaaaggaaa    31440
aggacagctt cttaaagttt atagtgattt tctatgaact atcaattccg ttttttttctg   31500 ttttactggt atgatggaaa ctaaatttcg agttgtaagt agtagataat tagactgcag    31560
ggtaagcctt gagattactt cttttcaggt aggaaactct actgtgtatt tggctagttc    31620
aacctatcat gggtagtcaa aaatagttac atatacaagt cagcattttt taaattgttc    31680
agttgtgctt aagattggtc ctttccagga acaatccagc tttatcaaaa aattattgcg    31740
tacatgtaaa gtgttctgac attttaatgc tcacaatagc cgaatgacgt gggtaagaat    31800
cttcgtcttc attttataga tgaagaaatg aagcacacaga gacataaatt aactgggcca    31860
gggtcctacc actagaatgt gatagatgat aatttgagct cagcacatag ttatttccct    31920 ataaatatttg ttttatgatt gtagatagt ctgctgacca accttaatct ctgctccta    31980 agattaacca ttctacaaag cagaaactgg aggtcattca aatgaaagct ctacacttt    32040 agagggccat taacaatgct caagttaaag aaaagcaatc aaagacaact aaaatactgg    32100
taccttcaaa cagtacttat gaattattta accttagata atttggcttt gagttagaaa    32160
gatagagtaa gatggaggaa ccaattcttc cctgggttga tatttattta tcttgctctt    32220
ttgaagtcta ggccaatcat cctatttatt ctgaatggcc cgttaacgtt tatccattta    32280
gggacagcag gttggcaca aatggattgg ttttctgagg tcttatgtag agggctgcac     32340
tgactgactt ctgaaagtcc cccctaaccc ttcaaatctc agggtcatct ggtctcaagc    32400
cttcaattat gaatacattt ctattgcctt tttgagtaac agcacaacac tgcaagctga    32460
cccactgggt ggatggaatg gggctcttgc cctaccaccc tttggcaaac aatttgaggg    32520
tggcattgtc actacctcat tgtatatagg gtctcttgag gcccagaatg gcaaaataat    32580
tttcccagtg tcacacagcg agttattgtc agagtaaata tcaattttga atttgtagac    32640
cacgtggttt tacctcatca tttctgtttg ttatgaaagt tttacaaata attagaagta    32700
gaaataatga ttaaaataaa gcataactac taaaaaatag tttattgcag caccacctaa    32760
attcatctca ccactctacc agtagcatac atttcacaat tgggttaaca ttgctctgga    32820
tcttatagct gttgaagaag acaaaattct ttccattctc cagcttatat tttccccatt    32880
tgtaaaacat aatggaagtg tacggaaaat aggagttgat aattttttaag gcccttgcca    32940 gcacattagt acataggatt cttgcaagtg gtggtttact tcacttcaac tatagaaggc    33000
ctatgcgaca ccacccatag agggtagttt gaaagaaaat gctagtgact acgtgtgttt    33060
ccttcctgac atatttttata gaaggtgatg agttccagca ttttttcaga cttggatctg    33120
gctttcattc cccttctcct cccaccctct aaaacaacag aggcagcaac catttacaca    33180
ctttccagaa gtaagtaagt aagactgtat tccagaaaca ccctatatca aaatggaaat    33240
atactccagt gccccaatga cccattgggc tagtttgaac gtgtgcagtc tctgtgctcc    33300
ccgttttagc ttaagcctac tccctaacct gtcatatgtc acccagccat ggagcctagg    33360
```

```
gcaatgactg ccatcatatc tgactttatg gcctctcagc tttcaatgac tagctttgta    33420
gcagaagttt agcctctcat ccccataact ttggaagtag tgttgagata aagaaacgtt    33480
gaattgaagg ttgtgttttc tagatttctt tcaattgctc cttaggcttt agaagataaa    33540
ttctcctaaa agagaggtgc tacaattaat ccaagcaaag ggaaagatgt cagtaaaact    33600 gcccctttc atagaggtgt ggcaactgct gggaaggaag aaattagcct gaggccatgt    33660
gattactaat aaactcaaag cggcattttt ttacttctca atatgaggtt gaaactataa    33720
gcttaaattg ctgactttct ggcagcacca acagtaagg aaaccacaaa gataaaccca    33780
aataatagag ccaattttct ttttttccgg gggggatgac ttctaactag tgatatgagg    33840
aaggataaga aaatgtttct ttgtaggaca tatgatcttt gctaagtgca ctgaatgtat    33900
gtagaggaga caagtctgct gagggtatga gaattgggcc aagatttaac acattttcaa    33960
agctccatga agaagcctac tgagcagtgg gagtggagca ggttggggat agtgaagtat    34020
ttgtaattca ttttaaaaa ggagagggag agagaaaagg aaaaactggg ccacccatcc    34080
tttgaaaaga aaccttgaaa gaggtccaaa tatccttaga aatccttgac ttcttaaaag    34140
tgatgtttgt ttttccccc tgacaattat agaggtcaga gagttttct tttctattac    34200 aaaacattga gagtgtgtag aaataattgt aggtagctta gccttggctg tagtcagaac    34260
ttttgtactg tgactttagg atctgtatgg aatcgtatga tatgcggata caccaaaaac    34320
tctatgggtt atcaaaatgg gatagcatta aaagaaatag tgcttttgtt tagaagaaga    34380
aatgaaatgc ttgtgtccag atgcttaaag gaaggcagtg cagactttca gaaactagac    34440
tttaagagct gtactcagat actgagaagg gctgatggct gaaggaggaa caatttaaaa    34500
gaataaccgt ctctcctctc cctgtatatt ggacataaaa gaatatccca ttcttttcag    34560
aaatgtaata caacagttta gcttgctagt aacttcacat gctatttcct ttacctctta    34620
tatttgaggt gtctatttgg agtgggctgt gtttctagct attctgttta tctggtttgt    34680
ttttgttggt gtaggaaact ggtataaatt ttatttgggt aaatatcacc tcaattttca    34740
actaaagctt tatttaagtt tcacatgaaa aagacaaatg aggcaaagga agagaaaaat    34800
gcattgtcag aatcagaatt atgagaaaaa aagtcaaaca aacatatttg aaatgtccag    34860
aaaacctgtg agtttttatg tatactatac aggaaagata ttctgtcatc tggttgccaa    34920
actatggagg gtgggagact tcgaattttt gtcaaaaagt attctttcat tagaaagata    34980
catgggtgtg cttccatgtc agcaacatga ctgcagacca ggaagtcctc acggagagct    35040
ggaatatggg tattttggac tctctggtta gatgcagctt ttacttcaca tcctcagtgg    35100
tactactgta aattttcatt ttcctgtgga atacccctatt tggttccatt gtatatagtt    35160
gacaactaga attcgttcgc tgttgcttga gcccaactat aacttcttgg cactatacct    35220
atcttctgat gtgcctgtgg aagagctacc ataatgaatg tgtacatgga caaaaaaaa    35280 gagagagaga gagagaatta aatcatgagt ttgtgccttg ggagctacag tttaaacatt    35340
tgctgttttt ctcacttaat gaaaaattta tttgaaaata acagcacaga aaggaagaaa    35400
gacaggctgg caagcatcct cctcctaata cacttatcca cgtttggata ccttggtctc    35460
agcctcagag gtcatatttt tagtaaaatg gccaccagaa ataaaggatt ttattttcca    35520
gactttggtg tttggagctg gtgtgctgag agctagcaga gaaagcccta ctcaggtaga    35580
tgtaccagag caggatggtt gctggtggat atggtggaat acctttatg tggttatctc    35640 ctccttgtaa ctcttggctg cataacccct attttctttt ctattttat tctctctctt    35700
```

```
ggaaaaaaaa ttggtggtaa attttcatgt gagccatatt gtcttttta  atagttttat   35760 taatataaaa tgtacgtacc ataaagcata cccatttaaa ctgtaaatgt caatgggttt   35820
ctctctctct ctctctttt  tttttttttt ttggatgctc agagttgtgc aacaattatc   35880
aaaatcaatt ttggaacaat ttcattgccc caaaaggaaa ccctctgccc attagcagtt   35940
actccccatt tcccccaccc cctgacccct caaccctagg caagcacaaa tgtactttct   36000
gtctctatag atttagccat tctggacatt tcatgtaaac agaatcatgc aatatgtcac   36060
cctttgtatc tggcttcttt cacttagcat gatgtttcca aggttcatct gcattgtagc   36120
atctgccaat acttcattcc ttatttatgg ctgaataata ttccattgta ttaatgtatc   36180
atatttgttt tttccaatca tcagttgatg gacatttggg ttgttttcat ccttttttta   36240 gctatttta  ataatgctgc tatgaacgtt cgtgtacaag ttttgtatg  aacatctgtt   36300 tttatttctc cttggtatac acctaggagt ggaattgctg ggtaatatgg tagcttaaca   36360
tttaatcttt tgaggaactg ccagatttt  ccaaagcagc agaatcattt tacattttga   36420
ccagaagtat atgagagttt tagttctcc  acatcctcaa caacactcat tattgtcatt   36480
gtccttttca gctttttga  taatagtaat ctcaatgggt gtgaattggg accccatcat   36540
gcttttgatt tgcatttcct tgaagagtaa ggatattgat catcttttca tgtgcttatt   36600
ggccgtttgt atattttttg atcctttgct catttccaaa ttgggttatt tgtctttgca   36660
ttattgagtt gtaagatctt acaatatatt ttggatgttt gtcattttag ggatgatact   36720
tcacagttat atgatgtttt ctagcaagca tttgcgttgt tctactggtg ttacatatct   36780
tagctgcatt agccactttg ctgggtatga atgccagcag aatctaagtg accttggctt   36840
cactactgag aatgcaaccc aagaacagaa atttgtcaga aatttagcac tgaagccccc   36900
cacttcccaa acttatctgg gacaaggaga atctacattt aaagctctat actttgtgtt   36960
gtgttttttt tactttagct tggttggatt taggatcttt tcttttgtt  ttgccttatg   37020 catacctaag cagaggcaag ggaggaaagg gatatgaacc tggtagaaaa gtaagtaagc   37080
tttattcaga ttggcatatc catcttaata tggttcaatt ggctgaagaa gtatctcaac   37140
taaaactctg gaatactttg aagtaccagc aatatgtacc aaatgtactt tttatttatg   37200
tttggtctct atgtacttgt gtgtgaaaca atgagcacaa ataataccct ccttgttttt   37260
aagcaattta tattggtgat ttaaaaataa aataaactca agtgggaaat catgaaaccc   37320
catgtaaaaa caataagagc atgttttaaa atcccacaga ctttagtttc aaatagtggt   37380
tttgctattt cttagctgtg tgtcactgtg caagttactt tgtttctctg agtctttatt   37440
ggtgatatat gtaaaaaccc accttctcaa attattgtga ggacaaaatg aagtaattaa   37500
cataaagttc ctggtgtata ataagtgttc atattttgta tttgagcaca gggcaactgg   37560 gttttttgaaa ctgcacatta ctgttgcagt caaatctggc atgaaattag tgcatagaca   37620
gaatgggctg ggaaaatgaa aggactttga acatttatat tctgctttat ttaggcataa   37680
gtgcttaata attattgata gtttcttctg gttatctgac attttgaaga tactattacc   37740
tagcagaaat tcttgtaat  aataatctct tacacttata tactgttttg tgcctttaga   37800
agtacttaat gctctttatt tcactatctg ttcataaaca ttctctgaag caagcataca   37860
gtcagtatga attccatttt tcagatgaga cagctgaggc tgaaagacat agagttactt   37920
gtctcaattc acaaagtaaa gtgccagagt ttgaaccaga gcccaggtct tctctctcaa   37980
cgtagctctt tttctccttc attatatcag gcatagtagc aacgtattct tttactagct   38040
ttttatcttg aatatccttt tagcgacttg cctttggtgt tagtgtgcct ataacattgt   38100
```

```
cgttgaatat cttaatacat ttagtggtct tggcaagcag ttttgtcttc agaaggacac  38160
tgaaatctgt ggaaaggact gcagaagatt gggtgggcag acacctatca ctttcggggc  38220
tggtagactt tctattgaag caatttgcaa ggctactttg tattgtctaa agcactact   38280 tcagaaaagg gttgtgatgt caaaataggc actttgagtg aagaaagggc tgtaagcatg  38340
ggtggaaaat gtggtagatg attgtcttga gttattttct ttaatgtcaa acaggcagtc  38400 cttgaatgc tacttcaaaa agtgttgtat aatgttgaag atacagttac agatttccaa   38460
cacgaaactc ataaatatgc aattccctgt cctcctaggc acatgaagga aaatttatga  38520
gcttcaggtt tctatgcagc tattaaagca tatttaatct gctttgagct caagctcact  38580
ctcgttggct ctcttcgttt cttcctctta catgagcaaa ctgcctttct ttttgtttaa  38640
aaatagtaag taggtttgtt ttcctccagg tgtcatgaat gcaaacattg taatttctca  38700
tctgttcagc ctttttgcac aacaaaatgg cagcacccag gaggttgaaa gggttaaatt  38760
gttccttctc tgagtagtac cataagttgt tagtctgcta ctctttctcc cagttggcac  38820
atgaccctaa catccaatcg ctagtggtgt ggccatttt tggtcttatt ttggcctttc    38880
ctcagccacc actcatcagt tctcatgcgt atttgtcaga tcctgctccc caactccaca  38940
gttcttagtt catcttaagc atatggctgt ctgtcttttc tctaaagatc ctcaagggaa  39000 aaaaaaaaa gcatctccag ggggaattta ctgcctcata gccctgacag agatttctga   39060
ccaaacccta acgaaaaaat ttcttccctc catttgtctt ttattgtttt tacaggggag   39120
atatgtaaca taataacaat tatattgcac ataataatta cttctacaaa taataatctg  39180
ttgtcaaaaa tatacacagc tttggatttc cttattatgg cccttcatta agttgtggtt  39240
taagaatagc tatgattatt acttttgtga taattataat ccataaatg gaaacttata    39300 aaattacctt taaagtgtta ctattattct ggccacagga tggaaagttg ttcgctagtt  39360
actcatttat aacctgaatg tactttttac tgaatctaaa ggtatcatct ttgcttggca  39420
attcccatga cttgtctttc tgactcttca gatctcagct taaaagctct cccttcaaag  39480
aagccttccc tgaccactct ggttttttct tcttttttta cctctactcc tttccccatt  39540
acttgctgtc atagcattct gtttgtttcc tttgaagtgc ctattccaat ttgtcattat  39600
gaatgagttt ttttgttctg ttgcttatta tccattttcc ccactagatt gtcaactctg  39660
tgagggcaga gaccatgata ctctgttcac tcctatatac attcccagca ctatcagact  39720
ttttggcaca tagaagatac tcagtaaata tttgttgaat gaataagtca taaagaagag  39780
tttatatttt aactcttagt tgaataatct aagccaagaa ttatcaacct gggttggacg  39840
tgagaatcat taatgaatct ttaaaacaat gacaaggcaa tctatttatt aattatctcc  39900
aggtctaaac tttagcacgt atatacattt taaaagccca taagtgattc ttacgtatag  39960
ccagtgctat ctgtctcttc tcctgtcctt tcccctcctc tccttactcc tctctcatag   40020
ttttaggatt agcatggccc cacaacaaat ctttaattca catggcaatt tctaggattt   40080
atcatggaaa atgagccaaa ttgccttcaa gaagttttta cgtacctctt atatagaatg  40140
tgatgtttta tatgtacctc ttatagaatg tgagcttta agaggcatat cttattgcaa    40200
gaaatttcaa tgttgaaaaa aatattgaat atttataaag tcaaaaatgc aaacttttat  40260
atgattttca aacctatgaa gttatatcat gttcaggcct tctttccagc atgtggctct  40320
cagccctggt actgtcctta accataaacc tcatctttgc cctctatagg gagaggttta   40380
tggttataat tactcatttt aaatagtgta tattagtaat gtacactatt tgtatatttg  40440
```

```
ttgactgcct cctatatgcc aaccactatg ctagaaattt tgtaatattc ttcacgatat    40500
tcaagatatt aacatatccg cattttataa atgaggaaac tgctctcaaa gaggttagtt    40560
tacacagcca gtaagccgct aagcctagat tggatggaag gtatgtgaga aaaaagcagc    40620
atccataagg ttttcattct cctaccctgt acgacagagg taatagaaat tattagttaa    40680
agaaataata gaattttaca agactctagg aagggagaat gtgaaggata cagttctcag    40740
ttactggaat gagtgccaga gtaccagtac atggcttgcc ttggggtttg gactacctat    40800
cttaactcct ttgctcctcc caatcttgat ctcatttgtt tgaaagatca tctgcccaac    40860
ataaaaatgc atttctaatt ctgtaattta agtcagtggc aagatcagat tcagttaaag    40920
tttactttcc tgacagcttt ttagtatcat atctattttg caaaactcta gtgataaatg    40980
tatgcacatt tacacataca gcatctcttc tgattctgac taagatatta ctgggttgtg    41040
tagaagtgat gggctcttta aagaaaggt ttgatatact actaatctaa ggactgaatt    41100
ttctcatctt tgtctttgcc ccttttgact gatgaccaga gcaggagcac ataacattct    41160
tttgtgctaa cagtatctct gcatcacatt gatcaggaga attggcatct ccagagccct    41220
gggatggtaa cttctctgtt gattttcagg aaagattagg tgatattttc tccatgggaa    41280
gaggatgttt gatgtgtgtt ggcttagca aaaggaagct tgtggagtca actgtaagta    41340
gacagaattg cctttgactt aatctgtttc agtcgttgtt catactcagg tcctccagag    41400
gacctttaag cattttatt gactttgtgg tctattacac gaaactaaag atactgattc    41460
tcagtcatga gtctgctcca aaattgccta gggaatcaaa ataattgta ccagttccta    41520 ttcctggaca ttatgattca tttggtctgg tatgaaggcc aggaatctgt attttttaaaa    41580 ttcactcaag caattttcat atatagctat aattgaaaat ctgtggctga acttctccac    41640
tcccgtatcc atcgcaatac ttccccaagg tggcatttaa gatgggccta gagggttata    41700
taagatttca atattaaaac atggattaaa agtgaagact tttcacatgg agataatttg    41760
gaagaaaaac ttgcaaaaat gtgagagcat tgagaacttt tctttcccaa ggaaagaagt    41820
ggcagcttca ttttttggtca ttgcaaacag cagtgccata catgaaagga agtggtggt    41880 gctcatcaac tttgaataac tttgtacaga acccttgaga ctcctctctg cttataaaga    41940
aaaagtgtca actgtaaagt tgatttattt atgaaccata ggctactatg aaatctctgt    42000
tcccagctag aggcctggga gagtaagata actacttgtt tattccacgg agccactat    42060 tagcttttc tatagcacat acctcaaatg aagcatttca ataaagaac cacattctat    42120 tcacatgctt cattttattc tgatttatgt aaaaattccc aaactcctca agcagtgttt    42180
ctttgtaagg caataatctt cagttctgtt gcaaaggtca ggagtgatag aatgaaaatg    42240
gtactagata caacagctct ttggtatttg catggccatt acattgccat ggggctgcaa    42300
gacttgtgag tgcttgatat tttgcttgtt gatgaatgag tctgtgtttg tgctaatgga    42360
gtgatttgag aggtagttct ccactgtcag tcaagaggtt ggttttgaaa gctgattgcc    42420
aatggtcatt ctgctaacca ctctggttct cctttagata gagacttatt cagattcaag    42480
tcttcatgta ctttgtggca taaacattgt acacaccaga tgtattcaac aaccataaaa    42540
aaaaacaatt aggactcaag tagtatgtca gagtgtagtc actgatgata tataattctc    42600
cactaccaag aagatggaag cacactgttg agtagctaca tcctacatat gttggccaga    42660
atttaggaat acacatgtga tctatacatt ttgaggtatt gtctgacccc tagaaaatcc    42720
tggtgaagtt tttctggtgt cagtttggtc ttaatgttta ggaaatgccc acagactact    42780
cctgctttct gcttattcac atagtaaacg caaagcacag gactagtttg tcatctggat    42840
```

```
caaggagaaa tgagttagca gatataaaat aaatcagaaa ggaggtagtt ctcaaatatt   42900
tactccatga atagttgctg gatgttcatt aactctatag catttgttac tacttattgg   42960
ggatcctgga aagaaaatat attgtctata tccactgttc actgaggccc tctccctacc   43020
cagaaactcc ctgtctccat cactcactct ccacattcat tgacccaggg gaacagttca   43080
tggatgagtg aacttgagct ctatcttaaa ggatggagtt cgatttcaag gcaagaggta   43140
taagagaaag ttcagagaca acactggcta tggtctttgt gaagaaaagt gaattgaata   43200
ggctcctgtg gagatcttaa gtaagtactt ctggagataa ggttgaggaa aagtaggttt   43260
gaatcttcat ccagaggtag cccctaaatg tgttgagttt attgaaagag tacttgactt   43320
ggattcagac agatctgcat ttgactcctg ttttgccatt tataagaatt tgagtaatta   43380
ttgtttctaa ataagagttt attgagccaa gcactcagta aatgtttgaa tgggaaaatt   43440
aactgccctg tttttctatt gtcagatggt cctcttcgtt ggataacttg gtaactgttg   43500
ataacctttt ctcaggaatc agaaggtaga aaggttggga aaatataaga aacaaaaagg   43560
catattccta ttttttatttt catattgtct tccaactctc ccaggcttct tgtttgcaa   43620 ggctgacttt tataatactt tttgggtaga gcaggtcctt cttTggtttg gggttaaacc   43680
gtgagtaacc ttattttcta ggtctcagcc aactttgaag ggcatgaact cacagtagcc   43740
tcactaggat cacttcagca gtgagaattt atctttcttg tataaaagtg taagagttga   43800
tggcggccag gcgcagtggc tcacgactgt aatcccagca ctttaggagg ttgagatggg   43860
tggatcacct gaggtcagga gttcaagacc agcctgacca acatggtgaa accccatgtc   43920
tactaaaaat acaaaaatta gttgggtgtg gtggcacatg cctgtaatcc cagctactca   43980
ggaggctgag acagaagaat tgcttgaacc tggaaagcag aggttggaga ttgcagtgag   44040
ccgagattgc accactgcac tccagcctgg gtgacagagt gagactgtca aaaaaaaaa   44100 aaaaaaagag ttgatagcaa ataactatc tgtagcataa acctcagtat tctttatcat   44160
tcagtatcaa cattattact gaaaacaata agcaatatgg actgagtttc tgtggggtgg   44220
aaatgtgaag tggatcatag catgatataa cttgtcattt ggcttccttt ataaacatta   44280
tcaactacct cagctctatc aatcacttgg cagtccgtag tgaacattat aactcaaatg   44340
actagtcagg tctgttcatt gcccatgtaa aggcatatac ctgaagtgag aagtctgagg   44400
taacttagca ataagcttgc agtacagtgt ttagtgaagc cgaggaattc aaggatttga   44460
gtcatgccag attgctccat aaccatagcc tatctttgtc acaagtaaga aggtttaaaa   44520
atcaccatac cattattggt cacaacgttt ggagatagggg aagagtttgt ggatggatca   44580
tggcagtgca tggacagtga ttagcccata acacaaccag tgaacactgt tgtacccaaa   44640
gcacataaat caccacatat actattaata tatttatgga tgacaacaga cactataatt   44700
ttatgtcagt gctttctgct gtgaaaaaca aagaaagtta agggtacctt ttttatattt   44760
gcatcatatc tccagacctt ttcctttatc tccttcttgc aagttcttct ttctttcagc   44820
tgactatctg ctgttcctgc tatggctccc agtggctttt caagagggta cttgtttttt   44880
aagagaagac ccttgaagga cagagagagc ctgaatcatt caaaataatg aattactcag   44940
gatgaaattt caataatttg caagtgtgtg gagatagata ttttgaggaa gcataatttt   45000
ctatgtaccc ctcaaatcgt ggctggagat gacagcctct tccacctcca tataagacca   45060
tttcatttcc ttctactttt ttctccctcc ttccccccaaa cacacaaaca tacacatatc   45120
ctgtgcttca gtcacacaga acttcttact atttcatttc aattctctat ggctttgcat   45180
```

-continued

```
gttctgctcc ttctgcctag aatgctcctt tccttttttc acctggaaac atcccaattc   45240
aaatgtcacc tcccttattt ataccaactt tgtctgtaac tcctttatca cacttcttcc   45300
tgtgattagt caattcactt gtctgctgtt acacctctat gagagatgaa aattccttct   45360
ccatctctgg aactcatgcc cttcgcatat agtaggcaat ctgtaaatgt ttgaaggttg   45420
agtgaattaa tgaatgacct tcaacctttc aggcttccaa ttttctctct gaaaaggaca   45480
gccaaatgaa aactcataat tttagaagat gaggttagac ggttggtagg tgcatgcaga   45540
gaccagttat tatttaggta ttatggaagt ttatagttct tgtatgttga gttcagtgta   45600
agagtggccc caaacatagt taatgaccac tccagaccca gttgttatag agttggcccc   45660
agctgtattg cttctatttt agactaggat aagaaatgac actttcctac tttttacctt   45720
attgaaaggg tagaggctca ctgttatcaa tctcagttca cttgttgatt gcactggctt   45780
gccaagtgag aatattagca cctctgcaca tttctatagc tctgccactt atgagatctt   45840
tccttcccat tgtcatattt aataatcagg atagccctat aaaatatgca ttctcatttc   45900
ccagatgagg atactaaggc tcaagtagga gaacttactt gtttagtaag atcatacagc   45960
taggaagtgg gagaggcaag agttgaaccc agatcttcct agctcctagt ccattgttct   46020
gtctactggg tcacactgga ccagccagga ggcaggaaaa tcagctgggg aatgtggtgc   46080
caacgtgtga tgtttgccta aatgtgtgca tccttgctgg aagccagcca tgattcatgc   46140
tgcataagta ttcattaatg ttcatttcat ttatttggct atccatatgc tttccagggc   46200
gaaggcaagc taggacaagg gcagacaagc agccttaaag tttgggtgct ttccttcgaa   46260
gttgagctgc ctgtttgaaa atcacacttt ttggtgatag aagatggttc cagtacagat   46320
tttatttatt actgcatcta catggataga catttccaa agcatagctg aaaatatgtg    46380
taagtcccag aatattttct gatttagaca cagactttga gcatgataac cacatttagc   46440
atgttaggaa attctgtcag aatgcttctg gaaaggctac ctttccagaa tgaaatgaaa   46500
aaagaaaagg atggactttg aaactggcta gatttgggtt atacttactc atagtgtgac   46560
cctggcaaat gatttaactt ctccgaattt cacttttctt attctttgaa gtgaattttt   46620
aaaatgccat cttgcctgat ttttgtgaga atgaaaatga gatcccacac caggaattta   46680
gaagctactc agtaaatatt gcttctctcc tttcccttc cccagtcctg tccccgaga    46740 cattcagtag ttattcacag gcatgcattc tgaagtctgc ctactgctcc atgttgaaat   46800
gcactgctct tgcaaggact gattatctat ttttctgtct tccaaggccc cctgtgttcc   46860
actccaccct cccaattctg ggggcttcca aagtgggcag gtacagaatg ttctgtggag   46920
catcggaggc tgttactcaa tatcttggcc agcactctca actgctcttt gcacacactc   46980
catatgaagg caaactccag atcttggagc ccatgtgtgt gtcatgcatt gtactgcttc   47040
ttgtacccaa atccatctca agggtgagta gaccaggctc agacttgtcc tgggagcaga   47100
tttctcaagc tgcccatgtc cccacactgt ttgattaaaa ggaggtgctt caaactcttt   47160
ggctttatat agactagaat cagaatgatt ggtggtgcct ctgttctcaa ggtatcccaa   47220
agcactttgt aaggaaatat gacaagcgct gaggccatgc aggccagtac aacagccgcc   47280
acccagcact tcacaattag tcatgcccag cctgggatca tcaagcctgt ttttattgga   47340
agagcaagag agagagggaa tgctagctgg caatttcccc aggtacccctt tatgaaagtg   47400 cccttggctc ttccaatttc atctgaataa ccagctcagg caaatttcc tctatcaaaa    47460 agcagaatgt gatagtgaca agctgatgcc cggctgatgc cccaggacat tgactaaata   47520
gacttggcct cacaattggt ttttattctc tatctccttt cttccctttt gttctttttc   47580
```

```
tgtgtttctt tccccattgc catctgcaga gtgttctcag tcagaagtca gctgtggggt  47640
ggacagtttg tcattttaag atcatcccta ttctgtctac ctttcttatc cctcatatca  47700
ttgcttttag agcaaggaca attctggaag tgaaactaca ataacactct gggctccttt  47760
ccctctagta gtactcaaca cacttgtaat tacatgttca aatttgtctt tcttatttct  47820
acttaggttc atgaaggcaa gggacatgcc tgtgttgctt actttctctt ggcaggcaca  47880
tacagcaagt cttcaaaaaa tgcttgttaa ctacaaatta agtgtttaag aagtccactg  47940
ttaattagcc gggcgcggtg gcgggcgcct gtagtcccag ctactcggga ggctgaggca  48000
ggagaatggc gtgaacccgg gaagcggagc ttgcagtgag ccgagattgc gccactgcag  48060
tccgcagtcc ggcctgggcg acagagcgag actccgtctc aaaaaaaaaa aaaaaaaga  48120 agtccactgt tagtatcttt tcccctgcct agtttgtaag caactggcct cttctatttg  48180
taagttacct gttttcattt ccatatgccc caaagcaaac tttagctcac ggccttacag  48240
agtgtgtatg ttagtatgtt aaaatgaaat caactttcct ctcccaggcc ttctaattga  48300
catgaatttg ggagtagact tgcattggcc tttgtcctga cagccaacag agtcctcttc  48360
tgttgtattc actgttgcct tccatgagga tcccatggag aaagtttgtc attgatatac  48420
attttgaggg cagactcaac ttgagtaaac ctgattgagc tttccccatc tgcctcccag  48480
agatcactgc ctgtgctttg ttaaaaagag aattatagga gtcctctcaa ggcagagagg  48540
cctaaaatta gacatggcag ccatgccttt ggtgtgcatg gaggttggat acaggcagcc  48600
agtttcccct ctgtttttctc ccttgcttac acagccaagg agtggagcca agcctcaagg  48660
ggaggagctg tatactcgag catgccctgt ggttcctggc cctgactgag ggactatttt  48720
atatatccca atagagaagc gtggaagaca tctaggttgc cactgtcatt tgaaattgga  48780 attttttaaaa gagaaacctg aagacttgaa gaaagctttc ttttgcctcc ccttacagtt  48840 gattttgag cttcttaaag ctacctagtc caaagtaccc acactcttat tcttttgtct  48900
ttcctactgg tttatttttt ttttcatctt cccaggtgtt tgatgatcac taagagcttc  48960
aacattgctc accctgacca ggtatgaagc caagagtttg gtttagggca taaaagaatg  49020
tcggaactca aggactaggt tgaggtgggg aaggggatg aaggcttctt tttttcttgg  49080
gttaagcaga aataacttag atctcagagt gaaagccttg aattatcaca tatatcactg  49140
gaaaagacta gttcctttgct atgataacaa ttgttcatca tctctcccct gaggattgg  49200 ggtcaaggcc tggctacacc ttttaatgat ttcagtcatg tgacttaacc tcttaaact  49260 tggattttct tcatctttac aatggaaatg atgacaataa tcactacctc acagatattg  49320
ataataatga tatctcacta ggaagagaat taagtaatat gagggataaa aaggcatttg  49380
taaatggtaa aatgagatta tgattttgaa agctattatt attttccttt cactgtctat  49440
tatctcaact cttctatttt cttgcctttt gtacagcatg gataatttag atgtgactct  49500
ggacagaggt atggatcaga tgacttctta agttatcttc cagtttagga gttcgtaaac  49560
tatactttct cctttccaga ctatcctagt aagaaaattc tcttttaaga cagagtagaa  49620
ctctggaatt catcagtttt gatgtttctt aaagtgtaat ctaagatagt gctcctgtat  49680
taagttctga tgtctgacca ttgttcaaat aaagagtaaa atgcaaatga caggaaattg  49740
gctgcgttct gaatcctatt tttatttggg ataacaataa gcctgtatgg tcactgtgac  49800
ctttgatttg ctgtttctgc aacctcacac ttgtctcagg attcttcttc cacttctgca  49860
ctttatattg ggtttcttcc aggcatcata ttaaacttta agccaggtat gtgtatatgc  49920
```

```
atgggctgtg ggcctgaaaa aaattagccc gagagagaaa aaaatttaag tagtgggcta    49980
gaagtaagca tgctactaga aacagaattt gggaacacag ctctgggcct agaaaagcga    50040
cctgtcaact tgttacagtt aacatcaata actataggat gggtttggtg gaaaattatg    50100
ctgaccaaca gggtgggaga gaatagggtc agaatatata tcgctgtaag gttgagaaaa    50160
aaagaagtga aaaaaaaga aatgcataga gagaaaaagg agtttagagg taacatgtta    50220
aagtgtgaga aataaactgg agagcttgac ttctcttgaa tatatttta aataaagtac     50280 tcctttcaac tccaaatgca gcaggcttgg ttcccttctc ctacctccat tgcggatgaa    50340
agcttaatct ttaagatggg cttggtgggg tagagtacgc cccttggtga gcactgtgct    50400
ctctgcaacc ccaataaggc ccaacagggc tctccaagga ggcaaaattc tgatgataca    50460
tttctgttta gtggaaaatg ggtagggaaa attatgtctt agaatcaatt aaccaaacat    50520
aaaatcctcc aagggcttg gtaggatgcc tagggaagag ccacgagata aaaactccag     50580
gctggaaggg cattgttgca gcactgtcat tctccagttt ctcttggagt tgtcaccacc    50640
ctctcctttg ttctcactgc tgacatcatt tgtaaaataa ttcttccct taaataaaca     50700 agacatacaa tcctctaaat gactaaagaa cagttaccta gaagaaacct tagtggaaag    50760
tattttcttc atctaacgga tgattgtctt tacagaggtg gagtaaagga tgtgcgaggg    50820
agcataatca agctaagaga tgcatgctga cttaaaaggc atgatatatg tgaaactaag    50880
ataatgtgtt caagagtgat gctttgttga tgcagaacca ctgaattcct tactattatg    50940
tttgcctgac tatcggcctc ttaataaaga acttgtggtt tgagtgttca ttgaaattag    51000
ccatattagg tttatgtggg gatgtgagga tctatgtcta ccaattgcag cctctgctgc    51060
aaattggagg cagaaatctg ggctgaacaa taggtaagag tgtcaactct acagatctct    51120
cacatgctaa gcaagcacaa tatagggcaa tccaggttta cacaaaggat taatttggga    51180
acaattatcc tcattttcac ttcctaaaaa gattttgaat aagatgtctt ttaagtaaga    51240
agctccctga atgcatttaa aatatgattt gattatgtac atttcagatt tttctacctt    51300
tctaggagta tctctgttgt ataaaaacac aaaattctgg aacttttgaa aggaagatgt    51360
gcctctcttc atacatttgt cattcttgaa cgattgtaaa atgaagtgac tgcatatcac    51420
gtcatgtgcc ctattgattt ctttctcttgt tttaggaata ttcccagaaa aaaaaaaac    51480 tttttttttt ttaaaatcta ctaagcatgc taggtaagac tgaagatgaa tctatttaag    51540
ttatgtcaat atctatttat aaagattttt gtgatattct tttcactgta gaacttcaag    51600
catatcctaa aaggaacggt tagataccte tacaaactgt ggcaatgact tactgagtaa    51660
ttgctggcaa ctgattttg gtgcttcttg ttttgatagt atagcagtgc gagtaggttt    51720
cagaagagca aaactaagac aatccaggga aatgccattt gagaatttct aactttaaaa    51780
aaacaagtaa aatagtgcca agaatattat ctaactaacc ccaaagtcta caatgtaact    51840 ctttatttt gataatgctg ttctaacct atctacttca gtccttccc acccagctgg      51900 tttaggaatc aaattcccaa tgtttcatca ctgttaacat tactgtttta ctcttcactt    51960
tagttcttaa atggcatagt gtcttaaatt ccctcagcct ctttcacatt tgatttcttt    52020
ggaaactttt taccttttca ttgaagccca tatgatcttt tccgaaacag acccttatct    52080
ttacctcctt ctttggagtc tttctcctac ttgaatttct gaacttctta aatggccgc    52140 tttgggttgg tgtcagtaat tcagtaataa gttttctttt cttttttttt ttttcttttt    52200
ttttgagaca gagtcttgct ctgtcaccag gctgcaggct gtagtgcagt ggagtgatct    52260
tggctcactg caacctccac ctcccgggtt caagcgattc ccttgcctca gactcccaag    52320
```

```
tagcaagtag cagcaccatg cccagctaat gtttgtattt ttagtagagt cggggtttcg   52380
ccatgttggc caggatggtc tcgatctctt gacctcatga tctgcccgcc ttgccctccc   52440
aaagtgctgg gattacaggc gtgtgccagt atgcccagcc agtaataagt tttcttaagt   52500
gctttcttaa tattctgata ttttttaaaaa agatctggac tattttgtca tacaggcaac   52560
agaatgttaa accatttcat aaaacaatga caaatataca tgaattttc atcagttata   52620 aatgcatttc ctttataaca ttgaacatgt ttttgcaact gaaataagta cggttttcat   52680
ttttagaagg cacatgataa agttaaggca gtggttaatt aatttttca gattaatttt   52740 tcagaaaagt gactgtttct gtctattgtc ttaaccccag gcatcaaagg attttaatca   52800
gaaagaaccg aggaataatt tggttatttt agtgcctttt tttgagacaa agtcttattc   52860
tgtctcccag gctggagtac agtagtcgc tcatggctta ctacagcctc gatctcctgg   52920
ttcaagtgat cctccaactt cactttccca gctaactggg accacaagtg ggcaccacac   52980
tctctgcaat ttattttaat ttttcataga aatgggtct cactatgttg ccctggctgg   53040
tctcagaatc ctaggttcaa gcaatccttc cacctcagcc tcctaaagtg ctgtgatttc   53100
aggcataagc cactcactc accctatttt agagctttgt caagctttgg aaagaaaacc   53160
atttataata taatagataa attatggata tttgaggcag tttttatcat agtatacatg   53220
gtaaaccaca gcccccttt ataatatttg tatttaataa aaatgaaaat attacttta   53280 tcttaaacat gttttaacaa agcaagcata tgtagattag cactaattaa aacaaaaacc   53340
tttgtaatga tagctgtttt ttatatgatt acaaaaaatt tactatacaa attttatcc   53400 taatcagtgt gaaaaactgc aaatattagc ttatagggct agtcttcaga gtcctcttcc   53460
tacctactac tgctaataag ccaatgaaaa actctctgat gtgtgtggtg gctcaggcct   53520
gtaatcccag cactttggga ggccaaggtg ggtggatcac ttgcactcag gagtttaaga   53580
ccagcctggg caacatggtg aaaccctgtc tctactaaaa atacaaaaaa ttagctaggc   53640
gttgtggtac gcacctgtag tcccagctac tcaggaggct gaggtgggag gatcacttga   53700
gcccaggagg ttgaggttgc agtgagccaa gatcacagga ctgcactcca gcctgagcta   53760
caaagtgaaa ccttgtcaaa agaaagaaa gaagagagag agagagagac aggctcctcc   53820 gcttttttcag ttcctaaata attttccaat ctagaatgca aaagattctg aaggaagaca   53880
gttaccattt cagatcggca gaagttgtgg ctttaatcta gactcgaata tgttttacat   53940
caaagggttg cctcaacagt gctcaaacct gcctctctga aaacatgctg agcacgaagg   54000
ttacttgaag tcttagcttg agtacttaag agagtgctat ggagggattg ttgatgagag   54060
ctgtgtcaca gctaattttt ctttagtaat taaaggttta taaaaatctt acactgtata   54120
ttgacaaatt tagcaacaaa atgagcttga gaaaaaatc aaggcctgcc atggcatctt   54180
tgcttttttt tcttaaaaaa aaactttttt agaaagatta tgcgactgta ttatctgtaa   54240
ctactgcaat ggtgtaaatc ctgatggtat aattgctttt ttaaagctat ctttacttca   54300
gtataactta gattaaattt attttaaatt taaatgatat ttttctcttt gtttattatt   54360
ttataatgtt tcccatagaa ttcacaaaat tcattagaaa gattttttt tacttcctta   54420 ggtcattaag attctgattt gtcaatggat ttcacataaa ccctgtcttt ccaaaaatat   54480
acaaaaaaaa aaaaaatagc caggcgtgat ggtgcgtgcc tatagtccca gctactcaga   54540
aggccgagtt gggaggattg cttgaaccca ggaagttatg gctgcagtga gctatggtca   54600
caccactgca ctccagcctg ggcaacaaag tgagaccca tctccaataa ataaataaac   54660
```

```
aaataagtaa ataattttca ccttgaaaag cttataaatg tatgaaatca caatgagggt    54720
cgctgatata gtttggatgt gtgtccctgc ccaaatttgg ttttgaattg taatccccag    54780
tgttggagat ggggcctgga gggaggtgat tggatcatga gggcagtttt tcatgaatg     54840 gctcagcacc atcccctcgg tgctgttgtg gtgatagtaa gttctcatga gatctggttg    54900
tatagcacct ccccccttgc tctcttgttc ctgctttcac catgtgacat gcctgctccc    54960
ccttcacctt ctgccataat tttaagttgc ctgaggcctc accagaagcc gaacagatgc    55020
cggcaccatg ctttctgcac agcttgcaaa gccatgagcc aattaaacct cttttttttt    55080
tttttataaa ttacccagtc tcaagtattc tttatagcaa ggcaagaatg gacttacaca    55140
gtctcttttg tatcagggag agggtcttct tggtgactcc acttcttttc tttgtttatg    55200
tatccttcca gatgatgtat ttatttcctt tgttttttcaa ttgatattta ctcttaaatt    55260
aaactaatta tttaaaaaag catttttaaag tctcatttta gattattttg actatctgat    55320
ttttaaaatg gtttaaaaaa tctatcttgg cctccatatg caatcaaata agaaacacat    55380
tttaagcata ttatttacct tgtggattct gccttcctca gtgtgttcag tctgtgtata    55440
ttcatttctc ccacactgta agaagctagt cagatgtata attggattat catgctacat    55500
aatcttagca cactcatttt aagcatacat agactagtga gcaccactca ttacatgtca    55560
tttctctaga gaaactagtt gggccatggc tgcaggactc tcacttgaaa agacatgtgt    55620
ggtgatgttt tctcaggcag ttaagcaata aagtgtaccc tgatttgcac tgaaaataaa    55680 gattcccttta aagggagcag ttctagttat ctctctcttt aggtaccata tgctgaacgt    55740
ttttctatgc actaaaacag caactaggtt ttatactctg ccttacagcc tacttcacac    55800
ccatttcaca gggagaggaa cagagaggta agtgatttgc cccaaattac ataactagga    55860
agttatttgc tcagtgtgga aacttgttca gaaggtcatt tcattgaaat gtaggaagag    55920
tttctggcac ttctcttgag caggagtcaa aaacctttt ttgcactagc ccagatagta    55980
aacattttag gctttgtggg ccatatgatc tctgtcaaaa ctcctctact tcgttgttgt    56040
agtgcaaaag cagctataca caatcctgaa atgaatgggt gtggccgtgt tccagtacaa    56100
ccttacagaa aaggcaatag gctggatttg gctctgagac tgtagtttgc tgacctcagc    56160
tcttgaactg agctctttaa ctgacctcag ctcttgaact atggtacaag atcccatggt    56220
cctgtttggt acctccattt gccctccttt tcactctctg ggagcatagc taagttcaaa    56280
attgaattag gtacttgtag taagagcata cttataatcc tgggatcttc atgttgccag    56340
atattaacct cttgaagttt ttcaccacaa cctgggcact tttctgattt gctcacttct    56400
agccccacct ttgggcccct tcataagcaa acatgcaggt tttccagaga gctgtatgct    56460
actgaatgca gaaaatttgg ctcatactgg cctatggact atctgctcac tgccctgata    56520 actatttttcc aagggagtgg gtgccctacc tttcctacat gaagtttttt gctagtcttg    56580
ccctaaaaat tctaggtatc ccttgctttt aggataaata tgtttcactg ggaccagctg    56640
gaaaacgaaa aatagaatta tccaactacc actttaaaat tggacaaaga cttttgttgt    56700
tgttgttgga gggggtggta aacatcattt tagcagacca aatatacttt tggtgaaagg    56760
cagcctgttg caaagacaca acacttggac aagattttga agcccggtt gcctttacta    56820 ctgacttaac tacagtattt gcggacttga gcaagttgct tcccttctgt gagcctcagg    56880
ttattcatct ttgaaatgag tataatacct gtgattataa ttacttatct ggattctgca    56940
gagaattgaa ggagataatg ggtgtaaaag tactttagcg cccagcactg ctccttatga    57000
aaatgaggaa ataattgaga tgagtgagcc attgaggcaa cagtacaaaa agtgctgaaa    57060
```

```
actcactgct taaataagca cctcttactg cttttgtggc actttgtagc aatgttttt     57120
ttttttttt  tgagacggag tcttgctgtc ttgcccaggc tggagttcag tggcacgatc    57180
tcggctcact gcaacctccg cctcacaggt tcaagcattc tctgacttca gcctcctgaa    57240
tagctggatt agaggtgcgt gccaccacgc ccagctaatt tttgtatttt tagtagagac    57300
ggggtttcac catgttgatc aggttggtct cgaactcctg acctcatgat ctgcccgcct    57360
tggcctccca aaatgctagg attacagatg tgagccaccg cacccacct  cagcaatgtg    57420
tttttattct gactagaaaa gtaatgtttg gttttgtttg gctctttgct taatataccc    57480
ataataaggg tacctatttg cctttggacc attagttcaa atattatttt attaatatgg    57540
aattactggg ctccagaagc catagtcttc ttagctgctc cctatcccca ctctcacctc    57600
aatttttttt tttcactttt gtttttcttc tcagggaaag gtttgaggca aagaatgtct    57660
tcttatgatc caaaccaag  catggtggtg atttattcac caagagattc ctaagtacct    57720
gtgtgatgga catggtagaa tctttgtcct gagggagcta tctagatcca ttccttctga    57780
tatgcagcca gtagccactt gtggtaatgg agcaatagaa acaacactag ttcaagtgga    57840
aacgtgagat gagaagtagg aggtggagag aactaaccag aagagggtac ccaaataaac    57900
cagaaatatg tatgtgttag agaagggggcc tattgagcgg gtggcagtgg catgtgtggc   57960
attacttgct cctgtattct ctgcttttta cttagttgtg gctttggtgg tatagtctca    58020
aatctaagtt acgtaggtaa tattgttatg tatcatgttt tggcaatgta gactaaatac    58080
ttgctcataa gagtacagga caatgaggat agtttggttt tgtttactgc atggaaaatg    58140
caggatgttt agtaaataga ttcatggcgt agtgagttca ctactaaaat cagactctga    58200
gaatgggttt gatttaaatg gctagtttag aagactgaat ttaggccact tgattgagaa    58260
aggccatttt gggtaattat aaaccaccaa cattgtgttt tgaatgttaa gcttatatt     58320
tgtcttccag ttaccagaat gtaagcttct tgaggaggga gagaggagtt ttcttaatct    58380
ctgaacctgc accttctct  tgtgcctagc ccagtgcctg gcaccaaaca ggtgctcaat    58440
caatgttgat tctatgctac caacaaaaat gagtccatga tgtttactat tcaacaaatg    58500
aatacaattt tagagtaaat ttttactgct tacactacat gtagattttc ttttagaga    58560
tttcgcaatg ctgatttatt tcaaaataag cttgaagcta agcgacaaag ctgaatgatg    58620
atttgttttt tatttatttt taaatccaaa cttacaattt tacatgtcat tgccagaaaa    58680
atcattaaat aaattatgat atgcgcatat ggaatacttt gcaaccatta aatcaaccat    58740
taaatactat gcaaccatta aatcaaccat taaatatgtt ggtatatgca aatgtgcata    58800
taccaacata ttatatagtt gagtaagaaa agctagtttc aaatgagtat gttaatatca    58860
tctgactctt gcaaaaggaa aaccatacat ttgaatgtac atatatgcat atgtttatat    58920
gtgcatagaa aaagctatga ggggatatac ctcaagttgc taaaagtggc tccacctgga    58980
gagggacatg gaaggagtt  ggctaaaaac tgaggtttgt tatggtatac accccctgcac   59040
agtttgattt tttaaaaaca atgattataa attacttttta ttatttataa aatatattatt  59100
taaaattttg gtactaaaaa cagagctcca tcaacaggtc aatggataaa gaaaatgtgg    59160
tacatatata caaccgagta ctattcgtca taaaaaaatg agaccctgtc atttttgcaa    59220
caaaatggat ggaactggaa attattatat taagtgaaat aaggcaggca cagaaaggca    59280
aacattgcat gttctcattt aatctgtgga atctaaaaat caaaacaatt gaactaatgg    59340
atatagaaag tagaaggatg gtaaccaaag gctagaaagg atagttggtg gggcagggga    59400
```

```
gggtgaggtg agcatgttta atgggcacaa aaaatagaa acaatgaata agacctatta    59460
tgtgatagca caataaggtg actatagtta ataataattt aattgtacat tttaaaataa    59520
ctaaagaggt ataataggat tgattgtaac acaaagaata aatgcttgag ggatgtatac    59580
ctcattctct ataatgtgat tagtacacat tgcatgcttc tatcaaaaat tttcatatac    59640
cccataaata tatacatcca ttgtgtactc acaaaattaa aaaaaactgt gcattaaaga    59700
aaaacaaaaa taaaaaccat agttcaagtt ataaacaaaa taaaggtaat ttggaggaaa    59760
actgtcttca gttatattgg atatttgggg gacatttttg tatgttagtt agcaaagatc    59820
acttgaaaaa gaagattctt ccttctatga ttcaagggag cctagcaaaa aataaatgaa    59880
atgaaataaa ataatacaaa gagaaaagat tattccataa attctgctta cttatttctg    59940
gcaaacttgt tgacagcaca tgtgaccttt tggtaaaaag acatttttat attttttagtt    60000
aagtttcaaa tataaattgt ttgtgttttt aaaataaatt aaatggatga tttcagccag    60060
atcattatga aaacacatga gatattgggt tatgcaatga ctaacagtgt gtaccttttc    60120
ttgatattta ttcataaact ggggaataaa agtacatttt ggcccattta ctccttaaat    60180
aattttatgt ctcccaagga gagttgtaag ttgcttgata gtaaatgcta tgtattttgt    60240
accttagtgt atatattatg ggatttcagc gttagaagag ctcttaaatg ccgtgttcat    60300
agtccaacct gtcttctgat gcttgaaatc cccttgcagt aggaaatgca aagtagagag    60360
cagacactca ataatgtagt tagtgaatta tttagaaaga ggcattttga gcccataatg    60420
tatgataggt acttctacat ttattatttt attctttgca gacctgcaga aaactgtaag    60480
aaaaaagttt atttcagatt catgtgttta tttgattaat ctcttcatag gtttcatttt    60540
tcagctcctg tcagaaaata cagattctta taaggttcac cttttaccca taagaataat    60600
agtataaagg ggataatgtg aaatacaatc acttcacaga ctgtttcaat taaataagag    60660
ctcgtagata attcagtcca ccacacccca ttttacagat gttgaaattg aagcccccac    60720
caaaaggaaa agacttgttc aaagtcacac agcaagtcag tggtgaacct aattaggccc    60780
cctgccttcc attttagtga gattcctgtg ctgatagtca tacccatatc aaatcctctt    60840
tggcagttat agcttgccca cagtaatgtg tcctgaaaaa tatgacaatt aattaagttg    60900
gagacagaac cataacctct ttataaaaat tttctggaaa gtttacatga cagtaagtaa    60960
tatataatta gaaaggataa ttcttatttc atatttatct ttttgtttca gaataataaa    61020
ctaagctatc tctactcagt ccatttaat acaaaaatat ttttacccgg actgagtttt    61080
tatgcttttt aggaactttg tatctgcctc acttagttaa aatcctagct gcactaatca    61140
cttactgtgg tgggcagaat tctagaatga ccctgaatac cttgtccttg tatgattcct    61200
tcctctttaa gtaaggataa aaactgtgaa tatgatatca ctcccttgat taggctttgt    61260
tatatggcac agttaacttt aagaaaggac caatcacaca agccatttga aagcagaggg    61320
tttgggtatt ttttaactgg tggcagaaag ccacgcagag atttgaacat tgagggaat    61380
ttgaatttga tgtgccagta ctaacttgaa gatagaggag gctgcatgga aagtggcctt    61440
taggagtgat ccctggctga cagccagtaa gaaaatgagg gcctcagacc tacagccata    61500
aagaattctg tcagtgaact tgaacttgga agtggattct tcctctagaa cttccatata    61560
agagtccagc ctgattgaca ccttgatttt ggacttgtga gaccctgagc agagaatcca    61620
gttgacttct gacctaaaaa aaagtcaga taataaatga gtattgtttt aaactgctaa    61680
ttttgtgata atttgttatg cagcaataaa aaactaatat atttaccatg caaggcaagg    61740
catttatcct ctcatgattc agtttcttttt tacctgacat aatggaatta atttatactg    61800
```

```
ctgtgaagtt gtagttgaga aacatgactt ctaaagtaat agaggacatg tattattaat   61860
tttagtagta ttaatagtaa tgatactgat tctcccaggc ctatacaaat cctttgatac   61920
acaaatgaat agtaaaggaa cataaattgt ctctaggtag actttccac aatgcaattt    61980 taggatacag aggtcatatg cctgttattc tactgtggca gagaaaatat ggagcctgga   62040
aaactgttca tttgcatcac atacatcttg ggagctcact ctgaacctgg taccataata   62100
agctctgtag acagtataaa gaggaaagga atcagacatg gtgtctgacc tcaagtgtct   62160
cataacgtag tagaagaggt aaaatatggg tcacactaac tctactgcaa agtaggaagt   62220
gcttgtcgcc ttgagattga caaaatttgg taagagttca gaggagattg tctgtgaact   62280
gggccttgaa gaatagttag gatttgaata ggagaaggtg aagaaggaag gcattccagc   62340
tagggagaag agcacaaaca aaagcataga taaccttgaa catcatcata tgggataatt   62400
caatagttca gtataatgga agtataagat gcataaaaat aagtgtagta ggaaacaagt   62460
ttaaaagtat agattggggt tagtcataca aggccttgaa tttcaggcta aggagtttag   62520
acattaacat ttgttttga acaaaggggt gaactgatca catctgtgat ttagaaagaa    62580
aattctagca atagtgtaga taaggggttga tggtaaagtt tggaaggtgg tgaggcgag   62640 gctggagaca gggagcacat ttaggataga aagatgataa agagatgatt tagaagagtt   62700
gttttggaaa aggagaagac agaaaatgtt ttagaggtgt catagagata aaattggcat   62760
ggcatggtgc aaggaggtaa agcccaatag ctttgtaagg tgctgagata gattgaaatc   62820
acagagttag gaagttttag agtcaggatt agtaccaaga cagcttggct ctagatctca   62880
tacttaacac ttacagtata attctgagag ggtgggtaac agcaatagtc agaggaaaga   62940
acccttttat acatgatggt acaggaacaa cactggcttc caaccccaca gctgctcttt   63000
aacagaaggt cagaagctgg ggagaaatat gtgtgtgtgt gtgtgtgtgt gtgtgtgtgt   63060
gtgtgtgtgt gtgtgtatgt gccatttctg ggactaagga tgggaagtag attagttgag   63120
gccactgcag tggggtctgc aagttgctag cactcacccg ttccaagagg ccttaaaggt   63180
gttgatctgt tccctgggca tcaccacatt ccacaaatta atgttcctct gagagaatag   63240
ggtgattcaa tttcactgtg cccgaaggtt acttttgggg ttcatgtttg ttctaagtct   63300
atgctaatga tctgccaact gtctgtttgt cactttctct aacccttagc atgtataaac   63360
tgatctgttg ggaaatgtgt agcatttata ggatggtagg atttgtaaca tgcgatcaca   63420
ggactgttta tatagagtcc ctgggaaggg gagagaagag tatttctgtt acaaatgtgg   63480
attctttggc ccctcctcaa acttactgag gttcaagaat tgacatttat aataagcaca   63540
tatccatttt caataaacat gaaagtttca taccctcttt taatgtttga aatcctcaaa   63600
taaattagtc attggtgcca gagtatcaaa taattatggt acagaatgta tttctctgaa   63660
tgacaccttc tcccagagat tctgatatat attcctctgc actcaccctg tttgataatt   63720
accagtatat ggaccattta cctgaagaat aagagtaggg tttcctactg ttgttgaaaa   63780
tttgcttgac tcttaacaac ttgtgtgtga ctgtaacaag atcacacagg gtaaacaata   63840
ttagcttatt caaccactgg ctgaagaaat ttaggaaagt gaacacattt ttctttacat   63900
ttctctttgt tctgtgagcc ttttatgctg gaatagtttt cactgcaggc tgttattgtc   63960
tgcctccaga ggagggagtt gacctagcag tggtaactgg agagtgtttt ttgaaacctc   64020
tttccaaggt tagttgccaa tggcatcttt ggaacagtgt ccttcacttt tgtccctcag   64080
ggaccagtgt gagaatggga actttatgat ctggagctgg ttaagtgaag tccaaaaata   64140
```

```
attaagaaag tgtttccttc cctgggaatg agttcagtag gaatctcaat gtattgtaga    64200
gcactaagga ctcagcctca ggcatttgca aaggattctt ccagttgcct gtgttacaga    64260
ggacacagtt ggcatttcct tttggtgttg aggggagatg tgtacatggt tgtgagatga    64320
ctcacccttt ttgcttagat agttccactt tcattgtgga cagactcttt ggagggccag    64380
tttggcatgc acgtgtgtgt tcattccatc ctggagcatt ctttatgaga aagccatttg    64440
ttgagtggtt tgccattttg ttttacagcc actctgtggg ctatgaaatg gtcatccggc    64500
cgctttattt gtccctaaaa aaagcagttt ttccctttct tatcttcatg gctgccaagc    64560
agcagaaaga gtaactcagg gaagccatgt gatagccttt tatctgtctg ttcagaaact    64620
gatgatgtat tggatttgat aattcatcaa atctgaggtt tactggtttg tatttgcctc    64680
aaaatgggca tataatattt tgtcaggtaa cataatagac agatcattgg cattgcttta    64740
ttgaagtgaa ttaattcaat aagcctgtaa gtgcctgaca tgtgccaggc actgtgctag    64800
gcattctgtt aacagatgag acaaatctct gtcttttagg tgttttcagt cgaacagggg    64860
agacaaatat atgagcaaat tgctattttt tttaaatttc atagtgtaca tgagtataag    64920
gtgctgaata tgtgattgat tctgagggaa aagagagata agggaaagtt ctcagagaaa    64980
gtcaagctga gggaagaaaa gcaccccaga cagagggact agcatagagc tatgctagta    65040
cattgagttt aagggaatgg cacatacttc actgttgctt cagcagacag caggcctgtt    65100
aggttacaaa gggccttgga tgacatgctg aggggttta aaattttatt taaatttaa     65160 ttgacaaaat ataattgtat atttctgtga ggtacaatgt gacgttatga tatatgtatg    65220
caatgtagaa tgattaaatc aagctaattt gtatatctac cacctcacat acttattttt    65280
tggttagaac atttaaaatt tattctctta acaactttga aatagacaac acattattat    65340
caactgtagt caccatgttg tgcagatctc aaaaacttct aacaaaaact ttttacccctt   65400 tgaagatatt gaactgtttt atgaacacaa tcttagaagg atttaaaaaa taatttgcta    65460
ttcaccaagt acttcttacg tacactgtgc atgaaatgat tattactttt tctaatatta    65520
gttttcttga ttgaggcttg gcaattatta gtttgtatgc ctttagaagg atcataagca    65580
gaggtttatc ccagtaggat ttgcatttta gaatgatgac tttgggagta aaatacagag    65640
aagtgaaacc agagatagtg ggatcattct ggagtctgtt gcctacactg aacagtagtt    65700
gagcgaaaaa ggatgggcag aatgtgttgg ttctgggtat tgcaaattca tggcacttga    65760
gtgaaaaagt ttaagccttc tattggctct ttgtgaatat cttcaacatg catgactaca    65820
aatagaacac atggttttgt tgttattgtt gttgtgtttt tgttttttttt tttatttgag    65880 atggagtttt gctcttcttg cccagactgg agtgcaatgg cacgaatttg gctcaccaca    65940
acctccgcct cccaggttca gcgattctc ctgcctcagc ctcctgagta gctgggatta    66000
gaatcatgcg ccaccacacc cggctaattt tgtattttta gtagaaacag gtttctcca     66060 tgttggtcag gctgtcttga actcccgacc tcagatgatc ctcccacctc ggcctcccaa    66120
agtactgaga ttacgggcat gagccaccgc gcccggccca cacggtatttt tgaaagaac    66180 agtgagcttg gattagaaca ctagtgtcca ggccctgctg ctactacata agtaattatg    66240
aatccatagc catcttgttg ctcttcttct ctgagccttg gtttctttag ctataaaatg    66300
ggaagttgaa actttctagc tacttctttg agttatgagt aacaagttag gtaatacact    66360
taaaagagaa tgtgctatac aaatactggt tcttaagaca gctgttgtta atgtactgag    66420
tattatgctt acctcacagg gttattgtga gcatcaaatg ggataatgga tttgtaagca    66480 tttttgtttaa agtgtgattc aaatgttaag aattagtaaa aatagtaaaa gaacaattca    66540
```

```
ttctccatcc agatgttctg tccccactgt gacttatgtg ctcattcaga gttgtacaga     66600
aaaacctcca cttaatttc acaagctgga gttccacatg taacagaatc atatgggacc      66660
aaaaaattct ctgtattggc ttcttccctg ccgtattttg gctctgggac caacaagaca     66720 cccatttgc atgagctgcc tgccaccaac tttgcgctca catctagttc tgttgcccat      66780
gtgcaagctg aatttgggcc cgggcccca gatctaacat gaaactcaag tttccttctg      66840
ttcaaactgt ccaggcataa tagtcttaaa gtccgatgcc cagcagagcc gtagattttt     66900
cactggccaa aaatcaacat gaaaccagat gtatctgtaa atctagtttc ataacacttt     66960
gtagtcaatg gaaatacagt agcaggcaga ccagaccaga gtttactatt tgcagtggaa     67020
ttaataacca catggaaact ttgcctttgg tatctgcgag atggaagata aggtgcgaa      67080 tcaaagcag ttcccacctt accctctaaa ttccaacata agaggcctt gaatgtcctt       67140 ctatcttatt gtatatttca ttaacagaag tatgttccta gctacttagt cattctatct     67200
ctattctcct tgttttaac ttcagtggtg ccagcttaag atgctctggc tttcagcttt      67260
catggagcac gtcatgtttt taaacttatc tttagggaca gaaatgttag aagatccta     67320 gttcctcatc tctttgctcc tgacaaggaa atttagaatt gcctaaagaa aggatgtatt     67380
ggccaaccta ataataaatc agtattagtg aatctaaagc atatttgaaa aatttgtaac     67440
atgagttgaa attcagacct gcaatgaagt gttttaaaa gatttaaaat cgaaataata     67500 taaagaatg ttaaaaacaa gtaaaacata tcactagtta atcactctac caaaattcat      67560
ttttatgttt gcatatttaa ccattttat tttctatatt tgtccatgaa catgtgtttt      67620
tatatattgt ttatattaaa catggtttta atcatggctt atttctttta tgttttactt     67680
cttttccttt gacataaaat attgtatttt ttaaatttta attgcttctt ggcatacct      67740 tccaatattg gtggctatat agattgaagt taaaactaat tacaatcaga gaaaattaac     67800 aattcatcc ttcaatctca ttagtcacaa gttaaatact caatagccac atctatctag      67860
ttgctactgt tttgaatagt acagatataa gacatttca tcaacacaga aaattcactt      67920
ggaaagcatt gccctggagt aaatgtgcca gactgtacta tatcatttt ctcttgttgg      67980 acatctaagt tatttcttat tttttaaata ttttatataa cttgacggtg aatataccta     68040
tgtacatagc tatttgcttt ggctgaatta tttcttagaa tcaatttcaa agtggagtt     68100 attaggtcaa agagcatgag aagattttt ggaacctgca gtgtattgcc atagtcctct      68160
caaaaaagtt tatgtcaact taaagtactt ctagcagcat atgattgtac taatttcgct     68220
gcaatctcaa caacactgga cattataagt ttttattcta ccctatttc cattaaaaga      68280 tagcttatgc ttgattgact ttgcatttta ttttattatt aataatgatg tggtttcctt     68340
ttttctagat tttattttta tttaaggcat cctttgattt taacctgatt ttttttctct     68400
aaaaattatt ctaagaaaag acaaaggtga tacgaaatat atcctgagtt tttattttt    68460 tcttgcatgg gatttgtata tttgcacctt tgcccattta tactatgatt tcttagtgtc     68520
ttccctggca attttaatga agacttcatg tatatcaatt tttccacaaa tataatcttt     68580
ctaaaaatat gttttttcca caatataatt cagacgtatt ctccgaaatg ttggaaaaac     68640
ttaagtaggc atcaaagcat ttgaagattt gtttaaaggt tgtttttata ccagttttaa     68700
attgtaattt aagggtcata aaataggtga aaattaaatc attttcagt aagggggcaa      68760 gaccacttaa ctcttggaaa atacaggaaa cgtagatttc tagaggccaa gaaggaggta     68820
gggattattt tgtaactgcc cccaaccttc taacctgtaa tgaaacaaac actgaaggcc     68880
```

| | | | | | |
|---|---|---|---|---|---|
| cttaaacatt | tttaggctta | attggctgtc | cttgtactta | gggcacatct | aaaaatcctg | 68940 |
| aggcaaccac | tcaagagaac | atgcttttgt | taattcaaag | ggagctgtcc | tacgagtgtc | 69000 |
| cagaatcctc | tgtagtcttg | ggcctggtgc | ttgagagacc | caaggaaag | gtcaatggaa | 69060 |
| ttacagctta | gtgttagagc | tttcatgcat | cacactaatt | aattaatgtc | ataaaggtct | 69120 |
| ctctcctgtt | atgggaaaaa | gcagcaaata | ggaacttctg | gtagggtgct | taaagttggt | 69180 |
| ttgatatttt | ttattagcat | ttttaactaa | tacaagtaat | acatgcttat | ggtagaatga | 69240 |
| taaaactgaa | aaaaaggta | tgaaaattta | gaagttctcc | tactcatgac | ctcacccctt | 69300 |
| ctttcactcc | cagtttcact | cctcagaggg | taaccacagt | gactagcttc | ttgtgtttgg | 69360 |
| ttcctgagat | tttctatgta | tatatattgt | tagatatatg | catggtatgt | tttcaaaatt | 69420 |
| cctgttacac | tataattact | gttctacaac | ttaattttt | cacttaatta | atagacctta | 69480 |
| tatatgcttt | tccatatcgg | tatatataga | tctatataag | ttttcttaaa | ggttgcacaa | 69540 |
| ctttcaattg | tatggctgtc | ttgtaattta | ctttttgttt | ccctactaa | tggatatttc | 69600 |
| atgtttccct | aactcttttg | atattaagag | tagtgctgca | attaacatcc | ttgagaggca | 69660 |
| gtatatatgg | tgtttaagat | gaatggttct | ggagccagac | tactttggat | tgaatattgg | 69720 |
| tgccaccaat | tccttgctgt | atgaccttag | gcaagttgct | taatttcttt | gcctcagtgt | 69780 |
| ccttgtgtga | aaaatggag | gcaataatgg | tcactatcca | gtagggcttt | tatgaggatt | 69840 |
| tagtaagtta | ataatgcact | ttaagaactt | agttattttt | agattaagta | gtgaaggact | 69900 |
| atataattgt | tagtataatt | gtataccttt | attatcatac | ttttgcatgt | atagcaataa | 69960 |
| gacaaattct | tagatgttta | accattggac | ataaggaatg | tacgcatttt | aagtactggt | 70020 |
| agatattacc | ttttccctgc | caaaaattgc | aaatattgga | tattaactttt | ttaaatctta | 70080 |
| gtaaatctga | taagtataaa | taacagttta | tcatcatttt | aagttgccta | tcttaattttt | 70140 |
| gtgtgaaaat | gattatcttt | tcacatgttt | ttttggccat | ttatgtttct | ttccatgtga | 70200 |
| actaactgtt | cctggccatt | gcctatttgt | tgttgctgtt | actatatggc | ttttcatctg | 70260 |
| tttcttattg | gtttatggag | ctctttgtat | atacaggaat | ttagcctcta | tttatatgtg | 70320 |
| tgacaaatac | ttttttccaat | ttatctttaa | aatttgttta | tgttttccta | ttcatcagtc | 70380 |
| taaaattatg | tagttaaatt | catcattgtt | ttttcttatg | actttagagt | ttggagatca | 70440 |
| tgcttcaaag | gtctttctag | gtggggatga | tttaaatcat | gtactggaag | tattttttgcc | 70500 |
| aaaaagactc | acgaattatg | gatgttagag | ctaaaggga | ccttagagat | ttcctagttc | 70560 |
| aaccacctttt | tcttcatacc | ttttttaattt | ttctctgcag | atgaaaagaa | gtttagtcct | 70620 |
| aaagaaagaa | aagagtctaa | aggttctcca | gtaagctaat | ggcaaaaatg | tagactggaa | 70680 |
| cttctagctc | ctgatgtgta | tttcagtgat | cattcaattt | aaccagatgg | tttcacaaaa | 70740 |
| agagctttct | actaaaaaat | aaaatacata | cttaagcaac | tcagagaatt | ttttttttat | 70800 |
| ttttcagatt | aattttcact | tagagattca | tcagcatatg | tactatacat | gtacaaatca | 70860 |
| cctgtgtgtt | ttggatattt | agttaaacaa | atgtgcaaat | atttttaacca | aaggagcata | 70920 |
| ttcatttgtg | ttttattttc | ttaatggttt | tcgttatgaa | tgtgaaatgt | gtatttacct | 70980 |
| taacagaaat | taagtatatt | tttggtctga | catatatgag | aactgaaaag | cattggcttg | 71040 |
| gctgctaact | gcattctcat | ctttctttct | ctgctttggc | aaagtctggg | attaaatcta | 71100 |
| atacctttta | aactgtttgg | gacttcagcc | agagtgacct | gtcttgaatt | cagaactgcg | 71160 |
| cagatcattc | cccattctaa | ggccctctca | tgcctcctca | ttgcctgtag | gatgagatcc | 71220 |
| aagtacctta | gcatagctta | tgcactgtag | tcacttgacc | tctagcacct | atgcagtctt | 71280 |

```
ccagtcttat ttacacattc ctttgcacat gctgtttccc cgtgtggggc aactttttc    71340 ttgcctgtct gcctgcctaa gccaacttaa ataaacatca tttctgtaac ttctgtgaag   71400
ccttttccaa tctctccact ccaagacgaa ggtgtttcta taggcatgac ttctggaatg   71460
gcagatcaag gatctggtgg accctctact cagtgaaaca accgtttaac tagtaaaaat   71520
gatcaatcaa ccatttaaaa tcttcagaaa atatcctaag ggcacatagc aaaagagaa    71580 acatttattc aagaaaagct attaagcctc agtaaaaaca gcaagagtct atggcatttg   71640
agtcatgacc tgttcctaat ccttccctta tctccattct tcaggcaagt gcaaccaaga   71700
agatggaggc ttcctctctc tcaaaatctt actccatagt tataatttca cccacaatgg   71760
ggcagaccac aagcatctct ttttttccc ccagccctat attacagaat cactgttcta    71820
ggaaggcata gcttagagga ttggagattc cttccacacc cactttctac gtatgagggc   71880
tttgccccag ggatggtaag tcaagaatac agggatcctg cttgtgcctg cctcagctca   71940
tatataaggt aaagcttcca cactaggaaa ggcaaattaa aggactagg gaatataccg    72000 ttatccccag ggtccacttg tagaacaggg gtgtcattct gggagaagca ggtcactgcc   72060
ccacttgtgg aacaggggag tcactcgtca ctgtccctgg ttcaaattct attgcagtga   72120
cagaggttct gtcccaggga aaggcaggtt gttaggatgg agaactccac agttctccct   72180
gaggtgactg actttatttg gaacagagca tgaagaagtt catgcctaag ggcactgtca   72240
aaaataatgg agatcttggt ggtgagcaat taagagtgga ttggtagctc catgatacta   72300
gtaacaacaa gcaaaacagc agaccagcat ggaggatacc agagaaccag acaaaggaat   72360
cactaagaag agcccttgtg gaattgcact cactgctggg tgtgtggaaa gttatgcatg   72420
tgtgctttac tgtaccctct caaaagcaac ctaaacagga tgtggggtag gctctaaagc   72480
attcctcaag ccacacatgg atccatcagt aaaatgtgga gggcttaagg ataaaaaggc   72540
ttaagtacaa tctctggccc tacattttct aaatgttatg ccaccctgac caaggggcaa   72600
ctcctacaaa gccaggcaaa ataataaaat catatttgtc tctagtggaa tggataacta   72660
tgcctaaaac tgtgcccttt gaaaagcaac tagagagata atttctgaag tgtttgtccc   72720
tacctgaatg tgtggcaaaa ttctaaactc cctgaagtgt gaaagtggtt tccaagccac   72780
atgcacatcc agtagtggta aagggtgaaa atctaactgg ctaagagggc ttcatagcaa   72840
cattaaccaa aaagtggttt atgtagtctt tgcctgcttc ataattccct aggcattcta   72900
tgctattctg tactcagaag gcttaaagtc aggttaggga aaggaggcct atgaggttac   72960
tgtgcagagc cagtgctggg aaataaatga agttaaataa atttaggcca tcgtggttta   73020
aagaatggat tgtggagata agaaggataa aggaaaccca gagtcaagaa aaataaaact   73080
tttcattggt gccatgccaa cccatatccg agcctgaggc aaaaggaaaa atgtgctccc   73140
tgatatacac ttatacaaaa tatcaactaa ttttatttgt tggactgaat agaaaagtc    73200 aacaaaaatt aaaaataaaa aaatcatgac tatattttta ataagtggtt tatgtaaacc   73260
cagagttgac caatgggatg ccagtctcaa ccataaaaac aaacaaaaca ttgtgagtaa   73320
caacaccaga agtctcaaag tgtcagggaa accaatttca cagaagcagt tcagccaagt   73380
cactaaacaa acaaacgact aagcaaaaaa caagaatgag tctcagaaag ggtcaagtca   73440
gtatccagag ttgttacaat atagtatcta aaatattgtt ttgaactaaa aattttgagg   73500
catgcaaaga atgaggaaag tatgactcat acatggtatt atatgaaaaa atcaacaaaa   73560
aactatccat gaggaaacaa agatgttgaa attcactagg gaaagacttt aaaaaccagc   73620
```

```
tatttaaata tattcaaaga actgaaggaa ctatgtctaa aatactaaaa taaagtataa    73680
taacaatttc ttgtcaagta gagaatgcca ataaagagat agaagttata aaaaagaaa     73740 aaaatggaaa atctggagtt gaaaattata ataactgaaa tgaaaaattc actagaaaag    73800
gtcacaagaa gatataactt ggcagaagaa acaatcagca aattagaaca tagatcaata    73860
tagattattc attttgaagg gtagaaagaa aaaagaatg aagaaaactg aagattccca     73920
aagaaatgta ggacatctta aagcacatc attaggagaa gaaagaagg gaaagaaaag      73980 agcagaaaga atatttttta aaaatggat aaaatcttcc aaaatttaat gaaaaacatc     74040
aacctacaca tcaaagaaaa ttttttttaaa acttcaagca ggaaaatgta acgatattga   74100
tacttagata catcatagtc aaaatattgg agtcaaatat aaagagaaaa ttttgaaatt    74160
agcaagagaa aaatgaaatg gaaccacaat aagattaaca gctgattctc atcagaaata    74220
acagagagca gaaggcagtg caatcccata ttctaaacgt tgaaagaata aaaaaactgt    74280
cagtcaagaa tcatatattc aacaaaacta tctttaaagg taaaaatgaa atgaagacat    74340
tcctaggtaa acaaaggctg agagaatttt tcattagctg acatgccttg caagaaatac    74400
taaaagcttc ctagacagta gctttaatct gcatgaaaaa aaattccaat aaagggaaat    74460 ttgtaaaataa taaaaataca tcattatata ttcttttcca cttaacttat ttaaaatcaa   74520
tttcttaaag cactatctgt aaaattgtat tgttatttga caataaaatg taaaagaggg    74580
gagtgggaat taagctaaat tggagtaagg aaatggtatc acatggtaaa ttgaatttac    74640
agaaagaaat gaaaaaatta agtggcaaat atgaagagta acattaaaaa cttctataaa    74700
ttaattgtgg cctcctttct tcccttagct tctgtaaaag acataagact attaaaaatg    74760
acaataatta taaacacatt gttttattag taataaacat agacaaatta tctacaacaa    74820
ttattattat acaaggagag ggaatggagc tgtagaggag taaagttttt ataacctact    74880
ggaactaagt cagtataaat atgatgtcga ttctgttaat ttgagatata tgttagaagc    74940
cccaaagtaa tcactgagaa aatgatgcaa aaatacagtt ttaaaaagtt aaaaacatag    75000
tttagcttat gtgtgcctag tactccatta ttattttttt attatatttt aagttctggg    75060
gtacatgtgc agaatgtgca ggtttgttac ataggcatac atgtgccatg gtggtttgct    75120
gcacccatca atccgtcata tacattaggt atttctccta atactatccc tcccctgtc     75180 ccctaaccc ctcaacaggc cctggtgtgt gatgttcccc tccctgtgtc catgtgttct     75240
cattgttcaa ctcccactta tgagtgagaa catgcggtgt ttcgttttct gttcttgtgt    75300
tagtttgctg agaatgatgg tttccagctt catccatgtc cttgcagagg acatgaactc    75360 atcctttta tggctgcata gtagtccatc gtgtatatgt gccacatttt ctttctgctt     75420
gttcccagga gaaagtggct gaagattcca gagagaagct gaatgcagtt taattctttt   75480
tgccataaac acgacaaccc attttcctgc aagctgtgtt agtttgctct cttcttggtt    75540
cattcattca tttattcata gcttccataa atatttaaca aacactaatt agggggccaag   75600 ccatgtgcta ggcacagggg ataaaactgt gaacaaaaca agccccagct actcttaagg    75660
aactgataga caaatggacc agcaaacacg ctggtcctgt tttgaaggca agcgcctgg     75720 tgctcctgat ctcatgagca cagagcattt agcctaagtc tcatcctcct aaggcctcag    75780
aaataaggcc ttatttaat aagtgcaagt cagtcatttg aagactaaat catagaatcc     75840
tagaaaacta gtaccgggag caaggcaaaa gaatgggatg agcatgaaac atatattcag    75900
aagttgtggt gtgtaggtat ataagccaag ctctttctt cacttgcttg ctaagtcact     75960
tagcttttct gccttttgt ttgctctgtc tggaaatgga gttaatgaaa tatatctaca     76020
```

```
tgatagggat attgagacga ttaaataaga tgctgctgtc acccagtatg ccttaccct    76080
gctgtactta gaagtatatg aaattcattt tctaaatttt tgtatgagtg tttcatgcat   76140
gcccaccacc atggaagcta ccttaagaca gtgagggact tgtttaact  tgtttgtact   76200
acatcctcag tctaatggtg tctggcttat ggtaggcacc aaatataatt ttattgacag   76260
aaaggatgat aatgaatgtg aaggcatttt taagtttatg aagtgttgtg catattgttg   76320
ttaattttaa gctgttacgt taaagaaccc ctaatccaac tctcttgagt tttatagata   76380
tcatagaaga tatatcttcc cttgacatag aagcttccct tgaaggttcc cttgactcat   76440
gtatttgcct cacagtgatt gtgcagatcc cacaagataa atttatgtga atgtgcttta   76500
tgtgcttgaa gtgctccaca aatatgggtt ttataagatg agaaaataga gtcagggaga   76560
aaggtgactg atccaaggtc atgcaaagag ttagtgtcag aatttataat ggaatttcag   76620
gctcccaact cccactccag tatactaagg cagattccag agaagaaaca gtggagagca   76680
ggcactgatg agggacaaag aaaagcaggc tccgtctggc tgcaacttgt ctcttcatgg   76740
caaaaagaaa ctaggaaagt gctatgccag agacgacatg ataactttgc agaatggaaa   76800
gagcttgttt accacattga atactttatc tgtgtttatc taacgacagt tccaccagct   76860
ctttaccact tgacttttgc ctaattcaaa aatataccaa ctatgaaaca ttttccttct   76920
cagttttttat tctagattac attttgttca actttatctt aatgtgtagt gtagaaagag   76980
taaggtaaga gtatagcaag tggttatttt ccatttctac tgaggacaga gaaataatct   77040
aagggatttg tattagagat gaagaagtgc atggccagga catgagagat actgtgatag   77100
aatggatatt gtgaagtctt tggtagtttt tgaggggaaa aaagagaagg ttttctttgt   77160
ctgatatagt ttagcaacgt cttaatttag gattcaaaag ttgttcaggg tccatcttgg   77220
ccttcaaatt aagatgccct tgagagata  acattgttgt tttcaaactc tgttctgtga   77280
cttaagaatg agaggagaag gaagaaaaga ggagaaaatt tgagggaaaa gtgcccaagc   77340
agcgtcaagg ctagacactg gaaatttatc aatgaaagcc acatggtgga tgggaatcag   77400
atatgtgcat caattatttg tgttccaatc catatagaag taccgtataa tgcaccaagc   77460
taataggtgc tttgaaagaa gaccatacaa gtggagatgt gttcctattc tatctaggga   77520
tagagtcagg aagggcttca ttgaataagt ggtagcctct tgggctgaga cctgagttat   77580
gagatgatgt ggcaaaggag acagatggct ggggcaaagg tggggtcatt gaaattggag   77640
gcagtagcaa tataagcaaa gctacagggg catgaaaaag caaggttaga ttagtgaatt   77700
gcaacagggt ggtactgctg gaaggtcaca tggaaaagat tgtgaaggta ttgagataag   77760
aagctagaaa taagctttga atgccatcct agtactttga atttgcatgc tgtaagccaa   77820
gtggttttca cttggtcatt taataaaatt acagattctc aggtctcacc tgtaacttca   77880
gattcagaag agtctgctaa ctgaaggtgg aatcagtgtt ccatattgct aattagctcc   77940
tcagaggatt ctaatatatc agtgagttat gaccactgct gtaagccata ggtagttatt   78000
gaaagctgct atggagagga gccacagaag cagatgtttt agataggatt cctctgggt    78060
cctgtgtaat ttatggactg gagaggatca gacaggaagc agaaagactt gaataagaca   78120
gttgcagtta ttttggaggc aaagattctc tctctctctc tctgtgtgtg tgtgtgtgtg   78180
tgtaattgta ggaactattt aggcagtaaa attaacagat attagtcact gattgactga   78240
gtggatggca gtgataggtg gggtgcgttg agggaagtgt attacattaa gtccaggatg   78300
actcatggtt ttctaagttg agtcattggg gattgccatc caatgtgaga aactatatag   78360
```

```
tcttatcata gttgatcttg gaggtagact tgaattaaaa tcttgaagcc atcaattgct   78420
gtatgtgggt cttgggcaga acacttaagg tttctggacc tcagttattt cttctgtaaa   78480
atgaggaaaa taatgcatac ctcatgcatt tgttgtaaag actaaatgag gttaaagtat   78540
gtagagtgta gtttagtaac tgggacgtat agtggtccag taaacatcag ctgttattat   78600
tgtgctatat gttgtgatgt gtactggagt gagatggggt aggggatttt ttagtctctg   78660
ccaatgactc ctctcccccat gatcaaaatc agaaaatcag tctcttatgt gttgaggagt   78720
gagacacttc tcccaagtgt ttaaggctaa taccttgcct tgttttgcct tgggccagac   78780
ctcactacac atctgtttaa gagatcaggg taagctctgt tcttggtgag tatctcaatg   78840
gggctgtttt tctagttctt gtagtttctt tgggccaaca tgaaatgtct aaccttggct   78900
tcttggttgt ggattctcgt caacatttca ctgctaccca agttgtgtct gcttacatga   78960
tgctatcttc cttcttttgg gtttctgaag ccctcagaca cttggctgaa catttttcac   79020
atttcttaag ctatatcatc tgtgttttcc ctgccacaga caaagtcaca aaaggacttt   79080
aagataggtt ttggttttttt ttttccccag gttttttata catttgggt aagggcaagt   79140 ggtaaatgct gcttttctgc cttaaccagt agtgtctgac agaggaggta gcatgatgat   79200
tgcagagctc actggactga aagtcagatg ctttacccgc ctagactcta gtaccaaggg   79260
gaagatggag tgagatgggg taaatgggga gaaattacca tttattttga gtgtgccagg   79320 cctttctctca tgtattgtct aatgcatttg tcacaattct ctttgggttt gaaatgtgat   79380
tttcttcatt ttatagataa ggaaacttat gggaagggag gttaggttca tcttgtgccc   79440
aactttacat ggctagtgat caataatagt gagattcaaa ctcagatttc tctgccccaa   79500
agcctttgct ttttcctctt ttgacactgt aactaatgag aagatgtatt taactctgag   79560
tctcatttgc ctcaactgta aaatggagct ctgtaactct tgctctgtat gacagtaaat   79620
ctcctcagac cagacttatg ataggggata aggatatttg tatctttggg cccctaatgt   79680
attgaaagtg cttctaagtg cctggcacat agaagggcac tcaataaata tttaccacat   79740
tttccagaaa gagggtagct ccataatggg tgagatacat tttggtggct actgtagtgt   79800 ttaatgctt accatctgt taaaatgatt ttggagtata gctagataac tgatgatggt   79860
tgttatatag attttttcat aggttgcctg ttccaaattc tatgccgtgg aagaagttaa   79920
atatccagaa tttgacagga atattattc tacaacagat ccctggcgta agaatgataa   79980
cacctgtgtt ctagtctcag acttgcctct gaataactgt ttctcctggt caattctctg   80040
tctctatcta ggcttgaaat ttcccccaaa tgatgaagga gttggactag tttagtgggg   80100
ttcagcctcg agtggccatt aaaattattt ggggatcttt gaaaaaaatt agatgcccag   80160 attttgtcg ttgttgttgt tgttttgtt tgtttgtttt ttaattatac tttaagttct   80220
gggatacatg tgcagaacat gcaggtttgt tacataggta tacacgtgcc atggtggttt   80280
gctgcaccca tcaacccgtc atctacatta ggtatttctc ctaatgctat ccctccctag   80340 tccctaacc ccagacaggc cctggtgtgt gatgttcccc tccctgtgtc tatgtgctct   80400
cattgttcag ctcccccctta tgagtgagaa cgtgcagtgt ttggttttct gttcctgtgt   80460
tagtttgctg agaatgatgg tttccagttt catccatgtt ctttcaaagg acatgaaccc   80520 atccttttt atggtggcct gatattccat ggtgtattga actgctcact ccagttcaat   80580
taaatcagaa tacagaatgt tgagaggagc atcagtattt taagaaggcc cctagtgaa    80640 gttcaatgtg cagccaaggg tgagaaacac tggactagat gattgataag gccatccaa    80700 cttttgatagt caacaagaga caatgctata gagtatggtg gacagagcat gggctttaga   80760
```

```
gttagccagg tatgcattca gaccctggct ctgttactta ctagttgtgt gatcttgaag  80820
aaatcaaaat ggagatacac tatgtacctg gcagtaatag ttgtgggat taagcacctt   80880 caccagagct taggacataa taagccccca gtaaatagct tctttaatat cagaagttca  80940 gatgaagat gtgagaaaaa tattggttca gtaagattta acaggtaaat taaaatcaag   81000
tatttgaaaa cattttcctg tttctttagc aatggattcc agaaacataa tgtggaaata  81060
gctctcagtc cttagatttg atgacattgc agaaagaaat ctggctagtc gtcccatggc  81120
tgattggcta tgatggctag aaagccattg gaaaaaaaa attggctcac agaagacagc   81180
agatgtggct tgggaaatgc aaggacatga ctgtaataag gatttgtcta ccagcccca   81240 tttatgagag tgattccagg agaaaggac agatttgtat tgtcagtggg atacgctgtt   81300
aaaaaacact tttgctacta ccactccagc tgtcttggca tgtttgttgg tgatgtaagc  81360
tacagaaaat ggaaatcacc aatagggcta tagcaacctg atgcatagtg acaagtaatt  81420
gttctattca tggttatgtg ttgtacagag cacttgctgc atgtcaggtt tgagacttga  81480
gtatgcatta gggccatgga cacccccatc ttatctttaa gtagatttca aagtaaatat  81540
ttgatgaata tgtaaaatat ttagtttggt cagtcatagg gctgagaaca tggtggcagt  81600
tacctcctag tatctgcaag caaaaaaagt ttttcttcc tatagcaatt gccatctcag   81660 ccactttgc agcatttctt tttgctacac tttgcattaa ccatttgtgc acttgtctta   81720
gcctcaaaca ggccatgaaa gctccttgag gatagggctc atgtctttt catctttata   81780 tatgcatcat ttagcagagc tgtccccttta taatgtacta attactgaat gaagggatgc  81840
atagatgaat aaatgaatga aagtaggag tgacctgtct tctctcttc ttcacgatgg    81900 ggactagtgt gtgtatataa ggggataatt tttgtgtcac ataaaatata accttactta  81960
gaaggcaaga cttccagaat ggtggaatga gaaccacccc cccgcccca taaatccgcc   82020 ctttcatgaa agcagtgaaa acgctagcaa acgttgtgaa aattaacttt tccagaactc  82080
tggaaaggaa acagaggctt ccaacaatct gagaagaatg tattcaagaa aaacttcggt  82140
aagctctctg atcacagtgg aaataataaa caattagtaa tagaaggata gttgggaaat  82200
tcaccatttg tgggatataa acagtggatc aaagaagaaa tcataaggga aatgagaaaa  82260
tactttgaga ttaatgaaaa tgaaaataca ttgttccaaa acttacagga tacagccaag  82320
ctaaagcagt acttaaaggg aaatttgtaa ctgcgaaggc ctatatcaac aaagacaaat  82380
gatctcaaat caagaaccta accttccacc ttagactagg aaaggaacag caaactacaa  82440
agaaagcagg aagaaagact aataaagact aaaagggaaa taaatgaaat aatagagtag  82500
aaaaacacta gaatcaatga aattaaacat tgattctttg aagagatcaa caaaactgaa   82560
aaaaacttta gtcagattga ataagaaaaa agagagaaaa attcaaatta tcaaaatgag  82620
caatgaaaat ggggccatca ctacctacct taaaaagaat tttcaaagga ttaaaagaaa  82680
atgccattgc attagttcat tctcacacaa ctataaaaaa gctacctgag atgggggtagt  82740 ttatgaagaa aagcgcttta attgactcac agttccacag tctgtacagc aggcatggat  82800
catgaggcct taggaaattt acatcaggtg aaaggctaag gggcatggaa gacatgtctt  82860
cacacggcag caggagagag agcaaagagg gaagtgccac acactttaa accatcagct   82920 ctcatgacaa ctcactcact atcatgagaa cagcaagggg aaaatctgcc ctcatgatcc   82980
aattacttcc taccaggtcc cttccccaac actggaaatt acaattcaac gtgcgatttg   83040
gatggtgtga cacagagcaa aaccatatca accatactgt atgccaaaaa attagatgac   83100
```

```
ctagatgaaa tggacaaata ctcagaaaaa cacaaactat ctaaagtgac cagtgaagaa    83160
acagaaaatc tgagtagtcc tgtaacaagt cctgtaacaa aactggatta gtaattaaga    83220
aacttcccac aaagaaaagc ccaggttcag tcttcactgg tgaatactat caaatattta    83280
aggaagattt aatccttcac aaattatttc aaaacttgga agaggctgga acccttccca    83340
actaattctg caaagtcagc attaccctga tgccaaaacc aaagatatga cacaaaaata    83400
aaactgcagg ctaatatcac atttgaatat agataacttt ctaaaaatct caacaaaatg    83460
ctagcaaaca gaattcagca acaaataaaa agggttataa agggtgacca agtaggattt    83520
atctctggaa tgtaaattaa cattcaaaaa cctaagaata ggaggaaact ttcttaactt    83580
tgtaatggac atctctgaaa aacacacagc taacatcata ctaaataggg aaagattgaa    83640 attttttcctt gtaagatcag gaacaagaca aggatgactg ttctcaccat ttcaatttac    83700
cattgtattg tagattcaag tcaaggcaat taggcaaaaa aaaaaaaaaa aaaaaaaaa     83760 aaaaagaaag aggtaaaagg cacccatatt ggaaaggaag aggtgaaaat atctatattc    83820
acagatgaca tgatcttata caaagaaaac cttaaggaat ccatgataaa ctattaaaac    83880
gagtaaacga gttcagcaag gtttcagaat acaagattaa tgtgcaaaaa tcaattgtat    83940
ttctgtacac tagcaatgag caatctgaaa atgagattaa gaaaacagtt cactcacaat    84000
ataatcaaaa taccagaata cttaaaaata aatttaacaa agaagcgta agacttgtat     84060 gctgcaaacc acaaaacact gtggaaagta attaaaaatc taaataaata gaaaacatc     84120 ccttgttcat gtactagagg actcaatatt gtcaagatgg aaatactccc caaagattga    84180
aggaaatccc tatcaaaata ctggctgttt tcttagcaga aatgaaaat ctgaccctaa      84240 aattaatatt taaatacatg gaacctagga taaccaaaat aatattgaga agaaaaaca      84300 aagtcggcgt acccatgctt cctgattcca aaccttatta caaagcagtg gtaatcaaga    84360
gtgtatggta ttggcataag gacaaacaga tcaataaatg gaatactatt gagaatccaa    84420
aagttaactc ttcacatttaa gaccaattga cttttcaaaag tgttgctaag acatttcaat    84480
gaggaaagaa tagtctttttc aataaattgt actggaaaaa ttggatatcc acatgaaaat    84540
aaaagatttt ggaccacttc aaacctgcaa aaaaaataaa atgatctcat ggtgtatcat    84600
ggatctaaat gctatagagc taagatgata aatctcagaa gaaaatatca aagtaaatct    84660
ttatgacctt gaagtaggca atggtttttt ggctataaca ccaaaagcac aagcaataag    84720
agaaaaaaaa tttttttaaa aaaacccttg attattttat taaaattttg ttgtgggtac    84780
aaagtaggtg tgtatattta tggggtatat gagatatttt gatacaggca tacaatgttc    84840
aatgatcata ttaggataaa tgaagtatcc agtacctcaa gcatttatca tttgtgttac    84900
aaacaatcca attatactct tttagttatt tttaaatgta cagtacatta ttattgtagt    84960
cattcccttg tgctatcaaa tactatatgt tattcattct atctaactat attattgtac    85020
ccattaacca tccccactcc cctgcctccc agctacactt cgtagcatct ggtaaccatg    85080
atttcctctt atctccatga gttcagtagt ttcagctcat ggagatagac agaactaatt    85140
ttattagctc ccacaaatta gctcccatgt cagaacatgt aaagtttgtc tttctgtgcc    85200
aggtttattt cacataacat aacgaactct agttccaacc atgttggtgc aaatgacagg    85260
ctctctcttt tttttttttt tttttttttt tgagatggag tctggctgtc tcccaggctg    85320
gactgcagtg gtgcaatctc agctcactgc aagctccgcc tcccaggttc atgccattct    85380
cctgcctcag cctcctgagt agctgggact acaggcaccc gccaccatgc ccgactaatt    85440
ttatatatat atatatatat atatatttat tattattata ctttaagttt tagggtacat    85500
```

```
gtgcacaatg tgcaggttag ttacatatgt atacatgtgc catgcaggtg cgctgcaccc    85560
actaactcat catctagcat taggtatatc tcccaatgct atccctcccc cctccccac     85620 cccacaacat tccccagagt gtgatgttcc ccttcctctg tccatgtgtt ctcattgttc    85680
aattcccacc tatgagtgag aacatgcggt gtttggtttt ttgttcttgc gatagtttac    85740
tgagaatgat gatttccaat ttcatccatg tccctacaaa ggacatgaac tcatcctttt    85800
ttatggctgc atagtattcc atggtgtata tgtgccacat tttcttaatc cagtctatca    85860
ttgttggaca tttgggttgg ttccaagtct ttgctattgt gaataatgcc gcaatgaaca    85920
tacgtgtgca tgtgtcttta tagcagcatg atttatagtc ctttgggtat atacccagta    85980
atgggatggc tggttcaaat ggtatttcta gttctagatc cctgaggaat caccacactg    86040
acttccacaa gggttgaact agtttacagt cccaccaaca gtgtcaaagt gttcctattt    86100
ctccacatcc tctccagcac ctgttgtttc ctgacttttt aatgattgcc attctaactg    86160
gcgtgagatg atatctcatt gtggttttga tttgcatttc tctgatggcc agtgatggtg    86220 agcattttt catgtgtttt ttgggtgcat aaatgtcttc tttttagaag tgtctgttca     86280
tatccttcgc ccactttttg atggggtcgt ttgtttttt cttgtaaatt tgtttgagtt     86340
cattgtagat tctggatatt agcccttttgt cagatgagta cgttgcgaaa attttctctc    86400
attttgtagg ttgcctgttc aatctgatgg tagtttcttt tgctgtgcag aagctcttta    86460
gttgaattag atcccatttg tcaattttga cttttggtgt tttagacatg cttttggtgt    86520
tttagacatg aagtccttgc ccatgcctat gtcctgaatg gtaatgccta ggttttcttc    86580
tagggttttt atggttttag gtctaacgtt taagtcttta atccatctcg aattgattt      86640 tgtataaggt gtaaggaagg gatccagttt cagctttcta catatggcta gccagttttt    86700
ccagcaccat ttattaaata gggaatcctt gccccattgc ttattttgt caggtttgtc      86760 aaagatcaga tagttgtaga tatgcggcat tatttctgag ggctctgttc tgtttcattg    86820
atctatatct ctcttttggt accagtacca tgctgttttg attactgtag ccttgtagta    86880
tagttagaag tcagggagtg tgatgcctcc agctttgttc ttttggctta ggattgactt    86940
ggggatgtgg gctcttttt ggttccatat gaactttaaa gtagttttt ccaattctgt      87000 gaagaaagtc atcagtagct tgatggggat ggcattgaat ctataaatta ccttgggcag    87060
tatggccatt ttcacgatat tgattcttcc tacccatgag catggaatgt tcttccattt    87120
gtttgtatcc tcttttattt ccttgagcag tggtttgtag ttctccttga agaggtcctt    87180
cacatccctt gaaagttgga ttcctaggta ttttattctc tttgaagcaa ttgtgaatgg    87240
gagttcactc atgatttggc tctctgtttg tctgttattg gtgtataaga atgctgtgat    87300
ttttgtacat tgattttgta tcctgagact ttgctgaagt tgcttatcag cttaaggaga    87360
ttttgggctg agacaacggg gttttctaga tatacaatca tgtcatctgc aaacagggac    87420
aatttgactt cctctttttcc taattgaata cccttatttt ccttcttctg cctaattgcc    87480
ctggccagaa cttccaacac tatgttgaat aggagtggtg agagagggca tccctgtctt    87540
gtgccagttt tcaaagagaa tgcttccagt ttttgaccat tcagtatgtt attggctgtg    87600
ggtttgtcat agatagctct tattatttta aaatacggcc catcaatacc taatttattg    87660
agagttttta gcatgaagcg ttattgaatt ttgtcaaagg cctttctgc atctattgag    87720 ataatcatgt ggttttgtc tttggttctg tttatatgct ggattacatt tattgatttg    87780
cgtatattga accagccttg catcccaagg atgaagccca cttgatcatg gtggataagc    87840
```

```
tttttgatgt gctgctggat tccgtttgcc agtatttat tgaggatttt tgcatcaatg    87900
ttcatcaagc atattggtct aaaattctct tttttggttg tgtctctgcc cgtctttggt    87960
atcaggatga tgctggcctc ataaaatgag ttagggagga ttccctcttt ttctattgat    88020
tggaatagtt tcagaaggaa tggtaccagt tcctccttgt acctctgata gaattcggct    88080
gtgaatccat ctggtcctgg actctttttg gttggtaagc tattgattat tgccacaatt    88140
tcagatcctg ttattggtct attcagagat tcaacttctt cctggtttag tcttgggagg    88200
gtgtatgtgt caaggaattt atccatttct tctagatttt ctagtttatt tgcgtagagg    88260
tgtttgtagt attctctgat ggtagtttgt atttctgtgg gatcggtggt gatatcccct    88320
ttatcatttt ttattgtgtc tatttgattc ttctctcttt ttttctttat tagtcttgct    88380
agcagtctat caattttgtt gatcctttca aaaaccacc tcctggattc attaattttt    88440
tgaagggttt tttgtgtctc tatttccttt agttctgctc tgatttagt tatttcttgc    88500 cttctgctag cttttgaatg tgtttgctct tgcttttcta gttcttttaa ttgtgatgtt    88560
agggtgtcaa ttttggatct ttcctgcttt ctcttgcggg catttagtgc tataaatttc    88620
cctctacaca ctgctttgaa tgtgtcccag agattctggt atgttgtgtc tttgttctct    88680
ttggtttcaa agaacatctt tatttctgcc ttcatttcgt tatgtaccca gtagtcattc    88740
aggagcaggt tgttcagttt ccatgtagtt gagcggtttt gagtgagatt cttaatactg    88800
agttctagtt tgattgcacg gtggtctgag agatagtttg ttataatttc tgttctttta    88860
catttgctga ggagagcttt acttccaact atgtggtcaa ttttggaata ggtgtggtgt    88920
ggtgctgaaa aaaatgtata ttctgttgat ttggggtaga gagttctgta gatgtctatt    88980
aggtctgctt ggtgcagagc tgagttcaat tcctgggtat ccttgttaac tttctgtctc    89040
gttgatctgt ctaatgttga cagtggggtg ttaaagtctc ccattattaa tgtgtgagag    89100
tctaagtctc tttgtaggtc actaaggact tgctttatga atctgggtgc tcctgtattg    89160
ggtgcatata tatttaggat acttagctct tcttgttgaa ttgatcccct taccattatg    89220
taatggcctt ctttgtctct tttgatcttt gttggtttaa agtctgtttt atcagagact    89280
agaattgtaa cccctgcctt ttttttgttt tccatttgct tggtagatct tcctccatcc    89340 ttttatttg agcctatgtg tgtctctgca tatgagatgg gtttcctgaa tacagcacac    89400
tgatgggtct tgactcttta tccaatttgc cagtctgtgt cttttaattg gagcatttag    89460
tccatttaca tttaaagtta atattgttat gtgtgaattt tatcctgtca ttatgatttt    89520
agctggttat tttgctcgtt agttgatgca gtttcttcct agtctcgatg gtctttacat    89580
tttggcatga ttttgcagcg gctggtaccg gtcgttcctt tccatgttta gtgcttcctt    89640
caggacctct tttagggcag gcctggtggt gacaaaatct ctcggcatt gcttgtctgt    89700 aaaggatttt atttctcctt cacttatgaa gcttagtttg gctggatatg aaattctggg    89760
ttgaaaattc ttttctttat gaatgttgaa tattggcccc tactctcttc tggcttgtaa    89820
agtttctgcc gagagatctg ctgttagtct gatgggcttc cctttgaggg taacctgacc    89880
tttctctctg gctgcccta acattttttc cttcatttca actttttga atctgacaat    89940 tatgtgtctt ggagttgctc ttctcaagga gtatctttgt ggcattctct gtatttcctg    90000
aatctgaatg ttggcctgcc ttgctagact ggggaggttc tcctggataa tatcctgcag    90060
agtgttttcc aacttggttc cattctcccc gtcactttca ggtacaccaa tcagacatag    90120
atttggtctt ttcccatagt cccatatttc ttggaggctt tgctcgtttc tttttattct    90180
tttttctcta agttccctt ctcacttcat ttcattcatt tcatcttcca tcgctgatac    90240
```

```
cctttcttcc agttgatcgc attggctcct gaggtttctg cattcttcac gtagttctcg   90300
agccttagtt ttcagctcca tcagctcctt taagcacttc tctgtattgg ttattctagt   90360
tatacattct tctaaatttt tttcaaagtt ttcaacttct ttgcctttgg tttgaatgtc   90420
ctcccatagc ttggagtaat ttgattgtct gaagccttct tctctcatct catcaaagtc   90480
attctctgtc cagctttgtt ccgttgctgg tgaggaactg cgttcctttg gaggaggaga   90540
ggcgctctgc ttttagtgt ttccagtttt tctgctctgt ttttcccat ctttgtggtt     90600 ttatctactt ttggtgtttg atgatggtga tgtacagatg gttttttggt gtggatgtcc   90660
tttctgtttt ttagttttcc ttctaagaga caggaccctc agctgcaggt ctgttggagt   90720
acccggccgt gtgaggtgtc agtctgcccc tgctgggggg tgcctcccag ttaggctgct   90780
caggggtcag gggtcaggga cccacttgag gaggcagtct gcccattctc agatctccag   90840
ctgcgtgctg ggagaaccac tgctctcttc aaagctgtcc aacagggaca tttaagtctg   90900
cagaggttac tgctgtcttt ttgtttgtct atgcccctgcc cccagaggtg aagcctatag   90960
aggcaggcag gcctccttga gctgtggtgg gctccaccca gttcgagctt cccagctgct   91020
ttgtttacct aagcaagcct gggcaatggc aggtgcccct cccccagcct cgctgccacc   91080
ttgcagtttg atctcagact gctgtgctag caataagcaa gactccatgg gcgtaggacc   91140
ctctgagcca tgtgcgggat ataatctcct ggtgcgccgt tttttaagcc cgtcagaaaa   91200
acgcagtatt tgggtgggag tgacccaatt ttccaggtgc cgtctgtcac cccttttcttt  91260 gactaggaat gggaactccc tgacccccttg cgcttcccga gtgaggcaat gcctcgccct  91320
gcttcggctc acacacggtg cgctgcaccc actgacctgc gcccactgtc tggcactccc   91380
tagtgagatg agcccgctac ctcagatgga aatgcagaaa tcacccgtct tctgcttcgc   91440
tcatgctggg agctgtagac ctgagctgtt cctattcggc catcttggct ccagaaaaaa   91500
aaattgttaa attggacttc atcaaatttg aaattttttgt gctgcaaatg ataccatcaa   91560
gaaagtgaaa atctcaccca cagaatgaga gaaagtattt gcaaatcata tatctgataa   91620
gggtattgaa tttagaatat ataaagaact cttgcaactc aatataaaaa gacaacccaa   91680
ttttaaaatg ggcaaagtat ttgaatagaa atttcttgat agaagatata caaatttaaa  91740
aatgctcaac atcattagtc attagggaaa tgcagatcaa aaccaaattg agataccggt   91800
ttacacctat taagatggct atagaataaa agaacaaata acaagtattg gctttaatgt   91860
ggaggagcca gaacccttat atattgctgg taaaatgtaa agtcatgcag ccctttgaaa   91920
tacagtctgc aagtctttaa aaaattacta tttgttattt ggttttttctt cacttttaat  91980 ttaggttcag aggtacatat gcaggtttgc tatatagcta aattgtgtgt cacaggagtt   92040
tagtgtacac attatttcat cacccaggta ataagcatgg tacccaatag gtagtttttc   92100
tatcctcacc ctcctcctac cctccaccat caagtaggcc ctggtgcctc ttgttctttt   92160
ctttgtgttc atatgtactc aatatttagc ttccacttat cagtgagaac atgtggtatt   92220
tggttttctg ttcctgcttt agtttgctta ggatactggc ctccagattc atccacgttg   92280
ctgcaaagga catgatctca ttcttttttgc atagtatact atggtgtaca tgtatcaaaa   92340
atgttactgt ttgacctagt aattctattc caaggtaaat actcaagaga aatgaaaaca   92400
tgtccacaca aatacttgta cacaaatgtt cattgcagca ttatttataa tagccaaaga   92460
gtggacgaca aatgtcttcc aaatgtgggc tccaaatgtc caccaactga taaatgaaa   92520 aacaaaatgt ggtatatcca tgccatggtt tatctgtcaa taataagaaa tgaagtactc   92580
```

-continued

```
atacatgctc aacatggat gaaccttgaa aacattatgc taggtgaaaa aagcaactca    92640
caaaagacta cactgtatga ttttatttgt attaaatgtc cataaaagaa aaatatttag    92700
agatagaaag gaaattagtt tttccagggt ctgggaggag acagtatgag gagtggctgc    92760
taatgggtac aggatttctt tttggagtga tataattgct ctaaaattag tttgcagtaa    92820
tagatgtgag tatgctaaaa tgggtgaatt ttatagtatg tgaaatataa ctcagtaagc    92880
ccattaaaaa caacctaatt aaattaaaac caagctataa cagaaatatt atatggcttt    92940
ggcagtttag aatagtggga aaatatggag taagggtggg gaaatagtcc caagtataat    93000
tctggttttg tcactactag tgtatggact tggacaagtc atttgctttc tctaagtatc    93060
agtttgcata tatgcaaaat agaggtaatg ataccctacct cagtggtacc ttttcaaaac    93120
cttgttcttc ctcatctctc ctctaccact ttctcataat attattacag taataaccat    93180
ttattaagca ctgtgtccgc agtggtgtgg ggctgcttta cctccacaac ttcactgaat    93240
cctcactgca gtcttgtggg atctttattt ctttgcccat tttacatgta aataaattga    93300
agtcaaatga gttgttcaag gtccttctgt tagcaagtgg cagagatgga catgaaaact    93360
agatcttcta cctatgtgtc tttccacttc aactaaagaa tttattaaag agaattgaaa    93420
agctatgaac taaatttcgg taatactttt aatagtaaac attgctgccc tcgtgaatga    93480
acacacacta aatttcaaat ctcacggtgg cagggaataa agatgctacc tatcttaagc    93540
cattacttca ccaacttctc caccaaaata ttccttgtaa ccacaaataa gtaagcacaa    93600
tagatctata aggagagaat aattgtgaac tctgatttta tcttaaaaag tcatgtaggg    93660
atgtcatgtt ccacaatgtg attaataaaa tatattttgt tactaaacac aaggaaaaat    93720
attatgttcc ataaagatgt ttggtggttg cctcgacctc ttttagtttg aaaagtaggt    93780
atgtatgaga aagatatgtg tttacatgtt taccccttgcc ttctctctgt ctcttcccct    93840
ctctctccct ccctccccaa cccctatgcc ctacaccccc gcaaccccca catgtattta    93900
cctttctcta aaagctctgc atagccaaga aaagtgctct tttttatttt taggatatta    93960
gatatttcat tttcttatgg taagacaaaa gattaaggca accaagactt acaatgtgcc    94020
taccatgtgg caggcacaga ggcaagggct tttacatgtt atttaatgta attgtaattc    94080
tcacaaaagc cgtctagagt tgaaaatatt tccaactcta aatgaggcaa atggagcaca    94140
gagagcctta attatttcac ccaaagttca gtggtagagg caggattcca acccaggtct    94200
ggtgggctcc aaatccttgt tgggttgcca ttcctcttgc taacaaataa aactggtctg    94260
tgacttttgc atttcacccc gcttccacag tcactggtgg gacttactta agttaatcag    94320
attcttcaaa gtatccccaa gtcctccttt gaaaagaaag ttgggggaca ggaggaggag    94380
cagaggagag gagataaaaa ggaaaggagt cagggagaga gagagagaga gagaacctg    94440 gtgatctcag ctgggtgcca aggtttccta agcccaagtt ccccatggtt gagcctgtat    94500
tgtcaggcca acagcttcta gtaatccact tttatttaat taatagtgaa actgttgaag    94560
aattgcaagt ggtgttctgg ttcagaaacc ttccgttcta tggggcactg cttttgcttc    94620
agattcataa aaccaaatgc tctgcctcaa gataataagt gaacgtgtaa ccctcgggag    94680
gtaagaaaaa acacaatgtc acgtgcaaat tctgcacttg ttctcaaagc aaacctctcc    94740
tgtgtttgca attaggatgt tatctaggag catattcaaa acttttgagg ttttttatttt    94800 agttttcctt tcattatgtg ctgtttagt aatatcaaag aatacatgta atatataatt    94860
tatatgtcat aacaataaaa ttaatgttga tgagcccaga ttaaagaatc aacaacatta    94920
acatcatgat tgcatcaacc ctattagaat ggaagctctg tgaaggcatg gattttgtc    94980
```

```
cattttgttc actgctatat ccccaggacc tagaggagtg tcagccacat aataggagct   95040
tagtcaatat tttaaaaata agagcataaa tctacttata tcctctttcc tcttaccatc   95100
actcccagcc tcccctcaga ggtaaccact atcctatatt tgggctttat tattcccttg   95160
cattttgata agttttcaca tgtatattcc caaataatat attgcttgct tttgcttctt   95220
tttaaacttt atataatgga atcatattgt atgtatccta ttgtgaatta tgtcttttac   95280
acaacattag tatttgagat tcaactatgt gtagctcgat tccattcctt ttcattgctg   95340
attgtagttt attggatatg tgtgccataa attattttc tcctgtcagt taatgtttat    95400
catttatgct ttaataaaca aaactgctat gactgttcct gcatgtgcct cctagtacat   95460
atgtgaccaa ctttctctag gatataagcc tgagagaggg actgcagttg gaatttacat   95520
ttccaaagcc caaagtttag ctcatgagtc agagctgcaa tgtgcccttt gtccacacta   95580
ggtcaggatc agtgggagtg ctacccaaaa tattttgcta gctggggagt cagggagaag   95640
cagagactga cctagtgagg ccaggaggca ctatctcagg tctctagtca aaatgggttg   95700
caattagtaa aagtccagat tctgaatccc cttcactatt tatcttcctc ttcctccttt   95760
acagttattt ttgttcaagg tgcactttat taaactcatg cctaacaaac aaaactctaa   95820
tgaatatttt gtctttcatt gattgtaaat tcaattaatt agattgcttg aaaaaatttt   95880 aactgtatt tcactttagt atggatgaaa atttcgattt cttaaaaaa cattttttaa     95940 taataacaca acataaagtc taccctcata acaaaattta agggcacaac accatattgt   96000
ttttttttta ttttattatt attatacttt aagttttagg gtacatgtgc acaacgtgca   96060
ggtttgttgc atatgtatac atgtgccatg ttggtgtgct gcacccatta actcgtcatt   96120
tagcattagg tatatctcct aatgctatcc ctccccctc cccccacccc acaacagtcc    96180
ccagtgtgtg atgttcccct tcctgtgtcc atgtgttctc aatgttcagt tcccacctat   96240
gagtgagaac atgtggtgtt tggttttttg tccttgccat agtttgctga ggatgatggt   96300
ttccagcttc atccatgtcc ctacaaagga catgaactca tccttttta tggctgcata    96360 gtattccacg gtgtatatgt gccacatttt cttaatccag tctatcattg ttggacattt   96420
gggttggttc caagtctttg ctattgtgaa tagtgccgca ataaacatac gtgtgcatga   96480
caacaccata ttgttaactg taggcacaat gttgtacagc agacgtctag aacttttct    96540 tcaggcttaa ctgaaacttt atagccattg aacagcaaca ctccatttcc gtttcttaaa   96600
ggtcctttac aaaatgagct ttctgcgtgt ttccattttg tttatctgat aacttttttt   96660
tcttttttta ttatacttta agttctgggg tacatgtgca gaatgtacag gtttgttaca   96720
taggtacaca catgccaggg tgtttggctg cacctatcaa cctgtcatct acattagata   96780
tttctcctaa tgctattccc tcccttgccc ctcaccctc actggcccca gtgtgtgatg    96840
ttccctagcc tgtgtccaag tgttctcatt gttcaactcc cacttttgag tgagaacatg   96900
cagtgtttga ttttctttc ttgtgttagt ttgctgagaa tgatggtttc cagcttcatc    96960
catgtccctg caaaggacat gaactcttcc ttttatatgg ctgcacaata ttccatggtg   97020
tatatgtgcc acaatttctt tatccaatct atcattgatg ggcatttcag ttgttccaag   97080
tctttgctat tgtgaatagt gccacagtag acataagtgt gcatgtgtct ttatggtaga   97140
atgatttata atcctttgtt tatatacca gtaatagaaa tgcttggtca aatggtattt    97200
ctagttctag atccttgagg aattgccaca ctgtcttcca caatggttga actaatttac   97260
actcccacca acaatgtaaa agcgttccta tttcttcaca tcctctccag cacctgttgt   97320
```

```
ttcctgactt tttaatgatc acgattctaa ctggcgtgag atggtatttc attgtggttt    97380
tgatttgcat ttctctaatg accagtgatg atgagctttt tttcatgttt gttgaccgca    97440
taaatgtctt cttttgagaa gtgcctgttc atttccttca cccactttt gatggggttg     97500 tttgtctttt tcttgtaaat ttgtttaagt tcattgcaca ttctggatat taattaacct    97560
ttcgtcagat ggatagactg cagaaatttt ctcccattct gtaggttgct tgttcactct    97620
gatgatcgtt tcttttgctg tgcagaagct cttgagttta attagatcac atttgtcaat    97680
cttggctctt gttgccattg cttttggtgt tttagtcatg tagtctttgc ccatgcctat    97740
gtcctgaatg gtattgccta ggttttcttc tagggttttc atggttttag gtcttacgtg    97800
actcatcttg atttaatttt tgtgtaaggt gtaaggaagg ggtccagttt cagttttctg    97860
catatggcta gctagttttc ccaacaccat ttattaaata gggaatcctt tccccattgc    97920
ttgtctttgt caggtttgtc aaagattaga tggttgtaga tgtgtggtat tatttctgag    97980
acctctgttc tgttccattg gtctatatat ctgttttggt accagtaccg tgctattttg    98040
gttactgtag cctgtagta tagtttgaag tcaggtagca tgatgcctcc agctttgtgc      98100
ttttggctta gaattgcctt ggctatgcag gctctttatt ggttccatat gaaatttaaa    98160
gtagtttttt tataattctg cgaagaaagt cattggcagc ttgatggggt tagtattgaa    98220
tctgtaaaac actttgggca gtttggccat tttcatgata atgattcttc ctatccatga    98280
gcatggaatg gttttccatt tatttttgtc ttctcttatt tccttgagca gtggtttgta    98340
attctccttg aagaggtcct tcacatccct tgtaagttgg attcctacat attttattct    98400
gtttgtagca attgtgaatg ggagttcact catgatttgg ctctctgttt gtctgttatt    98460
ggtgtatagg aatgcttgtg atttccgcac actgatttg tatcctgaga ctttgctgaa      98520
gttgcttgtc agcttaaggt gattttgggc tgagagaatg gggttttctg aatatacatt    98580
catgtcatct gcaaacagag acaatttgac ttcctgtttt cctatttgaa tatcctttat    98640
tgctttctct ttcctgattg ccctggccag aacttccaat actatgttga ataggggtgg    98700
tgagagacgg catccttgtc ttgttctggt tttcaaaggg agtgcttcca gttttttgacc   98760 attcagtatg atattgggtg tgggtttgtc ataaatagct cttattattt tgagatatat    98820
tccatcaata cctagtttat tgagagtttg agcatgaagc agtgttgtat tttgtcgaag    98880
gccttttctg catctattga gataatcata tggttttgtc attggttctg ttgatgtgat    98940
ggattatgtt tattgatttg tgtatgttga accagccttg catcccaggg gtgaagcgga    99000
cttgatcgtg gtggataagc ttttgatgt gctgctggat tgggtttgcc agtattttt      99060 tattgaggat ttttgcactg atgttcatca gggttattgg cctgacgttt tcttttttg     99120 ttgtgtctct gccaggtttt ggtatcagga tgatgctggc ccataaaatg agttagggag    99180
gattccttct ttttctgttg tttggaatag tttcggaagg aatggtacca gctcctcttt    99240
gtacatctgg tagaattcat ctgtgaatcc ttctggttct ggacttttt tggttggtag      99300 gctattaatt acttcctcaa tttcagaact tgttatagtt ctattcaggt atttgacttc    99360
ctgctttagg cttgggaggg tatatgcgtt caggaattta tctatttctt ctagattttc    99420
tattttattt gccccagagg tgtttatagt attctctgat ggtaatttgt atttctgtgg    99480
gatccgtggt gatatcccct ttatcatttt ttattgcatc tgtgattctt ctctcttttc    99540
ttctttagta gtctggctag tggtctatct acaaaataga ctgtttatct gatatttatt    99600
ttgtaattat ctaataataa ccatcattat catcatcagc attatcatta tcatctcctt    99660
tacccataca tacatttgtg tctttcaaat aataatccca tctttgaagt gcatcctcat    99720
```

```
ctttagcagt ctgcactctg ctttcttata tcatttatta tcttatttta taattattta   99780
tttccagtcc ttcttctcta acagatagta gtttcttagg gccaaggaaa tatctcgatc   99840
accactatat ccccagcacc taaccctgtg cctggtccat agggccagat gctaagagtt   99900
gagttgaacc attgtaccta atcttaacct tcattagcac aacatggttt gtcagtggtt   99960
aagaatctac actttggagt cagactcacc caggatggaa tcctggcatt gccacttatt  100020
attaatagat gcgtgatctt gaacaagttt acttaattgt tctgagcatc agtttcctct  100080
tctgcaatat agggatgata cacagctacc tggtaggttg ttgggaaaat taaatgggat  100140
gatatgtatg aaatggcctg gcatatagag tgcctaaata catgttcttc tgattctatt  100200
tggacagttt gtgttagtaa cagaagtcaa aaaggtggag aaaggagaaa ggtacttgtg  100260
aaaattttct atttcttctc catgtttcat tcaggactga ggaaggggc acagttttta   100320 cccaaggaaa tgacatttt agccaaaga aatgatctta gcatttagct gaattatata   100380
ttggaagtaa gctccttcca tgtggaactt atggccttgc tagccttggt ttgttggaag  100440
tgctcttgct ggctttctag ttagggtagg gaaaggaagg cttgtgggga atgaagatag  100500
gccatgatat caagccactg ggtttgcaaa tcagtagaat ttttattgc tttctgttgt    100560 acttgggact tgaataaagg ctgatatttg tgtcttgctg gtaaagtgct tgtaaagtga  100620
gtgaaagttt tctttgctct tgtcctgaca tagctgttca cttggggttg agggaggat   100680 aacctttcat gtttttttt tttcttcatt ctgatgactg tgctgaacat tcaaaccaaa   100740
aggccattgg tggaaagtaa aggtgagtgg tgagaagaca atagggtaat ggaaactgtg  100800
ttggacttgt aatcaaattg tcctgcactt cccctctcca agtcttaacg ttttttcatct 100860 gtacagtgga tattaaaatg agaaaataag cttgtcttca cagagtttc gttaggtgtt   100920 gacacaacaa acaggctccc attagggctc attttccttc attccttagt aaggaagaag  100980
tgcttataaa atatagcagt tgtgctcttg tgaatgatag catgggcagt tgtcatctcc  101040
ctgaagcaga tgtaacccag aatgtcactt gagttttgtt taatgcttag gcataagaca  101100
taggaatgac aaaagctgac ctttgggtag tgagaacaat gttccatttt gttcaaactt  101160 gaattttta ctataggaga ctgagaatta accttccatg aaggttttag gattggcttt   101220
ctggcccttc tccttcatat ccacctgaaa gagcttgggc gcagaagttc ttgcagaaag  101280
gcagttagac aaggtgactt ctgaagctcc agtggccaag tattttgatg gtagcctaaa  101340
agatgtccag aatcattgta catcatttt tcaacagaag cttcaggcat agggattatg   101400
cttggtactt tatgttgtgg aatggaatct ggcggatgtc catgtgatct atagaaacac  101460
ctaaggaaag tgaagaaatg agggaaaaaa aagaacaaga cttttatgat aatactaatc  101520
acgatccttg tgtatttatt ccaatggcat tttatccatt atctgattta tattaccact  101580
cacagcagca gctcaatagg atgggagata ttatctctat tttatagatg agatttgagg  101640
ctcacgaagc taaagcaagg aacatcaaat cactttgata tttggtctgg ttttgttata  101700 ggtctcccctt tggatgaggt aaagttacaa acctgggttc atatcattta attagtctga 101760
aaatgttgcc tggacaccac cttcagttag atatcttaac ctcaggcttc ctgccttcat  101820
tgctcccgca tatagacata gactatgaga ttggctaatc ccagagaact tccctaatcc  101880
cttggcaaga tccaaaaagg ctcagtcaca ccctacaacc atcatcttta ggagaagtct  101940
cagaaaattc agcttcacac taactaactt gagcaatgaa taatagtcat ttatgcctgc  102000
aggttaatgc tgaagacctg agacttcact tgcctatttc tgccattcag tgacatgtgt  102060
```

```
tgcattggtt ttttgtgtct ttccagtttg gagactgcca gggaccatgt tttgcccatt    102120
gactattact ttccacccca gaagacctgc ctgatctgtg gagatgaagc ttctgggtgt    102180
cactatggag ctctcacatg tggaagctgc aaggtcttct tcaaagagc cgctgaaggt     102240 aaagggtctt gcacatgcac ttctcttttcc ctttctcctt taccttccag agagagacac   102300
taacctttca gggcccagga ttttatcatc tcagaaatag agtcattggc aaggccctat    102360
caaataactt aggagcctaa ggaagcaaat ttttgtactt gctagttccc tggtttcagc    102420
agccttgttt gtacaggcaa tttaggcagt gaaggtggtc ccagctgggg cttgggctc     102480 agtgggtcct agaaatgaaa gaaaaattaa tgatttgaaa agatttaatt tcctcccttc    102540 ttgtttttcta ctctgctggc tagtaaagga aaaatttgtc cttattagag aggttagaag   102600
tggagaaacc ccaactgagt ccccagcctg ttccttggga tgaatatgag actgttcctt    102660
agcaaaggct tcctggcctc ggccccagaa agggagtgtt ctcactcttc agcagactat    102720
cagtctctgc acctgctccc tcctgttgtg gcctccttgg gacctgtctt tgcattaata    102780
gttcctaggt aggtaagaac tcagagtgaa gaaacacatt tattctcctc tccagagacc    102840
tgatctcaaa gcctgtccat tagtccctaa ccttaatcta aggtagcatc ttatatctgg    102900
ctaaattggc tcaagcccta gctccttagt tttatttagc ttagaacaac tcatgtctgc    102960
tcaacctcta gaggcgctca gcccacattc tgcagtagaa actcccattt tcaggcctct    103020
tatatacggt aatgtctcct tcctctaacc acccaggggc taagcttcct gcttatccac    103080
ttcaccctgt attgagggct ttcttctcaa agagacattg atgaggagcc cctagagaga    103140
gatgctgtgc tctgggacca gaccccttgt taaacaccag tattcacctc tgccccaact    103200
ttccccaaag aggtacttcc tgccaaggcc tttctctttc ctctcactgg ctggaagtgt    103260
tgagttccac ttcagaacca gaacagagaa cctttccttc tataagagct ataaaccttg    103320
agaacagtct taaaacatag gtatgtaggc cacaccattc accacgaatg tactgatact    103380
catcagaata tggaagaagc accagagagt ttgaagcatc tagagaaaag gtagaaagag    103440
aatgcccttt aactgacctc ctcagtgata gccaatcaca atgatgagtg ttgattcatc    103500
attttggcta ggtggcagaa atatctataa aacagaagct gccatgttgt tttcttccag    103560
tcctcagggc ctacaagaag gcagctatca tttggtatta ctgaaaacat gccccatgtt    103620
cagctcatac ccccaaatta cccattgcta ctgtttatgc tgggctaata tgaagcccag    103680
ggccctaatg tctaggtcta ggcagtaagg cctagagcag tgcctaaaga gcctgagagc    103740
agtgccttcc tttcttcaga gtactcatga aaggatggct gtcagaaaag gaaatgagga    103800
tgggttccag agacttcaga ccaccccaac ttccccagtg agaccctggc acctccccat    103860
accctctcac ctagcgggcc ctgtctatag agcagagaat gaaacagagc actcatctag    103920
aggtagtgtg tcagcaagcc caggcactgc accacagtaa tagcagccat atcagatggg    103980
aaaggagttc aagtgaacaa acaagcaaat tcaatagtca gatagattag attatacttg    104040
atgcttcctc tgagttttac aaatatgggt cactaaattg ttattttcag aaaacagggg    104100
aaatgctcaa tcacattgtg aaagggaaga ttttgctgtc atatcataca tcccacatgg    104160
gagctttctg cagaagttag agctgaagga gggaggcagg cagaagggca actggcaggg    104220
ctgcctggga ggagctctgc aatgaggtgg atcctgtgcc atttgagaac agggaagaaa    104280
agaaatgagg ttttggggag ggaatcaccc aactcacaga acacacagaa atccagcaag    104340
gtttcaaaac gctctacacc ttagagtctg ttaagttagg gaaactctgt gagctcatag    104400
ggccaaatgc acttgcctgc ttgaaatatg aaaaatcagc aatggattcc ttgaaaaaca    104460
```

```
atgaaaaggg aaccttctga gccccttggt tattttgaca tatggaccat agatttcagt 104520
cctgagccct ttgaaggtag gagaaggtgg tttagaaaac acacacacac acgcacacaa 104580
acacacacca gaatgaagca aaaaaaaaat tactggtgtt ttctttctcc tcccatctgt 104640
gaagctgttg gattgatttt actgccatca ttatccctgt ttgaaggcag ggggctgtct 104700
tattacccaa agaggacatt tattgatttg gttttctttt tccattttta caatgcatct 104760
ttatcgccca tatggccttt ctggaggtgg ttttcagtct ggcttgttga aacatcaaat 104820
tatacctgtc ttagagaaaa tagaaacaaa aatctttctc ttccttactt gcttgttgta 104880
gtcagttaac tcggactgag tattcagagt cttgattatc acttaattca tagtttcata 104940
aatctctgga atgggcatag gtacaggact aaaagcctg gcatctcaga cagaaatatg 105000
tttttagctt tggtggttta taacagatgg gacttttagg ctgtcattgg tgcagggctc 105060
agcacagagt cagttgtaat ctggacaggt tttgttgttg aggaagagtg ggaagaggga 105120
gtcctacatt ttctccttgt cagtaatgtt ggagaattgg ggtgagggtg aggctgggca 105180
gggagggtct gcatagaaaa aagggtgcgg tgagaaaaaa taatgctact aagccatgag 105240
ggtaaaatga ccaaattctg gttgagagaa acttggtcaa agtgtgtatg gggagagaaa 105300
gttggtcaaa gtctgtgtct gagtgcttgg tgggatgaac tctgggttag aaacaggcat 105360
ggagggaaat agttggttta tggagtgggt aggatgagtg gggtggtgaa agggaaggca 105420
ttttggatgc taagagacca ggaagtcaaa gcaaggcaat acacataaac agaggtaagg 105480
gctcagagag gttttagttg tgtagacttg gataagaaat tttccctttt ggacctcagt 105540
tttccttgtt tgtaaaacaa cggacttgaa ctagatattt taaaatgtgc ttccagctta 105600
gacattttgt gaccgttcta caaattacaa acataatcat catcatttca gcaaactcac 105660
atgtatttat acctgcataa gttttggtc ttgctttcct agaaggtgac taatcccaga 105720
tcctaatcaa ttaaagaagc aatcttcaga tggggataga gccagctgag agagtgtact 105780
atggatggag tgagttaaaa ctcaggactc agattttctc cttgtgatca ttgctgggta 105840
acttcctttc ttttctattt tctcatctgg aaaatcagga tatgaatccc catctctacc 105900
tcattatgtt tcaaagaggg ttaattaatc catcatgtgc attatgtgct caagaattta 105960 ctattttttca gacattttct agtaaaacat tgaagattat atgtccattt gttttgtaca 106020
catggagtgc tgtttggtac acatcataaa attgaaactg tagtttacat tctgaactca 106080
aagaattaca ccatcctcac tgatgtttac aataggtccc aatttagttt ctttagcaaa 106140
ttttatgtaa gtatggcttt gattctctct ctcactccag ttttgtgtta gggaagaaat 106200
gcaagtgaac cctcattgaa ctcttctgt cctttaaatc cattctttcc cacctcaact 106260
catgtggaat tgaatgttgc ctctagtttg gagtctagca gagagttttt ggtgcatatc 106320
agtgtcccct tcactccctg acttttcaag taacatttcc cagaggcaaa ttaactctgc 106380
taagaggatc tgcttgcagc ttcaacagag ccttcatcag gtatctttgg ccaaggagtt 106440
gactgatcct gactttgcga gtcctagaga tcttttcaca aagctcctct catgtttctg 106500
cctctgattt tcttaaatgt cacagacaga ctttagattt aggggttggt taacttttt 106560 tgtaaagggc catgtagtaa atattttagg ctttgtagat catatggtct ctgtgtcaac 106620
tactcaactc tgcctttgta ggatgaaagc agccatagac aatactggaa ctaatgggag 106680
tagctgtgtt ccaataaaac tttatgggca ctgaaatttg aatttcactt aatttccaca 106740
tgtcgtttaa tattattttt cttttttacc atttaaaaat ttagaaatca ttcttagctc 106800
```

```
tttgggcctc acaaaaacag atggtagagt ggatttggtt tatgggctgc agtttgttga    106860
cctgtgctttt agctaatcac ttctgtactt ataaatctgc ataggtttta tgtttttcca    106920
tctcttggta tcttagtagg ccagtcaaag tttgaacaac ttgttagcac agaatacctg    106980
gcctagtggc ttcttggtcc tgagcttatt tactaaacaa gagaaaaaat aaataagtct    107040
agaaatgcta gaagaggata cttttttgtt ttaatgatct agtagatcac tcctccttgc    107100
aatacccaga ggagaaactg aaaatatttc aaacattttc tagacttctg tgttgtaaat    107160
ttgtggataa ctatgaacta tatatgaatg aacttttctg gatgacacat atattccaga    107220
tggtaaaaag gaagggctttt ggggactctc tggtaccaag tgtcatggaa aaactgtgtg    107280
tctcatagaa agtagatccc aggaggccag cagagttgtg gatctgccat atattacctc    107340
atgattctgt cttcgcacac tcaccggctt aattctgggc ctccccataa acgactaga     107400
ccacaggctt gcagaagaaa taatttagct ctgtaactca ttgaagttgg tgcccaccca    107460
agtctctgtc agtgcccaat tcgggagcca tgccaagaat ttgccattgc tgcttcatgg    107520
tggccttgtg cctgcttatt tatagcctgt gcattttatg aaacagggat taataagaag    107580
ttgccatagc acttgcacca ttatgtaaat atctgtaatg cttacataac ttttgtcact    107640
tgcaagacct tttgagtcca ttgccttctg ctaccatgcc ttaccaattt cctagtccct    107700
tattattatt tttcaattca ttatatttaa cttctgtgat acacgttcag aatatgcagg    107760
tttcttatat aggtatacac gtgccgtggt ggtgtgctgc aaccaacaac ccgtcatcta    107820
cattaggtat ttctcctaat gctatccctc cactagccca ccaccccta ataagcccca     107880
gtgtgtgatg ttcccctccc tgtgtccatg tgttctcatt gttcaactcc cacttatgag    107940
tgagaacatg cagtgtttgg ttttctgttc ctgtgtttgt tttctgagaa tgatggtttc    108000
cagcttcatc cgtgtccctg caaaggacat gaactcatcc ttttttatga ctgcatagta    108060
ttccatggtg tatatgtgcc acattttctt tatccagtat atcattgatg ggcatttcgg    108120
ttggttccaa gtctgtgcta ttgtgaatag tgctgcaata aacatacgta tgcatgcgtc    108180
tttatagaag aatgacttat aatcctttgg gtatataccc agtaatggga tggctgggtc    108240
aaatggcatt tcaggttcta gatccttgag gaatctccac actgtcttcc acaatggttg    108300
aactgattta cacccccacc aacaatgtaa aagtgttcct atttctccat attctctcca    108360
gcatctgttg tttcctgact ttttaatgat cgccattcta actggcattg acatggtatc    108420
tcactgtggt tttgatttgc atttccctaa tgaccagtga tgataagctt ttttttcatat    108480
gtttgttggc cgcataaatg tcttcttttg agaagtgtct gttcatatcc ttcacccact    108540
ttctggtgtg gttggttatt ttttcttgt aaatttgttt aagttccttg tagattctgg     108600
atattagccc tttgtcagat ggatagattg cgaaaatttt ctctcattct gtaggttggt    108660
tgttcactct gatgatagtt tcttttgctg tgcagaagct ctttagttta attagatttc    108720
atttgtcaat tttggctttt gttgccattg cttttggtgt tttagccatg aagactttgc    108780
ccattcacaa ttgctacaaa gagaataaaa tacctaggaa tacaactcac aagggatgtg    108840
aaggacctct tcaaggagaa ctacaaacca ctgctcaagg caataagaga ggacacaaac    108900
aaaaggagaa acattccatg ctcatggata ggaacaatca atatcgtgaa aattgccata    108960
ctgcccaaag taaattatag attcaatgct atccccatta agctaccatt gactttcttc    109020
acagaattag aaaatactac tttaaatttc atatggaacc aaaaagagcc catatcccca    109080
agacaattct aagcaaaaag aataaagctg gaggtatcaa gctacctgac ttcaaactat    109140
actacaaggc tacagtaacc cttatcaatt ttttatgtgc ctctccatat tctgcagtca    109200
```

```
gaagcttctt cagtcctttc agggaattgc tgggtgacta tcaaactctg gtagttcatt    109260
tttgcagttg gctgctgttg tgaggataag agttagactc actttctctt cagagataga    109320
aattatgtat taattctctg ggttctagac ccacagcaag gagcatactg ctcctcaaaa    109380
taactgaatt ctgcgagaag ccatcattgt aaaacaacaa tatcttcagt tatagtagcc    109440
atgtgtgcaa cttctggaaa ctgttattca gattttcatg ttccttccct gtctcttcat    109500
agctaggcag ctgctttcag ccttgtacag atgctagtga gctttctacc tacaaacctg    109560
cagaaaattg aactgagatt tggaggtgaa agactcttga taaagggaac aaggtttaga    109620
attctcagtc cctttgctcc caggctgtgt tgtgactact gaggcactcc agtgaaatca    109680
ctattcctcc tatctagact aatgcctgtc tctgcagagc acctcataag aacaggcctg    109740
gtagtaatat cctcatgcat tcagtcagta aatatttaca gagtgcttac tacatatagg    109800
gtattgggct gacatatgca agatacaggg cctgcttcca ggaggttata gcttattgat    109860
cataaatgtg gcatttttt tttttgagac ggagtcttgc tctgtctgtc acccaggctg    109920
gagtgcagtg gcacgatctc ggctcactgc aacctccacc tcccaggttc atgtgatttt    109980
cctgcctcac cctcctgagc agctgagact acagggctc atcaccacac ccagctttt    110040 ttttttttc tgtattttta gtagagacag ggtttcacca tattggccag gctggtctcg    110100
aactcctgac ctcgtgatcc acccacctca gcctcccaaa gtgctgggat tacaggcgtg    110160
aaaatgtggc aatctttaaa gctcttcagt ggatgaaagg ccaccctatc tgctgtcctt    110220
ttgaacttcg caactttctt ggtacagagt gagaggttat tctcttggtt ttccatataa    110280
gtaaactgag gctttgccag ttcatcaaca ggtagtaaat aatatatttg gaatttgaac    110340
ccaagtcttc tggggtcaaa ggcagcattc actctgctct gtcacagcag ctcctcaaat    110400
aagccaacat agaaaccaag tactatgcct aggcaacaag aaaggcagca atgaagagca    110460
acagcagagt caaatatgag agaaggaagt taagaaagat gttaagtact gtggggagta    110520
actgagaaac caccaagtat cgctaacatc acagggaact tgtcttccta agaaaattcc    110580
aagcacttaa aaccgctggt agttcatcag caactctctt cattagatgt gcgagggaca    110640
tgtgggccat agtccttcta ctaacttata ttcttcaggg gaaagttctg attctgatga    110700
gacccagcat ggtagctctt aattcactgt tgtcacacga ctatagaaca ggaagcacaa    110760
cttaacacct gtgctcatga gaattttgct ccttatgacc aagctaaaga aagagcttag    110820
acaggatgtg tggctataaa tgtagattaa tggttccttg gctctttggt ttgagccttc    110880
tcagcagagc atcccacgga gtgttttcca tggggccacg agcaagagaa atccacttcc    110940
ctcctcctca atgtcagaaa atagagaata ttgtctttca ggatagaatt aaaaagtcat    111000
agaggcagca acttgttttc ctatattagg gttttaaaat tctgttttc cttcctctcc    111060 tgggtcagat cattgtgtgg atggaccttg atttcattgt ggtatctgta tgtggaccct    111120
gaagaccatg gacttctaac aattccttaa gttacataag cacattccta caggtcacaa    111180
gctcatttac ttacaggatg gttgatttgg tcacaggtta tttcatgaaa atacttaaaa    111240
gatttgcagt gttcaaaact gcagtatctt taaacactaa aacttgaagg aagggaattt    111300
agaaatcaaa aaatctggtc aaaccatttc atggaaaagg aaagtgaggc tcagagagag    111360
gaaattactt tcctgggttt gtatagccta taaatggcag aaatgagagc ctccctgcca    111420
tttctagttt tctgtctgag agactctcct gcctaatagc taattagcag agtcacagag    111480
gtcattacct tgcaattctc aagaattatg tgaggcagca tagtaagcat ttatggccct    111540
```

```
tggttcctag aaggagctta gtccctgata gtcatctctg cctttgccat tgtgtgagac  111600
tgtcttctgt aactgtatgt cttcctccct agtaagttaa tgagtaataa aggtattcta  111660
tagtgagagg actctgtaag acatttcttg gtgtgaggat tgttccaagg ttgttttgtg  111720
tgtatgtgca tgtataaact tttttaggga gcatattcat agcttttaca tggatctcag  111780
aggctctata acccagagaa gattacagaa taccagtctt gtctttggta aggattttat  111840
agacccatcc tgactacagt gatatccaac atggctatgt aatgactggc actttcccca  111900
cataacatat atttattcca cactcagtgc ctactgtgta catgagacct ataccgggca  111960
ctgggataag agacatgaaa taacagctaa aattgtttat tgagcagtca gtatgcatta  112020
gatgctttgt agtcattttc ttattcaatc tgtatacect caatttacaa atgaggaaac  112080
tgaggcacag aagagttgag tgatttgccc aaagtcatac aaatagtcag tggctatgtg  112140
atgaatagtt accaacataa aagagtgaga ttactgctgt actaaaagta ggtacataat  112200
cccctgagca gacagtatga gagaatgatt tattttacct ggaaagttta ggaaggcttc  112260
acagaggagt taaggttga tctgggtctt gagggatgga taagagtttg ccagatacaa  112320
aaaggtagga agagaacttc aggaggaggg aacaggctga gcaaagacac ggcgatgtga  112380
aagtgggagg cttgtttggg gaacattatg gaatctggag gttattgtgg ggaatctcat  112440
cagatgcagc aagctgtttg acaggccttc agttggctct ttgtaccttg ctccctccgc  112500
atgctgagct gtccatagct gccctaggct ggtgtctggg attttcggaa gaaggttact  112560
atccaggtag tgtaacaaga tgcagtgcaa aagcaccaga ttggggctct ggctctgctg  112620
ctgacttacc acctggcctt aagcatgtct agttccctct ttgtacatta aaatctccat  112680
tggaacagta acatggttgt attaaatgat cttgaagatt ttacctgcac gttttgcaca  112740
tgtaccctaa aacttaaagt ataataaaaa aattaaaata aaaaataaaa atataacaat  112800
ataaatcttt aacaataatt ttagtagtaa atctctacaa ttttacagat aatccagatg  112860
catccattgg ccaatggttc actttgtatg cataatattt gggaaacagg cagacccaat  112920
ttcaatcctt agttgtaaga cttaatacat atgtgatctc gagcaaatca cttttgtatg  112980
cctctataag gataataata gctcacagaa ttattttaag aactaaatga tgtgtaataa  113040
agctactggt actcagtaag ttttgtatcc ttttcctaga gtgagtcttg gtcataggca  113100
tgcgtatact tgcagcgtcc ctgggtaggc cgaaagagca aataagagat ggtatctatg  113160
gtattcccca ggtaaaggag gccttgggtt ggcataagat ttcacttctc tttagagtta  113220
cttaattagg gaccagaaag gccatcagca tttgtatgag aatataacaa aggtcaatct  113280
cttcctcttt acttttacc tcccagtaca ctgtgagtaa cattccccag ccagcccagc  113340
cagcacgtgt tcattgcctc tcttgacttc cagactttgg acttgaaggt gtcagagctc  113400
tctgtgtatc tttgtcccca acaagataag tctgacctcc ccagcaaatt caagtcctaa  113460
gccactgtcc aggagaaaag ctagcaaggt cataaattat tctccatatt ttccagccat  113520
tggtttccct tgtccagcca gaggtgtgtc tcaaagtatg ctgaggccag attcaataga  113580
aacctgagcc agcacctgtg taaataattt ttaaagctcc ttttcctgaa gctggatgaa  113640 tattttaaa aactaagctg gattgtcttt tatctagcat gccgtctcct acattcctag  113700
tgctatggac ctcttggagg aatgtggttt ggttatagtg gtattgtctt gtctgttgtg  113760
ggggagggag acatttcttt cagaagcaag gtaatacttt ggtctggtct atgactctat  113820
tttgttaaaa atgaaactat ggcagtatag tggtattcat tctgcttccc ataggttaac  113880
tttacatccc tctgtcttca cccactcttc agttctgatt cttttaaaag cagccaacca  113940
```

```
aaaccagcaa gtacatactg cttatctctg acttccacca gaatcaactt cagatcttgt 114000
ccaaagctcc atctgaagag aggggaataa cacccagcca agagccctca gggcccatca 114060
gtaagtagac atcctgtcct tgaggttcct taactctgct cagcttcaga atacagaagg 114120
ggttggttct tcatttgtgt tgtttataac taaaagcctc ctactcccca ctttttttgca 114180 tagcttcttc tgccatccca cctgtgtagc ctcttcaact cccccaaaac tcctctgtag 114240
cccatgtcac ttggaaagag ttttctttgt ctcttttgca acttgacaat gactagccag 114300
caagtttaag ttcaaattat tgttccatgg gagcagagat agatatagga aacaaaaaaa 114360
agggatatgg aggtatagag tgatttccca cctacctagt gagcactact gagatattca 114420
agtactctct acccaagaat tctattgata taaaggtaaa aaacttgatc ttaggtctaa 114480
tatccgttag tagtgtgacc ttgggaaaat gataccaccc ccaaaggctt agttttctta 114540
actgtaaaat aggcatacag atgaccaccc ccagaggatt cataaggata acatgagata 114600
aggcaacttg aaatttccta gcatagtgat agactttcga aaataaaatg aatcaaacac 114660
tgataacagt acttcctagt acacaaatga gaaatcagtc cctcatcaaa ttacagcaca 114720
ttttcaatgc tccaattatg tcactgtaga aatgctaatg tggattaaat aatttgtctg 114780
ttgctattta tacggataat ttgatagtag ttattttttgg acatggatag ctttgaagcc 114840
ttacagatga gtccatcccc aagtacccaa aactaaagaa agttggctag agtgatgaca 114900
aggtggcagc acagagctcc ctgcgttctg ggccctgtcc cctagctaga gagaactcca 114960
ggctataagc atttgtattc tcatagtcca atggcaggga agaagggctg gaggtgagta 115020
gttttcactc atttattttt tcaacaagca tgtatggtat caggccttgt atgcatccag 115080
agacaaatgt gaactagccg tgtcctcaag gagattccag tctggtgggc ctgccttcca 115140
aggtcagttg cagctttagc actataaaga gcacctacct gcggcagata caatgtgatg 115200
ggacatgaca gagaaaaaat ctataagcag agcctcccca ttcccaggca ttgaaacaat 115260
cctaaccaag actggcatag tacaatgagc ctgtccctat cagcaggttt ggaagcctta 115320
acaacaacaa caaaaacaat aataatggtg atgataatca tagagcctaa tgttaccaaa 115380
cattttccat gtgttaagta ctatactaag tgcatactta atcctcacaa caatgctata 115440
agatagtaga tactcttact actaccctga ttttacaaat gtggaaactg aggcacagaa 115500
gactaagaga acaggaatac acctaattca cctcagttca acaaacatca agcatctgtt 115560
ttatgtcagg cctcgtgctg gatggcaggg agagagagat gagtaaagca tagtttcagt 115620
ccagtgggag caaatgacag cacacagtgg ggcaggtata ttgcagccct tctgcttgat 115680
gctaagaact cagtgtcagt gatgaatgaa acacagtcat tctctcaaag atcttaaagc 115740
ttagtaggag atatctgtgt ggaaacaaaa attaaatact gctgtgataa gtgtcataag 115800
agataagtgg aaaatgagag agagagatca ctgtagcaat tgattggttt aaatcaaagc 115860
ccccaaaaaa atgttattga gaattataaa acaactaatt gatttaaatc aaagcccaaa 115920
cagaagtgtt tgctaatttt atttcaattt ggttgataat ttggttgaaa tgaatttatt 115980 tcattttta ttccatccatt acaatggaag attagtgctt gtttcccacc caaggatacc 116040
aggatatttc aggggctgta ttacaatata gttaaattat tcctttatct caaagcacat 116100
ccacactttc ccctatcctt acctttactc agggtatctc ttctgcctca ggtgcttttt 116160
ctccacattt ccatattctt aagtcctacc ttccttcagg gcctcactca aatgcctcct 116220
cctccatgaa gcattcaccc gactgaaagg taccccgccc tctcctgtac tccacatcac 116280
```

```
ttcatgggtg tctccacttc ctgctttatc tttcagtaat acacttacag ttctctttcc    116340
tccactagac tgagctcttc agaggaagac tcacttggct gaaaccatga ttttacttta    116400
aacacattga aaacctctac tggagtgcat tgtgtctggt gggcttcaac cttaattctt    116460
aagtatgtga aaacacatca cctatctgga ggtttacact ttctgctaat gactttattt    116520
ttaagcccac caccctaaca caacaaatac ttaaaacttg tcttcatttc ctttaggtct    116580
ggccctcatg catgcatata atttatagag tcactgtttt gctcggttgt cctcatgcct    116640
ctatattatt ggaggtttag attgtttcca tatactcagg ttgtattcat gtccttttt    116700
tcttttaaa tttccttagc atccatttcc accattggaa attcagggtc aaaacagggg    116760
tttgggattg gagcatgtct atcacagata accaatcatg tgttatgact taagaattta    116820
tgaaagggcc ctctacctga agatatcttg ctactgatgc tgtctcacag tgtctgaaac    116880
tcccatcata tgtggaattg ttttggaagg ctttgcctcc tgggacacat tcagccataa    116940
tcaagaaata gtattgagca ttagactgtc agtatgtcca ttagcaagac tgtggaggaa    117000
tggaatcacc aatattatat tttataggg atacagaata caagagaagt tctgaagaga    117060
aaattcttat gtagaatagg aaggcttaga tacagcatga aagctgcagg ctttgaggag    117120
ccagaggtca aatgaaagca ttgagtattt gtttagatga aagaacagaa agggaaaaag    117180
aagcagagga agggatagta gagagaaatg tataagtttt atccatttaa cttgtaattg    117240
tgtttggcta tgggcacaat agaagcagtg agatcacttt attttatttt attctttata    117300
gacagggtct tgctatgttg cccaggctgc agtgtgcagc tcttcacaag tgtgatcata    117360
gcgtactaca ccctcaaact cctggactca agcaatcctc ccatctcagc ctcctgagta    117420
gctgggacta caagtgcaca ccaccacgcc cagtgagatc acttgaaact agggagagat    117480
gtgtgagttc tgggcaacca gtagttggct ttacatagaa ctgtaggggt caaggccaaa    117540
ggggacgtcc tgttccaagt caccttcttt ggacattaga aaaccacgag gggtttggaa    117600
atcagaaaac cagcagaggc aggaaaactc agggcagcat gggagattca gtatatacaa    117660
aaaggttcac accagtaatc aaacagaatt ttaactgctg atgtggagta gaggcagctt    117720
tgtctgctgt gtgataacca aacctttacg aatagtaggt gtatatgggg aattggaggg    117780
agataggtgg ctgtgtttag taattggttg acttcactga gatggtttgg ggattgtggc    117840
ttccagatga tcagattttc tttttttaggt agagactcca acatcattac agaactataa    117900
attacatgtg gaaagaaag gcctcctatg ttagaataga aaataaaatg ctgtggggtt    117960
gagggacaga ggtgctgtct aggaagtcag atagcgtttt ccagttctgt ccctcagagt    118020
tccttgtcct cattgagact caatttctct tactttttt tttatacttt aagttttagg    118080
gtacatgtgc acaacatgca ggtttgttac atatgtatac atgtgccatg ttggtgtgct    118140
gcacccatta actcatcatt taacattagg tatatctcct aatgctatcc ttcccctctc    118200
ccctctcccc accacaggcc ctagtgtgtg atgttccct tcctgtgtcc atgtgttctc    118260
attgttcaat tctcacctgt gagtgagaac atgcggtgtt tggttttttg tccttgtgat    118320
agtttgctga gaatgatggt ttccagcttc atccatgtcc ctacaaagga catgaactct    118380
tcattttta tggctgcgta gtattccatg gtatatatgt gccacatttt cttaatccag    118440
tttatcattg atggacattt gggttggttc caaggctttg ctattgtgaa tagtgccatg    118500
ataaacatac gtgtgcatgt gtctttatag cagcatgatt tataatcctt agggtatata    118560
cccagtaatg ggatggctgg gtcaaatggt atttctagtt ctagatccct gaggaatcgc    118620
cacactgact tccacaatgg ttcaactagt ttacagtccc accaacagtg taaagggtt    118680
```

```
cctatttctc cacgtcctct ccagcacctg ttgtttcctg acttttaat gatcaccatt   118740 ctaattggtg tgagatggta tctcgtggtt ttgatttgca ttctctgat ggccagtgat   118800 gatgagcatt ttttcatgtg tctgttggct gtgtaaatgt cttctttgag acgtgtctgt   118860
tcatatcctt tgcccacttt ttgatagggt tgtttgtttt tttcttgtaa atttgtttga   118920
gttctttgta gattctggat attacccttt gtcagatgag tagattgcaa aagttttctc   118980
ccattctgta ggttgcctgt tcactctgat ggtagtttct tttgctatgc agaagttctt   119040
tagttgaatt agatcccatt tgtcaattt ggcttttgtt gccattgctt ttggtgtttt   119100
agacatgaag tccttgccca tgcctatgtc ctgaatggta ttgcgtaggt tttcttctag   119160 ggttttatg gttttaggtc taacatgtaa gtctttaatc catcttgaat taattttagt   119220
ataaggtgta aggaagggat ccagtttcag ctgtctacat atggctagcc agttttccca   119280
acaccattta ttaaataggg aatccttcc ccatttcttg tttttgtcag gtttgtcaaa   119340
gatcagatgg ttgtatatat gcggcattat ttctcagggc tctgttctgt tccattggtc   119400
tatatctctg ttttggtacc agtaccatgc tgttttggct actgtagcct tgtagtatag   119460
tttgaagtca gatagcgtga tgcctccagc tctgttcttt tggcttaggg ttgacttggc   119520
gattcaggct ctttttggt tccatatgaa ctttaaagta gttttttcca tttctgtgaa   119580
gaaagtcatg ggtagcttga tgaggatggc attgaatcta taaattacct tgggcagtat   119640
ggccattttc acaatattga ttcttcctac ccatgagcat ggaatgttct tccatttgtt   119700
tgtatcttct tttatttcat tgagcagtgg tttgtagttc tccttgaaga ggtccttcaa   119760
gtcccttgta agttggattc ctaggtattt tattctctta gaagcaattg caaatgggag   119820
ttcactcatg atttggctct ctgttttctg ttattggtgc ataagaatgc ttgtgatttt   119880
tgcacattga ttttgtatcc tgagactttg ctgaagttgc ttatcagctt aaggagattt   119940
tgggttgaga cgatggggtt ttctaggtat acaatcatgt catctgcaaa cagagacaat   120000
ttgacttcct ctttccctaa ttgaatgccc tttatttcct tctcctgcct gattgccctg   120060
gccagaactt ccaacagtat gttgaatagg agtggtgaga gagggcatcc ctgtcttgtg   120120
ccagttttca aagggaatgc ttccagtttt tgcccattca gtatgatatt ggctgtgggt   120180
ttgtcataga tagctcttat tattttgaga tacgtcccat caataactaa tttattgaga   120240 gttttttagca tgaagcgctg ttgaattttg ttaaaggcct tttctgcatc tattgagata   120300
atcatgtggt ttttgtcgtt ggttctgttt atatgctgga ttatgtttat tgatttgcgt   120360
atattgaacc agccttgcat cccagggatg aagcccactt gatcatagtg gatacgcttt   120420
ttgctggtat tttattgagg attttttgcat caatgtttat cagggatatc ggtctaaaat   120480 tctcttttt gttgtgtctc tgcctggctt tggtatcagg atgatgttgg cctcctaaaa   120540
tgagttaggg aggattccct ctttttctat ttattggaat agtttcagaa ggaagggtac   120600
cagctcctcc ttgtacctct ggtaggattc agctgtgaat ccatcggtt ctggactttt   120660 tttgattggt aagctattag ttatatcctc aatttcagag cctgttattg gtctattcag   120720
agattcaact tcttcctggt ttagtcttgg gatggtgtat gtgtcgagga atttatccat   120780
ttcttctaga ttttctagtt tatttgcata caggtgttta tagtatgctc tgatggtagt   120840
ttgtacttct gtgggatcgg tgattatatc cccttttatca ttttttattg cgtctatttg   120900
attcttctcc cttttcttct ttattagtct tgctagtggt ctatcaattt tgttgatctt   120960
ttcaaaaaac cagttcctgg attcattgat ttttgaagg gttttttaca tctctatttc   121020
```

```
cttcagttct gctctgatct tagttatttc ttgccttctg ctagcttttg aatgtgtttg   121080
cccttgcttc tctagttctt ttaattgtga tgttagggtt tcaattttgg atctttcctg   121140
ctttctcttg tgggcattta gtgctataaa tttccctctc cacactgctt tgaatgtgtc   121200
ccagagattc tggtatgttg tgtctttgtt ctcattggtt tcaaagaaca tctttatttc   121260
tgccttcatt tcattatgta cctagtagtc attaaggagt aggttgttca gtttccatgt   121320
agttgagcgg ttttgagtga gtttcttaat cctgagttct agtttgattg cactgtagtc   121380
tgagagacag tttgttataa tttctgttct tttacatttg ctgaggagtg ctttacttcc   121440
aactatgtgg tcaattttgg aataggtgtg gtgtggtgct gaaaagaatg tatattctgt   121500
tgatttgggg tggagagttc tgtagatgtc tgttaggtct gcttgacagt ggagtgttaa   121560
agtctcccat tattattgtg tgggagtcta agtctctttg taggtctcta aggacttgct   121620
ttatgaatct gggtgctcct gtattggttg catatatatt taggatagtt agctcttctt   121680
gttgaattga tccctttacc attatgtaat ggccttcttt gtctcttttg atctttgttg   121740
gtttaaagtc tgttttatct gagactagga ttgcaatccc tgccttttg tgttttccgt    121800 ttgcttgata aatcttcttc catccctta ttttgagcct atgtgtgtct ctgcatgtta    121860
gacgggtttc ctgaatacag cacactgatg ggtcttgtct ctttatccaa tttgccagtc   121920
tgtgtctttt aattggagca tttagcccat ttacatttaa ggttaatatt gttatgtgtg   121980
aatttgatcc tgtcattatg atgttagctg gttattttgc tcgttagttg atgcagtttc   122040
ttcctagcct cgacggtctt tacaatttgg tatgtttttg cagtggctgg taccggttgt   122100
tcctttccat gtttagtgct tccttcagga gctcctgcag tgcaggcctg gtggtgacaa   122160
aatttctcag catttgcttg tctgtaaagg attttatttc tccttcacct atgaaggtta   122220
gtttggctgg atatgaaatt ctggttttaa aattcttttc tttaagaatg ttgaatattg   122280
gcccccactc tcttctggct tgtagagttt ctgctgagag atcagctctt aatctgatgg   122340
gcttcccttt gtggggaacc tgacctgttt ctctggctgc ctttaacatt ttttccttca   122400
tttcaacttt ggtgaatctg acaattatgt gtcttggagt tgctcttctc aaggagtatc   122460
tttgtggtgt tctctgtatt tcctgaattt gaatattggc ctgccttgct agattgggga   122520
agttgtcctg gataatatcc tacagagtgt tttccaactt ggttccattc tccccatcac   122580
tttcaggtac accaatcaga catagatttg gtcttttcac atagtcccat atttcttgga   122640
ggctttgttc atttctttt attctttttc ctctgaactt ctcgcttcat ttcattcatt    122700
tgatcttcaa tcactgatac cctttcttcc agttgatcta atcggctact gaggcttgtg   122760
catttgtcac gtagttctcg tgctgtgttt ttcagctcca tcaggtcctt taaggacttc   122820
tctgcattgg ttattctagt tagccatttg tctaattttt tttcaaggtt tttaacttct   122880
ttgccatgcg ttcgaacttc ctcctttagc tcagagtagt ttgattgtct gaagccttct   122940
tctctcaact cgtcaaagtc attctccatc cagctttgtt ccattgctgg tgaggagctg   123000
cattcctttg gaggaagaaa ggcactctga ttttagagt ttccggtttt tctgctctgt    123060
tttttcccca tctttgtggt tttatctccc tttggtcttt gaagatggtg atgtacagat   123120
gagcgtttgg tgtggatgtc ctttctgttt gttagttttc cttctgtcag gaccctcagc   123180
tgcaggtctg ttggagtttg ctgcaggtcc actccagacc ctgtttgcct ggttatcagc   123240
agcagaggct gcagaacagt ggatattggt gaacagaaaa tgttgctggt tgatcattcc   123300
tctggaagtt ttgtctcaga ggaatacccg gatgtgtgag gtgtcagtct gcccctactt   123360
gggggtgcct cccagttagg ctactcgggg ttcagggaac cacttgagga ggcagtctgt   123420
```

```
ccgttctcag atctccagct gcatactggg agaaccacta ctctcttcaa agctgtcaga   123480
cagggacatt taagtctgca gaggtttctg ctgcctttg ttcggctatg ccctgccccc    123540
agaggtggag tctacagagg caggcaggcc tccttgagct gtggtgggct ccacccagtt   123600
cgagcttccc agctgctttg tttacctact caagcttcag caatggcggg caccoctccc   123660 ccagcctcgc tgctgccttg cagtttggtc tcagactgct atactagcaa tgagcgaggc   123720
tctgtgggcg taggaccctc tgagccaggc acaggatata atctcctggt gtgccgtttg   123780
tgaagaccat tgaaaaagtg cagtattatg gtgggagtga cccgattttc caggtgccat   123840
ctgtcacccc tttctttgac taggaaaggg aattctctga tcccttgtgc ttcctgggtg   123900
aggcgatgtc tcgccctgct ttggctcatg ctcggtgcgc tgcacccact gtcctgcacc   123960
caccatttga cactcccctg tgagatgaac ccggtacctc agttggaaat gcagaaatca   124020
cccatcttct gtgttgctca cgctgggagc tgtagactgg agctgttcct attcggccat   124080
cttcacaaaa atcttacttt ggtttctagt gttaccaccc actgttcttt ctcatctcaa   124140
ccctgagtat aagtacagat cacattcctt gggttcttag aaaataatag aaatgaactc   124200
tcattcatca aaatgcccat tagtaaatac tgagggagaa caaactagaa atccagtata   124260
gaaaataaaa ataggattat attccttgga atctcagaaa aaaacaatga agagctttct   124320
ttgggcatta gcactttcc cataaggtgg ctgactctct tttagtcatg tcagcttggc    124380
ccaatcttca cttggtagcc cttctttctt cttcattaat ccatctccta tgctcctatg   124440
gggtcctaga gaaatgccca tcatgtacac acacatctaa taacacaaag atcactctcg   124500
actagcaagc cctttatga tggtgtgagc atttgacacc cttgttgcta gtaacatcag    124560
tgagtgacct gacccatttt tggaacagaa tatgatcagt atgttgcctc aaggaggccc   124620
tcactgttct aggaaatata attccagagt ttgctgactc acaccatgga atatatgcat   124680
aaaatggatc ctgcagataa gccttctct gactagtttc agacattttt ttctgggtaa    124740
ttttaaagtt atttttatt tttgtgggta caaagtaggt gtatatatgt atgaggtacc     124800
tgaggcattt tgatacaagc atacagtgta taataatcac cagagttaat ggggtatccc   124860
tcaccacaag catttatcct ttctttgtga tacaaacaat ccaattatat tcttttagtt   124920
attttaagat gtataataaa ttattgttga ctgcagtcac cctgttgagc tatcaaatac   124980
tagatcttat tcattctaac tatacttttg tacccagtag ccatcccact tcctcccctc   125040
ccactaccct tcccagcctc tgataaccat cattccactc tctatctcta tgagctcaat   125100
tgttttaagt tttagctccc acaaatatgt gagaaaatgc caagtttgtc tttctgtgcc   125160
tggcttattt cacataatat aatgtcctct agttccatcc atgttattgc aaatgacagg   125220
atctctttct tttttatggc ttaatagtac tttattgtat gtatgtacca catttcttc    125280 atccatttgt ctgttgatag acaagagttg cttccaaata ttgactattg tgaatagtgc   125340
tgcaataaac gtgggaatgc agatctcttt gatatactga ttttctttct ttagggtgta   125400
tacccagcag tgggattgct gggtcatatg atagctctat tttagtatt tgtggaacc     125460 tcaaatctat tctacataat ggttttactg acttacatat ccaccaacag tgtatgagga   125520
tactcttttc tccacatcct caccagcatt cattactgcc tgttctttgg atgaaagcca   125580
ttttaactgt ggtgaaatga gatctcattg ttgttttgat gtgcacttct ctgatgatca   125640
gtgaggttga ggaccttgtc atatatctgt ttgtcatttg tatgttttat tttgagagat   125700
gtctacccag atcttttgcc cattttttaa tcagattgtt agatttttt tttcctacag    125760
```

```
agtgcttgag ctctttatat gccctagtta ctagtccctg gtcagatggg tagtttgcaa   125820
atagttgctc tcattctgtg ggttgtctct tcactttgtt gatcgaatca cttgctgtgc   125880
agaaggtttt taacttgatg tgacctcatt tgtccatttt tagttgcctg tgctggtgcg   125940
gtattactca agaaattttt gcccagatta atgttctgga gagtttcccc aatgttttct   126000
tgaagtagtt tcatggattg atgtcttaga tttaagtctt taatatgttt tgattttatt   126060
tttgtatttg ctgagagata gggctctagt ttccttctgc atatggatat ccagttttc    126120 tagcaccttt tgttaaagag actattcatt ctctaatata cgttcttggc acctttgttg   126180
aaaataagtt cactgtagat gtatggactt gtttctgggt tctctgttct gttccattgg   126240
tctatgtgtc tgcttttatg tgaataccat gttgttttgg ttgcaaaagc tctgtagtat   126300
aatttgaaat caggtaatgt gattcttcca gttttgctct gttcttttc ctcaagatag    126360 ctttgcctat cctgggtctc ttgtggttct atataaattt taggattatt ttttctattt   126420
atgtcaagaa tgtcattgat attttgatat aaattgcgtt gaatctgtag atagcttcag   126480
gtagtgtgga cattttaaca atatcaattc ttgaaatcca cgaacatgga atatccttct   126540
attatttgga tgtcttcttc aatttcttat attaatttt ttttagtttt cattgtagag    126600
atatttcatt tatttgacta agtttattgc taggtatttt atttatttt tacctattga    126660 caatgggatt gctttcttga tttctttttt agattgttca ctgttggcat acagaaatgc   126720
tactgatttt tatgtgatga ttttgtatcc cgcaacttta ctgaatttgt ttatcagttc   126780
taataggctt ttggtgcaga ctttaggctt ttccaaatat aagatcatat tatctgcaaa   126840
caagaataat ttgacttctt tcttttcaat ttggatgcct ttcatttctt tctcttgtct   126900
gattgctcta actaggactt ccagtactct gttgaataac agtggggaaa gttaacatcc   126960
ttgttttgtt tcagatctta tagccaaggc cttcagtttt tctgaattta gtatgatact   127020
agctatgggt ctgtcatata tggcttttat tatgttgaag tatgttccct agttttttga   127080
aggtttttat attttaagga agataaaaat tgaactttat caaatgcttt tcatgcaaca   127140
attgaaatga tcaagtgctt tttgtctttc attctgttga tacgatgtat cacactgatt   127200
gacttgtgta tttagaaacca tccttgcatc ccgtggtaaa tcccacttag tcatggtgaa   127260
tgaacttttt aatgtgttgt tgaattcagt ttgctagtat tttgttgggg attttttgcat  127320 cagtgtttat cagggatatt ggcctatagt ttttcctttt tttatgtgtc ttttgggttt   127380
tgttatcagg gtaatactgg ccttgtagaa tgagtttgga atgattctct cctctatttt   127440
ttgaaatact ttgaatagga ttgatgttac ttctttaaat gtttggtaaa attctgcact   127500
gaagccattg ggtcctgggc tttttactgc tggggagact tttcattaca gcttcaatct   127560
tattacttgt tattggtctg ttcaggcttt agatttttt catgaatcaa tcttcacaag    127620
ttgtctgttt ctcaaaattt atcaatttct tctaggtttt ccaatgtatt gtcatccagt   127680
tgctcataat gccctctaat gatgccttga atttttgcag taaccactgt aatgtttcct   127740
tttttaatct ctgatttttat ttgagctttc tcttttttc ttagtctagc taaatatttg    127800
tcaatgttgt tgttcatcc acaaaaccaa cttttcattt cactgatctt tgtattatt    127860 ttttcctttt aatttattt atttctattc tgatatttat catttcattt cttccagtta    127920
tttgagtttg gtttgctctt gcttttccag ttctttaaga tgcattgtta ggttatttat   127980
ttgaactttt ttgatatagg tgcatattgc tataaacttt caccataata ttgcttttgc   128040
tgtatcccat aggttttagt atgttgttta gtatgttcc aatttggtac atttcaataa    128100
atttttaaat tttcttcttt atttattgac atagtcattc cagagtatac tgtttaattt   128160
```

```
ccatgtggtt tgtatagttt ccaaaattcc tcttgttatt gatttctagt tttattccat  128220
tgtggtcaga gaagaagctt gatatgaatg caattgttaa taatttttt aaaacttgtt   128280
ttgtgaccta agatatgatc tgtcattgag aatgatccat atgctgagga aagaatgtat  128340
attctgcagc cattggataa aattgtcttt aaatatctat taggtccatt taagacataa  128400
tgcagattaa agccgatgtt tcattgttca tttttctgtc tggatgatct cttcagtgct  128460
gaaagtggtg tgttaaaatc tctaaatatt attgttttgg gatctttctc ttctttcaac  128520
tctgataata tttgctttag atacctgggt gctccagtgt tgggtgcata tatacttaaa  128580
attgttgtat cctcctgatg aattgacccc tttatcatta tataatgacc ttctttttct  128640
ctttgtgtag tgtttgtctt gaaatctatt tgtcggata ttagtattgc tgctaatttt    128700
tttggtttcc atttgcatga aatatctttt tcattccttt attttcaggc agcgtgtttc  128760
tttatattta ataggtgaaa tatgtttctt gtaaataaaa attattattt taaaatattt  128820
ttaaaataat actattttt aataagaaca attattattt tttaaaaaat ttcattagtt    128880
ttgggggcac aagtggattt tggttaaatg ggtgagttct ttagtagtgg attttgagat  128940
tttagtgcag cagccacctg agaagtgtac attacccata tattatatat atactatata  129000
tgctttatat atatagtgtg tatatataat atatatacaa ctacatattg ggtaatgtac  129060
acttctcagg tgactgctgc actaaaatct caaaatccac tactaaagaa ctcacccatt  129120
taaccaaaat ccacttgtgc ccccaaaact aatgaaattt tttaaaaaat aataattgtt  129180
cttattaaaa aatagtatta tttaaaaat attttaaaat aataattttt atttacaaga  129240
aacataattc acctattaaa tataaagaaa cacgctgcct gaaagtaaag gaatgaaaaa   129300
gatatttcat gcaaatggaa accaaaaaaa ttagcagcta tactaatata ttatatatat  129360
actacataaa gcatatatat agtatagtat atatataata catttataaa gcatatatat  129420
agtatgtaga taatatatgt ttatatactt taagttctgg gatacatgtg cagaacgtgc  129480
aggtttctta cataggtata ctcgtgccat ggtggtttgc tgcacccatc aacctgccat  129540
atacattaag tatttctcct aatgctatct ttccctagc cctacccac tccctgacag    129600
gccctggtgt atgatgttcc cctccctgtg tccatgtgtt ctcattgttc aactgccact  129660
tatgagtgag aacatgtggt gtttggtttt ctgttcttgt gttttagttt gctgaggatg  129720
atggtttcca gcttcatcca tgtccctgca aaggacatga actcatcctt tttgatggct  129780
gcatagtatt ccatggtgta tatgtgccac gttttcttta tccagtatat cattgatggg  129840
cattttggtt ggttccaagt ctttgctatt gtgaatagtg ctgcaataaa catacgtgtg  129900
catttgtctt tatagaagaa tgatttataa tcttttgggt atatacccag taatgggatt  129960
gctgagtcaa atgatatttc tggttctaga tccttaatga attgccacac tgtcttccac  130020
aatggttgaa ctaatttatg ctcccaccaa cagtgtaaaa gcgttcctat ttcttcaaat  130080
cctcaccagc atctgttgtt tcctgacttt ttaatcgcca ttctaactgg catgagatgg  130140
tatctcattg tggttttgat ttgcatttct ctaatgacca gtgatgatga ctttttttc    130200
atgtttgttg gcagcataaa tgtcttcttt tgagaagtgt ctgttcatat tcttcaccca  130260
cttttgatg gagtttatttg ttttcttctt gtaaatttgt ttaagttcct tgtcgattct  130320
ggatattagc tctttgtcag atgaatagat tgcaaaaatt ttctcccatt ctgtaagttg  130380
cctgttccct ctgctgatag tttcttctgc tgtgcagaag ctcttagtt taattagatc    130440
ccatttgtca attttggctt tgttgccat tgcttctggt gttttagtca tgaagtctct   130500
```

```
acccatgcct atgtcctgga tggtattgcc ttggttttct tctacagttt ttatggtttt    130560
aggtcttgca tttaagtctt taatccatct tgagttaatt ttgtataacg tgtaaggaag    130620
aggtccactt tcagttttct gcatgaggct aacgagtttt cccaacacca tttattaaat    130680
agggaatcct ttccccattg tttgtttttg tcaagtttgt caaagatcag gtggttgtag    130740
atgtgtggtg ttatttctga ggcctctgct ctgttccacg tgtctatatc tctgttttgg    130800
taccagtacc atgctgtttt gggtactgta ccacttgatt ggtgagagag ggaatccttg    130860
tcttgcactg gttttcaaag ggaatgcttc agcttttgcc tattcagtat gaccaatatg    130920
tagtctttta ttcctcaccc tctctcaaca ccccacccCC acggagtcct caaagtccat    130980
tatatcactc tgtatgtttt tgcgttctca tagcttagct cccacttata aatgagaaaa    131040
tacagtattt ggttttccat tctttggtta cttaattagt ataatggcct ccagctccat    131100
ccaggtgtct tgtttttcat ccattcagcc agtctataac ttttgcttgg agagtttcgt    131160
ccatttagat tcagcgttat gattgataac taagggctta ctcctgccat ttggttgttt    131220
tctggttatt ctgtggtctt ctcttccttt tttccttctt tcctgtctcc cttttagtga    131280
aagtggtttt ctctggtggt gtatttatt ttcttccttt ttattttttt ttgtgtgtat    131340
ttgttgcatg ttattgattt gaggttacca tgaggcttgt acataatatt ttctaactca    131400
ttatttcaaa ctgatgacaa cactctatcg cataaaaaaa catggaaaga gaaaactaat    131460
aaaaactcta cattttaact tcatctctct gcttgttgtc actttgtcgt ttctatttac    131520
atcttattgt actgtttatg tcttgaaaag tagtttcagt tattactttt gattggttca    131580
tctcatagtc tttctactca agatatgagt agttcacaca ccacaattac agtgttacaa    131640
tattctgtgt ttttctgtgt actttcaatt acccatgagt tttgtatttt cagataattt    131700
gttattgctc actaacatcc tattctttca gattaaagag ctcccttag catttcttgt    131760 aggaaaagtc tggtgttaat gaattccttc agctcttgtt gatctgtgaa agtctttatt    131820
tttccttcat gtttcaagga tattttcact ggatagtcta ttctagggta aaagtttttt    131880
tttttttttt cttcagccct tcaggtaagt catgccactc tctcctggcc tataaggcta    131940
ccactgaaaa gtctgctgcc agacatatat gagttccatt ctatgttact tgtttatttt    132000
ctcttgttac ttttaggatc ctttctttat cttgaccctt tgggagtttg attattaaat    132060
gccttgaggt ggtctttttt ggattaaatc ttccttcgtgt tcttgtactt ggatattaat    132120
atctttctct aggtttggga agttctctgt tattatccct ttgaataaac tttctaccaa    132180
gatctctctt tctctctctg tctctctctc tctctctctc tccttcttaa ggccaataac    132240
ttttagattt gcccttttga ggctgttttc tagatctcgt aggtgtgctt cattgtttgc    132300
tatttttttt tttttttttgt ctcttctgac tacattttca aatagcctgt tttaaaactc    132360
actaattctt tcttttgcct ggtcaattat gctgttaaga gactctgagg cattcttcag    132420
tgtgtcagtt gcattttttca gcaccagaat gtctgcttat tttttttag attatttcca    132480 tctctttgtt aaatatatct gatagaattc tgaattcttt cttagtgtta tctttaattt    132540
ccttgaattt cctcaacaca actattttga attatctgtc tgaaaggtca catatctcta    132600
tttttccagg attgctatct ggtgcttat ttagttcatt ttgtgaggtc atgtttttcct    132660 ggatggtgtt aatgctagta gatgtttttc agtgtctgag cattgaaaag ttagatgttt    132720
attgtagtct tcacagtctg ggcttgttca tacctgccct ccttgggaga ctttccaagt    132780
attcgaaggg atttggatgc tgtgatctta gtctttggtc actgcagcca tatctgcttt    132840
atggagcatc ccatgctcag taatgctgtg gctctttcag actcatagag ttactgcctg    132900
```

```
catgctcttg ggtaagagcc aggaaaattc cctggattac caagcagaga ctcttgttct   132960
cttctctcac tttcccccaa acaaatagag tctctctctc tctctctctt tctctctctc   133020
tctctccctc tcattctctg ccgacctgcc tgaatctggg gtagggatga cacaatcaca   133080
tttgtagtca acaccattgg gactgtgcta ggtcagaccc aaagctggca cagcactgag   133140
tctcgcccaa cgcccacaga gaccactccc tgggtaatgt ctgtgtttgc tcaaagccta   133200
agggctatac aatcagtcag tggtgaagcc agcctgtctt atgtccttcc cttcagggtg   133260
atgagttcct caagcaggtc cagggatggt gtccaggagc caaggcctcg agctgtgact   133320
gagctggcac ccaatccata agacaaagat ttttccaca ctttccttcc ttgtcctcaa    133380
gcaaaggagt ctctccctgt ggccaccacc accccatgt tcatggcaag tattgtctgg    133440
ctaccaccaa tcttcactca aggcccaggg gttctttagt tagcttatgg tgaatgctac   133500
caaggctgag tctctcccett caaggaagtg ggctcctctc tggcccaggg caggtccgga   133560
aatactatcc aagagccaag gcctggaatc agtttcccca agagtccatt tggtgctcta   133620
cacccactgt ggcagaacca gtacccaagc tgcaagacaa agtcctcttt actcttcctt   133680
ctcctttaca gagactctcc ctatagccac cacagctggg aatatgctgg gtcactcttg   133740
aagcaagaac agctctgagt ctcactcaaa actcctggca agtactgcct ggctatcaca   133800
ctgattattc agggcccaag ggctctttag tcagcaggag atgaatcctg ccagtactga   133860
ttccttccct tcaaggcagc cggtttcttt ctggcccagt gtgtatctag aaatatcatt   133920
tgggagctag ggcctggcat ggtgacctca ggactctgcc tggtgccctg ttctactgtg   133980
gctgatgtag tatccaaatt gcaagaccaa gtcctcttta ctctcccctc tcctgtcttc   134040
aagcagaagg aatgagtccg ccctggagtt gggagctgca ttgcctggga ttggaggagg   134100
ggtggcacaa gcactctctt ggtcaccca gctggtgtct tactaggtcg catgttcccc    134160
aagtccactg gctctgaggc tagcacacca ggatttgacc aagaattgca attcttgtgg   134220
cttacactgc ctttcaagtt tatttgagat cccagagcac tttagcccac agtgacaggg   134280
cttgccagaa tttagtttct gactgctgag atggacaatt gcgtctgat tagggctggt    134340
ctaagtgctc cttctgtggg cactggctga gttctgctcc atgttgcttt ctgctgtgac   134400
agggcaacat tgagtttcaa tgcaagtccc acagtcactg caatcttcct ctcccaagcc   134460
tgctctgaac accatgtggt tgctgctggg ggctggggga gggatgttgt aggcaattca   134520
agaatgtctt tcctacccett ttcggtgctt cttttccttgg tatgatatta aaaccagtta   134580
ctgtgattgc tcacctgatt tttggttctt atgaaggtgc tttttgtgt ggatcactgt    134640
tcaatttgtg cctgcaagcg gggatggggg acaattgctg gaggcttctc tttggccatc   134700
ttgctccacc tctaccctag tattagcaat ttcaaagcag ttgggatgga ggtagaagga   134760
aagggcgctt ggaatcagaa aatccatgtc ttagctttga gccttagaaa attcatttga   134820
cccttgtaag cctcagttgc ttcatctgta aagagaaat aatataatgg ctgaaaagat    134880
caaaggtgat aatgctttg aaaacactat agaaaatgac aaaatatcac atgagtatta    134940
ttttctagtt tctaggagtc tccttaccat tgtacaggac aaccatgtct attttttaaat  135000
aaattattat ttgcctctga gcaaccctgc aaagagttgc ctgtaggaga aacagcttta   135060
cttgcaaatc actccactgt tttctttgtg cacagcttat taatacataa ggcacatgtc   135120
ctccagcctg cagtaacatt ggaatcatta cctctttgga gtacctacca gagcttctca   135180
aagtgaattt tgtttatcac cacaaaaaat agtctgttgc agagataacc tccaaattca   135240
```

```
atgacaatat ttccaatcac tttttgcatga tgcagaaata gacaaatata taattttgct   135300
tatagagaca attattgtct cccaacaagt gatcagtagt cagaaaatgg ccaagaaata   135360
ccatggggtg tgccttccca taacagctta tctttgtgtt ttagttgcaa ggttactaaa   135420
agcctgtgca gggtttatgg caaaagtaaa acttgctcca ggagcaagcc cttgtttcat   135480
tgtctaatgt tcttaatccc cagcagacag gatttggatc tggcatttgg taacagggca   135540
gtttccaaag ttgctgtacg caacttgagg aagagaggtg atattatcgg aatgaatttc   135600
tttgttgtaa gttataaatg tatgggcttt tccaatccca tcacccttaa aactttattt   135660
gttttctgca gtgagggtgt ctccgttgtc tttaatatgc ttgctttgag ttcatggatg   135720
aacattcctg cctggctgac atgtggactc tctgaaattg ttataaggtc ttttctttg    135780
ttttttctt gatgcccaag ctgccaaggg tagtactggc agtggtgggc agacaaggag    135840
gtgatagcaa actttgtcct ctggcctccc ttgacccatt ccattcatta tctaagggac   135900
tccaagccag cattcacag agtgccctca ccaaactcac taagactgaa ggcgaaccag    135960
gattccaaac agccattatg aaaggaaaga gagagagact tagggtttgc aaaataagat   136020
accctgttga ttctttttat tccatacaga tactactatt ctttaggaaa acgttaaaat   136080
cacatgatct tccaggacct gggctgcttc tttaagaagc atgttacaga aagctttatt   136140
ggccaacaac atattgaaag atagattaat caatcattca ttcaaataag gtatattcag   136200
aattgaggta tattgtagcc agacagtgag actacaaaaa aagaatgcac cgtacccta    136260
tctcttgcac aatctaacga gggagataac cactctttca atttatagtg acctataaca   136320
tttcgtacac tgctgaatat ctttacatgg taataacaca atggaaagct tgcaaaatag   136380
acagaggcta ggggaagaag gattgagtgt gaatatagcc tcttataaat cgagaggaat   136440
ggtctgtgtc ttctgatcat acagagataa taaatatgga aatgatttca aactaacaaa   136500
gcaaatgtgc agaaaatact gagaatatag tgggcaggat acctgagttt tggttccatc   136560
tctgttattg actcattgtg taatctgagt caggtctgtt ctgctctctg gatctcaccc   136620
tttcctatct gtaaaatgag attgttggat tagatgatct ccatagaggt tctcacctat   136680
tctgacattc aaaaggactc ctaatttttc ttatataata ataatatata tgatctgtag   136740
agtgctttac actttatatg atattttgc atctgttatc tcatgtgaga aaagcactgg    136800
actgctggac tggcaatgag gacacctgga ttccttgtctc tgttttgaca ctgattcatg   136860
gtgtgatctt caagcaaatt ctctgagttt cagtttctca atctgtaaaa tagggggta    136920
tgaagattgg actaaatcag taggtctcta aaatgttcca caaagccctg ggtgggggg    136980
ctcctacaga gtttcgctaa ggcaaaccac aacgctaagc ctgcatggaa gaggagaaaa   137040
agagtggcct gacaagagaa gttcccagtt tcctatgcca accccaggca gattacattt   137100
aattttatct gatttatata gagagtttct atgtaatgtt ttattcttaa aaatagttta   137160
ctataaaaaa ctcaactggt ttgattttta aagattgcac atataagtga gatcatgcag   137220
tcagtatttg tcttctctatg cctggcttat ttcacttagc ataatgtctt ccagcatcat   137280
ctatgttgct gcaaatgaca gacttttctt ttcattaaag gctatatagt attccatcgt   137340
gtatgtacac cacattttct cttttgtaac tttcatttta ggtcagggg ttcatgtgca    137400
tgtttgatat ataggtaaac tgcatgtcag agaggtttct tgtacagatt atttcatcac   137460
ccaggtaata agcatagtat ctaatcaatt tttttctgat cctctccctt ctcccaccct   137520
acaacctcaa gtaggccctg gtgtcttattg ttcccctctt tgtgtccatt acaccacatt   137580
ttctttatcc acttatccat ccatggacac ttagtttgct tccatatgtt ggctattgtg   137640
```

```
aataatgctg aaaaaagtca aactcataga agcagagagt agaatggtgg ttaccaggga 137700
ctgggaggca gttgactgag ctaggaaaag agagataata aaagggtaca atgtgtcagt 137760
tatatagaag gaataagtta tattgaacta ttgcacagca tggtgaccat agttaataat 137820
aatgtattat atgtctcagt attgctaaaa gagtaaattt aaatattcta accacaaaaa 137880
attattagta ggcaaggtga tggatatgtt aatttgcttg atttaatctt tctagaatgc 137940
atacatatat caaaacatcc cactgtaccc cataaatata tacaattatt atttgtcaat 138000
ttagaaattt aaaaacttga tttagatgag ctctaaggcc ttaagtatta agtattaag 138060 tattaaagtg atatgtaacc aagtatattg tttggtaact tcattttgt tattatttta 138120 acaaaccaat atattgtgaa tatacttcca agtgaaaaga aaaagacat tgcagtcatc 138180 actaataact gcaaaacatt cctttgcaag aatatggaat aattcattta atcattcccc 138240
taatgttaga cattcaaatg tttccaactt tttctattta aataatgcta caataaactt 138300
ctattttgtg cttattgtat tattttctta caacacatcc ctagaagtgg aattcctaga 138360
agtttataca catttccaat tttttccaa atatatggca aaatttctct ctaaagtatt 138420
tttattccta ccagaaatac ctcttcacca acacgtagta tttaatctgt accaatctgg 138480
cttaagacaa tgatatttaa tttgtatttc tgtgatttct agctaaatta ataatcttc 138540 atatgcttat tggtcatttg tacttctaac tgctttctcc tgtctgttgc ccatttttct 138600
attgtgctgt ttatttttat atatcgaata tattgaccat tggttttaca tacttgatgc 138660
taataattat tcttagttta tggttttgtct ttgagttta taatggtgtt tatttcacat 138720
aagaaattat aaatgttttc taatgaaatt tatcaagtct gtcttcactt atgttttctt 138780
cattgtcaat aacttaaaat gacctttct acctttaaaa attttgaaat ttcctctgt 138840 attgtctaat agtacttaca tgatttcctc tttttaaattg acatatttaa tccatttgga 138900
atttattttg attttaacta gtaatttaac tttattttct tctccaaatg attcactagt 138960
tgttctgaca ttatttagtg aataattcat cctttcttca ctgaattgga atggcatatt 139020
ccatatactg tgtctggttt tggcttttct gatctcttcc actgatcaac ctaagctgga 139080
gccagtatca aactgttgta atcattatgc ctttagatac tttaaatgta cagcagggaa 139140
tgtcttatta ctcttatttt tcacaaatat cttggcattg tctcatgttt tattccttca 139200
gataaatttt gggattattt tgtcaagatt ttgtttgagt tgttttaaat ttttagattt 139260
cattgggaaa gaactgaaat ccttgaaata ttgcttcttc ttagccagga atatggtaca 139320
actttgcatt taattcagtt cttttcttaa ataccaccat gaagtttttt gttttgttca 139380
tataggtcct gcattaacac catatatata aagtgtgaga aatactacat tcttcaggat 139440
tctctgtagg ttaacaatga agatgatgac tcaacccttt ctttgtttgc ataatgtgat 139500
gccactaata gtgggtaact tctctgcctt acctcctctg ttccaaacag gattttcag 139560 aatgaacaaa ttaaaagaat cataatcaga cactaacccc aagccatact gcatggcagc 139620
accaatggga ctgacagaaa acaacagaaa taggaagaaa tcctacagag aaacaaactt 139680
gaaagctgtc tcatggcctt tgaatcatac ttaagttta tgatggaagg atacgactat 139740
gaagaaagac acagagcaac atcagacagt caagaatttc agagccagct ggcatgcagt 139800
ggacctcatg ccagcccatt ttatgactat ttaggtagtc aagggtttaa gattttcta 139860 ataagacagt tattatgcat ttcaatgagt gatttctttg cagctctaga gtgtggcctt 139920
acctacttca acatgagaag attttttgtat tttgtcagtc atttcacaat gacttttagt 139980
```

```
gagcccttca ttatagactg tggatacaac tttgctgttg gaaattaaca gtgtcaaaca 140040
actgggtata atgtttgtaa tatctgagga gggggagctg cctaggaagt tgtattccct 140100
gtgttaattt ttcagtctct taggttatag aggaccttct agaaccacct tacagcagga 140160
ttacatccca tttacacagt tctctgtcac ttgaatacag agaagggatc cacaaggcca 140220
tatgcttcct agacaaagag aaaagatttc tgccacactc agaacgcttt gtcttcagac 140280
tataatcacc cacaccatat ttcctttgga tccactttcc agattttgt gctggcacta 140340 acaccaactt gctgtggctt ggggcatgta atttcaatac tttgtgccca ttttcataag 140400
tgaagtgtca ggcatcacat tggacatttt aagattcttt acagcccaat gattctgtgt 140460
ttctaattag gcccaatggg ttagagctaa aaggaaacag tgagtttcct ggaaggaaag 140520
gacatataac acagtccaga ggtaaaatgg gctgtattca agaaaagata ggacaatact 140580
ttgcagggat gctgcagaga ggattcaagc cttgtatgga ggaatggatg tgatacaacc 140640
aaaaagtctt taaaaattct ttccaactaa tctgagattt gtaacctat ggactgtgat 140700 ttgcagcaaa ccaaggatgt gataaagact agtattgttt ctagaatgca aggatggttc 140760
aacatatgca aatcaatagt attaacagaa tgaaggacaa aaactatatg atcatctcaa 140820
tagatgcaga aaaataattt gacaaaattc aacatcattt tatgataaaa tctttcaaga 140880
aattgggtat tagaaggaat gtttctcaac acaataaagg ccatatcaga caagcccaca 140940
gctaacatta tattcaatga ccaggaatga gataaggatg ctcactctca ccacttctgt 141000
ttaacatagt actggaagtc ctagccaatt tcatattaat gagcctcatt ttcttcatca 141060
tagaatgaag tatataataa tccctgttat acttactttg cacagattat tattattatt 141120
taattattat tttgagacag ggtctcactc tgtcacccag gctggagtgc agtaccacaa 141180
tcacagctta cttcagccac gacctccag gcataaagga tcctagcccc tcagcctcct 141240
gagtagctgg gagtacaggt gcacaccacc acacctagct aatttttttt tttcattttt 141300
ttatagagac ggagtctcac tatgctgccc aggctggtct caaactcctg tgctcaagca 141360
atctttccac cttggccttc caaagtgctg ggattacagg agtgagccac tgcacctggc 141420
cttgcagatt attattaaac tttgtaaact aatcaaatga gagtgattat tgttactgtt 141480
aagaactctg atagcctcat ccatatattt ggagaaattg aataaataat aggaaagaaa 141540
taatagcatc ccaatgattt taccttggct ctaccatcat ttggggaagt gataattcag 141600
ataggagaag tgacttggaa gcagtcttga gagattgcct gttccatccc ctatctttgt 141660 ccttaaaacca aattgtacag ataaataagg tcttatttttt aggacttaca gaaaaaagat 141720
tcctttcata tccatctttg caatcctcaa ccacttctgt cactattatg tgtcatttca 141780
aacattaaat tcctcattct gctttgaagg aacacatgtg tcatgtgtac ccatttgtat 141840
gttttggtgt gttttatgct ttatgtgatc acccacatat gcacagataa ttccaaaatc 141900
cagtgtgtgg gtgttgtatt ccctgtgtta attattcagt cacactcaaa cacctatgca 141960
ctcacacata catgaataca cacatgtaca ttagcatgtt tatgcttatg ttgcatgtga 142020
ctggcaacat cagtgccttt ctaaggcaat gttaactacc ttgagttttg ggagagcttt 142080
agagaacaaa gacaagagac taaatgattc tagatgtaag agacaatgtt gcaataagtt 142140
actatcctaa aaagacagaa tacagggaca agagactatt attttggata gtttcttgct 142200
taccagtaat acttaagtcc tttacattaa aaaaaaaaa ctctgtaaat atattgcaga 142260
agaaatccag acatccttca agattcttag agctggaaaa gatttttaatg actttccagt 142320 ccaatctatc tcatgtaatc aatggggccc agagaggcaa aaggtcttgt ccaaggtcat 142380
```

```
atagtgagtt agtgataagg ctgaacaagg attcagatgt tggggcttcc agcccactgc   142440
tctttctctc atctgggatt tgtgtatttt tgttcattag agattttcct ctgtaacctc   142500
aatatccaat gcagggcctt gcacataata gattatcagt aaatgttaaa ttaatatgtc   142560
atggctttgg ttgtactggg cttttgcact tactcctgag taaattgtaa agaatatcta   142620
cgttttaggt tgccttgttt tagaccaaga ggtacccaga gaaaggtgt gaactatgct    142680 aaggaaatta tccgagttcc aaattgaaaa aaaaaaaaaa tcatgctttt ccgctataac   142740
ctctctcatt cacagagtga ttctctttca gaagggcaat ctagaactat tatgggagcc   142800
atattccatt ggtggtgcaa ccatttcttg acaaactagg gtccaagaaa gtattttcct   142860
ggggaagatg agatttctca agaaggcac gcactttcta acctaagctt atttcagtaa    142920
tcaatgtaac aagctggtct tgatgattgc agcagtacca atactgtggg agtgtaccag   142980
ttctagaaca gctacaacat tggaattgaa cgcactagaa ttggatacag gacctgtttt   143040
tgaggagcta acacccaaag gctgaacagc actcgtagca ccgtcctttc tgtgcacata   143100
tggtagtcct cagtttgcaa cagaaataaa gctgttagca aattatgtgt tctatttatg   143160
caaataaaat cttgtggtat gctagaaaga gcactggcct ggagacctta gttttctcat   143220
atgttaaaaa cccctaacac aggcctggtt catagtaggc acccaataaa tagtagtttt   143280
cttcctttgg gggcctccga ttcagtgtgc ttcttcaggt aagtcacttc cctgaactc    143340 ctccttggaa tgagagttgt actgttgtga tttttaacag ttccttcaag ccaagcattt   143400
tggaatcctt tcataaaggg agaaaggaag gaaagaagaa aggaaaatta aggaaaaag    143460 aacaaataaa acgttaaaaa ggaggaaagg aaaaaggatc ctttactaca ataaaactaa   143520
tcttatgttc ttgcaagtag cactttaagt aaaagaagtt ctttgctgac ctggttacta   143580
ctgaacctac tacataaaat agcctactat aatagatgca tttatgtgcc taatcttcac   143640
tttttaggct tagtaaaggg agaggaaagc tgatgtatag ttaaatttat gttttttagtt  143700 gttttttttt ctactctcaa atatcaatca ctctttagtt tctctttctt tttccgacca   143760
caagcattct tcctctgctt aaagaagctt ccctaaaatc ccagtctatc cagtaagcca   143820
aagcacagca ataaatttga ggaaaaaata ccagggactt agagacagaa aggagtgagg   143880
ggatgcagaa gctgaagctg gagcacggtt gcaagcatga gaagttctgc gtgtttcaga   143940
gcagccaagg atgtattttt gcctattcct gctggtgact ctgtgtgtct atgcatccat   144000
ctgctatatt tacatgttta gtcagtcaat ccacgtttgc tgagagcctg ctgtgtgcca   144060
ggattgtgct agcgtaaagg agcaaagtat tgagcaaaat atgtttgagc agctgtaatt   144120
ctgaggatct ctaggtctga gcatgtgtat gtgtgtgcgc ttctatgtat ctgtgacaac   144180
tccaggtgtt catgacagtg atctttgtta ctctgttggc ttcatcgaac ttccttttac   144240
ttgctgtgat tcactacata gagtgggctt tatctctgat tttataacc tgcaagactg    144300 ggggtatgat caccagcaat ctaaaaacag ttagaaatcc catggagtta tcttttgtag   144360
aaattttcct ctactaatat tatgaaaaat aagcatctta ttagctcgag tgtaattcta   144420
tgcatgatta caggtatcaa taggaagaaa cattgactga gttcaaatct cttctacgcc   144480
atgctaaagg ggtgacaagt tccacaatgg atcattttct catgggcatt tctgactttt   144540
ggtaaaagta gagcacctta tttttaaaaac cattgagtag tcctaatagt ggagatatca   144600
tcaggatctg aattgttcat ccctaaaaaa aacaccaatg gaaatcaaac aatatagtgc   144660
caaattaaac tgtttgaata tttaggttct gtatgatcaa attgtttggt gccatactct   144720
```

```
gtccactttt ttcatgtggt aggatataat ttcatatctt ttctgttcta gaaatacccg   144780
aagaaagaga ctctggaaac tcattatcag gtctatcaac tcttgtattt gttctcccag   144840
ggaaacagaa gtacctgtgc gccagcagaa atgattgcac tattgataaa ttccgaagga   144900
aaaattgtcc atcttgtcgt cttcggaaat gttatgaagc agggatgact ctgggaggta   144960
agatactttt cttctcttc ctcctccttc ctctctcccc cttctccctc attttctagt    145020
ctctctttag accagatttt cttctttgat gcttccaagg ggaccagcca tgctctagac   145080
acaggctgac cctttcatag gcaacgtggc catcagccag ctggtgcctt ttttttaatc   145140
cttatctata ccaatcccca ttccggggct cagcattaga gcaggcggtg tgaagcaggg   145200
atcaggagcc aacagaaggt gagtgaggat gcatctgact gggcagggcc cccaggggac   145260
ttaatgatac tggcctgatg ttgttcagtg gtagctagga tgagagaact aagaaatcca   145320
gaacagtcag aggtgcagga tgacccaggc ataggcgcag gatgacccag gcacaggctg   145380
atcctgaaca cctgggaata tcccttagct aactgctgcc tatgttgtag ggccagccac   145440
ctcgaatgag aagctacttc tctttggagc ctgtgactag gctgccacac agagccaatt   145500
tcctatccta tctctcccaa agatgagcag gtgttttaat aatttccttt tctttgcaaa   145560
gctattgacc atttccaaaa gcattttttt tcagtagcac agtaacgtga tagatggaag   145620
atacagctct ttcaagggcg ttcctctatc ataaggctct ctgtcccaca aacctgtcta   145680
ccatgagtgt tgtcaccatt ccagaaaggc ttgacatcag ttgattgaga cttatatttt   145740
ccctctccaa actccccat ctcttcatgt ttacatctgc ccaatgccag ggtcctcgct    145800
gctgcctgct acttccaaaa agatgtgtct ttcatgagaa aaacaagatc attaatccac   145860
ttcgatttgg aaatggaatt tgaagaaagg caagcctatt tctgagtgcc tgcaactgta   145920
gcctcatacc caattattca ttattagcct ggaaaaccca agtgcctaga atccaaccct   145980
ctcccctctc ctcttaagtc taatttagac cagttgtcta tctctggctt tctgtgaggt   146040
gttcaatacc ttgtctgcct atgtgcacat ttatagacaa caactagttc tcttatcctg   146100
gagcagggcc atgtgtggat cttcatatag ataactatat cctccccatc ctcacagggc   146160
agtagtatta tttaaacaga acaaagtacc tcacatgaat tgacccaggc tggatgagag   146220
acaatttcaa aagaatcatc tcaagtagcg tccagtactc ccaaacatca caggtagatg   146280
ttctgtgagt ggcttttccaa gcatccacat caaatgagac tcagatatct gagaaaactc   146340
aaccttgttt tggtttgctt ggtgcacccc aaagaaatcc aacaattgag gtctacagtg   146400
gagaagaagt aggactgggg tcagggagta cagaggcaaa ggcaggaagg gtgacaaagt   146460
gattgacaag aaaaaatgtt ctccatatga atgttgcagc cccatgttga gggttcttat   146520
acactcaact gtcaattatt tagccttctg tgaattatgt atagtataaa agatagggac   146580
tctcaagtag ggaacctctt ggcttgccat ctggcaatat gaattgcaag tccactttga   146640
tgcaggtaaa gtttaatggt aacaaaagtc ctcataacat ttggatgcaa atcttaacat   146700
taattccatg tctcagccaa cattctccat tattaagcag cctgtgatgt gattacagtg   146760
aaccactttt gaaaggagc ctgtgtataa cagatagttt cactatacta tataaccgtc    146820
agatgcaggc ttgtaaatta atttgttggt gacaatgttt cagtacattt tcaaattgat   146880
tcattggtat agtactcaaa tttgagtggg cttggtgaac acaatgaaga caagctgaga   146940
agtgctgtga ctggccttca tttcagttgc aggcccatga tattttgagt gtcttccatg   147000
tacaaggcac catgctaggc attagagctt gaggctggca aacttcagga agtgttcaca   147060
agataccagg attcttgatg ttgtgtaaat ggccttgcct ttagagtcag gcagatctag   147120
```

```
tttaaaggct cagctccttt atttactgtg tgccctctg agcctcaatt tcctcatctc  147180
tgatttagaa ataccatcct catagagtta taatgagtat cagatgacat gatgaatgtg  147240
aacatccttg ataaatagca aaatgctaga caaatatggg ggcttaatat gacattgagg  147300
tcactagtaa tttagctgga aagtctgtaa cacagcactt cccgatggct tttaccctaa  147360
gtaacttggt atgccatata atatgtaaca gcaccaacag gcagagaatc gccagaaaac  147420
actcttgatt acctcaaacg aaaaagtacc accaggatcc tgttcagaag ctaattttag  147480
taattaaggg aatcatatgc tatgttcaaa taccatgcca gtaaaaaccc aattgtttac  147540
cttcttaaat cactgcttga agagcaaatc tttccatttt gctgaatgaa cttatctcca  147600
cgttccctgc cctactgaca caacccctc ccaagtttat tgttaactta cacattcaat  147660
gcacagcaca cctttactca aacaatggaa aagaaagaaa gtgtcaattc aaagtggccc  147720
ttgtctattc cttaaggagt agacttccat tttcatcaga tttggattta gcatagacat  147780
attgattacc ttgaagaaga attcatataa ttttatcttc tgattcccat cactcaaatc  147840
aaaattacat aatatattcc aaaatggcaa ctaggaatgt ggccttgggc aagtcccttc  147900
tctcctctga tgcttggttt tcccatcata gaactggaat tgtggcttca ccgaggacct  147960
ttctggtgct aacattttgt gattctatgt aaaaagccac acagaaagga ttgttttca  148020 gccctttctt agattgtctg ttccctgctc ccagaagtat agatagtgag acttgagtgc  148080
tttgatacat cgtaattgta tctacctcca ttcacaccta cttaagatat ctgtctaaaa  148140
gtagactaga cagattattc agagagtgga gggcagaagg gctgtctctg tatcttaaag  148200
aagctggcac tcttcagctg atggctgctt ggtcttgagg cctcaagatc tttaatctgg  148260 cttctctat agtgtttcat tcactgtttg gtgatggaat ctcttcagtt cagagatact  148320
taatagatat agctttttct ttcctgcttc caggcctacc tacctgtttc ttgctttttt  148380
ttctagcagc tgttgttgtt tctgaaagaa tcttgagggt gtttggagtc tcagaatggc  148440
ttccttaaag actaccttca gactctcagc tgctcatcca aacagagat cagcctttct  148500 ttgtagatga ttcattcctg gctgcatttg aaaaccacat attgttaatt gcttgacgaa  148560
tttaaatccc ttgactactt ttcatttcag aaaacactta caaaaaaagt ccaaatgagg  148620
accttccctc cagtgaatta gctgtggctt tctcacagtc catagttagg ataaatgtaa  148680
agccatttct cattttttctc cgcacttttcc aagggtacac tccttgtttc caagatggaa  148740
tgagaaataa agaagtgccc ttcctgccat cttctcccct gacccttttcc tccttcccac  148800 tttcctccta ttcctccca aacatgattt attttctgcgt tttgcaactc ttgagttctc  148860
agcatttagt aaatggtgtt ggtccctgtt gattccttcc tctcctggac catggaaggt  148920
agtaggcctt tcagaaattt caggtagcag ccaaacccca gaagaagaga aggaacacag  148980
agacctagac catgtgagaa cctgaggtgt gcagcattta cttcacagat tcgtctagca  149040
tatttgagag gtgtctttcc tactaggaga ctgaactctg catctgagaa taaaaactta  149100
acatatctac aggttttgac aacctctgtg aattatctag ttgagaggat ggctcaagga  149160
gcctattgcc atggtctgat gtcgttatgg acgctatgaa catccttgca gtttccattg  149220
ttgaagacag ccctgatgcc agctgtctca tcattcccca tgttcaagag catcccagca  149280 ttgctaccctc aggatcccat gtcctgaatg caacagagtg atttcgctgc tgaattacta  149340
ttcatggcat ggctcttcac agcatttatt catccatgta tctatccatt catccttcca  149400
gccagccaag aagttcacgc tttcatcttt tcatccattt actcacctat ttattcattt  149460
```

```
agcaaatatt tattgagtac caactatgtg ccagacactc tgctaggcat tttggggaag  149520
cagaactgaa taagatacta ttcctttcct caaaaatttg agcaagagga gaaaggaagt  149580
aatgaggaat attccttagc cataaaggaa aaataagaaa tcacttggaa gaagttaggt  149640
gagatggaag gaaaaggaca tctaaggtaa agcgtacagt ttgaataaag gcacagagac  149700
atgaacaaaa tgcattgagg gttttgaggaa cagcaattgg tttaacatgg ccagagctgg  149760
ggaaatggta agggcaagct gaaaccacat tgaaagcaaa cttggttatt atactaggta  149820
gtttagactt caagcagttg aaaatctttg agcatgggat aggcatgatg acattgtgtt  149880
tatttgcatg tttctttaaa gaaaactggc agcagcacaa atgttttgtt gatgagggtt  149940
taaattgtag aaagtgagac aattttagga aggccagcta gagagaaatt tctagcatca  150000
aattttgcta acacctagg atttgtagtt acctccattt gggttgttac ctgcaagtac    150060
tgaccacgta tatgaagaag tactggttta gaccaaggca attggcttgt ataagaggcc  150120
taccctcata ccaaaagcca gtttccttgg tctaggccag tgtttactgg tatgtgtcct  150180
gagaaaacta gttccatgac atgttccatg aaaaatatga tttctattgt caaataagtg  150240
agggaaactt gcatatcatg gtcctgctca ggaagattta caatccttat tagcatatca  150300
caggtcctgg tgaatactgc ggtaaagtaa ccgaggagc ttgtaactca ggattcccga    150360
agttgattca accacaggac ctcatttatt cacataacac ctgttatcct acaaaaccac  150420
tgttctctgg aatacacttt cgaaaacatg ggtatagaca aaaactctat cctataggca  150480
gagaatacct atacctctag ctcaggtcat cattttgcag atgtgtgtgt cattaagaat  150540
cagtcaataa tgcattaatg atcaaaagca gaccatcctt accacatggt gcataagatt  150600
atgctattat gctattagct actaatgcca ctaaagttaa ttatgttggg tctgcaacgt  150660
tgtcatacac aaaggatagg atgcaaaact gtcctaggcc aaagcatggt tattgcccaa  150720
gttatctaat gtctgcaggt acatattcct ggcctaagga ttgtgctaaa gaagttattt  150780
ctaagaaata tagtgacttc cagcatcatg cagaatgacc atttaatatt ttgaatatct  150840
agacattctg ctgtagaatt taatagtcct tttatacact gtctgaccaa cattttgaca  150900
tttactcaga accccatcac agtgctacca cataacctca ttgctaaagt ggaggccta    150960 gaaatcacag atttgtagaa accatccaat gattgaatcc cctctacttc ctgttcagca  151020
ggcagcagag tgtcataaag aattaacaac gtggaactca gttactggga tttcttccat  151080
tctcctttga ttctctagac tagaattcca aagaccctca ggctggtgat gcaagtggga  151140
agtctcattt ctgagaagtg ctgcttccta cccacaattc tttgatagct gagtgcttta  151200
gctgatctgc ataactgagg tgtgcaccaa ggagcagaat tactctataa attttggcat  151260
caacatgtgc aacttgtgac tcagcacttt gaaactctgg ggattttttt gtttggttgg  151320
tttttgtttt aagatgtcct gtggtatagt ggaaatagta caatagactc agatacagag  151380
aggccttgtt tctagtcttg gttctgtcac ttactatctt gatgtccttg cacaaatcac  151440
cagacctctc tgagcctcag tttctccaac cacactgtgg gaataataaa atctttttta  151500
cggcattgtt gtaagtatgt agagaaactg gtacacagta ggcacacaat caatgtcacc  151560
gtacccttca gcccttcttt tgtggatgaa aaatggtctt tgtgctccca gtcaccactg  151620
gggtctgttc tctctctctc tgctgttaca gtgtggcttt tggttcttgt ttctttgttc  151680
tttggtctgt aaattaccct tgaaacaacc cttgaaattt ccactccatg acctaaatcg  151740
tcatccctaa attggttaca tacatatttg gtgcactttt ggaggggaaa agctttatgt  151800
ctctctaact gtagttctta agggaatttg catatggaaa aaacagagac tgcgtctctt  151860
```

```
aattcctcca aaccaaatta tctgggatag cacatatatg ttgtactctg tctctgagca    151920
tttgctctta gagaactatg gttagagcga agtaaatttt tctaatcata aaaattaatg    151980
ataccgcata tctgatactt gaatgagtac ctccttgtaa aatttatact taaatccttg    152040 agttttaaa  gtgtaatagc aatagaaaga ttttattgtt gttactttt  actgtgagtg    152100 ctccaaaatc cctcagttgc tcttgaaaga gcaagatgat gccataggca atattttcca    152160
aaggtagtag gcagaaaact gagtacacag cacacaatag gccatatata caaaagcaag    152220
tattttgcaa ataataataa ttcaggaaaa aagcttcact ttcgttggta acctgtttgt    152280
ttaaaaccat tttattattt attatttaaa aagagtgtca cttgttacag attgtgggat    152340
gtgttcctta agatcacaaa aatgtaaaat attttctttt tatactgaac acatgcatag    152400
acaacttacc tgagcaagct gcttttggga gacatttgca catcttttgg gatcacgttg    152460
ttaagaagta gaactaaggg aaaaacacgc agccacccag aaatcggtag agccttcagc    152520
tcatctgtta ttaatatttc tgtgacaaca gatatctagg aagtaaacag gaaattgcat    152580
cgctatcctg catcaccttt tttggaatca ggttccattc ttctcagtcc agttcaacct    152640
tgtgatactt tttagatctc aaccaaggca tagaaatata ttttcccttg cttaataccc    152700
catggaacca atgcccctgt ggttgaagta aaaattgatt gttgagggac atttcagccc    152760
tctagcagtc aacaattaaa aacatgtaag caccgagcac ctgcagaaaa cttgactgg    152820 catttggatc taagaagaaa atctgcatct tgaccaagat gaaaagtcac cagcccaagc    152880
ttgtgcagtg aagtgtcatg ttggccacaa tgaaactgaa agagactgat gactctcctc    152940
agggtggaaa atgaggcatg gaagctttga ttagtgagct gttaggcaca cagacattaa    153000
tttcaaagca ttctcatctc cagtctgagt aataatgctt atagtattat gcaattgttt    153060
ggctgctgca agaaattcag cagactccaa caagtagtct ttcttggtct ctgagtgact    153120
gtaacttaaa ttctacctcc cttctcttct cctacatctt ctcactcccc accccacccc    153180
cacatacaca caattcttgt ccactatgtt cagagagatg cacgcacaca tatatatgta    153240
tatatatagt atatttgtca ataaagcaga aagaagaaa  aaactccaag taaacaattt    153300
tccatttccc catctcactt ctgtcttaca agtggatagg aaaagaaaaa cccccagtaa    153360
aaaatggcaa ccgcccacct ccccaacttt acatgctgct tcctatgtta gaggatctgt    153420
cttaggcatc tgattatgga gcctgctaga tacaagcccg tatttagact gctacagtca    153480
acaatgtctc tctttcatac tagaaaaatt ccgggttggc aattgcaagc atctcaaaat    153540
gaccagaccc tgaagaaagg ctgacttgcc tcattcaaaa tgagggctct agagggctct    153600
agtggatagt ctggagaaac ctggcgtctg aggcttagga gcttaggttt ttgctcctca    153660
acacagactt tgacgttggg gttggggget actctcttga ttgctgactc cctccagcgg    153720
gaccaatagt gttttcctac ctcacaggga tgttgtgagg acgggctgta gaagtaatag    153780
tggttaccat tcatgtagtt gtgagtatca tgattattgt ttcctgtaat gtggcttggc    153840
attggcaaag tgcttttga  ttgttcttga tcacatatga tggggccag  gcactgactc    153900 aggcggatgc agtgaagctc tggctcagtc gcttgctttt cgtggtgtgc tgccaggaag    153960
aaactttgct gatgggactc aaggtgtcac cttggacaag aagcaactgt gtctgtctga    154020
ggttcctgtg gccatcttta tttgtgtatt aggcaattcg tatttccccc ttaggttcta    154080
gccttctgga tccagccag  tgacctagat cttagcctca ggccctgtca ctgagctgaa    154140
ggtagtagct gatccacaga agttcagtaa acaaggacca gatttctgct tctccaggag    154200
```

```
aagaagccag ccaacccctc tcttcaaaca cactgagaga ctacagtccg actttccctc   154260
ttacatctag ccttactgta gccacactcc ttgattgctc tctcacatca catgcttctc   154320
ttcatcagtt gtaagcctct cattcttctc ccaagccaga ctcaaatatt gtattgatgt   154380
caaagaagaa tcacttagag tttggaatat cttgttctct ctctgctcca tagcttccat   154440
attgacacca gtttctttct agtggagaag tggagtctgt gaagccaggg aaacacacat   154500
gtgagagtca gaaggactct ccctgacttg cctggggcct gtctttccca ccttctccag   154560
tctgtctaaa cacacacaca cacacacaca cacacacaca cacgctctct ctctctctcc   154620 cccccaaca cacacacact ctctctctct ctcacacaca cacacataca cacacattc   154680 tttctctttc ccctgactca gcaacattct ggagaaaagc caaggaagga cttcaggagg   154740
ggagtttccc ccttctcagg gcagaatttt aatctccaga ccaacaagaa gttccctaat   154800
gtggattgaa aggctaatga ggtttatttt taactacttt ctatttgttt gaatgttgca   154860
tatttctact agtgaaattt tcccttaata aagccattaa tacaccaatc gtattttctt   154920
atttacaaca gactgagaga attaatgctg ttaacattgg atcttttttc ttttttttt   154980 ttccttttt ttctctctcg tttgcttttcc aggtcatgct gacctgttca gcttggactg   155040
tttcacattt gttttaatg tcagtttaaa tgtaattgta aaagcatgta tgctctaaaa   155100
tcatgtagtt actttttca gtggaaaagc ctggtattcg aaagcatttc caggctctgc   155160
aatttcatat gagcaggttt ttggtaaaat cttttgtccc tcactcaggg tggtatctgg   155220
acagtgagcc cctttcttct ggctcagtag tcagagagag gagacttgga gacagtttct   155280
gctggatcct gtgctttggc aaggatgtgc agcattgcat atcattctat cattaattat   155340
gtttactcct ccatgaacta aaaaccatta gactaaatag tccaacataa accttgaaag   155400
ataaaatttg atattctttt gcctggccat ttctctgacc cagaattggg gctgggaggg   155460
gattggagac ttggggaaa gaatcaagga gccttcttgc ctgggggaat ttggcatgca   155520
cttattaatc ccatttggtt gcactcccta ctaatccctc actccatacc tgccaaggat   155580
tggctctgct ccctgcttct catccctgtc ctagttcttc ctcacctatc tccatttccc   155640
actactgatc cttctctcca gtaagatgct attcaacccg atgaaatata aagagtagca   155700
ccaccctgga agtcaggata ccttagtttt agctcctgct ctaccattat ctagctgtgt   155760
gacctggggc atgacttaac cttgctctt cagtctgaac agtctttaag aattggtttg   155820
gaggaggaag gaagggatag acaagatcca aggcctttga actcttttt ggaaatgggt   155880 ccttttcttc aaacaaaatt tgatgcagag tcccaaattt acctacagaa taaaatactg   155940
ctgttcttgt ttgaaaggaa gtggggtgct tggagccaca tgctcaggcc cactttgccc   156000
cctctcagga accctcgaaa aaacttatag gacttatagg actgttgggg atctgccaag   156060
tctctcttat gttacatttc agtccttgtg aaactctata tgtttcatca gttcacttttt  156120 tcagaaagtt cacctgcttg gggtaaaggt catgaagtgg agaatgtggg gctcagtaac   156180
tagcaatagt aaaaaacatc attgattggc ttgcagaatt tactctgttc taagcatctt   156240
acacacatac tcatccgaaa actcacaaca accttgtgag gtagatctgt tattatctta   156300
agattctgaa acctgccagc atgactctca atctttgact tgagaccagt tgcccaacat   156360
ggaaggttat acttttcaca gtttaccacc ataagcagtc tttcagagtg atttctagct   156420
agagatccat tcttagaaaa agtcagaacc tgcccattag catacactgt cacatggtgc   156480
agagtacctt cactgggttc atctcatttc ctcctaaaaa tagtcctatg cagtagtcca   156540
gtcatatcat caccattata tagatgagaa aaactgaggt gtaggagaaa tcaagagatc   156600
```

```
tgttcaaggt cacacattcc ataagactct gaataccacc atcaagaata ataaacctttt  156660
tatgtgaaaa gcatttttaga acttcagtgt cattattgca ttctgcctcc tggagttcag  156720
tgcactttt  caccatgctt taatcttgga gtcctggtgg tacagaatct gccttctact  156780
ctcagacaac accacagtgt ctttatccct cataacaaac ttatgaatta agtaatgata  156840
ttatccccat tttacaaatt agttaactga gataccaaga ggctaagtct gcccaaagt   156900
cacacagcta gtcagtgata gagccggagt tacaaatgag gcatcctgac tccagaatat  156960
ttgctcttaa ctactactct ttatacatat gtaaggaaac taaaagcaaa agagggaaag  157020
atgtccctga ggccccacag tgagctcccc tgactcacaa tccagtattc ctctgacctt  157080
ctaatcctaa agttatacag taaggtccct tgactctaat cctagtagat ggaaagatgg  157140
ctggcatgat ttaagccaga ggccacaaac tggcttcccc agagccagaa ttcacctgca  157200
gaattctgtt tgtccagcac agtgtttgtt tagaaaattg acgtagactg cccctaggca  157260
gggcatcaat cactgtcatt gtccccagcc ctccttattt atgtttgcca ggcttttta   157320
ctcatttatg tgtctgcctg acttgtgaag gtatttgagt ttatgacttt tagatttaag  157380
cattgcaata tataagcact gcacacatgc attcacaaaa gtatagccta gtctagcttc  157440
acaaagaatt tgtagcccta caccaaacac acctttatgt ttacttagtg tttagaatta  157500
gatttaagat cagaatttag tttcacaggc attcatgtgt ggaagaacct cagttattgt  157560
tttttgtttc atactgtctc acccttgctt tccctgctgt gtctggaccc ctgtcaatcc  157620
tgctttctgc cattcttcat gcctgagtta gggcccctgc aagccattca ctggttaatc  157680
tttaggaatg aatggagagt gaaaaccagt ttggagggtt cactgtgtcc caagcatcct  157740
ctcatttagt tctcataagt gtcctaagag acaggtagca gcacattcgt tttataaatg  157800
aggaaactaa atctcagaga agctgaacaa agacctcaaa gtcattaagg tagtaattaa  157860
cggagccggg atttgaacgc aagactgttg gactccagag cctattcttt tgccctacac  157920
cacagttcct tacaaggaag atgtattcat tttctattac tgcataacac attgccacaa  157980
atttagcagc ttcaaacatt tatcagctca ctgttttgta agtcagaagt ctggcacagc  158040
atggctagat tctcagttca gggtctctga aggatgaaac tgatgtgttt accaggatgc  158100
attctaatct gaagctcagg gttctcttcc aagctcatgt aattattgca ggattcagtt  158160
atttgtggtt gtaggactaa ggctccctct tcctttctgg ctaccagcca agggccattc  158220
tcagctcttg gaggctgccc tcttttccttta tcatgtggac cccaacgcct tcaaagccaa  158280
caacagagac tcttccttgt gttgaatgtt tctcactcta cggatgtctt tcctggagga  158340
tcccagtccc gtaagggctc acctgatgag gtcaggtaca tcaagaatag ccacccttca  158400
aattcaactg aattagcacc ttcattacat ctacctagcc ttttacaac agcatctagg  158460
ttagtgcttg actgaatgac tggaaactaa ggtctcagaa tctcggggac cgtcttagaa  158520
gtcagcctac tacagatgtt gattcttttc atgtgtcaaa tttcatagtg agatagggag  158580
aacagaaaca tcacatcctt gaccttaggt aaagggattc aaacttccta agactttgga  158640
aacttcacgc cactttcacc ttttccttaa tcatggttga gaaggcctat atcttggagt  158700
ggccaggagt gagactggaa cagtacctaa aggttaagga cgctaaagaa gttacagatt  158760
ggttacatct gctcctccct aggaatgatc catggaacct gatttgaaat ttttttctct  158820
ggtgctatag atagctccca caggggtcta atgcccagg  gctgaaaagt tagttcccca  158880
taggatccat ccaggcatga tatcaggcca ggtgttacaa tctcctaaag aggaggtatg  158940
```

```
gactggaaag cccccttgcca atggcccttt cttgtcactg ctctgaccca agactaacag   159000
ggcagagata gtgaactcac atactattaa aactatccac ttatacttcc ccctttctct   159060
ttgctttatc actccattta agtaaaccaa tgagtctctg ccttgacaca gtggcaagct   159120
gacctgtatc ttatatgaaa gaattagatt tgactctggg gctcaggtgc agagggcagg   159180
aggggcataa ggatggcctt catggaagaa aagaagtcct tggatactga gtaacagctg   159240
agactagcaa gcctcattgt ccaggattcc aagtcgtcta gcaacatcct ggtctctgct   159300
gcagacagaa cagaggatcc cccggcagaa tgaatggagt ctgatttcaa ttacgttcag   159360
tatagtcact ctctttaggc agagaagcca gaacacctgg tgcagctagg gccactgtgg   159420
tcacagggac aagcacacta cctgggtcct ggaggcaagt gggaatgcag ttttttcttcc   159480 ttaagcagat gccatatagg cctggggagg aggatgtgag aataccagcc aagttctcat   159540
tggcactata cagagaaagg ggaattattt catcttgatg gattctcccc acagtctctg   159600
cacatattga tcttacttgt aatgagtttg cttaggttca cgagtcatca tcccagggag   159660
atctgagtca ttggtgggaa agtcgaggcg acagattata tctcactgat ctcactgtca   159720
ccaattgctc tgtgtgtccc tccacctttt gaaaaagtcc atggattcat ttgtgtgtaa   159780
ttcatttgga tttatttctt cttttatcaat agctttagtg gggtattgca aatgggaaag   159840
ttgccccaga gaacagtgta cattcacagc attattcagt agaactttct gagatgatga   159900
aaatcttcta tatcttatgt tgtacaatat aatacagcca ctaactacat gtagcttttg   159960
aacactggaa atgtggcagg tgagactgag ggattatatt tttaattttt taatgttgta   160020
attaatttaa ttttttaaaa ttttttgcttt ctattttata gttaataat taaactaaac   160080 ttacgtagcc cacatgtggc tagttggcta ctatactgga cagtacaagt ctagaaggat   160140
ctcagagaga cacatgctga gatacagcag gaataagtca aaaagagagc caatgtaaca   160200
tagggaattc tggattggga attagagccc tggctctaat ctcagctctg ccactaggtg   160260
accttgccct ctctggcttc agcctccca tcttttgactt gaaaggttaa actaactaac   160320
gtcgaaagtc ccaaaatggt ggctatggac tgaattcaat tttgggatac acaagtttca   160380 ggaattttt aaaaatctat taatgccttc taggtgtgtg tatgcacgct tgcagacatg   160440
tgcccatgca caagcatggg aaggcagtaa ggcattcatt tcaattcacc agtgtactaa   160500
ccattcacac acacacacac acacacacac acacacacac atgcacacac accctactgt   160560
attgcctatg tagagcctga agatcttta atctgtcacc attggataag ataatttcta   160620
aggacccttc ctgttttgtc atgctgaaaa tctttaagcc actatagtgt cccaaatcta   160680
ttccagtttg ggcagatgac tggagtattc tcatagcctc ctgtctattc ccttctggat   160740
ttgatactag ttatgaagtt tggagtcaag ggtgaagaag ggaggcaggg atgatataac   160800
cccagcccca ctcctcaact ctgcttttga gttagaagta gggttcaggg cttcagattc   160860 cttgggagg cagtagagag aatatgggct ttataatcag aagatgaggt tcagatgatt   160920
gggttctcac cttttttata gctgtgttac ctcagtttat tcatttgtaa aataggata    160980 agaaatatct ttaacctcct aagatcatgt ggaattaagt gatgtaatgt gatgaagcga   161040
ggcacgcaga aggccctgaa aaaattagta gttacccta aggggactaa atggtctggc   161100
aactcccgag ctcaaagcta gaaaggtcca gtaatgggga agatggggtc tttctgtagg   161160
aactgtagca ggggagcaga tcctgtaggc caccagtctg tggagctgtg tccaagaact   161220
catgtttgca ataagcccac caaatgacaa gttattgtgg ggtcaggcc tctaactcaa   161280 gaagatggtc ttggcccaga tcataccttg cagcctgtgc cttggtggg atgtgggtgt   161340
```

```
tggcagtggc tatgcatatc tccttattac tggctgtgcc aaagccccgc agaaatgatt   161400
gttggacaaa gtcatcttgc actcagggct ggttttccag gcttccttgt tattttcccc   161460
tgagttcttc tgtgttcctc ttgcaacacc aaccccacta ttttcctctt ccctacccta   161520
gttgttggtc caaacatgta atccattctt gcagtgattt attgggtgac accatgactg   161580
gagtttgcat tgaaggactt ctttttctaa ttagaactaa aagtcagttc caggctgggt   161640
gtggtggctc acgcctataa tcccagcact ttgggaggcc gagatgggag gattgcttaa   161700
ggccaggagt ttgagtccag cctggacaac atagtgagat ccatctcta caaaaaatgt   161760 taaccaggag tggtagtgta caactctggt cccagctact gggagactg aggagggaga   161820 attgcttgag cccaggaagt tgaggctaca gtgagctttg atcgtgccac tgctctccag   161880
ctgggtgaca gaggaagatc ctccttcaaa aaataaataa aaactaaaaa aaagtcagt   161940 tccaggttgt atctttttc acaggggcca gacacagatg agagcaggtt ttgttgtatt   162000
tatccattta aattgagcaa taaaattctc tctttggttt ctacctttct tatttattat   162060
tattatgtta aagggattaa agtggttcat ggtctttctc agtgcaactg cttatgctag   162120
acctcagaat tatgaccttt tcaattattt atatttctgt ctatataaat actgaaaaa   162180 atagtacaaa gtaagcatcg gaatgcctaa ggacctctaa attgtgtgtg tgagcacatg   162240
gggaagatgg ttcttaaggt ttgagttttg gattattgtg gttgtcttaa ataatgttat   162300
ttctatcatt ctttccaatg actgtctcct agcatagttc ccattttaca gactgatggc   162360
agaggcagaa agattctctc acttctttga tactattgag gacttcagcc tttcaccgct   162420
cttctcccct ttgctaaaaa agaaaaaaat caatatgtat gttacagtgc atttttttaa   162480
atatttttta ttatactta agttctaggg tacgtgtgca caacttgcag gtttgttaca   162540
tatgtataca tgtgccaagt tggtgtgctg cacccattaa ctccttattt acattaagta   162600
tatctcctaa tgctatccct ccaccttcc ccaaccccac aacaggcccc agtgtgtgat   162660 gttcccttc ctgtgtccag gtgttctcat tgttcaattc ccacctgtga gtgagaacat   162720
gcagtgtttg gcttttttgtc cttgagatag tttgctgaga atgatggttt ccagcttcat   162780
ccatgtccct acaaaggaca tgaactcatc atttttttatg gctgcatagt attccatggt   162840
gtatatatgc cactttctct taatccagtc tatcattgat ggacatttgg gttggttcca   162900
aggctttgct attgtgaata gtgccacaat aaacatatgt gtgcatgtac ctttagcagca   162960 gcatgacata taatcctttg ggtatatacc caataatggg atggctgggt gcaatggtat   163020
ttctagttct agatccctga ggaatcacca cactgacttc cacaatggtt gaactagttt   163080
acagtcccac caacagtgta aaagtgttcc tatttctcca catcctttcc agcacctgtt   163140
gtttcctgac tttttaatga tcgccattct aactggtgtg agatggtatc tcattgtggt   163200
tttgatttgc atttctctga tggccagtga tgatgagcat ttttttcatgt gtctgttggc   163260 tgcataaatg tctttttttg agaagtatct gttaatatcc tctgcccact ttttgatggg   163320
gttgtttgtt ttttcttgt aaatttgttt gagttctttg tagattctgg gtatttgccc   163380
tttgtcagat gagtagatgg aaaaaatttt ctcccattct gtaggttgcc tgttcactct   163440
gatggtagtt tcttttgctg tgtagaagct ctttagttta attagatccc atttgtcaat   163500
tttggctttt gttgccattg cttttggtgt tttagacatg aagtccttgc cggtgcctat   163560
gtcatgaatg gtattgccta ggttttcttc tagggtttta tggttttagg tctaacattt   163620
aagtcttgaa tccatcttga attaattttt ctataaggtg taaggaaggg atccagtttc   163680
```

```
agctttctac atatggctaa ccagttttca cagcaccatt tgttaaatag ggaatctttt    163740
cccaatttct tgttttttgtc aggtttgtca aagatcagat ggttgtagat acgcagcatt    163800
atttctgagg gctctgttct gttccattga tctatatctc tgttttggta ccagtatcat    163860
gctgttttgg ttactgtagc cttgtagtat agtttgaagt caggtagcgt gatacctcca    163920
gctttgttct tttggcttag gattgtcttg gcaatgcagg ctcttttttg gttccatatg    163980
aactttaaag tagttttctc caattctgtg gagaaagtca ttgatagctt gatggggatg    164040
gcattgaatc tatgaattac cttgggcagt atggccattt tcacgatatt gattcttcct    164100
acccatgagc atggaatgtt cttccatttc tttgtatcct ctttttatttc attgagcagt    164160
ggtttgtagt tctccttgaa gaggtccttc acgtcccttg taagttggat tcctaggtat    164220
tttattctct tagaagcagt tgtgaatggg agttcactca tgatttggct tctgtttgtg    164280
tgttattggt gtataagaat gcttgtgatt tttgcacatt gattttgtat cctgagactt    164340
tgctgaagtt gctatcagc ttaaggagat tttgggctga gacaatgggg ttttctagat    164400
atacaatcat gtcatcggca aacagggaca atttgacttc ctcttttcct aattgaatac    164460
cctttatttc tttctgctgc ctgattgtcc tagccagaac ttccaacact atgttgaata    164520
ggaatggtga gagagggcat ccctgtcttg tgccagtttt caaagggagt gcttccagtt    164580
tttgcctatt cagtatgata ttggctgtgg gtttgtcata aatagctctt attattttga    164640
gatacgtccc atcaataccct aatttattga gagttttttag catgaagggc tgttgaattt    164700
tgtcaaaggc cttttctgca tctattgaga taatcatgtg gttttgtct ttggttctgt    164760
ttgtatgctc aattacattt attgatttgc atatgtggaa ccagtcttgc atcccaggga    164820
tgaagcccac ttgatcatgg tggataagct ttttgatgtg ctgctggatt cagtttgcca    164880
gtattgtatt gaggttttt gcatcgatat tcatcaggga tattggtgta aaattctctt    164940
tttttgttgt gtctctgcca ggctttggta tcaggatgat gctggcctca taaaatgagt    165000
tagggaggat tccctctttt tctagtgatt ggaatggttt cagaaggaat ggtaccagct    165060
cctccttgta cctctggtag aattcagctg tgaaatccat ctagtcctgg acttttttttg    165120
gctggtaagc tattaattat tgcctcaatt tcagaacctg ttattggtct attaagagat    165180
tcaacttcct cctagtttag tcttgggagg gtgtatgtgt cgaggaattt atccatttct    165240
tctagatttt ctagtttatt tgcatagagg tatttatagt attctctgat ggtagttgt    165300
atttctgtgg gatcggtggt gatctcccct ttatcatttt ttattgcatc tatttgattt    165360
ttctctcttt tcttctttat tagtcttgcc agcagtctat caattttgtt gatcttttca    165420
aaaaaccagc tcctggattc attgattttt tgaagggttt cccatgtctc tatctccttc    165480
agttcttctc tgatcttggt tatttcttgc cttctgctag cttttgaatg tgtttgctct    165540
tccttctcta gttcttttaa ttgtgatgtt agggtgtcaa ttttagatct ttcctgcttt    165600
ctcttgtggg aatttggtgc tataaatttc cctctacaca ctactttaaa tgtgtcccag    165660
agattctggt atgttgtgtc tttgttctca ttggtttcaa ggaacatctt tatttctgcc    165720
ttcatttcat tatgtaccca gtagtcattc aggagcaggt tgttcagttt ccatgtagta    165780
gagtggtttt gagtgagttt cttaatcctg agttccagtt tgattgcact gtggtctgag    165840
agacagtttg ttataatttc tgttctttta catttgctga ggagtgtttt acttccaact    165900
cagtggtcaa ttttggaata ggtgtggtgt ggtgctgaga agaatgtata ttctgttgat    165960
ttgggggtgga gagttctgta taagtctatt aggtccactt ggtacagagc tgagttcaat    166020
tcctggatat ccttttgtgtc ttgttgatct gtctaatgtt gacagtgggg tgttaaagtc    166080
```

```
tcccttgatt attgtgtggg agtctaagtc tctttgtagg tctctaagta atcactttat    166140
gaatctggtt gttcctgtat tggtgcatat atatttagga tagttagttc ttcttgttga    166200
actgatccct ttaccattat gtaatggcct tctttgtctc ttttgatctt tgttggttta    166260
aagtctgttt tatcagagac tagcattgca atccctgcct cttttggttt tccatttgct    166320
tggtagatct tcctccatcc ctttgttttg agcctatatg tgtctctgca catgagatgg    166380
gtttcctgaa tacagcacac tgatgggtct tgactcttta tccaatttgc cagtctgtgt    166440
cttttaattg gagcatttag gttaatattt acgtttaagg ttaatattgt tatatgtgaa    166500
tttgatcctg tcattgtgat gttagctggt tcttttgctc gttggttgat gcagtttctt    166560
cctagcctcg atggtcttta caatttggca tgttttgca gtggctggta ccggttgttc    166620
cttccatgt ttagtgcttc cttcaggagc tcctgtagtg caggcctggt ggtgacaaaa    166680
tctctcagca tttgcttgtt tttaaagtat tttatttctc cttcacttat gaagcttagt    166740
ttggctggat atgaaattct gggttgaaaa ttcttttctt taagaatgat gaatattggc    166800
ccccactctc ttctggcttg tagagtttct gccaagaaat ccactgttag tctgatggct    166860
tcccttgtg ggtaacccga cctttctctc tggctgccct taacattgta tccttcattt    166920
caactttggc gaatctgata attatgtgtc ttggagttgc tcttctcgag gagtatcttt    166980
gtggcgttct ctgtatttcc tgaatgtgaa tgttggcctg tcttgctagg ttgggtaagt    167040
tctcctgggg aatatcctgc agagtgtttt ccaacttggt tccattctcc ctgtcacttt    167100
caggtacacc aatcagatgt agatttggtc ttttcacata gtcccatatt tcttggaggc    167160
tttgttcgtt tcttttttact cttttttttct ctaaacttct cttctcgctt catttcattc    167220
atttgatctt caatcactga tacccttttt tccagttgat cgaatcagct actgaagctt    167280
gtgcattcgt catatagttc tcgtgccatg gttttcagct ccatcaggtc atttaaggcc    167340
gtctctacat tgattattct agttagccat tcgtctaatc ttttttcaag gttttttaact    167400
tctttgcgat gggttcaaac ttcctccttt agcttggaga aatttggtca tctgaagcct    167460
tctctcaact catcaaagtc attctccgtc caggtttgtt ctgttgctgg tgaggagctg    167520
tgttcctttg gaggagaaga ggggctctga ttttagaat gtttcagttt ttctgctctg    167580
ttttttcccc atctttgtgg ttttatctac ctttggtctt tgatgatggt gacatacaga    167640
tgggattttg gtgtggatgt cctttctgtt tgttagtttt ccttctaaca gtcaggaccc    167700
tcagctgcag gtctgttgga gtttgctgga ggtccactct agaccctgtt tgcctgggtg    167760
tcggcagcag aggctcagaa cagcgaatat tgctgaacag caaatgttgc tgcctactca    167820
ttcttctgga agtttcgtct cagagggta cctagccatg tgaggtatca gtctgcccct    167880
actggtgggt gtctcccagt taggctactc gggggtcagg gagccacttg aggaggcagt    167940
ctgtccgttc tcagatctcc agctgtgtgc tgggagaacc actactctct tcaaagctgt    168000
cagacaggga catttaagtc tgcagaggtt tctgctgcct tttgttcggc tatgccctgc    168060
ccccagaggt ggagtctaca gaggcatgca ggcctccttg agttgcggta ggctccaccc    168120
agttcgagct tcccagctgc tttgtttacc tactcaagcc tcagcaatgg cgggtgcccc    168180
tcccccagcc tcactgctgc cttgcagttc gatttcagac tgctctgcta gcagtgagcg    168240
atgctccatg ggcgtgggac cctccgagcc aggtgtggga tataatctcc tggtgtgccg    168300
tttgctaaga ccattggaaa agtgcagtat tagggtggga gtgacccaat tttccaggtg    168360
ccatctgtca cagctttgct tggctaggaa agggaatttc ctgacccttt gcacttcccg    168420
```

```
ggtgaggcga tgcctctccc tgctttggct cacacttggt gcactgcacc cactgtcctg   168480
tacccactgt ccaacaagcc ccagtgagat gaacccggta cctcagtcgg aaatgcagaa   168540
atcactcatc ttctgcgtca ctcacgctgg gagctgtaga ctggagctgt tcctattcgg   168600
ccatcttatg aatcatgcat gttcaactat gagcaactat gtgtattcaa tgggaaatgg   168660
aataccataa aattgtcata tgttgagccc aaaatgatag gatagaattt gatagtctga   168720
ggatggaaag gaccttcaag gccactttta aaaacccat tcccatatga tgcttgaatt    168780
cttaaccact gtgtgtctag tattttctca tttccagtga tatgtgtgcc tgccaacctt   168840
tccgtctcca agagctttaa ctatcaaaat gtatgtgtgt gtgttttttgt gtgtgcatgt  168900
gtgtgtgagt gtgcgtgtgt gtgtgtgtgt gtttagagag agagagagag acagaaagag   168960
aaggagagac taaaatccaa ttcactgttc tttctgggac ccaaagaaca agtctagtca   169020
ttctccattt ctagtctctt tccctagcaa tcggctagac atgctagaca tagacacatg   169080
tacatcactc ctttgaatta caacattcag tatttgtcta tcacttatat gataaaatac   169140
aaacttagct tttattttta ttttttttaga gacagtgttt tactatgtca cccaggctag   169200
agcatcagtg gcacaatcat agcccactgc agcctggaac ccctgggctc aaggaatcct   169260
tccacctctg cctcctgagt agcagagact acagatgtgc accaccagac ccagctaatt   169320
tggttttta ctattttttg tggagatggt gtattgtctt gtggtgttgc tcaggctgat    169380
cttgagctcc tggcctcaag cactcctccc atctcagcct cccaaaatgc tgggattaca   169440
ggcatgaacc accttaccca gccaaatttc ttaatatgat atacatgctc ctttaaaatc   169500
aagcaccatc tttgctttca acctcattat taaccacttt cccatatatg caacatatgt   169560
ttcagccata ctagtgtcta gttttttcccct gaacactcct tggtgctttt gtttatgccc  169620
tttctgccca cctttgcctg gtgaaatcct catcaatctt caaattctat caaatactat   169680
cttccatata aagcattttc taaacccacc tatgtaaaaa gattagtgtt ttcctatttt   169740
gttgatgcct ccattgcagc attttccagt ccaacgtttt ctagaattga ttgtggccag   169800
gctaccagac tgggccaggg cctgtgtctt ttctgtcacc cagaagcaaa ggtctaacaa   169860
tggatatctg ctgaatgaat gaacgaaaat gaatcattaa tatattagta aatacgttaa   169920
ttaaagttcc aggtatgaat actgaaggct gcattcaggc agagctggat ccaaggatat   169980
gctaggttgg tctagcacaa gaatcagagt tttcctctgc aagctatgaa aaatttgggt   170040
ttagcaggta tttgggatga tgaattatac atttaaccag tgttgaatga gcacttgtcc   170100
ttaaggagtt tagagtctgt gaccagggag aatggtgatt ttcttagcta gggcagtttt   170160
tctaaaaagg tagttgcatt gtgtgttttt gaccactgat gataaattca agtctctctt   170220
ccttcccaat agcccggaag ctgaagaaac ttggtaatct gaaactacag gaggaaggag   170280
aggcttccag caccaccagc cccactgagg agacaaccca gaagctgaca gtgtcacaca   170340
ttgaaggcta tgaatgtcag cccatctttc tgaatgtcct ggaagccatt gagccaggtg   170400
tagtgtgtgc tggacacgac aacaaccagc ccgactcctt tgcagccttg ctctctagcc   170460
tcaatgaact gggagagaga cagcttgtac acgtggtcaa gtgggccaag gccttgcctg   170520
gtaaggaaaa gggaagtggg agcatgagat aaggggatc atatttagtg aacgctccta    170580
tggaccagcc accatgtctg gtgcttttct gcccattaac tcaggcagtc ttcatcataa   170640
ccctgtggga gagggattgt tacaagtctc aatttaaaca tacagggatc gaaactcaga   170700
aagcaaagag aaagatagta ttatcgggtg tcttatgtgg cccacattga tgcacagcag   170760
tcatgctttc atattcaact cacaaaaatg gtcagcaaat tttccattaa tcacaaatca   170820
```

-continued

```
catagacata cccatatatg ccttaggatg ctcttctata tttgcacaca caggctcacc  170880
ccaaagataa tctctagttt gactgacatt ctgtcttcaa tgtcatcttt aggagctata  170940
tcatgggaac tctcataata tggtatggtg gaaagaacat gaggttggga atcagaacac  171000
ttcgggtctg ctcttagctc tgctagtaac ttattgtgtg atcccttccc cttctgggtc  171060
tcaatttctc tatctgtata atgtataaag cgtggtttgt atcaaattga tggtttccag  171120
tttttgaaaa aaggaacgct ttttgcacct taaactacct aaggaatcat aatgagagga  171180
aagattaggt aatagtgaaa gaattaccaa gtgttggtct aacagaagtt ggataacaga  171240
agttcctcag tgatggggaa ctcacttctt tcttatgtca tctgttgttt aaacaagtct  171300
ggttattaaa atattacagc ttaaggaatt cttagagatc ctctatccaa tgattcacaa  171360
actttccttt agcagccaag tgctttattt ctcaaaagaa ttgtacacag atacaagtgg  171420
agctagttta tttaaagcca gagcctgtag cttgggcctc accagttcag cctctttctc  171480
tctatcccag ggaagcccta ggtcactctt gcaaaatctt agggctccaa ggaacacagt  171540
ttgaaaacca gtgaagtata tgccctttaa aggttctcct aatcctgcaa ttatgattca  171600
aagattcttt tgaaataaca acaaccaaac cttctcttgt ggagtcaaag attaacctgc  171660
ctttcaataa taactgccat tcaggtagaa atttatagtg aacagagcaa ttttgtatgt  171720
attacctgaa ttgattctta taggaatcct ataacatgag attctttctc ttattttaca  171780
gaccaaatag ggaagctgtg agaatgatgt gattggccta tagttacata gtcagaaaat  171840
agcaggacca gaacttgagc ccaggttctc tcctgattcc aaattctctc tattccactc  171900
cacctgtagg ctgtagcacc actgcagttc tgtagctctg ggctttacag tgaggggcca  171960
aggcttcatt gaaggccact tgggtcatag tatgggcttg ttgcatttga agacatttca  172020
tgttggctgt caagtcttag atttgtattt ccaactcaca gggcctggtc acagccctaa  172080
ccatctctta taccttctca gcttgggaag ctgaggtcga ctagccaata gaacactgg   172140
gaaggaaacc caaggactct gactggatat gctctgtgcc aaaacagagg gttcactcag  172200
agaggaaaaa tataaaaaag aaaaaggaga aggttgcttt aattcttatc acttttttcat  172260
ctggatattt tgatatcatg tgtttgacag agattcaaag tttaatcttc ccaagcagtt  172320
tccaaacact tatctcattt ataggctac agagcttttt catatatatg atcccactta   172380
atctttacaa caattctatg aatcatagag actattattt ccatttcaca tgccaaggct  172440
caaagaggtt aactaacttg ctccatttgg tcacttaaca catggaacca gaacttgacc  172500
tagaccttcg ggtttctaaa ttggttatct tgacaataac ctagtgcaaa acactatagc  172560
agaatttgta tgacttggga tcactggggc tttccttggc ccaaccacca agatggaaag  172620
ccccctcccc ttacattaac aaatctgcaa gccaatatca gttcaccatc tagcttgcca  172680
gactaaatga tttctgaccc caagtctttt aaaagaatag cttcaaaaga aagccaatta  172740
ccacattcac aagaactgtt cttcatatta tctataatta cctacaagta caagtaattt  172800
gctaattcaa tagattgagt tcttgacctg taagatgaac tgtgctaggc ccctaataag  172860
ataaattttg ttttaagttt tctgtgacag taaagatgta tgaaaattgc ctagtagagt  172920
acctggcaca ttaataaatg ataactgtta atttggagtg ggtgagtaga ctgggtgtgc  172980
acagtatatt tagaatcaaa tttatctggt ttggaatcct agctatggac tagttctgtg  173040
accttgagca aatcacatgt cttctctgtg cttctgtgtc ctcatttgta agatgataga  173100
ataatcacta cctttcaaat tgttgtcaac aaaaagatta tgtataaaga gcacctagta  173160
```

```
acgtagcctg aaacatagtc aatgctctgt aaatggtggt ttattattat gagacttgaa  173220
tgctaagcca ctgctttcac gaaactcaat tttagctacc acttgccttg cctagaagct  173280
catgcatgga ccccaaggtg aaattgtgtt ctctgaagac ctcggctggc agatgtacta  173340
cagcagcaaa gatttccaaa ctggcctttc tttgagccca ttctcccaga ctagacagga  173400
gactacaagt ttctgctgca catgaaaaaa atatgatgtc aatcggattc tagtgagaaa  173460
acagagtctc aaagaaactg cttctgctcc ctagcgtgtt taatgtgttt cagaacctga  173520
gaatgactcc tctctgtttc tccagaacag cctaacacag tggcaaatgg gtgttgagtg  173580
aatgcatact taaggaaatc tgtagggttg cagctactct ttcctcaagt aatcccttga  173640
tagtcatgta ggctacttca gagattgggc attagagaac agagtcaggt attataatca  173700
gattagactc tagggaggtt agccagccat attgctgata tgtgcacagt tactgggttt  173760
gagtgctaag cagctctcat taaggacggt taattaatat tatggccaaa ttaagctttc  173820
ccttttctct cctctttgtt agttcggtgg cattttaggg agaaaaaaat aagcatcagt  173880
atggacaatt tgcttgatac ctgtacaatt taattctcat ccttccatgt gccttcacat  173940
tcacacattc caccagaaga ccaaggttca ccagccaaaa gctttcttg ctccccactg  174000 cctcctaccc aagatattca gggtcaacct cccaggcctc ttctctaaga gatccttggt  174060
tgctacatgc ttagaccctg cttcttattt cctgctgaga agggtcagtc caaggcattc  174120
tgtgctacag aagggttcca agcaggaact actctgggat ctgaggctcc agccggtctg  174180
tcagcgtgtc attacagtga aggtgggaag cacaggcctg ggagctaaga ctgctaagat  174240
gagggactct agaatccctg atacctggaa ggcctaggct ctaaaagaaa gaacaggga  174300 aatggggcta tatgagtgga cagggaccaa ccaagcagaa caatgtgtct ggataatgta  174360
gacttcagac ctgatcctat ggctgacaaa agctggtgac cttggtagtt cctgagctgt  174420
aaccttcatt agtggagtag aaaaaacact ggagaagaga atcagaacac ctgggttcta  174480
gtattagttc agccacatat aaaccatatg accttgggta agtcagttta tttctctggc  174540
cctcatgttc cttgttggta aaataagtgc cacatcacct aacctctggg attattgtga  174600
gagttaaatt aggtcatcaa caggaaagtg agaagtttga tctaaatttg gggaagcatt  174660
cctaatgagg tatgatgaca aaatttcaga taattctgga tttgttggtg agaagagaga  174720
gtgttggtag ggacgagctc tgaggtgatg cctttataac tttaagcatc caactgtttc  174780
aaaaactcca ggagaacatg gccatgtctg ttctacctgt gtattattgt agacgtagct  174840
tctgggagcc tctgctctct gagcttaagg gaggtaattt ggagatcatt taattctcat  174900
tttacaaaag gaaaaaaaat tgagggtctt taggccattt gtttaggtaa tatttcttaa  174960
gtgcccactc aaatacgtgg actgtactaa gtactaggga ggtaaagata aataagaaga  175020
tatggtccct gtcttcaaga agctccaagt cttgtggggg agacagacat gtatatacat  175080
agacttcaat gctgtgtaat gactgctata attgggtgag gctacacaag gtgcaatgag  175140
aatgtaaaag aagaatcttt aagccttctt cttggatgag ttgggaaagc cttcacgaaa  175200
gaggtagcct ttgagtgaag acttgaaaga tgagtagtgt ttaccggatg aaaggcctga  175260
gaaggaggaa tgcattctag gcaaaagtaa ctgcctgtgc agagataaca gagatataga  175320
ggcatgtgag agcgcaagtg gcaagagatc agtctaggta ggcaggtcat aaagggccta  175380
ttcatgtata atgatggcag taagatgagg atggcagtag ggtgggaaat tagtagggcc  175440
agggtaccta ttgagtagaa aagaatggag aggaaatgcc aggcagaaag aggatggacg  175500
caagagaggg aacatgaaag tggtgaacag gtggcagtgg ctgtcaagac atctctccat  175560
```

```
accctgtaca ctgtatgtaa tatccatctc ccagggttgt tagaagggtc aaaccagatc  175620
gtagctggaa aacagctttg tgaagtgaaa actgctgttt atgtggggga aatgattgtt  175680
aaactgcatc tttggaaagg tgaagtgatc aagagcacag accttggaat ctgactgctt  175740
tgctttgtaa cttggtctgc caattactag ctgtatgatc ttggacaagt tccttaacct  175800
ctctctgact cacttgtact ggttcacaga atggagataa taatagtact taccttactc  175860
attgttgtga atgttaaatg agataatata agtaaagtgc ttagaaaaga gttaaatgta  175920
ccccataaat acatacaact atcatgtacc caaaattatt tttaattttt ttaaaaaaga  175980
gcaatccaat agcaaaagaa aaaagagtt cactcatata agcagtcaat aagtgttaga  176040
ttattttttct cttacaactg acaatgccct ttttgtctcc atcatcatct catttgagca  176100
gctcagggaa gtagggagga taaggaatat tatcctcacc atatagtttg tgcttttccc  176160
caccacccct taatggccag cctggatggt ccctggggat ccttagggga tgcccgaata  176220
ccagagcatc tctgcccaac agggactcag acttagctca acccgtcagt acccagactg  176280
accactgcct ctgcctcttc ttctccaggc ttccgcaact tacacgtgga cgaccagatg  176340
gctgtcattc agtactcctg gatggggctc atggtgtttg ccatgggctg gcgatccttc  176400
accaatgtca actccaggat gctctacttc gcccctgatc tggttttcaa tgagtaagtg  176460
ctcctggggc ccagacctca ctaaaataca gcagcttggc cagacctggt tggtggtgat  176520
ggtgatgggg tgacagtgaa gcttagctca tttgatctgc agttgtcgca gcggatgccc  176580
cagccagcca atccagtatg aggcggcttt gccctggctt tcagccaact ggcaggagcc  176640
caggaggatg gtgctgagac cacccctttc acacccaaga accaatccta gtcatatttc  176700
tggtctgctt tgcagcttat ctcaaaacca catggaaaga ttcctccccct tcacatataa  176760
aagaggcaga aagactctgg ctttaagggc tggagtttct tgggttcttt tgctaccacc  176820
aaaggctact tctagtcacc atttgctgag caactagttt gtgccaagac tatgctagat  176880
actttctaaa tcctagctca ttgagtcctc atggtgacct gacctcacct ttttatagat  176940
aacactattt ttttatggat ggggaaaatc aggctcagca aaataaagtg actcacccaa  177000
agtcacagag ctagtgcctg ttggagacaa gattcaaacg tatgtccctg tcgatctcag  177060
ctcttctgcg tcatggtggt aactgatggg aaggagtacc tctaccgctc tctggctgtg  177120
tgaccttggt actgccattt tccttccctt aaacagcttt aattaatacc tgccctgcca  177180
ccagctccat ataacatcat gaatttggcc agtggctcag attttggaat tacatttttc  177240
tccactaaaa tctcagttct actatttttct tagtcagcat ctttgggaaa gacctttaac  177300
ttttccgacc ctcaatttct tcatccatta atgataacag aaccttcata agtaatttct  177360
tatgataact aaatgggaat tgacagatgt ggaatgtctg gcccatagta ggcaagaagg  177420
aaaaaaaaag tcccttttctg attcacccctt tccctaatag tgatacattt ttttccccg  177480
agatggggtt ttgctctgcc acccaggctg gagggcagtg gcgcaatgat ctcagcccag  177540
tgcaacctcc acctccctgg ttcaagcaat tctcctgcct cagcttcccg agtagctggg  177600
attatagatg cccgccaccg tgtccatcta attttgtat ttttggtaga cgggatttt  177660
caccatgtta gccaggctgg tctcaaactc ctgacctcat gatctgcccg cctcagccgg  177720
gcatgataat ctttttctatg tctgctgtat gaggtccctc gatggcattg tgaatggagc  177780
tggccagaga aatcttccca aggaccttga gctagtctca ccacagagaa tccttccagt  177840
caggacagga attgaccttc ccccctcttc agccctctaa cccagaagag tcttaaaata  177900
```

```
aaatctacag gccaatggtt ccttccagta cagcactgca atgcgaggga gagtgagcgt   177960
ccccagctgc cctctcccaa ccctgccagc ctggtagcca aaagctaaga ataaccacta   178020
ggcttttggc acaaactgct ttgtggtttt cagatctccg caaagttgcc tatgatgcca   178080
tcttctgggg caggccttga aaagccccct aactgttcat ctcccatcct taaaccccctg   178140 ctgcccttaa gcagttgaat caactccatg agcacctgct ctaccttccc cagagccctg   178200
agacctttgg agctttgaaa agtgataatt ggttgttctc taaatcctca tttccttctc   178260
tgcctctaag taagcatgtg gcatcccacc tcggcttcct ggtccagtct tgttcatctt   178320 ataaaaggc ctccctacgg ggtcagaggc ctagacccat caaacccagg gctcctgaaa    178380
caataggacc cctattcctc ctgtaggaag ccactgtgtt agagctctca gggtgtctac    178440
aaacatctag ataagtgttt ctcaacatgg attctgttga catattggga aaataatttt    178500
tgtcattatg tagaatatgg ttaacatacc tggcaccagc ctactctata ccaaatagga    178560
ttccagtcat tctgacagcc caaactgctc ccacacattt ctgacaccca ctgaagaggc    178620
agtactctcc agttgagtgc aactaatccc tgccagcctt cctaaggtgc taatgggggag   178680 cctcagaccc aaagagagag agaagaactt gtccaatgta ggtcaaccca tttgctgatc    178740
tcttcaacac caagctctat tatcagcccct gttttttct ttctttctct ctttgtagag    178800
atcacatgtt gtgaggataa tgagcttgaa ccttagctgt gtgaccttgg gcaaattact    178860
gaacttctat gtgccgcaaa ttttatctgg agactgctga agagtattat aatagcacct    178920
ttctatatgt catttattga acacctgcta tgtgtcaggc actgtgctca gtgttttcca    178980
atcttcattt ctcctcttat tttctctctt gcactcccac caaccttgtt ctcttcctaa    179040
attccattcc tgcctcattt ttctaccctc cattctcctc tctcttcctt cctttaactg    179100 tctcccctagt atttttcccc ttttccccct ttcttttccc cttcccccat gaatttcttc    179160
tctttccttt cccctttctct ttcctccatt ccccacttttt tctgcccctg aggcctgcag    179220
caatgttaaa ggaatcctca ttccagcatt gtgatttcaa tggtaaaaag attgcagcat    179280
tgtcatcaac agaggtggga aagtacattg gagactggag cagagccaga cctcagggtc    179340
agccaatctt actaaaaaat tctctacagt gaaagagctt ggagcaacac tgttctgctc    179400
aattgatttg tgataccatc taaacacttc ctctttctag ttgggcttca gcctgagttg    179460
ataattctat caccatctgc cctcttctct ctttctccag acagccaag atctctctga    179520 gataggatgc tgagcttcca cccagacaat accaggcctg ctcatcctat ggagtaggct   179580
agtggcttgg aaaccaaaat gtcaaaccat agcctttagg ctccatctgg gaggtctttg    179640
tcctcaccac ttaagtgggt gtcaaatttc cttcccttc tgcacacgct gcacaatcaa    179700
tttctgtctt acacacacac acacacacac acacacacac gatttttgaa gtgctgaaaa   179760
ctggaaggcc tactagcatg aggatgctgt gtcttctctt agaggtatgc catggtcagc    179820 catgaaccg agaggttgct cttccttgaa aagctggcca agcattggcc acttccccat    179880
ataatttata ggtgataatg tggtgatctg ttcagaagtg actataataa atgcaactca    179940
catatgtcta cagttccaa actgtggtaa ggagcagcca gcatatgagg gaatgggctc    180000
cccttcagca ggggacattt aaactagaca ttcaaaaaca ctccctggca gatttaacat   180060
tggaactcgt tttgaaagaa caatgtggaa tctccttcac tgggagtttt tgaataagta   180120
tgaaatttct agtattccag gccagaggca aaggggtcaa caggatgacc aaacacttcg   180180
ggtcatttgc aaatcttgat gtcctgatgt taagagctga ctactggggc ttctcctaaa    180240
aatccttcat gttgagctgc ctggaaggca ggttctcatt ctggctgtag ctgagatgtt    180300
```

```
agaactgtag tcagggagac catgtgcctc ccccattgtg ttcatttggt taggctttcc   180360
tgtccctgac tcagaaaaca gaaggggcac agagacctgg aaattccatg tgctaaccca   180420
tatcctggcc agagaagatg agtagttatc agggtgtcag gattttggaa aacagagaga   180480
gaaaaaaaac aaacaaacag acaaacaaac aaaaaaacct tttcctggtc cctggagcac   180540
cagcaggaga aacagcaagc tcttcttgga aaacctggcg agggatggca atcagagaca   180600
ttccctctgg gcttattgta aacttcccct cattcctttt tcctctgtgt atctccttcc   180660
caggtaccgc atgcacaagt cccggatgta cagccagtgt gtccgaatga ggcacctctc   180720
tcaagagttt ggatggctcc aaatcacccc ccaggaattc ctgtgcatga aagcactgct   180780
actcttcagc attagtaagt gcctagaagt gcagggaatg cccctgagg gcacagagat   180840 tcagagagga ccacttttgc cattaaaaca ttattaggga aaagccagct cctggacatt   180900
tcccttcttc attcccctc cccatcccca ctctactctc tctcagcatc attttcctaa   180960
caagaaacaa tttcatgact agaagccaat ttatttgcta gaagtcaacc tccatcagat   181020
tccccaccta tccccagtct gtctttggga caaggccttt ttgactggtt acagcaggtc   181080
tctgaatttt tccatagctt ctgctataga aacagacatg ggccaccttg tattctttgc   181140
agggcagtag agcaggaggc atttcctcct ggaaagattt cctcttctgc caacaggagg   181200
agatctatgt aagcaactca gataggattt gtatggcagc caaggaactt ttctttaata   181260
tcttttctaa gagccctctc ttagccccta cggagggaga agggcaaaat ttgatattca   181320
aagctatgtg ttttggttat ctaaatcagg gttttactgt gaatgacata aaagcttagg   181380
tcctaaaaaa tgagtatctg agaagagtag aaaaagaaaa ggttcaggaa atttgattta   181440
cttgactcct ttcagatcgg atccagctat cctttcccct gagatctccc tgacagactg   181500
aaggccccaa gcacacagac ttcaactaac aggaagccaa gtagatggtt ccctgtgggg   181560 gtggggtca agtctgtggt cagaaaactt ggtgctttgt ctaatgctcc ttcgtgggca   181620
tgcttcccct ccccattctg tcttcatccc acatcagttc cagtggatgg gctgaaaaat   181680
caaaaattct ttgatgaact tcgaatgaac tacatcaagg aactcgatcg tatcattgca   181740
tgcaaaagaa aaaatcccac atcctgctca agacgcttct accagctcac caagctcctg   181800
gactccgtgc agcctgtaag caaacgatgg agggtgcttt atcagggaga acagcctgat   181860
agagccaatg ataatatgct tctctagagt ctggcaccac ctgttgggag gtgcttccat   181920
tcccctctgg ctttgagtgt ggtccaggaa gaaaatgtgg tgaagaaaag aacacgggtc   181980
acagtgtccc agctggatat tgtgaaaggg gtggaggagt tgagaacaga gcagttggga   182040
ctcagggaag ggacttgcag cagatgaatt ctctaggcag acaaaacaga cctggatgtt   182100
tttcccctct tctttgagtc atgttcatgt gagtttgtct gtctgtgtgt gtgtgtgtgt   182160
gtgtgtgtgt gtgtgtgtgt gtgtcagaga gagagagaga gagagagaga tggagtgcgg   182220
aggcttgggt gagagcacaa gctggagaag tcttgagtca gagagcttac aatggtataa   182280
gacatctctt gggagccctc agtgactcca tggagaccat ttctttctct ctctctcgct   182340
gtctctctct aacacacaca cacacacaca cgacctcatg ggggaggacc aaggaagtac   182400
ggggaagggg gaggaaacaa aaggctgaaa gaccaaaaat cagaggttgg ggaagaggct   182460
agcagaggcc acctccttgt caaccctgtt tttctccctc ttattgttcc ctacagattg   182520
cgagagagct gcatcagttc acttttgacc tgctaatcaa gtcacacatg gtgagcgtgg   182580
actttccgga aatgatggca gagatcatct ctgtgcaagt gcccaagatc ctttctggga   182640
```

```
aagtcaagcc catctatttc cacacccagt gaagcattgg aaaccctatt tccccacccc 182700
agctcatgcc ccctttcaga tgtcttctgc ctgttataac tctgcactac tcctctgcag 182760
tgccttgggg aatttcctct attgatgtac agtctgtcat gaacatgttc ctgaattcta 182820
tttgctgggg tttttttttc tctttctctc ctttcttttt cttcttccct ccctatctaa 182880
ccctcccatg gcaccttcag actttgcttc ccattgtggc tcctatctgt gttttgaatg 182940
gtgttgtatg cctttaaatc tgtgatgatc ctcatatggc ccagtgtcaa gttgtgcttg 183000
tttacagcac tactctgtgc cagccacaca aacgtttact tatcttatgc cacgggaagt 183060
ttagagagct aagattatct ggggaaatca aaacaaaaac aagcaaacaa aaaaaaaag 183120
caaaacaaa acaaaaaata agccaaaaaa ccttgctagt gttttttcct caaaaataaa 183180
taaataaata aataaatacg tacatacata cacacataca tacaaacata tagaaatccc 183240
caaagaggcc aatagtgacg agaaggtgaa aattgcaggc ccatgggag ttactgattt 183300
tttcatctcc tccctccacg ggagacttta ttttctgcca atggctattg ccattagagg 183360
gcagagtgac cccagagctg agttgggcag ggggtggac agagaggaga ggacaaggag 183420
ggcaatggag catcagtacc tgcccacagc cttggtccct gggggctaga ctgctcaact 183480
gtggagcaat tcattatact gaaaatgtgc ttgttgttga aaatttgtct gcatgttaat 183540
gcctcaccc caaacccttt tctctctcac tctctgcctc caacttcaga ttgactttca 183600
atagttttc taagacctt gaactgaatg ttctcttcag ccaaaacttg gcgacttcca 183660
cagaaaagtc tgaccactga gaagaaggag agcagagatt taaccctttg taaggcccca 183720
tttggatcca ggtctgcttt tcatgtgtg agtcagggag gagctggagc cagaggagaa 183780
gaaaatgata gcttggctgt tctcctgctt aggacactga ctgaatagtt aaactctcac 183840
tgccactacc ttttccccac ctttaaaga cctgaatgaa gttttctgcc aaactccgtg 183900
aagccacaag caccttatgt cctcccttca gtgttttgtg ggcctgaatt tcatcacact 183960
gcatttcagc catggtcatc aagcctgttt gcttcttttg ggcatgttca cagattctct 184020
gttaagagcc cccaccacca agaaggttag caggccaaca gctctgacat ctatctgtag 184080
atgccagtag tcacaaagat ttcttaccaa ctctcagatc gctggagccc ttagacaaac 184140
tggaaagaag gcatcaaagg gatcaggcaa gctgggcgtc ttgcccttgt cccccagaga 184200
tgataccctc ccagcaagtg gagaagttct cacttccttc tttagagcag ctaaaggggc 184260
tacccagatc agggttgaag agaaaactca attaccaggg tgggaagaat gaaggcacta 184320
gaaccagaaa ccctgcaaat gctcttcttg tcacccagca tatccacctg cagaagtcat 184380
gagaagagag aaggaacaaa gaggagactc tgactactga attaaaatct tcagcggcaa 184440
agcctaaagc cagatggaca ccatctggtg agtttactca tcatcctcct ctgctgctga 184500
ttctgggctc tgacattgcc catactcact cagattcccc acctttgttg ctgcctctta 184560
gtcagaggga ggccaaacca ttgagacttt ctacagaacc atggcttctt tcggaaaggt 184620
ctggttggtg tggctccaat actttgccac ccatgaactc agggtgtgcc ctgggacact 184680
ggttttatat agtcttttgg cacacctgtg ttctgttgac ttcgttcttc aagcccaagt 184740
gcaagggaaa atgtccacct actttctcat cttggcctct gcctccttac ttagctctta 184800
atctcatctg ttgaactcaa gaaatcaagg gccagtcatc aagctgccca ttttaattga 184860
ttcactctgt ttgttgagag atagttttct gagtgacatg atatgatcca caagggtttc 184920
cttccctgat ttctgcattg atattaatag ccaaacgaac ttcaaaacag ctttaaataa 184980
caagggagag gggaacctaa gatgagtaat atgccaatcc aagactgctg gagaaaacta 185040
```

```
aagctgacag gttcccttt tgggtggga tagacatgtt ctggttttct ttattattac   185100
acaatctggc tcatgtacag gatcactttt agctgttta aacagaaaaa aatatccacc   185160
actcttttca gttacactag gttacatttt aataggtcct ttacatctgt tttggaatga   185220
ttttcatctt ttgtgataca cagattgaat tatatcattt tcatatctct ccttgtaaat   185280
actagaagct ctcctttaca tttctctatc aaattttca tctttatggg tttcccaatt   185340
gtgactcttg tcttcatgaa tatatgtttt tcatttgcaa aagccaaaaa tcagtgaaac   185400
agcagtgtaa ttaaaagcaa caactggatt actccaaatt tccaaatgac aaaactaggg   185460
aaaaatagcc tacacaagcc tttaggccta ctctttctgt gcttgggttt gagtgaacaa   185520
aggagatttt agcttggctc tgttctccca tggatgaaag gaggaggatt ttttttttct   185580
tttggccatt gatgttctag ccaatgtaat tgacagaagt ctcatttgc atgcgctctg   185640 ctctacaaac agagttggta tggttggtat actgtactca cctgtgaggg actggccact   185700
cagacccact tagctggtga gctagaagat gaggatcact cactgaaaaa gtcacaagga   185760
ccatctccaa acaagttggc agtgctcgat gtggacgaag agtgaggaag agaaaaagaa   185820
ggagcaccag ggagaaggct ccgtctgtgc tgggcagcag acagctgcca ggatcacgaa   185880
ctctgtagtc aaagaaaaga gtcgtgtggc agtttcagct ctcgttcatt gggcagctcg   185940
cctaggccca gcctctgagc tgacatggga gttgttggat tctttgtttc atagcttttt   186000
ctatgccata ggcaatattg ttgttcttgg aaagtttatt attttttaa ctcccttact   186060 ctgagaaagg gatattttga aggactgtca tatatctttg aaaaagaaa atctgtaata   186120 catatatttt tatgtatgtt cactggcact aaaaaatata gagagcttca ttctgtcctt   186180
tgggtagttg ctgaggtaat tgtccaggtt gaaaaataat gtgctgatgc tagagtccct   186240
ctctgtccat actctacttc taaatacata taggcataca tagcaagttt tatttgactt   186300
gtactttaag agaaaatatg tccaccatcc acatgatgca caaatgagct aacattgagc   186360
ttcaagtagc ttcaagtgt ttgttcatt aggcacagca cagatgtggc ctttcccccc   186420
ttctctccct tgatatctgg cagggcataa aggcccaggc cacttcctct gccccttccc   186480
agccctgcac caaagctgca tttcaggaga ctctctccag acagcccagt aactacccga   186540
gcatggcccc tgcatagccc tggaaaaata agaggctgac tgtctacgaa ttatcttgtg   186600
ccagttgccc aggtgagagg gcactgggcc aagggagtgg ttttcatgtt tgacccacta   186660
caaggggtca tgggaatcag gaatgccaaa gcaccagatc aaatccaaaa cttaaagtca   186720
aaataagcca ttcagcatgt tcagtttctt ggaaaaggaa gttctaccc ctgatgcctt   186780 tgtaggcaga tctgttctca ccattaatct ttttgaaaat cttttaaagc agttttaaa   186840 aagagagatg aaagcatcac attatataac caaagattac attgtacctg ctaagatacc   186900
aaaattcata agggcagggg gggagcaagc attagtgcct cttgataag ctgtccaaag   186960 acagactaaa ggactctgct ggtgactgac ttataagagc tttgtgggtt tttttttccc   187020
taataatata catgtttaga agaattgaaa ataatttcgg gaaaatggga ttatgggtcc   187080
ttcactaagt gatttataa gcagaactgg ctttccttt ctctagtagt tgctgagcaa   187140
attgttgaag ctccatcatt gcatggttgg aaatggagct gttcttagcc actgtgtttg   187200
ctagtgccca tgttagctta tctgaagatg tgaaacccct gctgataagg gagcatttaa   187260
agtactagat tttgcactag agggacagca ggcagaaatc cttatttctg cccactttgg   187320
atggcacaaa aagttatctg cagttgaagg cagaaagttg aaatacattg taaatgaata   187380
```

```
tttgtatcca tgtttcaaaa ttgaaatata tatatatata tatatatata tatatatata   187440
tatatagtgt gtgtgtgtgt tctgatagct ttaactttct ctgcatcttt atatttggtt   187500
ccagatcaca cctgatgcca tgtacttgtg agagaggatg cagttttgtt ttggaagctc   187560
tctcagaaca aacaagacac ctggattgat cagttaacta aaagttttct ccctattgg    187620
gtttgaccca caggtcctgt gaaggagcag agggataaaa agagtagagg acatgataca   187680
ttgtacttta ctagttcaag acagatgaat gtggaaagca taaaaactca atggaactga   187740
ctgagattta ccacagggaa ggcccaaact tggggccaaa agcctaccca agtgattgac   187800
cagtggcccc ctaatgggac ctgagctgtt ggaagaagag aactgttcct tggtcttcac   187860
catccttgtg agagaagggc agtttcctgc attggaacct ggagcaagcg ctctatcttt   187920
cacacaaatt ccctcacctg agattgaggt gctcttgtta ctgggtgtct gtgtgctgta   187980
attctggttt tggatatgtt ctgtaaagat tttgacaaat gaaaatgtgt ttttctctgt   188040
taaaacttgt cagagtacta gaagttgtat ctctgtaggt gcaggtccat ttctgcccac   188100
aggtagggtg ttttctttg attaagagat tgacacttct gttgcctagg acctcccaac    188160
tcaaccattt ctaggtgaag gcagaaaaat ccacattagt tactcctctt cagacatttc   188220
agctgagata acaaatcttt tggaattttt tcacccatag aaagagtggt agatatttga   188280
atttagcagg tggagtttca tagtaaaaac agcttttgac tcagctttga tttatcctca   188340
tttgatttgg ccagaaagta ggtaatatgc attgattggc ttctgattcc aattcagtat   188400
agcaaggtgc taggtttttt cctttcccca cctgtctctt agcctgggga attaaatgag   188460
aagccttaga atgggtggcc cttgtgacct gaaacacttc ccacataagc tacttaacaa   188520
gattgtcatg gagctgcaga ttccattgcc caccaaagac tagaacacac acatatccat   188580
acaccaaagg aaagacaatt ctgaaatgct gtttctctgg tggttccctc tctggctgct   188640
gcctcacagt atgggaacct gtactctgca gaggtgacag gccagatttg cattatctca   188700
caaccttagc ccttggtgct aactgtccta cagtgaagtg cctgggggt tgtcctatcc     188760
cataagccac ttggatgctg acagcagcca ccatcagaat gacccacgca aaaaaagaa     188820
aaaaaaatt aaaagtcccc ctcacaaccc agtgacacct ttctgctttc ctctagactg     188880
gaacattgat tagggagtgc ctcagacatg acattcttgt gctgtccttg gaattaatct   188940
ggcagcagga gggagcagac tatgtaaaca gagataaaaa ttaattttca atattgaagg   189000
aaaaaagaaa taagaagaga gagagaaaga aagcatcaca caaagatttt cttaaaagaa   189060
acaattttgc ttgaaatctc tttagatggg gctcatttct cacggtggca cttggcctcc   189120
actgggcagc aggaccagct ccaagcgcta gtgttctgtt ctcttttgt aatcttggaa     189180
tcttttgttg ctctaaatac aattaaaaat ggcagaaact tgtttgttgg actacatgtg   189240
tgactttggg tctgtctctg cctctgcttt cagaaatgtc atccattgtg taaaatattg   189300
gcttactggt ctgccagcta aaacttggcc acatcccctg ttatggctgc aggatcgagt   189360
tattgttaac aaagagaccc aagaaaagct gctaatgtcc tcttatcatt gttgttaatt   189420
tgttaaaaca taagaaatc taaaatttca gatgaatgtc atcagagttc ttttaattag    189480
ctcttttat tggctgtttt tattgaagtc aagagttggt atcatgcccg gttgcgtttt    189540
atgctatttt gatttcata tattttaaa agtctttgca caagggttac aaatttgccc     189600
tgtggtggcc ttagcataag ctgacctggg accaccaaaa taacaaggaa tttgggctag   189660
aaagcacaga tggacactgg tgacccatca caacttctct tgaaaaccc caaacttgtc    189720
agctggggaa aagccacaca aagcccagct gcccaccttc acatccttat ccttgtagga   189780
```

```
gcataaaatg gtgtcatcac tgcccagttc taaccaagct tcagttaaag aatgggtacc  189840
ttcacatctt cactattttt caggggcctt accgtccttg accacccaag taaaatctaa  189900
atcagccttc ttttgggttc ttcagttcaa gcaaggcctc ttcttgtggc ctctcagtat  189960
taatatttat gaggttgcag attgaatttt tgggcctgag atacaagcca tcaatgaggt  190020
gtgacaaagc atgtcaatga ataataagaa aattatctat tcttccatat cctcccctgt  190080
aataagggtt gtcagaatgc cttctttctg ggctgggttg aggattcagt gagaacatat  190140
gtgacacagc tggtgggcta ttaagctctg gctttgctcc ctgttaaaat gccagaaccc  190200
ttgagaggga tcccacattg agccatgttt atcactgacc accttagaat ggatggattt  190260
ctcagatttt tcctgagatc aatgcttgat ggagaggaga ggagaacaat agattcttgg  190320
gatgtgtgtt atgcatgtgt ttaagtaaga gacagagagt atgtttattt gcaggttgtg  190380
tgtgtaaagt cagagcctgc ctccagagga tcttctctaa ccaccattgc ttaggtcctg  190440
ttcgtttgca tctacagcga atgacccttac agccatctga cttggcttca ctcaccactc  190500
agctcctgcc taaacagacg aggtggttag catccaccat aagttttcca aggagtagca  190560
aagcacaaag acacctatt gggttgaaaa gagcctagag gcatgagtcc tgtgtgtgac  190620 tgttcatag tcatgcagct agtgtatagc taggattctc ccctgctgat ttactatgtg  190680
acactaggca gcaatctgcc cttgctggac ctcggttttc taatctgtaa aatgtgtgga  190740
gtaaaactac atgagatggg aagtcccttc tagtgcagat gccatggtta ttgaaaactg  190800
cagcaacatc tttcttaatc gtaagggaa agaaaaagac catttactac tcctagaaca  190860
gttttggagc tagaatattc acatttgcac tcaataatta tttacaaaac aactagtgtg  190920
gagagggtca aaacaacagc tgagtcctgt gtaatagata ttgtcaaccc cttgatggat  190980
gaggaagggg ctcaaaggga a                                             191001
```

<210> SEQ ID NO 2
<211> LENGTH: 10661
<212> TYPE: DNA
<213> ORGANISM: Homo sapiens
<220> FEATURE:
<221> NAME/KEY: CDS
<222> LOCATION: (1116)..(3878)

<400> SEQUENCE: 2

```
cgagatcccg gggagccagc ttgctgggag agcgggacgg tccggagcaa gcccagaggc   60
agaggaggcg acagagggaa aaagggccga gctagccgct ccagtgctgt acaggagccg  120
aagggacgca ccacgccagc cccagcccgg ctccagcgac agccaacgcc tcttgcagcg  180
cggcggcttc gaagccgccg cccggagctg cccttcctc ttcggtgaag ttttaaaag   240 ctgctaaaga ctcggaggaa gcaaggaaag tgcctggtag gactgacggc tgcctttgtc  300
ctcctcctct ccacccgcc tccccccacc ctgccttccc ccctccccc gtcttctctc   360 ccgcagctgc ctcagtcggc tactctcagc caacccccct caccacccct ctccccaccc  420 gccccccgc cccgtcggc ccagcgctgc cagcccgagt ttgcagagag gtaactccct  480
ttggctgcga gcgggcgagc tagctgcaca ttgcaaagaa ggctcttagg agccaggcga  540
ctggggagcg gcttcagcac tgcagccacg accggcctgg ttaggctgca cgcggagaga  600
accctctgtt ttccccccact ctctctccac ctcctcctgc cttccccacc ccgagtgcgg  660
agccagagat caaagatga aaaggcagtc aggtcttcag tagccaaaaa acaaaacaaa  720
caaaaacaaa aaagccgaaa taaagaaaa agataataac tcagttctta tttgcaccta   780
```

```
cttcagtgga cactgaattt ggaaggtgga ggatttttgtt ttttctttt aagatctggg      840 catctttga atctaccctt caagtattaa gagacagact gtgagcctag cagggcagat      900
cttgtccacc gtgtgtcttc ttctgcacga gactttgagg ctgtcagagc gcttttttgcg     960 tggttgctcc cgcaagtttc cttctctgga gcttcccgca ggtgggcagc tagctgcagc    1020
gactaccgca tcatcacagc ctgttgaact cttctgagca agagaagggg aggcggggta    1080
agggaagtag gtggaagatt cagccaagct caagg atg gaa gtg cag tta ggg      1133
                                        Met Glu Val Gln Leu Gly
                                         1               5 ctg gga agg gtc tac cct cgg ccg ccg tcc aag acc tac cga gga gct      1181
Leu Gly Arg Val Tyr Pro Arg Pro Pro Ser Lys Thr Tyr Arg Gly Ala
         10                  15                  20 ttc cag aat ctg ttc cag agc gtg cgc gaa gtg atc cag aac ccg ggc      1229
Phe Gln Asn Leu Phe Gln Ser Val Arg Glu Val Ile Gln Asn Pro Gly
     25                  30                  35 ccc agg cac cca gag gcc gcg agc gca gca cct ccc ggc gcc agt ttg      1277
Pro Arg His Pro Glu Ala Ala Ser Ala Ala Pro Pro Gly Ala Ser Leu
 40                  45                  50 ctg ctg ctg cag cag cag cag cag cag cag cag cag cag cag cag         1325
Leu Leu Leu Gln Gln Gln Gln Gln Gln Gln Gln Gln Gln Gln Gln
55                  60                  65                  70 cag cag cag cag cag cag cag cag cag caa gag act agc ccc agg cag      1373
Gln Gln Gln Gln Gln Gln Gln Gln Gln Glu Thr Ser Pro Arg Gln
                 75                  80                  85 cag cag cag cag cag ggt gag gat ggt tct ccc caa gcc cat cgt aga      1421
Gln Gln Gln Gln Gln Gly Glu Asp Gly Ser Pro Gln Ala His Arg Arg
         90                  95                 100 ggc ccc aca ggc tac ctg gtc ctg gat gag gaa cag caa cct tca cag      1469
Gly Pro Thr Gly Tyr Leu Val Leu Asp Glu Glu Gln Gln Pro Ser Gln
        105                 110                 115 ccg cag tcg gcc ctg gag tgc cac ccc gag aga ggt tgc gtc cca gag      1517
Pro Gln Ser Ala Leu Glu Cys His Pro Glu Arg Gly Cys Val Pro Glu
    120                 125                 130 cct gga gcc gcc gtg gcc gcc agc aag ggg ctg ccg cag cag ctg cca      1565
Pro Gly Ala Ala Val Ala Ala Ser Lys Gly Leu Pro Gln Gln Leu Pro
135                 140                 145                 150 gca cct ccg gac gag gat gac tca gct gcc cca tcc acg ttg tcc ctg      1613
Ala Pro Pro Asp Glu Asp Asp Ser Ala Ala Pro Ser Thr Leu Ser Leu
                155                 160                 165 ctg ggc ccc act ttc ccc ggc tta agc agc tgc tcc gct gac ctt aaa      1661
Leu Gly Pro Thr Phe Pro Gly Leu Ser Ser Cys Ser Ala Asp Leu Lys
        170                 175                 180 gac atc ctg agc gag gcc agc acc atg caa ctc ctt cag caa cag cag      1709
Asp Ile Leu Ser Glu Ala Ser Thr Met Gln Leu Leu Gln Gln Gln Gln
    185                 190                 195 cag gaa gca gta tcc gaa ggc agc agc agc ggg aga gcg agg gag gcc      1757
Gln Glu Ala Val Ser Glu Gly Ser Ser Ser Gly Arg Ala Arg Glu Ala
200                 205                 210 tcg ggg gct ccc act tcc tcc aag gac aat tac tta ggg ggc act tcg      1805
Ser Gly Ala Pro Thr Ser Ser Lys Asp Asn Tyr Leu Gly Gly Thr Ser
215                 220                 225                 230 acc att tct gac aac gcc aag gag ttg tgt aag gca gtg tcg gtg tcc      1853
Thr Ile Ser Asp Asn Ala Lys Glu Leu Cys Lys Ala Val Ser Val Ser
                235                 240                 245 atg ggc ctg ggt gtg gag gcg ttg gag cat ctg agt cca ggg gaa cag      1901
Met Gly Leu Gly Val Glu Ala Leu Glu His Leu Ser Pro Gly Glu Gln
        250                 255                 260
```

```
ctt cgg ggg gat tgc atg tac gcc cca ctt ttg gga gtt cca ccc gct    1949
Leu Arg Gly Asp Cys Met Tyr Ala Pro Leu Leu Gly Val Pro Pro Ala
    265                 270                 275 gtg cgt ccc act cct tgt gcc cca ttg gcc gaa tgc aaa ggt tct ctg    1997
Val Arg Pro Thr Pro Cys Ala Pro Leu Ala Glu Cys Lys Gly Ser Leu
280                 285                 290 cta gac gac agc gca ggc aag agc act gaa gat act gct gag tat tcc    2045
Leu Asp Asp Ser Ala Gly Lys Ser Thr Glu Asp Thr Ala Glu Tyr Ser
295                 300                 305                 310 cct ttc aag gga ggt tac acc aaa ggg cta gaa ggc gag agc cta ggc    2093
Pro Phe Lys Gly Gly Tyr Thr Lys Gly Leu Glu Gly Glu Ser Leu Gly
            315                 320                 325 tgc tct ggc agc gct gca gca ggg agc tcc ggg aca ctt gaa ctg ccg    2141
Cys Ser Gly Ser Ala Ala Ala Gly Ser Ser Gly Thr Leu Glu Leu Pro
        330                 335                 340 tct acc ctg tct ctc tac aag tcc gga gca ctg gac gag gca gct gcg    2189
Ser Thr Leu Ser Leu Tyr Lys Ser Gly Ala Leu Asp Glu Ala Ala Ala
            345                 350                 355 tac cag agt cgc gac tac tac aac ttt cca ctg gct ctg gcc gga ccg    2237
Tyr Gln Ser Arg Asp Tyr Tyr Asn Phe Pro Leu Ala Leu Ala Gly Pro
360                 365                 370 ccg ccc cct ccg ccg cct ccc cat ccc cac gct cgc atc aag ctg gag    2285
Pro Pro Pro Pro Pro Pro Pro His Pro His Ala Arg Ile Lys Leu Glu
375                 380                 385                 390 aac ccg ctg gac tac ggc agc gcc tgg gcg gct gcg gcg cag tgc        2333
Asn Pro Leu Asp Tyr Gly Ser Ala Trp Ala Ala Ala Ala Gln Cys
                395                 400                 405 cgc tat ggg gac ctg gcg agc ctg cat ggc gcg ggt gca gcg gga ccc    2381
Arg Tyr Gly Asp Leu Ala Ser Leu His Gly Ala Gly Ala Ala Gly Pro
            410                 415                 420 ggt tct ggg tca ccc tca gcc gcc gct tcc tca tcc tgg cac act ctc    2429
Gly Ser Gly Ser Pro Ser Ala Ala Ala Ser Ser Ser Trp His Thr Leu
        425                 430                 435 ttc aca gcc gaa gaa ggc cag ttg tat gga ccg tgt ggt ggt ggt ggg    2477
Phe Thr Ala Glu Glu Gly Gln Leu Tyr Gly Pro Cys Gly Gly Gly Gly
        440                 445                 450 ggt ggt ggc ggc ggc ggc ggc ggc ggc ggc ggc ggc ggc ggc ggc ggc    2525
Gly Gly Gly Gly Gly Gly Gly Gly Gly Gly Gly Gly Gly Gly Gly Gly
455                 460                 465                 470 ggc ggc ggc gag gcg gga gct gta gcc ccc tac ggc tac act cgg ccc    2573
Gly Gly Gly Glu Ala Gly Ala Val Ala Pro Tyr Gly Tyr Thr Arg Pro
            475                 480                 485 cct cag ggg ctg gcg ggc cag gaa agc gac ttc acc gca cct gat gtg    2621
Pro Gln Gly Leu Ala Gly Gln Glu Ser Asp Phe Thr Ala Pro Asp Val
        490                 495                 500 tgg tac cct ggc ggc atg gtg agc aga gtg ccc tat ccc agt ccc act    2669
Trp Tyr Pro Gly Gly Met Val Ser Arg Val Pro Tyr Pro Ser Pro Thr
        505                 510                 515 tgt gtc aaa agc gaa atg ggc ccc tgg atg gat agc tac tcc gga cct    2717
Cys Val Lys Ser Glu Met Gly Pro Trp Met Asp Ser Tyr Ser Gly Pro
520                 525                 530 tac ggg gac atg cgt ttg gag act gcc agg gac cat gtt ttg ccc att    2765
Tyr Gly Asp Met Arg Leu Glu Thr Ala Arg Asp His Val Leu Pro Ile
535                 540                 545                 550 gac tat tac ttt cca ccc cag aag acc tgc ctg atc tgt gga gat gaa    2813
Asp Tyr Tyr Phe Pro Pro Gln Lys Thr Cys Leu Ile Cys Gly Asp Glu
            555                 560                 565 gct tct ggg tgt cac tat gga gct ctc aca tgt gga agc tgc aag gtc    2861
Ala Ser Gly Cys His Tyr Gly Ala Leu Thr Cys Gly Ser Cys Lys Val
        570                 575                 580
```

| | | | | | | | | | | | | | | | |
|---|---|---|---|---|---|---|---|---|---|---|---|---|---|---|---|
| ttc | ttc | aaa | aga | gcc | gct | gaa | ggg | aaa | cag | aag | tac | ctg | tgc | gcc | agc | 2909 |
| Phe | Phe | Lys | Arg | Ala | Ala | Glu | Gly | Lys | Gln | Lys | Tyr | Leu | Cys | Ala | Ser | |
| | | 585 | | | | 590 | | | | | 595 | | | | | |
| aga | aat | gat | tgc | act | att | gat | aaa | ttc | cga | agg | aaa | aat | tgt | cca | tct | 2957 |
| Arg | Asn | Asp | Cys | Thr | Ile | Asp | Lys | Phe | Arg | Arg | Lys | Asn | Cys | Pro | Ser | |
| | 600 | | | | | 605 | | | | | 610 | | | | | |
| tgt | cgt | ctt | cgg | aaa | tgt | tat | gaa | gca | ggg | atg | act | ctg | gga | gcc | cgg | 3005 |
| Cys | Arg | Leu | Arg | Lys | Cys | Tyr | Glu | Ala | Gly | Met | Thr | Leu | Gly | Ala | Arg | |
| 615 | | | | | 620 | | | | | 625 | | | | | 630 | |
| aag | ctg | aag | aaa | ctt | ggt | aat | ctg | aaa | cta | cag | gag | gaa | gga | gag | gct | 3053 |
| Lys | Leu | Lys | Lys | Leu | Gly | Asn | Leu | Lys | Leu | Gln | Glu | Glu | Gly | Glu | Ala | |
| | | | | 635 | | | | | 640 | | | | | 645 | | |
| tcc | agc | acc | acc | agc | ccc | act | gag | gag | aca | acc | cag | aag | ctg | aca | gtg | 3101 |
| Ser | Ser | Thr | Thr | Ser | Pro | Thr | Glu | Glu | Thr | Thr | Gln | Lys | Leu | Thr | Val | |
| | | | 650 | | | | | 655 | | | | | 660 | | | |
| tca | cac | att | gaa | ggc | tat | gaa | tgt | cag | ccc | atc | ttt | ctg | aat | gtc | ctg | 3149 |
| Ser | His | Ile | Glu | Gly | Tyr | Glu | Cys | Gln | Pro | Ile | Phe | Leu | Asn | Val | Leu | |
| | | 665 | | | | | 670 | | | | | 675 | | | | |
| gaa | gcc | att | gag | cca | ggt | gta | gtg | tgt | gct | gga | cac | gac | aac | aac | cag | 3197 |
| Glu | Ala | Ile | Glu | Pro | Gly | Val | Val | Cys | Ala | Gly | His | Asp | Asn | Asn | Gln | |
| | | 680 | | | | | 685 | | | | | 690 | | | | |
| ccc | gac | tcc | ttt | gca | gcc | ttg | ctc | tct | agc | ctc | aat | gaa | ctg | gga | gag | 3245 |
| Pro | Asp | Ser | Phe | Ala | Ala | Leu | Leu | Ser | Ser | Leu | Asn | Glu | Leu | Gly | Glu | |
| 695 | | | | | 700 | | | | | 705 | | | | | 710 | |
| aga | cag | ctt | gta | cac | gtg | gtc | aag | tgg | gcc | aag | gcc | ttg | cct | ggc | ttc | 3293 |
| Arg | Gln | Leu | Val | His | Val | Val | Lys | Trp | Ala | Lys | Ala | Leu | Pro | Gly | Phe | |
| | | | | 715 | | | | | 720 | | | | | 725 | | |
| cgc | aac | tta | cac | gtg | gac | gac | cag | atg | gct | gtc | att | cag | tac | tcc | tgg | 3341 |
| Arg | Asn | Leu | His | Val | Asp | Asp | Gln | Met | Ala | Val | Ile | Gln | Tyr | Ser | Trp | |
| | | | 730 | | | | | 735 | | | | | 740 | | | |
| atg | ggg | ctc | atg | gtg | ttt | gcc | atg | ggc | tgg | cga | tcc | ttc | acc | aat | gtc | 3389 |
| Met | Gly | Leu | Met | Val | Phe | Ala | Met | Gly | Trp | Arg | Ser | Phe | Thr | Asn | Val | |
| | | 745 | | | | | 750 | | | | | 755 | | | | |
| aac | tcc | agg | atg | ctc | tac | ttc | gcc | cct | gat | ctg | gtt | ttc | aat | gag | tac | 3437 |
| Asn | Ser | Arg | Met | Leu | Tyr | Phe | Ala | Pro | Asp | Leu | Val | Phe | Asn | Glu | Tyr | |
| 760 | | | | | 765 | | | | | 770 | | | | | | |
| cgc | atg | cac | aag | tcc | cgg | atg | tac | agc | cag | tgt | gtc | cga | atg | agg | cac | 3485 |
| Arg | Met | His | Lys | Ser | Arg | Met | Tyr | Ser | Gln | Cys | Val | Arg | Met | Arg | His | |
| 775 | | | | | 780 | | | | | 785 | | | | | 790 | |
| ctc | tct | caa | gag | ttt | gga | tgg | ctc | caa | atc | acc | ccc | cag | gaa | ttc | ctg | 3533 |
| Leu | Ser | Gln | Glu | Phe | Gly | Trp | Leu | Gln | Ile | Thr | Pro | Gln | Glu | Phe | Leu | |
| | | | | 795 | | | | | 800 | | | | | 805 | | |
| tgc | atg | aaa | gca | ctg | cta | ctc | ttc | agc | att | att | cca | gtg | gat | ggg | ctg | 3581 |
| Cys | Met | Lys | Ala | Leu | Leu | Leu | Phe | Ser | Ile | Ile | Pro | Val | Asp | Gly | Leu | |
| | | | 810 | | | | | 815 | | | | | 820 | | | |
| aaa | aat | caa | aaa | ttc | ttt | gat | gaa | ctt | cga | atg | aac | tac | atc | aag | gaa | 3629 |
| Lys | Asn | Gln | Lys | Phe | Phe | Asp | Glu | Leu | Arg | Met | Asn | Tyr | Ile | Lys | Glu | |
| | | | 825 | | | | | 830 | | | | | 835 | | | |
| ctc | gat | cgt | atc | att | gca | tgc | aaa | aga | aaa | aat | ccc | aca | tcc | tgc | tca | 3677 |
| Leu | Asp | Arg | Ile | Ile | Ala | Cys | Lys | Arg | Lys | Asn | Pro | Thr | Ser | Cys | Ser | |
| | 840 | | | | | 845 | | | | | 850 | | | | | |
| aga | cgc | ttc | tac | cag | ctc | acc | aag | ctc | ctg | gac | tcc | gtg | cag | cct | att | 3725 |
| Arg | Arg | Phe | Tyr | Gln | Leu | Thr | Lys | Leu | Leu | Asp | Ser | Val | Gln | Pro | Ile | |
| 855 | | | | | 860 | | | | | 865 | | | | | 870 | |
| gcg | aga | gag | ctg | cat | cag | ttc | act | ttt | gac | ctg | cta | atc | aag | tca | cac | 3773 |
| Ala | Arg | Glu | Leu | His | Gln | Phe | Thr | Phe | Asp | Leu | Leu | Ile | Lys | Ser | His | |
| | | | | 875 | | | | | 880 | | | | | 885 | | |
| atg | gtg | agc | gtg | gac | ttt | ccg | gaa | atg | atg | gca | gag | atc | atc | tct | gtg | 3821 |
| Met | Val | Ser | Val | Asp | Phe | Pro | Glu | Met | Met | Ala | Glu | Ile | Ile | Ser | Val | |

```
              890                 895                 900
caa gtg ccc aag atc ctt tct ggg aaa gtc aag ccc atc tat ttc cac    3869
Gln Val Pro Lys Ile Leu Ser Gly Lys Val Lys Pro Ile Tyr Phe His
        905                 910                 915 acc cag tga agcattggaa accctatttc cccacccag ctcatgcccc              3918
Thr Gln
    920 ctttcagatg tcttctgcct gttataactc tgcactactc ctctgcagtg ccttggggaa    3978 tttcctctat tgatgtacag tctgtcatga acatgttcct gaattctatt tgctgggctt    4038 tttttttctc tttctctcct ttcttttttct tcttccctcc ctatctaacc ctcccatggc   4098 accttcagac tttgcttccc attgtggctc ctatctgtgt tttgaatggt gttgtatgcc    4158 tttaaatctg tgatgatcct catatggccc agtgtcaagt tgtgcttgtt tacagcacta    4218 ctctgtgcca gccacacaaa cgtttactta tcttatgcca cgggaagttt agagagctaa    4278 gattatctgg ggaaatcaaa acaaaaacaa gcaaacaaaa aaaaaagca aaaacaaaac     4338 aaaaaataag ccaaaaaacc ttgctagtgt ttttccctca aaaataaata aataaataaa    4398 taaatacgta catacataca cacatacata caaacatata gaaatcccca agaggccaa     4458 tagtgacgag aaggtgaaaa ttgcaggccc atggggagtt actgattttt tcatctcctc    4518 cctccacggg agactttatt ttctgccaat ggctattgcc attagagggc agagtgaccc    4578 cagagctgag ttgggcaggg gggtggacag agaggagagg acaaggaggg caatggagca    4638 tcagtacctg cccacagcct tggtccctgg gggctagact gctcaactgt ggagcaattc    4698 attatactga aaatgtgctt gttgttgaaa atttgtctgc atgttaatgc ctcacccca     4758 aaccctttc tctctcactc tctgcctcca acttcagatt gactttcaat agtttttcta    4818 agaccttga actgaatgtt ctcttcagcc aaaacttggc gacttccaca gaaaagtctg     4878 accactgaga agaaggagag cagagattta accctttgta aggccccatt tggatccagg    4938 tctgctttct catgtgtgag tcagggagga gctggagcca gaggagaaga aaatgatagc    4998 ttggctgttc tcctgcttag gacactgact gaatagttaa actctcactg ccactacctt    5058 ttccccacct ttaaaagacc tgaatgaagt tttctgccaa actccgtgaa gccacaagca    5118 ccttatgtcc tcccttcagt gttttgtggg cctgaatttc atcacactgc atttcagcca    5178 tggtcatcaa gcctgtttgc ttcttttggg catgttcaca gattctctgt taagagcccc    5238 caccaccaag aaggttagca ggccaacagc tctgacatct atctgtagat gccagtagtc    5298 acaaagattt cttaccaact ctcagatcgc tggagcccctt agacaaactg aaagaaggc    5358 atcaagggga tcaggcaagc tgggcgtctt gcccttgtcc cccagagatg ataccctccc    5418 agcaagtgga gaagttctca cttccttctt tagagcagct aaaggggcta cccagatcag    5478 ggttgaagag aaaactcaat taccagggtg gaagaatga aggcactaga accagaaacc     5538 ctgcaaatgc tcttcttgtc acccagcata tccacctgca gaagtcatga gaagagagaa    5598 ggaacaaaga ggagactctg actactgaat taaaatcttc agcggcaaag cctaaagcca    5658 gatggacacc atctggtgag tttactcatc atcctcctct gctgctgatt ctgggctctg    5718 acattgccca tactcactca gattcccac ctttgttgct gcctcttagt cagagggagg     5778 ccaaaccatt gagactttct acagaaccat ggcttctttc ggaaaggtct ggttggtgtg    5838 gctccaatac tttgccaccc atgaactcag ggtgtgccct gggacactgg ttttatatag    5898 tcttttggca cacctgtgtt ctgttgactt cgttcttcaa gccagtgc aagggaaaat     5958 gtccacctac tttctcatct tggcctctgc ctccttactt agctcttaat ctcatctgtt    6018
```

```
gaactcaaga aatcaagggc cagtcatcaa gctgcccatt ttaattgatt cactctgttt    6078
gttgagagga tagtttctga gtgacatgat atgatccaca agggtttcct tccctgattt    6138
ctgcattgat attaatagcc aaacgaactt caaaacagct ttaaataaca agggagaggg    6198
gaacctaaga tgagtaatat gccaatccaa gactgctgga gaaaactaaa gctgacaggt    6258
tccctttttg gggtgggata gacatgttct ggttttcttt attattacac aatctggctc    6318
atgtacagga tcacttttag ctgttttaaa cagaaaaaaa tatccaccac tcttttcagt    6378
tacactaggt tacattttaa taggtccttt acatctgttt tggaatgatt ttcatctttt    6438
gtgatacaca gattgaatta tatcattttc atatctctcc ttgtaaatac tagaagctct    6498
cctttacatt tctctatcaa attttctcatc tttatgggtt tcccaattgt gactcttgtc    6558
ttcatgaata tatgttttc atttgcaaaa gccaaaaatc agtgaaacag cagtgtaatt    6618
aaaagcaaca actggattac tccaaatttc caaatgacaa actagggaa aaatagccta    6678 cacaagcctt taggcctact ctttctgtgc ttgggtttga gtgaacaaag gagattttag    6738
cttggctctg ttctcccatg gatgaaagga ggaggatttt ttttttcttt tggccattga    6798
tgttctagcc aatgtaattg acagaagtct cattttgcat gcgctctgct ctacaaacag    6858
agttggtatg gttggtatac tgtactcacc tgtgagggac tggccactca gacccactta    6918
gctggtgagc tagaagatga ggatcactca ctggaaaagt cacaaggacc atctccaaac    6978
aagttggcag tgctcgatgt ggacgaagag tgaggaagag aaaaagaagg agcaccaggg    7038
agaaggctcc gtctgtgctg ggcagcagac agctgccagg atcacgaact ctgtagtcaa    7098
agaaaagagt cgtgtggcag tttcagctct cgttcattgg gcagctcgcc taggcccagc    7158
ctctgagctg acatgggagt tgttggattc tttgtttcat agcttttct atgccatagg    7218 caatattgtt gttcttggaa agtttattat ttttttaact cccttactct gagaaaggga    7278
tattttgaag gactgtcata tatctttgaa aaagaaaat ctgtaataca tatattttta    7338
tgtatgttca ctggcactaa aaaatataga gagcttcatt ctgtcctttg ggtagttgct    7398
gaggtaattg tccaggttga aaaataatgt gctgatgcta gagtccctct ctgtccatac    7458
tctacttcta aatacatata ggcatacata gcaagtttta tttgacttgt actttaagag    7518
aaaatatgtc caccatccac atgatgcaca aatgagctaa cattgagctt caagtagctt    7578
ctaagtgttt gtttcattag gcacagcaca gatgtggcct ttccccccctt ctctcccttg    7638 atatctggca gggcataaag gcccaggcca cttcctctgc cccttcccag ccctgcacca    7698
aagctgcatt tcaggagact ctctccagac agcccagtaa ctacccgagc atggcccctg    7758
catagccctg gaaaaataag aggctgactg tctacgaatt atcttgtgcc agttgcccag    7818
gtgagagggc actgggccaa gggagtggtt ttcatgtttg acccactaca aggggtcatg    7878
ggaatcagga atgccaaagc accagatcaa atccaaaact taaagtcaaa ataagccatt    7938
cagcatgttc agtttcttgg aaaaggaagt ttctaccccct gatgcctttg taggcagatc    7998
tgttctcacc attaatcttt ttgaaaatct tttaaagcag tttttaaaaa gagagatgaa    8058
agcatcacat tatataacca aagattacat tgtacctgct aagataccaa aattcataag    8118 ggcaggggg gagcaagcat tagtgcctct ttgataagct gtccaaagac agactaaagg    8178
actctgctgg tgactgactt ataagagctt tgtgggtttt ttttcccta ataatataca    8238 tgtttagaag aattgaaaat aatttcggga aaatggggatt atgggtcctt cactaagtga    8298
ttttataagc agaactggct ttcctttct ctagtagttg ctgagcaaat tgttgaagct    8358
```

```
ccatcattgc atggttggaa atggagctgt tcttagccac tgtgtttgct agtgcccatg    8418
ttagcttatc tgaagatgtg aaacccttgc tgataaggga gcatttaaag tactagattt    8478
tgcactagag ggacagcagg cagaaatcct tatttctgcc cactttggat ggcacaaaaa    8538
gttatctgca gttgaaggca gaaagttgaa atacattgta aatgaatatt tgtatccatg    8598
tttcaaaatt gaaatatata tatatatata tatatatata tatatatata tatagtgtgt    8658
gtgtgtgttc tgatagcttt aactttctct gcatctttat atttggttcc agatcacacc    8718
tgatgccatg tacttgtgag agaggatgca gttttgtttt ggaagctctc tcagaacaaa    8778
caagacacct ggattgatca gttaactaaa agttttctcc cctattgggt ttgacccaca    8838
ggtcctgtga aggagcagag ggataaaaag agtagaggac atgatacatt gtactttact    8898
agttcaagac agatgaatgt ggaaagcata aaaactcaat ggaactgact gagatttacc    8958
acagggaagg cccaaacttg gggccaaaag cctacccaag tgattgacca gtggcccct     9018
aatgggacct gagctgttgg aagaagagaa ctgttccttg gtcttcacca tccttgtgag    9078
agaagggcag tttcctgcat tggaacctgg agcaagcgct ctatctttca cacaaattcc    9138
ctcacctgag attgaggtgc tcttgttact gggtgtctgt gtgctgtaat ctggttttg    9198
gatatgttct gtaaagattt tgacaaatga aaatgtgttt ttctctgtta aaacttgtca    9258
gagtactaga agttgtatct ctgtaggtgc aggtccattt ctgcccacag gtagggtgtt    9318
tttctttgat taagagattg acacttctgt tgcctaggac ctcccaactc aaccatttct    9378
aggtgaaggc agaaaaatcc acattagtta ctcctcttca gacatttcag ctgagataac    9438
aaatcttttg gaattttttc acccatagaa agagtggtag atatttgaat ttagcaggtg    9498
gagtttcata gtaaaaacag cttttgactc agctttgatt tatcctcatt tgatttggcc    9558
agaaagtagg taatatgcat tgattggctt ctgattccaa ttcagtatag caaggtgcta    9618
ggtttttttcc tttccccacc tgtctcttag cctggggaat taaatgagaa gccttagaat    9678
gggtggccct tgtgacctga aacacttccc acataagcta cttaacaaga ttgtcatgga    9738
gctgcagatt ccattgccca ccaaagacta gaacacacac atatccatac accaaaggaa    9798
agacaattct gaaatgctgt ttctctggtg gttccctctc tggctgctgc ctcacagtat    9858
gggaacctgt actctgcaga ggtgacaggc cagatttgca ttatctcaca accttagccc    9918
ttggtgctaa ctgtcctaca gtgaagtgcc tggggggttg tcctatccca taagccactt    9978
ggatgctgac agcagccacc atcagaatga cccacgcaaa aaaagaaaaa aaaaaattaa   10038
aaagtccccct cacaacccag tgacaccttt ctgctttcct ctagactgga acattgatta   10098
gggagtgcct cagacatgac attcttgtgc tgtccttgga attaatctgg cagcaggagg   10158
gagcagacta tgtaaacaga gataaaaatt aattttcaat attgaaggaa aaagaaata   10218
agaagagaga gagaaagaaa gcatcacaca aagattttct taaaagaaac aattttgctt   10278
gaaatctctt tagatggggc tcatttctca cggtggcact tggcctccac tgggcagcag   10338
gaccagctcc aagcgctagt gttctgttct cttttttgtaa tcttggaatc ttttgttgct   10398
ctaaatacaa ttaaaaatgg cagaaacttg tttgttggac tacatgtgtg actttgggtc   10458
tgtctctgcc tctgctttca gaaatgtcat ccattgtgta aaatattggc ttactggtct   10518
gccagctaaa acttggccac atcccctgtt atggctgcag gatcgagtta ttgttaacaa   10578
agagacccaa gaaagctgc taatgtcctc ttatcattgt tgttaatttg ttaaaacata   10638
aagaaatcta aaatttcaaa aaa                                            10661
```

```
<210> SEQ ID NO 3
<211> LENGTH: 8112
<212> TYPE: DNA
<213> ORGANISM: Homo sapiens
<220> FEATURE:
<221> NAME/KEY: CDS
<222> LOCATION: (163)..(1329)

<400> SEQUENCE: 3
gctgcgagca gagagggatt cctcggaggt catctgttcc atcttcttgc ctatgcaaat      60
gcctgcctga agctgctgga ggctggcttt gtaccggact ttgtacaggg aaccagggaa     120
acgaatgcag agtgctcctg acattgcctg tcactttttc cc atg ata ctc tgg        174
                                                Met Ile Leu Trp
                                                  1 ctt cac agt ttg gag act gcc agg gac cat gtt ttg ccc att gac tat       222
Leu His Ser Leu Glu Thr Ala Arg Asp His Val Leu Pro Ile Asp Tyr
  5                  10                  15                  20 tac ttt cca ccc cag aag acc tgc ctg atc tgt gga gat gaa gct tct       270
Tyr Phe Pro Pro Gln Lys Thr Cys Leu Ile Cys Gly Asp Glu Ala Ser
                 25                  30                  35 ggg tgt cac tat gga gct ctc aca tgt gga agc tgc aag gtc ttc ttc       318
Gly Cys His Tyr Gly Ala Leu Thr Cys Gly Ser Cys Lys Val Phe Phe
             40                  45                  50 aaa aga gcc gct gaa ggg aaa cag aag tac ctg tgc gcc agc aga aat       366
Lys Arg Ala Ala Glu Gly Lys Gln Lys Tyr Leu Cys Ala Ser Arg Asn
         55                  60                  65 gat tgc act att gat aaa ttc cga agg aaa aat tgt cca tct tgt cgt       414
Asp Cys Thr Ile Asp Lys Phe Arg Arg Lys Asn Cys Pro Ser Cys Arg
 70                  75                  80 ctt cgg aaa tgt tat gaa gca ggg atg act ctg gga gcc cgg aag ctg       462
Leu Arg Lys Cys Tyr Glu Ala Gly Met Thr Leu Gly Ala Arg Lys Leu
85                  90                  95                 100 aag aaa ctt ggt aat ctg aaa cta cag gag gaa gga gag gct tcc agc       510
Lys Lys Leu Gly Asn Leu Lys Leu Gln Glu Glu Gly Glu Ala Ser Ser
                105                 110                 115 acc acc agc ccc act gag gag aca acc cag aag ctg aca gtg tca cac       558
Thr Thr Ser Pro Thr Glu Glu Thr Thr Gln Lys Leu Thr Val Ser His
            120                 125                 130 att gaa ggc tat gaa tgt cag ccc atc ttt ctg aat gtc ctg gaa gcc       606
Ile Glu Gly Tyr Glu Cys Gln Pro Ile Phe Leu Asn Val Leu Glu Ala
        135                 140                 145 att gag cca ggt gta gtg tgt gct gga cac gac aac aac cag ccc gac       654
Ile Glu Pro Gly Val Val Cys Ala Gly His Asp Asn Asn Gln Pro Asp
    150                 155                 160 tcc ttt gca gcc ttg ctc tct agc ctc aat gaa ctg gga gag aga cag       702
Ser Phe Ala Ala Leu Leu Ser Ser Leu Asn Glu Leu Gly Glu Arg Gln
165                 170                 175                 180 ctt gta cac gtg gtc aag tgg gcc aag gcc ttg cct ggc ttc cgc aac       750
Leu Val His Val Val Lys Trp Ala Lys Ala Leu Pro Gly Phe Arg Asn
                185                 190                 195 tta cac gtg gac gac cag atg gct gtc att cag tac tcc tgg atg ggg       798
Leu His Val Asp Asp Gln Met Ala Val Ile Gln Tyr Ser Trp Met Gly
            200                 205                 210 ctc atg gtg ttt gcc atg ggc tgg cga tcc ttc acc aat gtc aac tcc       846
Leu Met Val Phe Ala Met Gly Trp Arg Ser Phe Thr Asn Val Asn Ser
        215                 220                 225 agg atg ctc tac ttc gcc cct gat ctg gtt ttc aat gag tac cgc atg       894
Arg Met Leu Tyr Phe Ala Pro Asp Leu Val Phe Asn Glu Tyr Arg Met
    230                 235                 240 cac aag tcc cgg atg tac agc cag tgt gtc cga atg agg cac ctc tct       942
```

| | |
|---|---|
| His Lys Ser Arg Met Tyr Ser Gln Cys Val Arg Met Arg His Leu Ser<br>245                             250                       255                   260 | |
| caa gag ttt gga tgg ctc caa atc acc ccc cag gaa ttc ctg tgc atg<br>Gln Glu Phe Gly Trp Leu Gln Ile Thr Pro Gln Glu Phe Leu Cys Met<br>                 265                       270                      275 | 990 |
| aaa gca ctg cta ctc ttc agc att att cca gtg gat ggg ctg aaa aat<br>Lys Ala Leu Leu Leu Phe Ser Ile Ile Pro Val Asp Gly Leu Lys Asn<br>        280                     285                     290 | 1038 |
| caa aaa ttc ttt gat gaa ctt cga atg aac tac atc aag gaa ctc gat<br>Gln Lys Phe Phe Asp Glu Leu Arg Met Asn Tyr Ile Lys Glu Leu Asp<br>295                       300                     305 | 1086 |
| cgt atc att gca tgc aaa aga aaa aat ccc aca tcc tgc tca aga cgc<br>Arg Ile Ile Ala Cys Lys Arg Lys Asn Pro Thr Ser Cys Ser Arg Arg<br>    310                   315                     320 | 1134 |
| ttc tac cag ctc acc aag ctc ctg gac tcc gtg cag cct att gcg aga<br>Phe Tyr Gln Leu Thr Lys Leu Leu Asp Ser Val Gln Pro Ile Ala Arg<br>325                       330                     335                   340 | 1182 |
| gag ctg cat cag ttc act ttt gac ctg cta atc aag tca cac atg gtg<br>Glu Leu His Gln Phe Thr Phe Asp Leu Leu Ile Lys Ser His Met Val<br>                 345                       350                     355 | 1230 |
| agc gtg gac ttt ccg gaa atg atg gca gag atc atc tct gtg caa gtg<br>Ser Val Asp Phe Pro Glu Met Met Ala Glu Ile Ile Ser Val Gln Val<br>        360                     365                     370 | 1278 |
| ccc aag atc ctt tct ggg aaa gtc aag ccc atc tat ttc cac acc cag<br>Pro Lys Ile Leu Ser Gly Lys Val Lys Pro Ile Tyr Phe His Thr Gln<br>375                       380                     385 | 1326 |
| tga agcattggaa accctatttc cccaccccag ctcatgcccc ctttcagatg | 1379 |
| tcttctgcct gttataactc tgcactactc ctctgcagtg ccttgggaa tttcctctat | 1439 |
| tgatgtacag tctgtcatga acatgttcct gaattctatt tgctgggctt ttttttctc | 1499 |
| tttctctcct ttcttttct tcttccctcc ctatctaacc ctcccatggc accttcagac | 1559 |
| tttgcttccc attgtggctc ctatctgtgt tttgaatggt gttgtatgcc tttaaatctg | 1619 |
| tgatgatcct catatggccc agtgtcaagt tgtgcttgtt tacagcacta ctctgtgcca | 1679 |
| gccacacaaa cgtttactta tcttatgcca cgggaagttt agagagctaa gattatctgg | 1739 |
| ggaaatcaaa acaaaaacaa gcaaacaaaa aaaaaagca aaaacaaaac aaaaaataag | 1799 |
| ccaaaaaacc ttgctagtgt tttttcctca aaaataaata aataaataaa taaatacgta | 1859 |
| catacataca cacatacata caaacatata gaaatcccca aagaggccaa tagtgacgag | 1919 |
| aaggtgaaaa ttgcaggccc atggggagtt actgattttt tcatctcctc cctccacggg | 1979 |
| agactttatt ttctgccaat ggctattgcc attagagggc agagtgaccc cagagctgag | 2039 |
| ttgggcaggg gggtggacag agaggagagg acaaggaggg caatggagca tcagtacctg | 2099 |
| cccacagcct tggtccctgg gggctagact gctcaactgt ggagcaattc attatactga | 2159 |
| aaatgtgctt gttgttgaaa atttgtctgc atgttaatgc ctcaccccca aacccttttc | 2219 |
| tctctcactc tctgcctcca acttcagatt gactttcaat agttttctta agaccttga | 2279 |
| actgaatgtt ctcttcagcc aaaacttggc gacttccaca gaaaagtctg accactgaga | 2339 |
| agaaggagag cagagattta acccttgta aggccccatt tggatccagg tctgctttct | 2399 |
| catgtgtgag tcaggagga gctggagcca gaggagaaga aaatgatagc ttggctgttc | 2459 |
| tcctgcttag gacactgact gaatagttaa actctcactg ccactacctt ttccccacct | 2519 |
| ttaaaagacc tgaatgaagt tttctgccaa actccgtgaa gccacaagca ccttatgtcc | 2579 |
| tcccttcagt gttttgtggg cctgaatttc atcacactgc atttcagcca tggtcatcaa | 2639 |

```
gcctgtttgc ttcttttggg catgttcaca gattctctgt taagagcccc caccaccaag    2699
aaggttagca ggccaacagc tctgacatct atctgtagat gccagtagtc acaaagattt    2759
cttaccaact ctcagatcgc tggagccctt agacaaactg aaagaaggc atcaaaggga     2819 tcaggcaagc tgggcgtctt gcccttgtcc cccagagatg ataccctccc agcaagtgga    2879
gaagttctca cttccttctt tagagcagct aaagggcta cccagatcag ggttgaagag     2939
aaaactcaat taccagggtg ggaagaatga aggcactaga accagaaacc ctgcaaatgc    2999
tcttcttgtc acccagcata tccacctgca gaagtcatga gaagagagaa ggaacaaaga   3059
ggagactctg actactgaat taaaatcttc agcggcaaag cctaaagcca gatggacacc    3119
atctggtgag tttactcatc atcctcctct gctgctgatt ctgggctctg acattgccca    3179
tactcactca gattccccac ctttgttgct gcctcttagt cagagggagg ccaaaccatt    3239
gagactttct acagaaccat ggcttctttc ggaaaggtct ggttggtgtg ctccaatac     3299 tttgccaccc atgaactcag ggtgtgccct gggacactgg ttttatatag tcttttggca    3359
cacctgtgtt ctgttgactt cgttcttcaa gcccaagtgc aagggaaaat gtccacctac    3419
tttctcatct tggcctctgc ctccttactt agctcttaat ctcatctgtt gaactcaaga    3479
aatcaagggc cagtcatcaa gctgcccatt ttaattgatt cactctgttt gttgagagga    3539
tagtttctga gtgacatgat atgatccaca agggtttcct tccctgattt ctgcattgat    3599
attaatagcc aaacgaactt caaaacagct ttaaataaca agggagaggg gaacctaaga    3659
tgagtaatat gccaatccaa gactgctgga gaaaactaaa gctgacaggt tccctttttg    3719
gggtgggata gacatgttct ggttttcttt attattacac aatctggctc atgtacagga    3779
tcacttttag ctgtttttaaa cagaaaaaaa tatccaccac tcttttcagt tacactaggt    3839 tacatttaa taggtccttt acatctgttt tggaatgatt ttcatctttt gtgatacaca     3899
gattgaatta tatcattttc atatctctcc ttgtaaatac tagaagctct cctttacatt    3959
tctctatcaa attttttcatc tttatggggtt tcccaattgt gactcttgtc ttcatgaata  4019 tatgttttc atttgcaaaa gccaaaaatc agtgaaacag cagtgtaatt aaaagcaaca     4079
actggattac tccaaatttc caaatgacaa aactagggaa aaatagccta cacaagcctt    4139
taggcctact cttttctgtgc ttgggtttga gtgaacaaag gagatttttag cttggctctg  4199 ttctcccatg gatgaaagga ggaggatttt tttttttcttt tggccattga tgttctagcc   4259
aatgtaattg acagaagtct cattttgcat gcgctctgct ctacaaacag agttggtatg    4319
gttggtatac tgtactcacc tgtgagggac tggccactca gacccactta gctggtgagc    4379
tagaagatga ggatcactca ctggaaaagt cacaaggacc atctccaaac aagttggcag    4439
tgctcgatgt ggacgaagag tgaggaagag aaaaagaagg agcaccaggg agaaggctcc    4499
gtctgtgctg ggcagcagac agctgccagg atcacgaact ctgtagtcaa agaaaagagt    4559
cgtgtggcag tttcagctct cgttcattgg gcagctcgcc taggcccagc ctctgagctg    4619
acatgggagt tgttggattc tttgtttcat agcttttct atgccatagg caatattgtt     4679
gttcttggaa agtttattat ttttttaact cccttactct gagaaaggga tatttttgaag  4739 gactgtcata tatctttgaa aaagaaaat ctgtaataca tatatttta tgtatgttca      4799 ctggcactaa aaatataga gagcttcatt ctgtcctttg ggtagttgct gaggtaattg     4859
tccaggttga aaaataatgt gctgatgcta gagtccctct ctgtccatac tctacttcta    4919
aatacatata ggcatacata gcaagttta tttgacttgt actttaagag aaaatatgtc     4979
caccatccac atgatgcaca aatgagctaa cattgagctt caagtagctt ctaagtgttt    5039
```

```
gtttcattag gcacagcaca gatgtggcct ttcccccctt ctctcccttg atatctggca    5099
gggcataaag gcccaggcca cttcctctgc cccttcccag ccctgcacca aagctgcatt    5159
tcaggagact ctctccagac agcccagtaa ctacccgagc atggcccctg catagccctg    5219
gaaaaataag aggctgactg tctacgaatt atcttgtgcc agttgcccag gtgagagggc    5279
actgggccaa gggagtggtt ttcatgtttg acccactaca aggggtcatg ggaatcagga    5339
atgccaaagc accagatcaa atccaaaact taaagtcaaa ataagccatt cagcatgttc    5399
agtttcttgg aaaaggaagt ttctacccct gatgcctttg taggcagatc tgttctcacc    5459
attaatcttt ttgaaaatct tttaaagcag ttttaaaaa gagagatgaa agcatcacat    5519
tatataacca agattacat tgtacctgct aagataccaa aattcataag ggcagggggg     5579
gagcaagcat tagtgcctct ttgataagct gtccaaagac agactaaagg actctgctgg    5639
tgactgactt ataagagctt tgtgggtttt ttttcccta ataatataca tgtttagaag    5699
aattgaaaat aatttcggga aaatgggatt atgggtcctt cactaagtga ttttataagc    5759
agaactggct ttcctttct ctagtagttg ctgagcaaat tgttgaagct ccatcattgc     5819
atggttggaa atggagctgt tcttagccac tgtgtttgct agtgcccatg ttagcttatc    5879
tgaagatgtg aaaccttgc tgataaggga gcatttaaag tactagattt tgcactagag     5939
ggacagcagg cagaaatcct tatttctgcc cactttggat ggcacaaaaa gttatctgca    5999
gttgaaggca gaaagttgaa atacattgta aatgaatatt tgtatccatg tttcaaaatt    6059
gaaatatata tatatatata tatatatata tatatatata tatagtgtgt gtgtgtgttc    6119
tgatagcttt aactttctct gcatctttat atttggttcc agatcacacc tgatgccatg    6179
tacttgtgag agaggatgca gttttgtttt ggaagctctc tcagaacaaa caagacacct    6239
ggattgatca gttaactaaa agttttctcc cctattgggt ttgacccaca ggtcctgtga    6299
aggagcagag ggataaaaag agtagaggac atgatacatt gtactttact agttcaagac    6359
agatgaatgt ggaaagcata aaaactcaat ggaactgact gagatttacc acagggaagg    6419
cccaaacttg gggccaaaag cctacccaag tgattgacca gtggccccct aatgggacct    6479
gagctgttgg aagaagagaa ctgttccttg gtcttcacca tccttgtgag agaagggcag    6539
tttcctgcat tggaacctgg agcaagcgct ctatctttca cacaaattcc ctcacctgag    6599
attgaggtgc tcttgttact gggtgtctgt gtgctgtaat tctggttttg gatatgttct    6659
gtaaagattt tgacaaatga aaatgtgttt ttctctgtta aaacttgtca gagtactaga    6719
agttgtatct ctgtaggtgc aggtccattt ctgcccacag gtagggtgtt tttctttgat    6779
taagagattg acacttctgt tgcctaggac ctcccaactc aaccatttct aggtgaaggc    6839
agaaaaatcc acattagtta ctcctcttca gacatttcag ctgagataac aaatcttttg    6899
gaatttttc acccatagaa agagtggtag atatttgaat ttagcaggtg gagtttcata    6959
gtaaaaacag cttttgactc agctttgatt tatcctcatt tgatttggcc agaaagtagg    7019
taatatgcat tgattggctt ctgattccaa ttcagtatag caaggtgcta ggttttttcc    7079
tttccccacc tgtctcttag cctggggaat taaatgagaa gccttagaat gggtggccct    7139
tgtgacctga aacacttccc acataagcta cttaacaaga ttgtcatgga gctgcagatt    7199
ccattgccca ccaaagacta gaacacacac atatccatac accaaaggaa agacaattct    7259
gaaatgctgt ttctctggtg gttccctctc tggctgctgc ctcacagtat gggaacctgt    7319
actctgcaga ggtgacaggc cagatttgca ttatctcaca accttagccc ttggtgctaa    7379
```

-continued

```
ctgtcctaca gtgaagtgcc tgggggttg tcctatccca taagccactt ggatgctgac      7439
agcagccacc atcagaatga cccacgcaaa aaaagaaaa aaaaattaa aaagtccct        7499 cacaacccag tgacacctttt ctgctttcct ctagactgga acattgatta gggagtgcct   7559
cagacatgac attcttgtgc tgtccttgga attaatctgg cagcaggagg gagcagacta    7619
tgtaaacaga gataaaaatt aattttcaat attgaaggaa aaagaaata agaagagaga     7679 gagaaagaaa gcatcacaca aagattttct taaaagaaac aattttgctt gaaatctctt    7739 tagatgggc tcatttctca cggtggcact tggcctccac tgggcagcag gaccagctcc     7799
aagcgctagt gttctgttct ctttttgtaa tcttggaatc ttttgttgct ctaaatacaa    7859 ttaaaatgg cagaaacttg tttgttggac tacatgtgtg actttgggtc tgtctctgcc    7919
tctgctttca gaaatgtcat ccattgtgta aatattggc ttactggtct gccagctaaa    7979
acttggccac atccctgtt atggctgcag gatcgagtta ttgttaacaa agagacccaa    8039
gaaaagctgc taatgtcctc ttatcattgt tgttaatttg ttaaaacata agaaatcta    8099 aaatttcaaa aaa                                                        8112
```

<210> SEQ ID NO 4
<211> LENGTH: 3641
<212> TYPE: DNA
<213> ORGANISM: Homo sapiens
<220> FEATURE:
<221> NAME/KEY: CDS
<222> LOCATION: (328)..(2265)

<400> SEQUENCE: 4

```
gacactgaat ttggaaggtg gaggatttttg ttttttttctt ttaagatctg ggcatctttt    60
gaatctaccc ttcaagtatt aagagacaga ctgtgagcct agcagggcag atcttgtcca   120
ccgtgtgtct tcttctgcac gagactttga ggctgtcaga gcgcttttttg cgtggttgct  180 cccgcaagtt tccttctctg gagcttcccg caggtgggca gctagctgca gcgactaccg   240
catcatcaca gcctgttgaa ctcttctgag caagagaagg ggaggcgggg taagggaagt  300
aggtggaaga ttcagccaag ctcaagg atg gaa gtg cag tta ggg ctg gga agg   354
                                Met Glu Val Gln Leu Gly Leu Gly Arg
                                 1               5 gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10              15                  20                  25 ctg ttc cag agc gtg cgc gaa gtg atc cag aac ccg ggc ccc agg cac      450
Leu Phe Gln Ser Val Arg Glu Val Ile Gln Asn Pro Gly Pro Arg His
             30                  35                  40 cca gag gcc gcg agc gca gca cct ccc ggc gcc agt ttg ctg ctg cag     498
Pro Glu Ala Ala Ser Ala Ala Pro Pro Gly Ala Ser Leu Leu Leu Gln
         45                  50                  55 cag cag cag cag cag cag cag cag cag cag cag cag cag cag cag cag      546
Gln Gln Gln Gln Gln Gln Gln Gln Gln Gln Gln Gln Gln Gln Gln Gln
     60                  65                  70 cag cag cag cag cag cag cag cag cag cag caa gag act agc ccc         594
Gln Gln Gln Gln Gln Gln Gln Gln Gln Gln Gln Glu Thr Ser Pro
 75                  80                  85 agg cag cag cag cag cag cag cag ggt gag gat ggt tct ccc caa gcc cat  642
Arg Gln Gln Gln Gln Gln Gln Gly Glu Asp Gly Ser Pro Gln Ala His
 90                  95                 100                 105 cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                 110                 115                 120
```

```
tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
        125                 130                 135 cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
    140                 145                 150 ctg cca gca cct ccg gac gag gat gac tca gct gcc cca tcc acg ttg      834
Leu Pro Ala Pro Pro Asp Glu Asp Asp Ser Ala Ala Pro Ser Thr Leu
        155                 160                 165 tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185 ctt aaa gac atc ctg agc gag gcc agc acc atg caa ctc ctt cag caa      930
Leu Lys Asp Ile Leu Ser Glu Ala Ser Thr Met Gln Leu Leu Gln Gln
            190                 195                 200 cag cag cag gaa gca gta tcc gaa ggc agc agc agc ggg aga gcg agg      978
Gln Gln Gln Glu Ala Val Ser Glu Gly Ser Ser Ser Gly Arg Ala Arg
                205                 210                 215 gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
                220                 225                 230 act tcg acc att tct gac aac gcc aag gag ttg tgt aag gca gtg tcg     1074
Thr Ser Thr Ile Ser Asp Asn Ala Lys Glu Leu Cys Lys Ala Val Ser
235                 240                 245 gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265 gaa cag ctt cgg ggg gat tgc atg tac gcc cca ctt ttg gga gtt cca     1170
Glu Gln Leu Arg Gly Asp Cys Met Tyr Ala Pro Leu Leu Gly Val Pro
                270                 275                 280 ccc gct gtg cgt ccc act cct tgt gcc cca ttg gcc gaa tgc aaa ggt     1218
Pro Ala Val Arg Pro Thr Pro Cys Ala Pro Leu Ala Glu Cys Lys Gly
                285                 290                 295 tct ctg cta gac gac agc gca ggc aag agc act gaa gat act gct gag     1266
Ser Leu Leu Asp Asp Ser Ala Gly Lys Ser Thr Glu Asp Thr Ala Glu
                300                 305                 310 tat tcc cct ttc aag gga ggt tac acc aaa ggg cta gaa ggc gag agc     1314
Tyr Ser Pro Phe Lys Gly Gly Tyr Thr Lys Gly Leu Glu Gly Glu Ser
315                 320                 325 cta ggc tgc tct ggc agc gct gca gca ggg agc tcc ggg aca ctt gaa     1362
Leu Gly Cys Ser Gly Ser Ala Ala Ala Gly Ser Ser Gly Thr Leu Glu
330                 335                 340                 345 ctg ccg tct acc ctg tct ctc tac aag tcc gga gca ctg gac gag gca     1410
Leu Pro Ser Thr Leu Ser Leu Tyr Lys Ser Gly Ala Leu Asp Glu Ala
            350                 355                 360 gct gcg tac cag agt cgc gac tac tac aac ttt cca ctg gct ctg gcc     1458
Ala Ala Tyr Gln Ser Arg Asp Tyr Tyr Asn Phe Pro Leu Ala Leu Ala
                365                 370                 375 gga ccg ccg ccc cct ccg ccg cct ccc cat ccc cac gct cgc atc aag     1506
Gly Pro Pro Pro Pro Pro Pro Pro Pro His Pro His Ala Arg Ile Lys
                380                 385                 390 ctg gag aac ccg ctg gac tac ggc agc gcc tgg gcg gct gcg gcg gcg     1554
Leu Glu Asn Pro Leu Asp Tyr Gly Ser Ala Trp Ala Ala Ala Ala Ala
                395                 400                 405 cag tgc cgc tat ggg gac ctg gcg agc ctg cat ggc gcg ggt gca gcg     1602
Gln Cys Arg Tyr Gly Asp Leu Ala Ser Leu His Gly Ala Gly Ala Ala
410                 415                 420                 425 gga ccc ggt tct ggg tca ccc tca gcc gcc gct tcc tca tcc tgg cac     1650
Gly Pro Gly Ser Gly Ser Pro Ser Ala Ala Ala Ser Ser Ser Trp His
                430                 435                 440
```

```
act ctc ttc aca gcc gaa gaa ggc cag ttg tat gga ccg tgt ggt ggt    1698
Thr Leu Phe Thr Ala Glu Glu Gly Gln Leu Tyr Gly Pro Cys Gly Gly
            445                 450                 455 ggt ggg ggt ggt ggc ggc ggc ggc ggc ggc ggc ggc ggc ggc ggc        1746
Gly Gly Gly Gly Gly Gly Gly Gly Gly Gly Gly Gly Gly Gly Gly
        460                 465                 470 ggc gag gcg gga gct gta gcc ccc tac ggc tac act cgg ccc cct cag    1794
Gly Glu Ala Gly Ala Val Ala Pro Tyr Gly Tyr Thr Arg Pro Pro Gln
    475                 480                 485 ggg ctg gcg ggc cag gaa agc gac ttc acc gca cct gat gtg tgg tac    1842
Gly Leu Ala Gly Gln Glu Ser Asp Phe Thr Ala Pro Asp Val Trp Tyr
490                 495                 500                 505 cct ggc ggc atg gtg agc aga gtg ccc tat ccc agt ccc act tgt gtc    1890
Pro Gly Gly Met Val Ser Arg Val Pro Tyr Pro Ser Pro Thr Cys Val
                510                 515                 520 aaa agc gaa atg ggc ccc tgg atg gat agc tac tcc gga cct tac ggg    1938
Lys Ser Glu Met Gly Pro Trp Met Asp Ser Tyr Ser Gly Pro Tyr Gly
            525                 530                 535 gac atg cgt ttg gag act gcc agg gac cat gtt ttg ccc att gac tat    1986
Asp Met Arg Leu Glu Thr Ala Arg Asp His Val Leu Pro Ile Asp Tyr
        540                 545                 550 tac ttt cca ccc cag aag acc tgc ctg atc tgt gga gat gaa gct tct    2034
Tyr Phe Pro Pro Gln Lys Thr Cys Leu Ile Cys Gly Asp Glu Ala Ser
    555                 560                 565 ggg tgt cac tat gga gct ctc aca tgt gga agc tgc aag gtc ttc ttc    2082
Gly Cys His Tyr Gly Ala Leu Thr Cys Gly Ser Cys Lys Val Phe Phe
570                 575                 580                 585 aaa aga gcc gct gaa ggg aaa cag aag tac ctg tgc gcc agc aga aat    2130
Lys Arg Ala Ala Glu Gly Lys Gln Lys Tyr Leu Cys Ala Ser Arg Asn
                590                 595                 600 gat tgc act att gat aaa ttc cga agg aaa aat tgt cca tct tgt cgt    2178
Asp Cys Thr Ile Asp Lys Phe Arg Arg Lys Asn Cys Pro Ser Cys Arg
            605                 610                 615 ctt cgg aaa tgt tat gaa gca ggg atg act ctg gga gaa aaa ttc cgg    2226
Leu Arg Lys Cys Tyr Glu Ala Gly Met Thr Leu Gly Glu Lys Phe Arg
        620                 625                 630 gtt ggc aat tgc aag cat ctc aaa atg acc aga ccc tga agaaaggctg     2275
Val Gly Asn Cys Lys His Leu Lys Met Thr Arg Pro
    635                 640                 645 acttgcctca ttcaaaatga gggctctaga gggctctagt ggatagtctg gagaaacctg   2335
gcgtctgagg cttaggagct taggttttg ctcctcaaca cagactttga cgttggggtt    2395
gggggctact ctcttgattg ctgactccct ccagcgggac caatagtgtt ttcctacctc   2455
acagggatgt tgtgaggacg ggctgtagaa gtaatagtgg ttaccactca tgtagttgtg   2515
agtatcatga ttattgtttc ctgtaatgtg gcttggcatt ggcaaagtgc ttttgattg    2575
ttcttgatca catatgatgg gggccaggca ctgactcagg cggatgcagt gaagctctgg   2635
ctcagtcgct tgcttttcgt ggtgtgctgc caggaagaaa cttgctgat gggactcaag    2695
gtgtcacctt ggacaagaag caactgtgtc tgtctgaggt tcctgtggcc atctttattt   2755
gtgtattagg caattcgtat ttccccctta ggttctagcc ttctggatcc cagccagtga   2815
cctagatctt agcctcaggc cctgtcactg agctgaaggt agtagctgat ccacagaagt   2875
tcagtaaaca aggaccagat ttctgcttct ccaggagaag aagccagcca ccctctct     2935
tcaaacacac tgagagacta cagtccgact ttccctctta catctagcct tactgtagcc   2995
acactccttg attgctctct cacatcacat gcttctcttc atcagttgta agcctctcat   3055
```

-continued

```
tcttctccca agccagactc aaatattgta ttgatgtcaa agaagaatca cttagagttt    3115
ggaatatctt gttctctctc tgctccatag cttccatatt gacaccagtt tctttctagt    3175
ggagaagtgg agtctgtgaa gccagggaaa cacacatgtg agagtcagaa ggactctccc    3235
tgacttgcct ggggcctgtc tttcccacct tctccagtct gtctaaacac acacacacac    3295
acacacacac acacacacac acacacacac gctctctctc tctctccccc cccaacacac    3355
acacactctc tctctcacac acacacacat acacacacac ttctttctct ttcccctgac    3415
tcagcaacat tctggagaaa agccaaggaa ggacttcagg aggggagttt ccccttctc     3475 agggcagaat tttaatctcc agaccaacaa gaagttccct aatgtggatt gaaaggctaa    3535
tgaggtttat ttttaactac tttctatttg tttgaatgtt gcatatttct actagtgaaa    3595
ttttccctta ataaagccat taatacaccc aaaaaaaaaa aaaaaa                   3641
```

```
<210> SEQ ID NO 5
<211> LENGTH: 2430
<212> TYPE: DNA
<213> ORGANISM: Homo sapiens
<220> FEATURE:
<221> NAME/KEY: CDS
<222> LOCATION: (328)..(2274)

<400> SEQUENCE: 5
```

```
gacactgaat ttggaaggtg gaggattttg ttttttctt ttaagatctg ggcatctttt      60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct    180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaagg atg gaa gtg cag tta ggg ctg gga agg    354
                                Met Glu Val Gln Leu Gly Leu Gly Arg
                                 1               5 gtc tac cct cgg ccg ccg tcc aag acc tac cga gga gct ttc cag aat    402
Val Tyr Pro Arg Pro Pro Ser Lys Thr Tyr Arg Gly Ala Phe Gln Asn
 10                  15                  20                  25 ctg ttc cag agc gtg cgc gaa gtg atc cag aac ccg ggc ccc agg cac    450
Leu Phe Gln Ser Val Arg Glu Val Ile Gln Asn Pro Gly Pro Arg His
                 30                  35                  40 cca gag gcc gcg agc gca gca cct ccc ggc gcc agt ttg ctg ctg cag    498
Pro Glu Ala Ala Ser Ala Ala Pro Pro Gly Ala Ser Leu Leu Leu Gln
             45                  50                  55 cag cag cag cag cag cag cag cag cag cag cag cag cag cag cag cag    546
Gln Gln Gln Gln Gln Gln Gln Gln Gln Gln Gln Gln Gln Gln Gln Gln
         60                  65                  70 cag cag cag cag cag cag cag cag cag cag caa gag act agc ccc agg    594
Gln Gln Gln Gln Gln Gln Gln Gln Gln Gln Glu Thr Ser Pro Arg
     75                  80                  85 cag cag cag cag cag cag ggt gag gat ggt tct ccc caa gcc cat cgt    642
Gln Gln Gln Gln Gln Gln Gly Glu Asp Gly Ser Pro Gln Ala His Arg
 90                  95                 100                 105 aga ggc ccc aca ggc tac ctg gtc ctg gat gag gaa cag caa cct tca    690
Arg Gly Pro Thr Gly Tyr Leu Val Leu Asp Glu Glu Gln Gln Pro Ser
                110                 115                 120 cag ccg cag tcg gcc ctg gag tgc cac ccc gag aga ggt tgc gtc cca    738
Gln Pro Gln Ser Ala Leu Glu Cys His Pro Glu Arg Gly Cys Val Pro
            125                 130                 135 gag cct gga gcc gcc gtg gcc gcc agc aag ggg ctg ccg cag cag ctg    786
Glu Pro Gly Ala Ala Val Ala Ala Ser Lys Gly Leu Pro Gln Gln Leu
```

-continued

```
                140                 145                 150
cca gca cct ccg gac gag gat gac tca gct gcc cca tcc acg ttg tcc      834
Pro Ala Pro Pro Asp Glu Asp Asp Ser Ala Ala Pro Ser Thr Leu Ser
    155                 160                 165 ctg ctg ggc ccc act ttc ccc ggc tta agc agc tgc tcc gct gac ctt      882
Leu Leu Gly Pro Thr Phe Pro Gly Leu Ser Ser Cys Ser Ala Asp Leu
170                 175                 180                 185 aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200 cag cag gaa gca gta tcc gaa ggc agc agc agc ggg aga gcg agg gag      978
Gln Gln Glu Ala Val Ser Glu Gly Ser Ser Ser Gly Arg Ala Arg Glu
            205                 210                 215 gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
        220                 225                 230 tcg acc att tct gac aac gcc aag gag ttg tgt aag gca gtg tcg gtg     1074
Ser Thr Ile Ser Asp Asn Ala Lys Glu Leu Cys Lys Ala Val Ser Val
    235                 240                 245 tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265 cag ctt cgg ggg gat tgc atg tac gcc cca ctt ttg gga gtt cca ccc     1170
Gln Leu Arg Gly Asp Cys Met Tyr Ala Pro Leu Leu Gly Val Pro Pro
                270                 275                 280 gct gtg cgt ccc act cct tgt gcc cca ttg gcc gaa tgc aaa ggt tct     1218
Ala Val Arg Pro Thr Pro Cys Ala Pro Leu Ala Glu Cys Lys Gly Ser
            285                 290                 295 ctg cta gac gac agc gca ggc aag agc act gaa gat act gct gag tat     1266
Leu Leu Asp Asp Ser Ala Gly Lys Ser Thr Glu Asp Thr Ala Glu Tyr
        300                 305                 310 tcc cct ttc aag gga ggt tac acc aaa ggg cta gaa ggc gag agc cta     1314
Ser Pro Phe Lys Gly Gly Tyr Thr Lys Gly Leu Glu Gly Glu Ser Leu
    315                 320                 325 ggc tgc tct ggc agc gct gca gca ggg agc tcc ggg aca ctt gaa ctg     1362
Gly Cys Ser Gly Ser Ala Ala Ala Gly Ser Ser Gly Thr Leu Glu Leu
330                 335                 340                 345 ccg tct acc ctg tct ctc tac aag tcc gga gca ctg gac gag gca gct     1410
Pro Ser Thr Leu Ser Leu Tyr Lys Ser Gly Ala Leu Asp Glu Ala Ala
                350                 355                 360 gcg tac cag agt cgc gac tac tac aac ttt cca ctg gct ctg gcc gga     1458
Ala Tyr Gln Ser Arg Asp Tyr Tyr Asn Phe Pro Leu Ala Leu Ala Gly
            365                 370                 375 ccg ccg ccc cct ccg ccg cct ccc cat ccc cac gct cgc atc aag ctg     1506
Pro Pro Pro Pro Pro Pro Pro Pro His Pro His Ala Arg Ile Lys Leu
        380                 385                 390 gag aac ccg ctg gac tac ggc agc gcc tgg gcg gct gcg gcg cag         1554
Glu Asn Pro Leu Asp Tyr Gly Ser Ala Trp Ala Ala Ala Ala Gln
    395                 400                 405 tgc cgc tat ggg gac ctg gcg agc ctg cat ggc gcg ggt gca gcg gga     1602
Cys Arg Tyr Gly Asp Leu Ala Ser Leu His Gly Ala Gly Ala Ala Gly
410                 415                 420                 425 ccc ggt tct ggg tca ccc tca gcc gcc gct tcc tca tcc tgg cac act     1650
Pro Gly Ser Gly Ser Pro Ser Ala Ala Ala Ser Ser Ser Trp His Thr
                430                 435                 440 ctc ttc aca gcc gaa gaa ggc cag ttg tat gga ccg tgt ggt ggt ggt     1698
Leu Phe Thr Ala Glu Glu Gly Gln Leu Tyr Gly Pro Cys Gly Gly Gly
            445                 450                 455 ggg ggt ggt ggc ggc ggc ggc ggc ggc ggc ggc ggc ggc ggc ggc         1746
```

| | | |
|---|---|---|
| Gly Gly Gly Gly Gly Gly Gly Gly Gly Gly Gly Gly<br>460          465          470 | | |
| gag gcg gga gct gta gcc ccc tac ggc tac act cgg ccc cct cag ggg<br>Glu Ala Gly Ala Val Ala Pro Tyr Gly Tyr Thr Arg Pro Pro Gln Gly<br>475          480          485 | 1794 | |
| ctg gcg ggc cag gaa agc gac ttc acc gca cct gat gtg tgg tac cct<br>Leu Ala Gly Gln Glu Ser Asp Phe Thr Ala Pro Asp Val Trp Tyr Pro<br>490          495          500          505 | 1842 | |
| ggc ggc atg gtg agc aga gtg ccc tat ccc agt ccc act tgt gtc aaa<br>Gly Gly Met Val Ser Arg Val Pro Tyr Pro Ser Pro Thr Cys Val Lys<br>510          515          520 | 1890 | |
| agc gaa atg ggc ccc tgg atg gat agc tac tcc gga cct tac ggg gac<br>Ser Glu Met Gly Pro Trp Met Asp Ser Tyr Ser Gly Pro Tyr Gly Asp<br>525          530          535 | 1938 | |
| atg cgt ttg gag act gcc agg gac cat gtt ttg ccc att gac tat tac<br>Met Arg Leu Glu Thr Ala Arg Asp His Val Leu Pro Ile Asp Tyr Tyr<br>540          545          550 | 1986 | |
| ttt cca ccc cag aag acc tgc ctg atc tgt gga gat gaa gct tct ggg<br>Phe Pro Pro Gln Lys Thr Cys Leu Ile Cys Gly Asp Glu Ala Ser Gly<br>555          560          565 | 2034 | |
| tgt cac tat gga gct ctc aca tgt gga agc tgc aag gtc ttc ttc aaa<br>Cys His Tyr Gly Ala Leu Thr Cys Gly Ser Cys Lys Val Phe Phe Lys<br>570          575          580          585 | 2082 | |
| aga gcc gct gaa ggg aaa cag aag tac ctg tgc gcc agc aga aat gat<br>Arg Ala Ala Glu Gly Lys Gln Lys Tyr Leu Cys Ala Ser Arg Asn Asp<br>590          595          600 | 2130 | |
| tgc act att gat aaa ttc cga agg aaa aat tgt cca tct tgt cgt ctt<br>Cys Thr Ile Asp Lys Phe Arg Arg Lys Asn Cys Pro Ser Cys Arg Leu<br>605          610          615 | 2178 | |
| cgg aaa tgt tat gaa gca ggg atg act ctg gga gca gct gtt gtt gtt<br>Arg Lys Cys Tyr Glu Ala Gly Met Thr Leu Gly Ala Ala Val Val Val<br>620          625          630 | 2226 | |
| tct gaa aga atc ttg agg gtg ttt gga gtc tca gaa tgg ctt cct taa<br>Ser Glu Arg Ile Leu Arg Val Phe Gly Val Ser Glu Trp Leu Pro<br>635          640          645 | 2274 | |
| agactacctt cagactctca gctgctcatc cacaacagag atcagccctt ctttgtagat | 2334 | |
| gattcattcc tggctgcatt tgaaaaccac atattgttaa ttgcttgacg aatttaaatc | 2394 | |
| ccttgactac ttttcatttc aaaaaaaaaa aaaaaa | 2430 | |

```
<210> SEQ ID NO 6
<211> LENGTH: 2427
<212> TYPE: DNA
<213> ORGANISM: Homo sapiens
<220> FEATURE:
<221> NAME/KEY: CDS
<222> LOCATION: (328)..(2271)

<400> SEQUENCE: 6
```

| | |
|---|---|
| gacactgaat tggaaggtg gaggattttg ttttttctt ttaagatctg ggcatcttt | 60 |
| gaatctaccc ttcaagtatt aagagacaga ctgtgagcct agcagggcag atcttgtcca | 120 |
| ccgtgtgtct tcttctgcac gagactttga ggctgtcaga gcgcttttg cgtggttgct | 180 |
| cccgcaagtt tccttctctg gagcttcccg caggtgggca gctagctgca gcgactaccg | 240 |
| catcatcaca gcctgttgaa ctcttctgag caagagaagg ggaggcgggg taagggaagt | 300 |
| aggtggaaga ttcagccaag ctcaagg atg gaa gtg cag tta ggg ctg gga agg<br>              Met Glu Val Gln Leu Gly Leu Gly Arg<br>              1           5 | 354 |
| gtc tac cct cgg ccg ccg tcc aag acc tac cga gga gct ttc cag aat | 402 |

```
Val Tyr Pro Arg Pro Ser Lys Thr Tyr Arg Gly Ala Phe Gln Asn
 10              15                  20                  25 ctg ttc cag agc gtg cgc gaa gtg atc cag aac ccg ggc ccc agg cac    450
Leu Phe Gln Ser Val Arg Glu Val Ile Gln Asn Pro Gly Pro Arg His
             30                  35                  40 cca gag gcc gcg agc gca gca cct ccc ggc gcc agt ttg ctg ctg cag    498
Pro Glu Ala Ala Ser Ala Ala Pro Pro Gly Ala Ser Leu Leu Leu Gln
             45                  50                  55 cag cag cag cag cag cag cag cag cag cag cag cag cag cag cag cag    546
Gln Gln Gln Gln Gln Gln Gln Gln Gln Gln Gln Gln Gln Gln Gln Gln
         60                  65                  70 cag cag cag cag cag cag cag cag cag caa gag act agc ccc agg        594
Gln Gln Gln Gln Gln Gln Gln Gln Gln Glu Thr Ser Pro Arg
     75                  80                  85 cag cag cag cag cag cag ggt gag gat ggt tct ccc caa gcc cat cgt    642
Gln Gln Gln Gln Gln Gln Gly Glu Asp Gly Ser Pro Gln Ala His Arg
 90                  95                 100                 105 aga ggc ccc aca ggc tac ctg gtc ctg gat gag gaa cag caa cct tca    690
Arg Gly Pro Thr Gly Tyr Leu Val Leu Asp Glu Glu Gln Gln Pro Ser
             110                 115                 120 cag ccg cag tcg gcc ctg gag tgc cac ccc gag aga ggt tgc gtc cca    738
Gln Pro Gln Ser Ala Leu Glu Cys His Pro Glu Arg Gly Cys Val Pro
             125                 130                 135 gag cct gga gcc gcc gtg gcc gcc agc aag ggg ctg ccg cag cag ctg    786
Glu Pro Gly Ala Ala Val Ala Ala Ser Lys Gly Leu Pro Gln Gln Leu
             140                 145                 150 cca gca cct ccg gac gag gat gac tca gct gcc cca tcc acg ttg tcc    834
Pro Ala Pro Pro Asp Glu Asp Asp Ser Ala Ala Pro Ser Thr Leu Ser
             155                 160                 165 ctg ctg ggc ccc act ttc ccc ggc tta agc agc tgc tcc gct gac ctt    882
Leu Leu Gly Pro Thr Phe Pro Gly Leu Ser Ser Cys Ser Ala Asp Leu
170                 175                 180                 185 aaa gac atc ctg agc gag gcc agc acc atg caa ctc ctt cag caa cag    930
Lys Asp Ile Leu Ser Glu Ala Ser Thr Met Gln Leu Leu Gln Gln Gln
             190                 195                 200 cag cag gaa gca gta tcc gaa ggc agc agc agc ggg aga gcg agg gag    978
Gln Gln Glu Ala Val Ser Glu Gly Ser Ser Ser Gly Arg Ala Arg Glu
             205                 210                 215 gcc tcg ggg gct ccc act tcc tcc aag gac aat tac tta ggg ggc act   1026
Ala Ser Gly Ala Pro Thr Ser Ser Lys Asp Asn Tyr Leu Gly Gly Thr
             220                 225                 230 tcg acc att tct gac aac gcc aag gag ttg tgt aag gca gtg tcg gtg   1074
Ser Thr Ile Ser Asp Asn Ala Lys Glu Leu Cys Lys Ala Val Ser Val
             235                 240                 245 tcc atg ggc ctg ggt gtg gag gcg ttg gag cat ctg agt cca ggg gaa   1122
Ser Met Gly Leu Gly Val Glu Ala Leu Glu His Leu Ser Pro Gly Glu
250                 255                 260                 265 cag ctt cgg ggg gat tgc atg tac gcc cca ctt ttg gga gtt cca ccc   1170
Gln Leu Arg Gly Asp Cys Met Tyr Ala Pro Leu Leu Gly Val Pro Pro
             270                 275                 280 gct gtg cgt ccc act cct tgt gcc cca ttg gcc gaa tgc aaa ggt tct   1218
Ala Val Arg Pro Thr Pro Cys Ala Pro Leu Ala Glu Cys Lys Gly Ser
             285                 290                 295 ctg cta gac gac agc gca ggc aag agc act gaa gat act gct gag tat   1266
Leu Leu Asp Asp Ser Ala Gly Lys Ser Thr Glu Asp Thr Ala Glu Tyr
             300                 305                 310 tcc cct ttc aag gga ggt tac acc aaa ggg cta gaa ggc gag agc cta   1314
Ser Pro Phe Lys Gly Gly Tyr Thr Lys Gly Leu Glu Gly Glu Ser Leu
             315                 320                 325
```

-continued

| | | |
|---|---|---|
| ggc tgc tct ggc agc gct gca gca ggg agc tcc ggg aca ctt gaa ctg<br>Gly Cys Ser Gly Ser Ala Ala Ala Gly Ser Ser Gly Thr Leu Glu Leu<br>330               335                       340               345 | | 1362 |
| ccg tct acc ctg tct ctc tac aag tcc gga gca ctg gac gag gca gct<br>Pro Ser Thr Leu Ser Leu Tyr Lys Ser Gly Ala Leu Asp Glu Ala Ala<br>                      350                       355                     360 | | 1410 |
| gcg tac cag agt cgc gac tac tac aac ttt cca ctg gct ctg gcc gga<br>Ala Tyr Gln Ser Arg Asp Tyr Tyr Asn Phe Pro Leu Ala Leu Ala Gly<br>               365                       370                     375 | | 1458 |
| ccg ccg ccc cct ccg ccg cct ccc cat ccc cac gct cgc atc aag ctg<br>Pro Pro Pro Pro Pro Pro Pro His Pro His Ala Arg Ile Lys Leu<br>         380                     385                       390 | | 1506 |
| gag aac ccg ctg gac tac ggc agc gcc tgg gcg gct gcg gcg gcg cag<br>Glu Asn Pro Leu Asp Tyr Gly Ser Ala Trp Ala Ala Ala Ala Ala Gln<br>     395                     400                     405 | | 1554 |
| tgc cgc tat ggg gac ctg gcg agc ctg cat ggc gcg ggt gca gcg gga<br>Cys Arg Tyr Gly Asp Leu Ala Ser Leu His Gly Ala Gly Ala Ala Gly<br>410                   415                       420               425 | | 1602 |
| ccc ggt tct ggg tca ccc tca gcc gcc gct tcc tca tcc tgg cac act<br>Pro Gly Ser Gly Ser Pro Ser Ala Ala Ala Ser Ser Ser Trp His Thr<br>                      430                       435                     440 | | 1650 |
| ctc ttc aca gcc gaa gaa ggc cag ttg tat gga ccg tgt ggt ggt ggt<br>Leu Phe Thr Ala Glu Glu Gly Gln Leu Tyr Gly Pro Cys Gly Gly Gly<br>               445                       450                     455 | | 1698 |
| ggg ggt ggt ggc ggc ggc ggc ggc ggc ggc ggc ggc ggc ggc ggc ggc<br>Gly Gly Gly Gly Gly Gly Gly Gly Gly Gly Gly Gly Gly Gly Gly Gly<br>                      460                       465                     470 | | 1746 |
| gag gcg gga gct gta gcc ccc tac ggc tac act cgg ccc cct cag ggg<br>Glu Ala Gly Ala Val Ala Pro Tyr Gly Tyr Thr Arg Pro Pro Gln Gly<br>475                   480                       485 | | 1794 |
| ctg gcg ggc cag gaa agc gac ttc acc gca cct gat gtg tgg tac cct<br>Leu Ala Gly Gln Glu Ser Asp Phe Thr Ala Pro Asp Val Trp Tyr Pro<br>490                   495                     500               505 | | 1842 |
| ggc ggc atg gtg agc aga gtg ccc tat ccc agt ccc act tgt gtc aaa<br>Gly Gly Met Val Ser Arg Val Pro Tyr Pro Ser Pro Thr Cys Val Lys<br>               510                       515                     520 | | 1890 |
| agc gaa atg ggc ccc tgg atg gat agc tac tcc gga cct tac ggg gac<br>Ser Glu Met Gly Pro Trp Met Asp Ser Tyr Ser Gly Pro Tyr Gly Asp<br>                      525                       530                     535 | | 1938 |
| atg cgt ttg gag act gcc agg gac cat gtt ttg ccc att gac tat tac<br>Met Arg Leu Glu Thr Ala Arg Asp His Val Leu Pro Ile Asp Tyr Tyr<br>     540                     545                     550 | | 1986 |
| ttt cca ccc cag aag acc tgc ctg atc tgt gga gat gaa gct tct ggg<br>Phe Pro Pro Gln Lys Thr Cys Leu Ile Cys Gly Asp Glu Ala Ser Gly<br>555                   560                     565 | | 2034 |
| tgt cac tat gga gct ctc aca tgt gga agc tgc aag gtc ttc ttc aaa<br>Cys His Tyr Gly Ala Leu Thr Cys Gly Ser Cys Lys Val Phe Phe Lys<br>570                   575                       580               585 | | 2082 |
| aga gcc gct gaa ggg aaa cag aag tac ctg tgc gcc agc aga aat gat<br>Arg Ala Ala Glu Gly Lys Gln Lys Tyr Leu Cys Ala Ser Arg Asn Asp<br>                      590                       595                     600 | | 2130 |
| tgc act att gat aaa ttc cga agg aaa aat tgt cca tct tgt cgt ctt<br>Cys Thr Ile Asp Lys Phe Arg Arg Lys Asn Cys Pro Ser Cys Arg Leu<br>               605                       610                     615 | | 2178 |
| cgg aaa tgt tat gaa gca ggg att ctg gga gca gct gtt gtt gtt tct<br>Arg Lys Cys Tyr Glu Ala Gly Ile Leu Gly Ala Ala Val Val Val Ser<br>         620                     625                       630 | | 2226 |
| gaa aga atc ttg agg gtg ttt gga gtc tca gaa tgg ctt cct taa<br>Glu Arg Ile Leu Arg Val Phe Gly Val Ser Glu Trp Leu Pro<br>               635                       640               645 | | 2271 |

```
                                            -continued agactacctt cagactctca gctgctcatc cacaacagag atcagccctt ctttgtagat    2331
gattcattcc tggctgcatt tgaaaaccac atattgttaa ttgcttgacg aatttaaatc    2391
ccttgactac ttttcatttc aaaaaaaaaa aaaaaa                              2427

<210> SEQ ID NO 7
<211> LENGTH: 4039
<212> TYPE: DNA
<213> ORGANISM: Homo sapiens
<220> FEATURE:
<221> NAME/KEY: CDS
<222> LOCATION: (328)..(2376)

<400> SEQUENCE: 7
gacactgaat ttggaaggtg gaggattttg ttttttttctt ttaagatctg ggcatctttt    60
gaatctaccc ttcaagtatt aagagacaga ctgtgagcct agcagggcag atcttgtcca    120
ccgtgtgtct tcttctgcac gagacttga ggctgtcaga gcgcttttg cgtggttgct      180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaagg atg gaa gtg cag tta ggg ctg gga agg   354
                                Met Glu Val Gln Leu Gly Leu Gly Arg
                                  1               5 gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25 ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40 cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55 cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70 cag cag cag cag cag cag cag cag cag cag cag caa gag act agc ccc      594
Gln Gln Gln Gln Gln Gln Gln Gln Gln Gln Gln Glu Thr Ser Pro
     75                  80                  85 agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105 cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120 tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135 cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
        140                 145                 150 ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165 tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185 ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200
```

| | | |
|---|---|---|
| cag cag cag gaa gca gta tcc gaa ggc agc agc agc ggg aga gcg agg<br>Gln Gln Gln Glu Ala Val Ser Glu Gly Ser Ser Ser Gly Arg Ala Arg<br>205 210 215 | | 978 |
| gag gcc tcg ggg gct ccc act tcc tcc aag gac aat tac tta ggg ggc<br>Glu Ala Ser Gly Ala Pro Thr Ser Ser Lys Asp Asn Tyr Leu Gly Gly<br>220 225 230 | | 1026 |
| act tcg acc att tct gac aac gcc aag gag ttg tgt aag gca gtg tcg<br>Thr Ser Thr Ile Ser Asp Asn Ala Lys Glu Leu Cys Lys Ala Val Ser<br>235 240 245 | | 1074 |
| gtg tcc atg ggc ctg ggt gtg gag gcg ttg gag cat ctg agt cca ggg<br>Val Ser Met Gly Leu Gly Val Glu Ala Leu Glu His Leu Ser Pro Gly<br>250 255 260 265 | | 1122 |
| gaa cag ctt cgg ggg gat tgc atg tac gcc cca ctt ttg gga gtt cca<br>Glu Gln Leu Arg Gly Asp Cys Met Tyr Ala Pro Leu Leu Gly Val Pro<br>270 275 280 | | 1170 |
| ccc gct gtg cgt ccc act cct tgt gcc cca ttg gcc gaa tgc aaa ggt<br>Pro Ala Val Arg Pro Thr Pro Cys Ala Pro Leu Ala Glu Cys Lys Gly<br>285 290 295 | | 1218 |
| tct ctg cta gac gac agc gca ggc aag agc act gaa gat act gct gag<br>Ser Leu Leu Asp Asp Ser Ala Gly Lys Ser Thr Glu Asp Thr Ala Glu<br>300 305 310 | | 1266 |
| tat tcc cct ttc aag gga ggt tac acc aaa ggg cta gaa ggc gag agc<br>Tyr Ser Pro Phe Lys Gly Gly Tyr Thr Lys Gly Leu Glu Gly Glu Ser<br>315 320 325 | | 1314 |
| cta ggc tgc tct ggc agc gct gca gca ggg agc tcc ggg aca ctt gaa<br>Leu Gly Cys Ser Gly Ser Ala Ala Ala Gly Ser Ser Gly Thr Leu Glu<br>330 335 340 345 | | 1362 |
| ctg ccg tct acc ctg tct ctc tac aag tcc gga gca ctg gac gag gca<br>Leu Pro Ser Thr Leu Ser Leu Tyr Lys Ser Gly Ala Leu Asp Glu Ala<br>350 355 360 | | 1410 |
| gct gcg tac cag agt cgc gac tac tac aac ttt cca ctg gct ctg gcc<br>Ala Ala Tyr Gln Ser Arg Asp Tyr Tyr Asn Phe Pro Leu Ala Leu Ala<br>365 370 375 | | 1458 |
| gga ccg ccg ccc cct ccg ccg cct ccc cat ccc cac gct cgc atc aag<br>Gly Pro Pro Pro Pro Pro Pro Pro Pro His Pro His Ala Arg Ile Lys<br>380 385 390 | | 1506 |
| ctg gag aac ccg ctg gac tac ggc agc gcc tgg gcg gct gcg gcg gcg<br>Leu Glu Asn Pro Leu Asp Tyr Gly Ser Ala Trp Ala Ala Ala Ala Ala<br>395 400 405 | | 1554 |
| cag tgc cgc tat ggg gac ctg gcg agc ctg cat ggc gcg ggt gca gcg<br>Gln Cys Arg Tyr Gly Asp Leu Ala Ser Leu His Gly Ala Gly Ala Ala<br>410 415 420 425 | | 1602 |
| gga ccc ggt tct ggg tca ccc tca gcc gcc gct tcc tca tcc tgg cac<br>Gly Pro Gly Ser Gly Ser Pro Ser Ala Ala Ala Ser Ser Ser Trp His<br>430 435 440 | | 1650 |
| act ctc ttc aca gcc gaa gaa ggc cag ttg tat gga ccg tgt ggt ggt<br>Thr Leu Phe Thr Ala Glu Glu Gly Gln Leu Tyr Gly Pro Cys Gly Gly<br>445 450 455 | | 1698 |
| ggg ggt ggt ggc ggc ggc ggc ggc ggc ggc ggc ggc ggc ggc<br>Gly Gly Gly Gly Gly Gly Gly Gly Gly Gly Gly Gly Gly Gly Gly Gly<br>460 465 470 | | 1746 |
| ggc gag gcg gga gct gta gcc ccc tac ggc tac act cgg ccc cct cag<br>Gly Glu Ala Gly Ala Val Ala Pro Tyr Gly Tyr Thr Arg Pro Pro Gln<br>475 480 485 | | 1794 |
| ggg ctg gcg ggc cag gaa agc gac ttc acc gca cct gat gtg tgg tac<br>Gly Leu Ala Gly Gln Glu Ser Asp Phe Thr Ala Pro Asp Val Trp Tyr<br>490 495 500 505 | | 1842 |
| cct ggc ggc atg gtg agc aga gtg ccc tat ccc agt ccc act tgt gtc<br>Pro Gly Gly Met Val Ser Arg Val Pro Tyr Pro Ser Pro Thr Cys Val | | 1890 |

```
                510                 515                 520
aaa agc gaa atg ggc ccc tgg atg gat agc tac tcc gga cct tac ggg   1938
Lys Ser Glu Met Gly Pro Trp Met Asp Ser Tyr Ser Gly Pro Tyr Gly
            525                 530                 535 gac atg cgt ttg gag act gcc agg gac cat gtt ttg ccc att gac tat   1986
Asp Met Arg Leu Glu Thr Ala Arg Asp His Val Leu Pro Ile Asp Tyr
        540                 545                 550 tac ttt cca ccc cag aag acc tgc ctg atc tgt gga gat gaa gct tct   2034
Tyr Phe Pro Pro Gln Lys Thr Cys Leu Ile Cys Gly Asp Glu Ala Ser
    555                 560                 565 ggg tgt cac tat gga gct ctc aca tgt gga agc tgc aag gtc ttc ttc   2082
Gly Cys His Tyr Gly Ala Leu Thr Cys Gly Ser Cys Lys Val Phe Phe
570                 575                 580                 585 aaa aga gcc gct gaa ggg aaa cag aag tac ctg tgc gcc agc aga aat   2130
Lys Arg Ala Ala Glu Gly Lys Gln Lys Tyr Leu Cys Ala Ser Arg Asn
                590                 595                 600 gat tgc act att gat aaa ttc cga agg aaa aat tgt cca tct tgt cgt   2178
Asp Cys Thr Ile Asp Lys Phe Arg Arg Lys Asn Cys Pro Ser Cys Arg
            605                 610                 615 ctt cgg aaa tgt tat gaa gca ggg atg act ctg gga gga ttt ttc aga   2226
Leu Arg Lys Cys Tyr Glu Ala Gly Met Thr Leu Gly Gly Phe Phe Arg
        620                 625                 630 atg aac aaa tta aaa gaa tca tca gac act aac ccc aag cca tac tgc   2274
Met Asn Lys Leu Lys Glu Ser Ser Asp Thr Asn Pro Lys Pro Tyr Cys
    635                 640                 645 atg gca gca cca atg gga ctg aca gaa aac aac aga aat agg aag aaa   2322
Met Ala Ala Pro Met Gly Leu Thr Glu Asn Asn Arg Asn Arg Lys Lys
650                 655                 660                 665 tcc tac aga gaa aca aac ttg aaa gct gtc tca tgg cct ttg aat cat   2370
Ser Tyr Arg Glu Thr Asn Leu Lys Ala Val Ser Trp Pro Leu Asn His
                670                 675                 680 act taa gttttatgat ggaaggatac gactatgaag aaagacacag agcaacatca   2426
Thr gacagtcaag aatttcagag ccagctggca tgcagtggac ctcatgccag cccatttat   2486 gactatttag ggaaacagaa gtacctgtgc gccagcagaa atgattgcac tattgataaa   2546
ttccgaagga aaaattgtcc atcttgtcgt cttcggaaat gttatgaagc agggatgact   2606
ctgggagaaa aattccgggt tgcaattgc aagcatctca aaatgaccag accctgaaga   2666
aaggctgact tgcctcattc aaaatgaggg ctctagaggg ctctagtgga tagtctggag   2726
aaacctggcg tctgaggctt aggagcttag gttttgctc ctcaacacag actttgacgt   2786
tggggttggg ggctactctc ttgattgctg actccctcca gcgggaccaa tagtgttttc   2846
ctacctcaca gggatgttgt gaggacgggc tgtagaagta atagtggtta ccactcatgt   2906
agttgtgagt atcatgatta ttgttcctg taatgtggct tggcattggc aaagtgcttt   2966
ttgattgttc ttgatcacat atgatggggg ccaggcactg actcaggcgg atgcagtgaa   3026
gctctggctc agtcgcttgc ttttcgtggt gtgctgccag gaagaaactt tgctgatggg   3086
actcaaggtg tcaccttgga caagaagcaa ctgtgtctgt ctgaggttcc tgtggccatc   3146
tttatttgtg tattaggcaa ttcgtatttc ccccttaggt tctagccttc tggatcccag   3206
ccagtgacct agatcttagc ctcaggccct gtcactgagc tgaaggtagt agctgatcca   3266
cagaagttca gtaaacaagg accagatttc tgcttctcca ggagaagaag ccagccaacc   3326
cctctcttca aacacactga gagactacag tccgactttc cctcttacat ctagccttac   3386
tgtagccaca ctccttgatt gctctctcac atcacatgct tctcttcatc agttgtaagc   3446
```

```
ctctcattct tctcccaagc cagactcaaa tattgtattg atgtcaaaga agaatcactt    3506
agagtttgga atatcttgtt ctctctctgc tccatagctt ccatattgac accagtttct    3566
ttctagtgga gaagtggagt ctgtgaagcc agggaaacac acatgtgaga gtcagaagga    3626
ctctccctga cttgcctggg gcctgtcttt cccaccttct ccagtctgtc taaacacaca    3686
cacacacaca cacacacaca cacacacaca cacacacgct ctctctctct ctcccccccc    3746
aacacacaca cactctctct ctcacacaca cacacataca cacacacttc tttctctttc    3806
ccctgactca gcaacattct ggagaaaagc caaggaagga cttcaggagg ggagtttccc    3866
ccttctcagg gcagaatttt aatctccaga ccaacaagaa gttccctaat gtggattgaa    3926
aggctaatga ggtttatttt taactacttt ctatttgttt gaatgttgca tatttctact    3986
agtgaaattt tcccttaata aagccattaa tacacccaaa aaaaaaaaaa aaa           4039

<210> SEQ ID NO 8
<211> LENGTH: 3922
<212> TYPE: DNA
<213> ORGANISM: Homo sapiens
<220> FEATURE:
<221> NAME/KEY: CDS
<222> LOCATION: (328)..(2259)

<400> SEQUENCE: 8
gacactgaat ttggaaggtg gaggattttg ttttttctct ttaagatctg ggcatctttt      60
gaatctaccc ttcaagtatt aagagacaga ctgtgagcct agcagggcag atcttgtcca     120
ccgtgtgtct tcttctgcac gagacttga ggctgtcaga gcgcttttg cgtggttgct       180 cccgcaagtt tccttctctg gagcttcccg caggtgggca gctagctgca gcgactaccg     240
catcatcaca gcctgttgaa ctcttctgag caagagaagg ggaggcgggg taagggaagt     300
aggtggaaga ttcagccaag ctcaagg atg gaa gtg cag tta ggg ctg gga agg    354
                              Met Glu Val Gln Leu Gly Leu Gly Arg
                                1               5 gtc tac cct cgg ccg ccg tcc aag acc tac cga gga gct ttc cag aat       402
Val Tyr Pro Arg Pro Pro Ser Lys Thr Tyr Arg Gly Ala Phe Gln Asn
 10                  15                  20                  25 ctg ttc cag agc gtg cgc gaa gtg atc cag aac ccg ggc ccc agg cac       450
Leu Phe Gln Ser Val Arg Glu Val Ile Gln Asn Pro Gly Pro Arg His
                 30                  35                  40 cca gag gcc gcg agc gca gca cct ccc ggc gcc agt ttg ctg ctg cag       498
Pro Glu Ala Ala Ser Ala Ala Pro Pro Gly Ala Ser Leu Leu Leu Gln
             45                  50                  55 cag cag cag cag cag cag cag cag cag cag cag cag cag cag cag cag       546
Gln Gln Gln Gln Gln Gln Gln Gln Gln Gln Gln Gln Gln Gln Gln Gln
         60                  65                  70 cag cag cag cag cag cag cag cag cag cag cag caa gag act agc ccc       594
Gln Gln Gln Gln Gln Gln Gln Gln Gln Gln Gln Glu Thr Ser Pro
     75                  80                  85 agg cag cag cag cag cag cag ggt gag gat ggt tct ccc caa gcc cat       642
Arg Gln Gln Gln Gln Gln Gln Gly Glu Asp Gly Ser Pro Gln Ala His
 90                  95                 100                 105 cgt aga ggc ccc aca ggc tac ctg gtc ctg gat gag gaa cag caa cct       690
Arg Arg Gly Pro Thr Gly Tyr Leu Val Leu Asp Glu Glu Gln Gln Pro
                110                 115                 120 tca cag ccg cag tcg gcc ctg gag tgc cac ccc gag aga ggt tgc gtc       738
Ser Gln Pro Gln Ser Ala Leu Glu Cys His Pro Glu Arg Gly Cys Val
            125                 130                 135 cca gag cct gga gcc gcc gtg gcc gcc agc aag ggg ctg ccg cag cag       786
Pro Glu Pro Gly Ala Ala Val Ala Ala Ser Lys Gly Leu Pro Gln Gln
```

-continued

```
        140                 145                 150
ctg cca gca cct ccg gac gag gat gac tca gct gcc cca tcc acg ttg    834
Leu Pro Ala Pro Pro Asp Glu Asp Asp Ser Ala Ala Pro Ser Thr Leu
    155                 160                 165 tcc ctg ctg ggc ccc act ttc ccc ggt tta agc agc tgc tcc gct gac    882
Ser Leu Leu Gly Pro Thr Phe Pro Gly Leu Ser Ser Cys Ser Ala Asp
170                 175                 180                 185 ctt aaa gac atc ctg agc gag gcc agc acc atg caa ctc ctt cag caa    930
Leu Lys Asp Ile Leu Ser Glu Ala Ser Thr Met Gln Leu Leu Gln Gln
                    190                 195                 200 cag cag cag gaa gca gta tcc gaa ggc agc agc agc ggg aga gcg agg    978
Gln Gln Gln Glu Ala Val Ser Glu Gly Ser Ser Ser Gly Arg Ala Arg
                205                 210                 215 gag gcc tcg ggg gct ccc act tcc tcc aag gac aat tac tta ggg ggc   1026
Glu Ala Ser Gly Ala Pro Thr Ser Ser Lys Asp Asn Tyr Leu Gly Gly
            220                 225                 230 act tcg acc att tct gac aac gcc aag gag ttg tgt aag gca gtg tcg   1074
Thr Ser Thr Ile Ser Asp Asn Ala Lys Glu Leu Cys Lys Ala Val Ser
        235                 240                 245 gtg tcc atg ggc ctg ggt gtg gag gcg ttg gag cat ctg agt cca ggg   1122
Val Ser Met Gly Leu Gly Val Glu Ala Leu Glu His Leu Ser Pro Gly
250                 255                 260                 265 gaa cag ctt cgg ggg gat tgc atg tac gcc cca ctt ttg gga gtt cca   1170
Glu Gln Leu Arg Gly Asp Cys Met Tyr Ala Pro Leu Leu Gly Val Pro
                    270                 275                 280 ccc gct gtg cgt ccc act cct tgt gcc cca ttg gcc gaa tgc aaa ggt   1218
Pro Ala Val Arg Pro Thr Pro Cys Ala Pro Leu Ala Glu Cys Lys Gly
                285                 290                 295 tct ctg cta gac gac agc gca ggc aag agc act gaa gat act gct gag   1266
Ser Leu Leu Asp Asp Ser Ala Gly Lys Ser Thr Glu Asp Thr Ala Glu
            300                 305                 310 tat tcc cct ttc aag gga ggt tac acc aaa ggg cta gaa ggc gag agc   1314
Tyr Ser Pro Phe Lys Gly Gly Tyr Thr Lys Gly Leu Glu Gly Glu Ser
        315                 320                 325 cta ggc tgc tct ggc agc gct gca gca ggg agc tcc ggg aca ctt gaa   1362
Leu Gly Cys Ser Gly Ser Ala Ala Ala Gly Ser Ser Gly Thr Leu Glu
330                 335                 340                 345 ctg ccg tct acc ctg tct ctc tac aag tcc gga gca ctg gac gag gca   1410
Leu Pro Ser Thr Leu Ser Leu Tyr Lys Ser Gly Ala Leu Asp Glu Ala
                    350                 355                 360 gct gcg tac cag agt cgc gac tac tac aac ttt cca ctg gct ctg gcc   1458
Ala Ala Tyr Gln Ser Arg Asp Tyr Tyr Asn Phe Pro Leu Ala Leu Ala
                365                 370                 375 gga ccg ccg ccc cct ccg ccg cct ccc cat ccc cac gct cgc atc aag   1506
Gly Pro Pro Pro Pro Pro Pro Pro Pro His Pro His Ala Arg Ile Lys
            380                 385                 390 ctg gag aac ccg ctg gac tac ggc agc gcc tgg gcg gct gcg gcg gcg   1554
Leu Glu Asn Pro Leu Asp Tyr Gly Ser Ala Trp Ala Ala Ala Ala Ala
        395                 400                 405 cag tgc cgc tat ggg gac ctg gcg agc ctg cat ggc gcg ggt gca gcg   1602
Gln Cys Arg Tyr Gly Asp Leu Ala Ser Leu His Gly Ala Gly Ala Ala
410                 415                 420                 425 gga ccc ggt tct ggg tca ccc tca gcc gcc gct tcc tca tcc tgg cac   1650
Gly Pro Gly Ser Gly Ser Pro Ser Ala Ala Ala Ser Ser Ser Trp His
                    430                 435                 440 act ctc ttc aca gcc gaa gaa ggc cag ttg tat gga ccg tgt ggt ggt   1698
Thr Leu Phe Thr Ala Glu Glu Gly Gln Leu Tyr Gly Pro Cys Gly Gly
                445                 450                 455 ggt ggt ggt ggt ggc ggc ggc ggc ggc ggc ggc ggc ggc ggc ggc ggc   1746
```

|  |  |  |  |  |  |  |  |  |  |  |  |  |
|---|---|---|---|---|---|---|---|---|---|---|---|---|
| Gly | Gly | Gly | Gly | Gly | Gly | Gly | Gly | Gly | Gly | Gly | Gly |  |
|  |  | 460 |  |  |  | 465 |  |  |  | 470 |  |  |

| ggc | gag | gcg | gga | gct | gta | gcc | ccc | tac | ggc | tac | act | cgg | ccc | cct | cag | 1794 |
|---|---|---|---|---|---|---|---|---|---|---|---|---|---|---|---|---|
| Gly | Glu | Ala | Gly | Ala | Val | Ala | Pro | Tyr | Gly | Tyr | Thr | Arg | Pro | Pro | Gln |  |
|  | 475 |  |  |  | 480 |  |  |  |  | 485 |  |  |  |  |  |  |

| ggg | ctg | gcg | ggc | cag | gaa | agc | gac | ttc | acc | gca | cct | gat | gtg | tgg | tac | 1842 |
|---|---|---|---|---|---|---|---|---|---|---|---|---|---|---|---|---|
| Gly | Leu | Ala | Gly | Gln | Glu | Ser | Asp | Phe | Thr | Ala | Pro | Asp | Val | Trp | Tyr |  |
| 490 |  |  |  | 495 |  |  |  | 500 |  |  |  |  | 505 |  |  |  |

| cct | ggc | ggc | atg | gtg | agc | aga | gtg | ccc | tat | ccc | agt | ccc | act | tgt | gtc | 1890 |
|---|---|---|---|---|---|---|---|---|---|---|---|---|---|---|---|---|
| Pro | Gly | Gly | Met | Val | Ser | Arg | Val | Pro | Tyr | Pro | Ser | Pro | Thr | Cys | Val |  |
|  |  |  | 510 |  |  |  | 515 |  |  |  |  | 520 |  |  |  |  |

| aaa | agc | gaa | atg | ggc | ccc | tgg | atg | gat | agc | tac | tcc | gga | cct | tac | ggg | 1938 |
|---|---|---|---|---|---|---|---|---|---|---|---|---|---|---|---|---|
| Lys | Ser | Glu | Met | Gly | Pro | Trp | Met | Asp | Ser | Tyr | Ser | Gly | Pro | Tyr | Gly |  |
|  | 525 |  |  |  | 530 |  |  |  |  | 535 |  |  |  |  |  |  |

| gac | atg | cgt | ttg | gag | act | gcc | agg | gac | cat | gtt | ttg | ccc | att | gac | tat | 1986 |
|---|---|---|---|---|---|---|---|---|---|---|---|---|---|---|---|---|
| Asp | Met | Arg | Leu | Glu | Thr | Ala | Arg | Asp | His | Val | Leu | Pro | Ile | Asp | Tyr |  |
| 540 |  |  |  | 545 |  |  |  | 550 |  |  |  |  |  |  |  |  |

| tac | ttt | cca | ccc | cag | aag | acc | tgc | ctg | atc | tgt | gga | gac | gaa | gct | tct | 2034 |
|---|---|---|---|---|---|---|---|---|---|---|---|---|---|---|---|---|
| Tyr | Phe | Pro | Pro | Gln | Lys | Thr | Cys | Leu | Ile | Cys | Gly | Asp | Glu | Ala | Ser |  |
| 555 |  |  |  | 560 |  |  |  | 565 |  |  |  |  |  |  |  |  |

| ggg | tgt | cac | tat | gga | gct | ctc | aca | tgt | gga | agc | tgc | aag | gtc | ttc | ttc | 2082 |
|---|---|---|---|---|---|---|---|---|---|---|---|---|---|---|---|---|
| Gly | Cys | His | Tyr | Gly | Ala | Leu | Thr | Cys | Gly | Ser | Cys | Lys | Val | Phe | Phe |  |
| 570 |  |  |  | 575 |  |  |  | 580 |  |  |  |  | 585 |  |  |  |

| aaa | aga | gcc | gct | gaa | gga | ttt | ttc | aga | atg | aac | aaa | tta | aaa | gaa | tca | 2130 |
|---|---|---|---|---|---|---|---|---|---|---|---|---|---|---|---|---|
| Lys | Arg | Ala | Ala | Glu | Gly | Phe | Phe | Arg | Met | Asn | Lys | Leu | Lys | Glu | Ser |  |
|  |  |  | 590 |  |  |  | 595 |  |  |  |  | 600 |  |  |  |  |

| tca | gac | act | aac | ccc | aag | cca | tac | tgc | atg | gca | gca | cca | atg | gga | ctg | 2178 |
|---|---|---|---|---|---|---|---|---|---|---|---|---|---|---|---|---|
| Ser | Asp | Thr | Asn | Pro | Lys | Pro | Tyr | Cys | Met | Ala | Ala | Pro | Met | Gly | Leu |  |
|  |  |  | 605 |  |  |  | 610 |  |  |  |  | 615 |  |  |  |  |

| aca | gaa | aac | aac | aga | aat | agg | aag | aaa | tcc | tac | aga | gaa | aca | aac | ttg | 2226 |
|---|---|---|---|---|---|---|---|---|---|---|---|---|---|---|---|---|
| Thr | Glu | Asn | Asn | Arg | Asn | Arg | Lys | Lys | Ser | Tyr | Arg | Glu | Thr | Asn | Leu |  |
|  |  | 620 |  |  |  | 625 |  |  |  |  | 630 |  |  |  |  |  |

| aaa | gct | gtc | tca | tgg | cct | ttg | aat | cat | act | taa | gttttatgat | ggaaggatac | 2279 |
|---|---|---|---|---|---|---|---|---|---|---|---|---|---|
| Lys | Ala | Val | Ser | Trp | Pro | Leu | Asn | His | Thr |  |  |  |  |
|  | 635 |  |  |  |  | 640 |  |  |  |  |  |  |  |

| gactatgaag | aaagacacag | agcaacatca | gacagtcaag | aatttcagag | ccagctggca | 2339 |
|---|---|---|---|---|---|---|
| tgcagtggac | ctcatgccag | cccattttat | gactatttag | ggagacagaa | gtacctgtgc | 2399 |
| gccagcagaa | atgattgcac | tattgataaa | ttccgaagga | aaaattgtcc | atcttgtcgt | 2459 |
| cttcggaaat | gttatgaagc | aggggtgact | ctggagaaaa | aattccgggt | tggcaattgc | 2519 |
| aagcatctca | aaatgaccag | accctgaaga | aaggctgact | tgcctcattc | aaaatgaggg | 2579 |
| ctctagaggg | ctctagtgga | tagtctggag | aaacctggcg | tctgaggctt | aggagcttag | 2639 |
| gtttttgctc | ctcaacacag | actttgacgt | tggggttggg | ggctactctc | ttgattgctg | 2699 |
| actccctcca | gcgggaccaa | tagtgttttc | ctacctcaca | gggatgttgt | gaggacgggc | 2759 |
| tgtagaagta | atagtggtta | ccactcatgt | agttgtgagt | atcatgatta | ttgtttcctg | 2819 |
| taatgtggct | tggcattggc | aaagtgcttt | ttgattgttc | ttgatcacat | atgatgggga | 2879 |
| ccaggcactg | actcaggcgg | atgcagtgaa | gctctggctc | agtcgcttgc | ttttcgtggt | 2939 |
| gtgctgccag | gaagaaactt | tgctgatggg | actcaaggtg | tcaccttgga | caagaagcaa | 2999 |
| ctgtgtctgt | ctgaggttcc | tgtggccatc | tttatttgtg | tattaggcaa | ttcgtatttc | 3059 |
| ccccttaggt | tctagccttc | tggatcccag | ccagtgacct | agatcttagc | ctcaggccct | 3119 |
| gtcactgagc | tgaaggtagt | agctgatcca | cagaagttca | gtaaacaagg | accagatttc | 3179 |
| tgcttctcca | ggagaagaag | ccagccaacc | cctctcttca | aacacactga | gagactacag | 3239 |

-continued

```
tccgactttc cctcttacat ctagccttac tgtagccaca ctccttgatt gctctctcac    3299
atcacatgct tctcttcatc agttgtaagc ctctcattct tctcccaagc cagactcaaa    3359
tattgtattg atgtcaaaga agaatcactt agagtttgga atatcttgtt ctctctctgc    3419
tccatagctt ccatattgac accagtttct ttctagtgga gaagtggagt ctgtgaagcc    3479
agggaaacac acatgtgaga gtcagaagga ctctccctga cttgcctggg gcctgtcttt    3539
cccaccttct ccagtctgtc taaacacaca cacacacaca cacacacaca cacacacaca    3599
cacacacgct ctctctctct ctccccccccc aacacacaca cactctctct ctcacacaca    3659
cacacataca cacacacttc tttctctttc ccctgactca gcaacattct ggagaaaagc    3719
caaggaagga cttcaggagg ggagtttccc ccttctcagg gcagaatttt aatctccaga    3779
ccaacaagaa gttccctaat gtggattgaa aggctaatga ggtttatttt taactacttt    3839
ctatttgttt gaatgttgca tatttctact agtgaaattt tcccttaata aagccattaa    3899
tacacccaaa aaaaaaaaaa aaa                                            3922
```

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9

```
tccttcacca atgtcaactc c                                                21
```

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10

```
gagccatcca aactcttgag a                                                21
```

<210> SEQ ID NO 11
<211> LENGTH: 22
<212> TYPE: DNA
<213> ORGANISM: Artificial Sequence
<220> FEATURE:
<223> OTHER INFORMATION: Probe

<400> SEQUENCE: 11

```
agtaccgcat gcacaagtcc cg                                               22
```

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 12

```
gcgctctgac agcctc                                                      16
```

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligonucleotide -continued

<400> SEQUENCE: 13
cacctgcggg aagctc                                                    16

<210> SEQ ID NO 14
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 14
ggctgtgatg atgcgg                                                    16

<210> SEQ ID NO 15
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 15
cttcgcgcac gctctg                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 16
atggtgctgg cctcgc                                                    16

<210> SEQ ID NO 17
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 17
ggtcgaagtg ccccct                                                    16

<210> SEQ ID NO 18
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 18
gacaccgaca ctgcct                                                    16

<210> SEQ ID NO 19
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 19
cccgaagctg ttcccc                                                    16

<210> SEQ ID NO 20

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 20
cttgcctgcg ctgtcg                                                    16

<210> SEQ ID NO 21
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 21
gttgtagtag tcgcga                                                    16

<210> SEQ ID NO 22
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 22
aagttgtagt agtcgc                                                    16

<210> SEQ ID NO 23
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 23
gcgctgccgt agtcca                                                    16

<210> SEQ ID NO 24
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 24
aggatgagga agcggc                                                    16

<210> SEQ ID NO 25
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 25
gctcccgcct cgccgc                                                    16

<210> SEQ ID NO 26
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 26
```
cgctttcctg gcccgc                                                     16

<210> SEQ ID NO 27
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 27
gccgccaggg taccac                                                     16

<210> SEQ ID NO 28
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 28
ccaaacgcat gtcccc                                                     16

<210> SEQ ID NO 29
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 29
agcttcatct ccacag                                                     16

<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 30
tcccttcagc ggctct                                                     16

<210> SEQ ID NO 31
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 31
tttctgctgg cgcaca                                                     16

<210> SEQ ID NO 32
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 32
gttcattcga agttca                                                     16

<210> SEQ ID NO 33
<211> LENGTH: 16
<212> TYPE: DNA

<213> ORGANISM: Artificial Sequence
<220> FEATURE:
<223> OTHER INFORMATION: Synthetic Oligonucleotide

<400> SEQUENCE: 33
gaggatcatc acagat                                              16

<210> SEQ ID NO 34
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 34
ctaaacttcc cgtggc                                              16

<210> SEQ ID NO 35
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 35
gttgatttaa tggttg                                              16

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 36
atggttgatt taatgg                                              16

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37
ggttgattta atggtt                                              16

<210> SEQ ID NO 38
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 38
tggttgattt aatggt                                              16

<210> SEQ ID NO 39
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 39
acagcactgg agcggc                                              16

<210> SEQ ID NO 40
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 40
aacttcaccg aagagg                                                        16

<210> SEQ ID NO 41
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 41
agtctttagc agcttt                                                        16

<210> SEQ ID NO 42
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 42
gcttcctccg agtctt                                                        16

<210> SEQ ID NO 43
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 43
ccttgcttcc tccgag                                                        16

<210> SEQ ID NO 44
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 44
gcactttcct tgcttc                                                        16

<210> SEQ ID NO 45
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 45
tcagtcctac caggca                                                        16

<210> SEQ ID NO 46
<211> LENGTH: 16
<212> TYPE: DNA
<213> ORGANISM: Artificial Sequence
<220> FEATURE:

<223> OTHER INFORMATION: Synthetic Oligonucleotide

<400> SEQUENCE: 46
gactgaggca gctgcg                                                              16

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 47
ccgactgagg cagctg                                                              16

<210> SEQ ID NO 48
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 48
gctagctcgc ccgctc                                                              16

<210> SEQ ID NO 49
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 49
cagctagctc gcccgc                                                              16

<210> SEQ ID NO 50
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 50
gcaatgtgca gctagc                                                              16

<210> SEQ ID NO 51
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 51
gtcgcctggc tcctaa                                                              16

<210> SEQ ID NO 52
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 52
ctggctccgc actcgg                                                              16

```
<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
atctctggct ccgcac                                                     16

<210> SEQ ID NO 54
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 54
tgatctctgg ctccgc                                                     16

<210> SEQ ID NO 55
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 55
agtgtccact gaagta                                                     16

<210> SEQ ID NO 56
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 56
aggctcacag tctgtc                                                     16

<210> SEQ ID NO 57
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 57
gacacacggt ggacaa                                                     16

<210> SEQ ID NO 58
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 58
agaagacaca cggtgg                                                     16

<210> SEQ ID NO 59
<211> LENGTH: 16
<212> TYPE: DNA
<213> ORGANISM: Artificial Sequence
<220> FEATURE:
<223> OTHER INFORMATION: Synthetic Oligonucleotide
```

```
<400> SEQUENCE: 59
cgctctgaca gcctca                                                  16

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 60
gtcgctgcag ctagct                                                  16

<210> SEQ ID NO 61
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 61
ggtagtcgct gcagct                                                  16

<210> SEQ ID NO 62
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 62
gcggtagtcg ctgcag                                                  16

<210> SEQ ID NO 63
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 63
atgcggtagt cgctgc                                                  16

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 64
gtgatgatgc ggtagt                                                  16

<210> SEQ ID NO 65
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 65
ctgtgatgat gcggta                                                  16

<210> SEQ ID NO 66
<211> LENGTH: 16
```

```
<212> TYPE: DNA
<213> ORGANISM: Artificial Sequence
<220> FEATURE:
<223> OTHER INFORMATION: Synthetic Oligonucleotide

<400> SEQUENCE: 66
gaagagttca acaggc                                                    16

<210> SEQ ID NO 67
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 67
gcttggctga atcttc                                                    16

<210> SEQ ID NO 68
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 68
ccttgagctt ggctga                                                    16

<210> SEQ ID NO 69
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 69
atccttgagc ttggct                                                    16

<210> SEQ ID NO 70
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 70
tccatccttg agcttg                                                    16

<210> SEQ ID NO 71
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 71
gtaggtcttg gacggc                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 72
```
gattctggaa agctcc                                                     16

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73
gctctggaac agattc                                                     16

<210> SEQ ID NO 74
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 74
cgcgcacgct ctggaa                                                     16

<210> SEQ ID NO 75
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 75
tcacttcgcg cacgct                                                     16

<210> SEQ ID NO 76
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 76
tggatcactt cgcgca                                                     16

<210> SEQ ID NO 77
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 77
gttctggatc acttcg                                                     16

<210> SEQ ID NO 78
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 78
cgctcgcggc ctctgg                                                     16

<210> SEQ ID NO 79
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 79
tgcgctcgcg gcctct        16

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80
gctgcgctcg cggcct        16

<210> SEQ ID NO 81
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 81
aggtgctgcg ctcgcg        16

<210> SEQ ID NO 82
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 82
gctgttcctc atccag        16

<210> SEQ ID NO 83
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 83
tgctgcggca gcccct        16

<210> SEQ ID NO 84
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 84
ggtgctggcc tcgctc        16

<210> SEQ ID NO 85
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 85
tgcatggtgc tggcct        16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 86
gttgcatggt gctggc                                               16

<210> SEQ ID NO 87
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 87
tgctgttgct gaagga                                               16

<210> SEQ ID NO 88
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 88
ggatactgct tcctgc                                               16

<210> SEQ ID NO 89
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 89
tcggatactg cttcct                                               16

<210> SEQ ID NO 90
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 90
tgccttcgga tactgc                                               16

<210> SEQ ID NO 91
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 91
ctcgctctcc cgctgc                                               16

<210> SEQ ID NO 92
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 92
tgtccttgga ggaagt                                                        16

<210> SEQ ID NO 93
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 93
tggtcgaagt gccccc                                                        16

<210> SEQ ID NO 94
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 94
cagaaatggt cgaagt                                                        16

<210> SEQ ID NO 95
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 95
tgttcccctg gactca                                                        16

<210> SEQ ID NO 96
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 96
agctgttccc ctggac                                                        16

<210> SEQ ID NO 97
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 97
gaagctgttc ccctgg                                                        16

<210> SEQ ID NO 98
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 98
ccgaagctgt tcccct                                                        16

<210> SEQ ID NO 99

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 99
gtacatgcaa tccccc                                                     16

<210> SEQ ID NO 100
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 100
acagcgggtg gaactc                                                     16

<210> SEQ ID NO 101
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 101
ggacgcacag cgggtg                                                     16

<210> SEQ ID NO 102
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 102
gtgggacgca cagcgg                                                     16

<210> SEQ ID NO 103
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 103
tgcattcggc caatgg                                                     16

<210> SEQ ID NO 104
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 104
cctttgcatt cggcca                                                     16

<210> SEQ ID NO 105
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 105
```

```
aacctttgca ttcggc                                              16

<210> SEQ ID NO 106
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 106
gctcttgcct gcgctg                                              16

<210> SEQ ID NO 107
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 107
cagtgctctt gcctgc                                              16

<210> SEQ ID NO 108
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 108
ttcagtgctc ttgcct                                              16

<210> SEQ ID NO 109
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 109
tcttcagtgc tcttgc                                              16

<210> SEQ ID NO 110
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 110
actcagcagt atcttc                                              16

<210> SEQ ID NO 111
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 111
atactcagca gtatct                                              16

<210> SEQ ID NO 112
<211> LENGTH: 16
<212> TYPE: DNA
```

```
<213> ORGANISM: Artificial Sequence
<220> FEATURE:
<223> OTHER INFORMATION: Synthetic Oligonucleotide

<400> SEQUENCE: 112
tttggtgtaa cctccc                                                  16

<210> SEQ ID NO 113
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 113
cctttggtgt aacctc                                                  16

<210> SEQ ID NO 114
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 114
ctaggctctc gccttc                                                  16

<210> SEQ ID NO 115
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 115
cagcctaggc tctcgc                                                  16

<210> SEQ ID NO 116
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 116
agcagcctag gctctc                                                  16

<210> SEQ ID NO 117
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 117
ctgccagagc agccta                                                  16

<210> SEQ ID NO 118
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 118
tcgcgactct ggtacg                                                  16
```

```
<210> SEQ ID NO 119
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 119
gtagtcgcga ctctgg                                                      16

<210> SEQ ID NO 120
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 120
tagtagtcgc gactct                                                      16

<210> SEQ ID NO 121
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 121
agttgtagta gtcgcg                                                      16

<210> SEQ ID NO 122
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 122
tctccagctt gatgcg                                                      16

<210> SEQ ID NO 123
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 123
cagcgggttc tccagc                                                      16

<210> SEQ ID NO 124
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 124
ccttcttcgg ctgtga                                                      16

<210> SEQ ID NO 125
<211> LENGTH: 16
<212> TYPE: DNA
<213> ORGANISM: Artificial Sequence
<220> FEATURE:
```

<223> OTHER INFORMATION: Synthetic Oligonucleotide

<400> SEQUENCE: 125
ggtccataca actggc                                            16

<210> SEQ ID NO 126
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 126
acacatcagg tgcggt                                            16

<210> SEQ ID NO 127
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 127
cgccagggta ccacac                                            16

<210> SEQ ID NO 128
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 128
catgccgcca gggtac                                            16

<210> SEQ ID NO 129
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 129
accatgccgc cagggt                                            16

<210> SEQ ID NO 130
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 130
ctgctcacca tgccgc                                            16

<210> SEQ ID NO 131
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 131
acacaagtgg gactgg                                            16

```
<210> SEQ ID NO 132
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 132
cccttcagcg gctctt                                                         16

<210> SEQ ID NO 133
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 133
cagagtcatc cctgct                                                         16

<210> SEQ ID NO 134
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 134
caccctcaag attctt                                                         16

<210> SEQ ID NO 135
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 135
aaggtagtct ttaagg                                                         16

<210> SEQ ID NO 136
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 136
gttttcaaat gcagcc                                                         16

<210> SEQ ID NO 137
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 137
gccatgagac agcttt                                                         16

<210> SEQ ID NO 138
<211> LENGTH: 16
<212> TYPE: DNA
<213> ORGANISM: Artificial Sequence
<220> FEATURE:
<223> OTHER INFORMATION: Synthetic Oligonucleotide
```

```
<400> SEQUENCE: 138
attcttgact gtctga                                                      16

<210> SEQ ID NO 139
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 139
gcatgccagc tggctc                                                      16

<210> SEQ ID NO 140
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 140
cgcgcaggta ggagcc                                                      16

<210> SEQ ID NO 141
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 141
tctaaacatg acggtt                                                      16

<210> SEQ ID NO 142
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 142
atgcaattgc ctgcca                                                      16

<210> SEQ ID NO 143
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 143
atgggagtaa cttttg                                                      16

<210> SEQ ID NO 144
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 144
catattattg tgctgc                                                      16

<210> SEQ ID NO 145
<211> LENGTH: 16
```

```
<212> TYPE: DNA
<213> ORGANISM: Artificial Sequence
<220> FEATURE:
<223> OTHER INFORMATION: Synthetic Oligonucleotide

<400> SEQUENCE: 145
gagttgtgat ttcagg                                                   16

<210> SEQ ID NO 146
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 146
ttgatggaat gctgat                                                   16

<210> SEQ ID NO 147
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 147
ggttaacttt ctctga                                                   16

<210> SEQ ID NO 148
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 148
tggattgtaa attacg                                                   16

<210> SEQ ID NO 149
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 149
tcaatctaga taccat                                                   16

<210> SEQ ID NO 150
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 150
cacatcagaa ggagta                                                   16

<210> SEQ ID NO 151
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 151
```
gagtgttaat gaagac                                              16

<210> SEQ ID NO 152
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 152
ctgattagct atgacc                                              16

<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153
aaaccttttg ctgggt                                              16

<210> SEQ ID NO 154
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 154
atgagtcctc agaatc                                              16

<210> SEQ ID NO 155
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 155
gtagattcta gctttg                                              16

<210> SEQ ID NO 156
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 156
acaggctctg actagg                                              16

<210> SEQ ID NO 157
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 157
tgtgtgaccc ttggac                                              16

<210> SEQ ID NO 158
<211> LENGTH: 16
<212> TYPE: DNA
<213> ORGANISM: Artificial Sequence

```
<220> FEATURE:
<223> OTHER INFORMATION: Synthetic Oligonucleotide

<400> SEQUENCE: 158
aagtatgagc atggtt                                                    16

<210> SEQ ID NO 159
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 159
ggattctcta cacaca                                                    16

<210> SEQ ID NO 160
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 160
ccatttgtgc caaacc                                                    16

<210> SEQ ID NO 161
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 161
aggttaggga gtaggc                                                    16

<210> SEQ ID NO 162
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 162
tagggtttgg tcagaa                                                    16

<210> SEQ ID NO 163
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 163
gttatcttac tctccc                                                    16

<210> SEQ ID NO 164
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 164
gattgtgtat agctgc                                                    16
```

```
<210> SEQ ID NO 165
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 165
ggttatggtt ctgtct                                                   16

<210> SEQ ID NO 166
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 166
cttcattgca ggtctg                                                   16

<210> SEQ ID NO 167
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 167
tagccaactt tcttta                                                   16

<210> SEQ ID NO 168
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 168
tttggtaaca ttaggc                                                   16

<210> SEQ ID NO 169
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 169
atggttgtcc tgtaca                                                   16

<210> SEQ ID NO 170
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 170
tcttatgttt ccgaaccgtt                                               20

<210> SEQ ID NO 171
<211> LENGTH: 21
<212> TYPE: DNA
<213> ORGANISM: Artificial Sequence
<220> FEATURE:
<223> OTHER INFORMATION: Primer
```

```
<400> SEQUENCE: 171
gcccctggat ggatagctac t                                              21

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
ccacagatca ggcaggtctt c                                              21

<210> SEQ ID NO 173
<211> LENGTH: 24
<212> TYPE: DNA
<213> ORGANISM: Artificial Sequence
<220> FEATURE:
<223> OTHER INFORMATION: Probe

<400> SEQUENCE: 173
actgccaggg accatgtttt gccc                                           24

<210> SEQ ID NO 174
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 174
gagaaccatc ctcacc                                                    16

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
ggaccaggta gcctgt                                                    16

<210> SEQ ID NO 176
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 176
cccctggact cagatg                                                    16

<210> SEQ ID NO 177
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 177
gcacaaggag tgggac                                                    16

<210> SEQ ID NO 178
```

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 178
gctgtgaaga gagtgt                                                       16

<210> SEQ ID NO 179
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 179
tttgacacaa gtggga                                                       16

<210> SEQ ID NO 180
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 180
gtgacaccca gaagct                                                       16

<210> SEQ ID NO 181
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 181
catccctgct tcataa                                                       16

<210> SEQ ID NO 182
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 182
accaagtttc ttcagc                                                       16

<210> SEQ ID NO 183
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 183
cttggcccac ttgacc                                                       16

<210> SEQ ID NO 184
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 184
```
tcctggagtt gacatt                                                    16

<210> SEQ ID NO 185
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 185
cactggctgt acatcc                                                    16

<210> SEQ ID NO 186
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 186
catccaaact cttgag                                                    16

<210> SEQ ID NO 187
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 187
gctttcatgc acagga                                                    16

<210> SEQ ID NO 188
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 188
gaagttcatc aaagaa                                                    16

<210> SEQ ID NO 189
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 189
agttccttga tgtagt                                                    16

<210> SEQ ID NO 190
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 190
ttgcacagag atgatc                                                    16

<210> SEQ ID NO 191
<211> LENGTH: 16
<212> TYPE: DNA

```
<213> ORGANISM: Artificial Sequence
<220> FEATURE:
<223> OTHER INFORMATION: Synthetic Oligonucleotide

<400> SEQUENCE: 191
gatgggcttg actttc                                                      16

<210> SEQ ID NO 192
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 192
caggcagaag acatct                                                      16

<210> SEQ ID NO 193
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 193
cccaaggcac tgcaga                                                      16

<210> SEQ ID NO 194
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 194
gctgacattc atagcc                                                      16

<210> SEQ ID NO 195
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 195
tggggagaac catcctcacc ctgc                                             24

<210> SEQ ID NO 196
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 196
tccaggacca ggtagcctgt gggg                                             24

<210> SEQ ID NO 197
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 197
tgttcccctg gactcagatg ctcc                                             24
```

<210> SEQ ID NO 198
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 198
tggggcacaa ggagtgggac gcac                                          24

<210> SEQ ID NO 199
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 199
ttcggctgtg aagagagtgt gcca                                          24

<210> SEQ ID NO 200
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 200
cgcttttgac acaagtggga ctgg                                          24

<210> SEQ ID NO 201
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 201
catagtgaca cccagaagct tcat                                          24

<210> SEQ ID NO 202
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 202
gagtcatccc tgcttcataa catt                                          24

<210> SEQ ID NO 203
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 203
gattaccaag tttcttcagc ttcc                                          24

<210> SEQ ID NO 204
<211> LENGTH: 24
<212> TYPE: DNA
<213> ORGANISM: Artificial Sequence
<220> FEATURE:

<210> SEQ ID NO 205
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 204
aggccttggc ccacttgacc acgt                                    24

<210> SEQ ID NO 205
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 205
agcatcctgg agttgacatt ggtg                                    24

<210> SEQ ID NO 206
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 206
gacacactgg ctgtacatcc ggga                                    24

<210> SEQ ID NO 207
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 207
gagccatcca aactcttgag agag                                    24

<210> SEQ ID NO 208
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 208
cagtgctttc atgcacagga attc                                    24

<210> SEQ ID NO 209
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 209
attcgaagtt catcaaagaa tttt                                    24

<210> SEQ ID NO 210
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 210
atcgagttcc ttgatgtagt tcat                                    24

```
<210> SEQ ID NO 211
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 211
gcacttgcac agagatgatc tctg                                          24

<210> SEQ ID NO 212
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 212
aatagatggg cttgactttc ccag                                          24

<210> SEQ ID NO 213
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 213
ataacaggca gaagacatct gaaa                                          24

<210> SEQ ID NO 214
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 214
attccccaag gcactgcaga ggag                                          24

<210> SEQ ID NO 215
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 215
atgggctgac attcatagcc ttca                                          24

<210> SEQ ID NO 216
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 216
ctgtgaagag agtg                                                     14

<210> SEQ ID NO 217
<211> LENGTH: 12
<212> TYPE: DNA
<213> ORGANISM: Artificial Sequence
<220> FEATURE:
<223> OTHER INFORMATION: Synthetic Oligonucleotide
```

```
<400> SEQUENCE: 217
tgtgaagaga gt                                                            12

<210> SEQ ID NO 218
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 218
ttgacacaag tggg                                                          14

<210> SEQ ID NO 219
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 219
tgacacaagt gg                                                            12

<210> SEQ ID NO 220
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 220
tgacacccag aagc                                                          14

<210> SEQ ID NO 221
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 221
gacacccaga ag                                                            12

<210> SEQ ID NO 222
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 222
ccaagtttct tcag                                                          14

<210> SEQ ID NO 223
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 223
caagtttctt ca                                                            12
```

```
<210> SEQ ID NO 224
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 224
actggctgta catc                                                         14

<210> SEQ ID NO 225
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 225
ctggctgtac at                                                           12

<210> SEQ ID NO 226
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 226
gttccttgat gtag                                                         14

<210> SEQ ID NO 227
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 227
ttccttgatg ta                                                           12

<210> SEQ ID NO 228
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 228
atgggcttga cttt                                                         14

<210> SEQ ID NO 229
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 229
tgggcttgac tt                                                           12

<210> SEQ ID NO 230
<211> LENGTH: 14
<212> TYPE: DNA
<213> ORGANISM: Artificial Sequence
<220> FEATURE:
<223> OTHER INFORMATION: Synthetic Oligonucleotide
```

```
<400> SEQUENCE: 230
ccaaggcact gcag                                                        14

<210> SEQ ID NO 231
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 231
caaggcactg ca                                                          12
```

METHODS OF TREATING KENNEDY'S DISEASE

SEQUENCE LISTING

The present application is being filed along with a Sequence Listing in electronic format. The Sequence Listing is provided as a file entitled BIOL0195USASEQ_ST25.txt, created Apr. 9, 2015, which is 380 Kb in size. The information in the electronic format of the sequence listing is incorporated herein by reference in its entirety.

FIELD

Certain embodiments are directed to methods of ameliorating, treating, or preventing Kennedy's Disease in a subject carrying a mutation in the Androgen Receptor (AR) gene, such as expansion of a CAG trinucleotide repeat, which is associated with Kennedy's Disease, by administering an antisense compound targeted to AR.

BACKGROUND

Kennedy's Disease, also known as Spinal Bulbar Muscular Atrophy, bulbo-spinal atrophy, X-linked bulbospinal neuropathy (XBSN), or X-linked spinal muscular atrophy type 1 (SMAX1), is a neuromuscular degenerative disease affecting males who carry a mutation in the Androgen Receptor (AR) gene on the X chromosome. Kennedy's Disease is caused by expansion of a trinucleotide CAG repeat in exon 1 of the androgen receptor gene that encodes a polyglutamine tract in the androgen receptor protein.

There is a positive correlation between CAG repeat length and disease severity, and a negative correlation between repeat length and the age of disease onset. The number of CAG repeats in Kennedy's Disease patients varies, but can be in the range of about 36-62 repeats. Kennedy's Disease is characterized by the degeneration and loss of lower motor neurons in the brainstem and spinal cord, together with progressive weakness, atrophy and fasciculation of proximal limb and bulbar muscles combined with sensory impairment. Kennedy's Disease usually develops in middle adult life, but onset and severity of the disease can vary from adolescence to old age.

Currently there are no cures or treatments for Kennedy's Disease. Males suffering from Kennedy's Disease commonly end up in a wheelchair as a result of motor neuron degeneration and muscle wasting, and are subsequently at higher risk of developing other ailments.

SUMMARY

Several embodiments provided herein relate to the discovery that antisense compounds targeting Androgen Receptor can ameliorate, treat, or prevent Kennedy's Disease in a subject carrying a mutation in the Androgen Receptor gene, such as expansion of a CAG trinucleotide repeat, which is associated with Kennedy's Disease. Certain embodiments are drawn to increasing muscle strength, improving muscle atrophy, and/or inhibiting muscle denervation in a subject having Kennedy's Disease, thereby treating Kennedy's Disease. Certain embodiments relate to preventing the onset of Kennedy's Disease and its symptoms or complications in a subject having an Androgen Receptor (AR) gene mutation associated with Kennedy's Disease. Certain embodiments are drawn to preventing muscle strength loss, preventing muscle atrophy, and/or preventing muscle denervation in a subject having an Androgen Receptor (AR) gene mutation associated with Kennedy's Disease, thereby preventing Kennedy's Disease.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Androgen Receptor", it is implied that Androgen Receptor levels are inhibited within a range of 63% and 77%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying" or "selecting" an animal with Kennedy's Disease or having an AR gene mutation associated with Kennedy's Disease means identifying or selecting a subject having been diagnosed with Kennedy's Disease, or an AR gene mutation associated with Kennedy's Disease such as a CAG trinucleotide repeat expansion in the AR gene; or, identifying or selecting a subject having any symptom of Kennedy's Disease, including, but not limited to, muscle fatigue, muscle cramping, muscle weakness, muscle atrophy, muscle twitching or tremoring; and/or bulbar signs such as difficulty with breathing, swallowing, and/or talking.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Prevent" refers to delaying or forestalling the onset or development of a disease, disorder, or condition for a period of time from minutes to indefinitely. Prevent also means reducing risk of developing a disease, disorder, or condition. It will be understood that the term "prevent" includes, but does not require, complete prevention. Prevent can also refer to delaying or forestalling the onset or development of symptoms that typically appear in adulthood as a result of an inherited gene mutation.

"Preventing Kennedy's Disease" refers to performing actions that delay or forestall the onset or development of symptoms in a subject that typically appear in adulthood as a result of the subject having an inherited AR gene mutation associated with Kennedy's Disease. Prevention of Kennedy's Disease includes, but is not limited to, preventing muscle strength loss, preventing muscle atrophy, and/or preventing muscle denervation in a subject having an inherited AR gene mutation associated with Kennedy's Disease, such as a CAG trinucleotide repeat expansion.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Symptom(s)" of Kennedy's Disease include, but are not limited to, any one or more of the following: bulbar signs, such as difficult breathing, swallowing, or talking; dysphagia; intention tremor; hand tremors; lower motor neuropathy; muscle weakness and/or atrophy; muscle denervation; numbness or loss of sensation; decreased deep tendon reflexes; muscular fasciculations (e.g. unintentional muscle twitching); muscle cramps; muscle spasms; hypertrophied calf muscles; gynecomastia (enlarged breasts); effeminate effect of androgen deficiency; impotence; erectile dysfunction; reduced fertility; testicular atrophy; muscle asymmetry; and/or elevated serum creatine kinase.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Treating Kennedy's Disease" refers to performing actions that lead to amelioration of Kennedy's Disease or of the symptoms accompanied therewith. The combination of said actions is encompassed by the term "treatment." Amelioration of Kennedy's Disease includes, but is not limited to, increasing muscle strength, improving muscle atrophy, and/or inhibiting muscle denervation in a subject having Kennedy's Disease.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Treating Kennedy's Disease

Certain embodiments provided herein relate to ameliorating or treating Kennedy's Disease in a subject by administering an antisense compound targeted to Androgen Receptor. For example, several embodiments are drawn to increasing muscle strength, improving muscle atrophy, and/or inhibiting muscle denervation in a subject having Kennedy's Disease by administering an antisense compound targeted to Androgen Receptor. A subject suffering from Kennedy's Disease can be identified and confirmed by molecular diagnostic techniques available in the art, such as PCR-based assays for detecting CAG repeat expansions in the androgen receptor gene from a blood sample. The subject can have, for example, an expansion of about 36-62 trinucleotide repeats.

In certain embodiments, a method of ameliorating or treating Kennedy's Disease in a subject comprises administering to the subject an antisense compound or modified oligonucleotide targeted to human androgen receptor (AR), thereby ameliorating or treating Kennedy's Disease in the subject.

In certain embodiments, a method of increasing muscle strength in a subject having Kennedy's Disease comprises administering to the subject an antisense compound or modified oligonucleotide targeted to human androgen receptor (AR), thereby increasing muscle strength and ameliorating or treating Kennedy's Disease in the subject. In several aspects, the muscle is a proximal limb muscle (e.g. arms and legs) or bulbar muscle (e.g. mouth, tongue, and throat).

In certain embodiments, a method of improving muscle atrophy in a subject having Kennedy's Disease comprises administering to the subject an antisense compound or modified oligonucleotide targeted to human androgen receptor (AR), thereby improving muscle atrophy and ameliorating or treating Kennedy's Disease in the subject. In several aspects, improving muscle atrophy increases muscle cell size. In several aspects, the muscle is a proximal limb muscle (e.g. arms and legs) or bulbar muscle (e.g. mouth, tongue, and throat).

In certain embodiments, a method of inhibiting muscle denervation in a subject having Kennedy's Disease comprises administering to the subject an antisense compound or modified oligonucleotide targeted to human androgen receptor (AR), thereby inhibiting muscle denervation and ameliorating or treating Kennedy's Disease in the subject. In several aspects, the muscle is a proximal limb muscle (e.g. arms and legs) or bulbar muscle (e.g. mouth, tongue, and throat).

In certain embodiments, a method of inhibiting AR expression in a subject having Kennedy's Disease comprises administering to the subject an antisense compound or modified oligonucleotide targeted to human androgen receptor (AR), thereby ameliorating or treating Kennedy's Disease in the subject.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 21 linked nucleosides. In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 16 linked nucleosides, a gap segment consisting of 10 linked deoxynucleosides, a 5' wing segment consisting of three linked nucleosides, a 3' wing segment consisting of three linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 16 linked nucleosides, a gap segment consisting of 9 linked deoxynucleosides, a 5' wing segment consisting of three linked nucleosides, a 3' wing segment consisting of four linked nucleosides; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are each a constrained ethyl (cEt) sugar; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of four linked nucleosides, a 3' wing segment consisting of four linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of seven linked nucleosides, a 3' wing segment consisting of two linked nucleosides; the seven linked nucleosides of the 5' wing segment are a 2'-O-methoxyethyl sugar, a constrained ethyl (cEt) sugar, a constrained ethyl (cEt) sugar, a 2'-O-methoxyethyl sugar, a 2'-O-methoxyethyl sugar, a constrained ethyl (cEt) sugar, and a constrained ethyl (cEt) sugar in the 5' to 3' direction; the two linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of six linked nucleosides, a 3' wing segment consisting of three linked nucleosides; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

Certain embodiments provide a method of reducing AR expression in a subject having Kennedy's Disease or an AR gene mutation associated with Kennedy's Disease comprising administering to the subject a compound as described herein. In certain embodiments, the compound comprises a modified oligonucleotide 12 to 30 linked nucleosides in length targeted to AR. In certain embodiments, the compound comprises a modified oligonucleotide 15 to 30 linked nucleosides in length targeted to AR. In certain embodiments, the compound comprises a modified oligonucleotide 18 to 21 linked nucleosides in length targeted to AR. In certain embodiments, the compound comprises a modified oligonucleotide 17 to 35 linked nucleosides in length targeted to AR. In certain embodiments, the compound comprises a modified oligonucleotide 17 to 25 linked nucleosides in length targeted to AR. In certain embodiments, the compound comprises a modified oligonucleotide 17 to 24 linked nucleosides in length targeted to AR. In certain embodiments, the compound comprises a modified oligonucleotide 17 to 23 linked nucleosides in length targeted to AR. In certain embodiments, the compound comprises a modified oligonucleotide 17 to 22 linked nucleosides in length targeted to AR. In certain embodiments, the compound comprises a modified oligonucleotide 17 to 21 linked nucleosides in length targeted to AR.

Certain embodiments provide a method for treating a subject with Kennedy's Disease comprising: a) identifying said subject with Kennedy's Disease, and b) administering to said subject a therapeutically effective amount of a compound comprising a modified oligonucleotide consisting of 12 to 30 linked nucleosides and having a nucleobase sequence at least 90% complementary to any of SEQ ID NOs: 1-8 as measured over the entirety of said modified oligonucleotide. In certain embodiments, the therapeutically effective amount of the compound administered to the subject treats or reduces Kennedy's Disease, or a symptom thereof, in the subject.

Certain embodiments provide a method for treating a subject with Kennedy's Disease comprising: a) identifying said subject with Kennedy's Disease, and b) administering to said subject a therapeutically effective amount of a compound comprising a modified oligonucleotide consisting of 12 to 30 linked nucleosides and having a nucleobase sequence 100% complementary to any of SEQ ID NOs: 1-8 as measured over the entirety of said modified oligonucleotide. In certain embodiments, the therapeutically effective amount of the compound administered to the subject treats or reduces Kennedy's Disease, or a symptom thereof, in the subject.

Certain embodiments are drawn to a method of ameliorating or treating a subject with Kennedy's Disease comprising administering to the subject an antisense compound or modified oligonucleotide targeted to human androgen receptor (AR) upstream of the 3' end of exon 3 and/or upstream of the ligand binding domain. In certain embodiments, an antisense compound provided herein targets AR within exon 1 encoding the N-terminal domain or exons 2 and 3 encoding the DNA binding domain, but not within exons 4-8 encoding the ligand binding domain. In certain embodiments, an antisense compound provided herein targets AR within exon 1, for example within nucleotide regions 2863-5593 (exon 1) or 27672-27853 (exon 1B) of SEQ ID NO: 1. In certain aspects, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In several aspects, the compound targeted to human androgen receptor (AR) within exon 1 is capable of inhibiting AR to a greater extent than an antisense compound targeted to the ligand binding domain, such as EZN-4176, which is targeted to exon 4 and corresponds to SEQ ID NO: 58 described in U.S. Pat. No. 7,737,125.

Certain embodiments are drawn to a method of ameliorating or treating a subject with Kennedy's Disease comprising administering to the subject an antisense compound or modified oligonucleotide targeted to human androgen receptor (AR) within intron 1. In certain embodiments, an antisense compound provided herein targets AR within intron 1, for example within nucleotide regions 5594-27671 or 27854-102086 of SEQ ID NO: 1. In certain aspects, an antisense compound provided herein targeted to intron 1 of AR is complementary within any of the following nucleotide regions of SEQ ID NO: 1: 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58722-58737, 58723-58738, 58724-58739, 58725-58740, 58752-58767, 58753-58768, 58754-58769, 58755-58770, 60902-60917, or 67454-67469.

In several aspects, the compound targeted to human androgen receptor (AR) within intron 1 is capable of inhibiting AR to a greater extent than an antisense compound targeted to the ligand binding domain, such as EZN-4176, which is targeted to exon 4 and corresponds to SEQ ID NO: 58 described in U.S. Pat. No. 7,737,125.

Certain embodiments are drawn to a method of ameliorating or treating a subject with Kennedy's Disease comprising administering to the subject an antisense compound or modified oligonucleotide targeted to human androgen receptor (AR) within exon 2. In certain embodiments, an antisense compound provided herein targets AR within exon 2, for example within nucleotide regions 102087-102238 (exon 2) or 139551-139834 (exon 2c) of SEQ ID NO: 1. In certain aspects, an antisense compound provided herein targeted to exon 2 of AR is complementary within any of the following nucleotide regions of SEQ ID NO: 1: 102156-102171, 139682-139697, 139762-139777, or 139782-139797.

Certain embodiments are drawn to a method of ameliorating or treating a subject with Kennedy's Disease comprising administering to the subject an antisense compound or modified oligonucleotide targeted to human androgen receptor (AR) within intron 2. In certain embodiments, an antisense compound provided herein targets AR within intron 2, for example within nucleotide regions 102239-139550 or 139835-144840 of SEQ ID NO: 1. In certain aspects, an antisense compound provided herein targeted to intron 2 of AR is complementary within any of the following nucleotide regions of SEQ ID NO: 1: 114874-114889, 115365-115380, or 134971-134986.

Certain embodiments are drawn to a method of ameliorating or treating a subject with Kennedy's Disease comprising administering to the subject an antisense compound or modified oligonucleotide targeted to human androgen receptor (AR) within exon 3. In certain embodiments, an antisense compound provided herein targets AR within exon 3, for example within nucleotide regions 144841-144957 (exon 3), 148380-148594 (exon 3b), or 153504-154908 (exon 3d) of SEQ ID NO: 1. In certain aspects, an antisense compound provided herein targeted to exon 3 of AR is complementary within any of the following nucleotide regions of SEQ ID NO: 1: 144856-144871, 144938-144953, 148406-148421, 148443-148458, or 148520-148535.

Certain embodiments are drawn to a method of ameliorating or treating a subject with Kennedy's Disease comprising administering to the subject an antisense compound or modified oligonucleotide targeted to human androgen receptor (AR) within exon 7. In certain embodiments, an antisense compound provided herein targets AR within exon 7, for example within nucleotide region 181658-181815 of SEQ ID NO: 1. In certain aspects, an antisense compound provided herein targeted to exon 7 of AR is complementary within nucleotide region 181695-181710 of SEQ ID NO: 1.

Certain embodiments are drawn to a method of ameliorating or treating a subject with Kennedy's Disease comprising administering to the subject an antisense compound or modified oligonucleotide targeted to human androgen receptor (AR) within exon 8. In certain embodiments, an antisense compound provided herein targets AR within exon 8, for example within nucleotide region 182517-189455 of SEQ ID NO: 1. In certain aspects, an antisense compound provided herein targeted to exon 8 of AR is complementary within nucleotide regions 182958-182973 or 183049-183064 of SEQ ID NO: 1.

Certain embodiments are drawn to a method of ameliorating or treating a subject with Kennedy's Disease comprising administering to the subject an antisense compound or modified oligonucleotide targeted to human androgen receptor (AR) within the exon 1 and exon 2 junction. In certain aspects, an antisense compound provided herein targeted to the exon 1 and exon 2 junction of AR is complementary within nucleotide region 2721-2736 of SEQ ID NO: 2.

Certain embodiments are drawn to a method of ameliorating or treating a subject with Kennedy's Disease comprising administering to the subject an antisense compound or modified oligonucleotide targeted to human androgen receptor (AR) within the exon 2 and exon 3 junction. In certain aspects, an antisense compound provided herein targeted to the exon 2 and exon 3 junction of AR is complementary within nucleotide regions 2870-2885 or 2721-2736 of SEQ ID NO: 2.

In certain embodiments a method of ameliorating or treating Kennedy's Disease in a subject comprises administering to the subject an antisense compound or modified oligonucleotide targeted to AR, with the proviso that the antisense compound does not have a nucleobase sequence consisting of any of SEQ ID NOs: 174-231, described in U.S. Pat. No. 7,737,125 as SEQ ID NOs: 2-80 & 86-106 (herein incorporated by reference) and identified in Table A.

TABLE A

| SEQ ID NO: | Sequence |
|---|---|
| 174 | GAGAACCATCCTCACC |
| 175 | GGACCAGGTAGCCTGT |
| 176 | CCCCTGGACTCAGATG |
| 177 | GCACAAGGAGTGGGAC |
| 178 | GCTGTGAAGAGAGTGT |
| 179 | TTTGACACAAGTGGGA |
| 180 | GTGACACCCAGAAGCT |
| 181 | CATCCCTGCTTCATAA |
| 182 | ACCAAGTTTCTTCAGC |
| 183 | CTTGGCCCACTTGACC |
| 184 | TCCTGGAGTTGACATT |
| 185 | CACTGGCTGTACATCC |
| 186 | CATCCAAACTCTTGAG |
| 187 | GCTTTCATGCACAGGA |
| 188 | GAAGTTCATCAAAGAA |
| 189 | AGTTCCTTGATGTAGT |
| 190 | TTGCACAGAGATGATC |
| 191 | GATGGGCTTGACTTTC |
| 192 | CAGGCAGAAGACATCT |
| 193 | CCCAAGGCACTGCAGA |
| 194 | GCTGACATTCATAGCC |
| 195 | TGGGGAGAACCATCCTCACCCTGC |
| 196 | TCCAGGACCAGGTAGCCTGTGGGG |
| 197 | TGTTCCCCTGGACTCAGATGCTCC |
| 198 | TGGGGCACAAGGAGTGGGACGCAC |
| 199 | TTCGGCTGTGAAGAGAGTGTGCCA |
| 200 | CGCTTTTGACACAAGTGGGACTGG |
| 201 | CATAGTGACACCCAGAAGCTTCAT |
| 202 | GAGTCATCCCTGCTTCATAACATT |
| 203 | GATTACCAAGTTTCTTCAGCTTCC |
| 204 | AGGCCTTGGCCCACTTGACCACGT |
| 205 | AGCATCCTGGAGTTGACATTGGTG |
| 206 | GACACACTGGCTGTACATCCGGGA |
| 207 | GAGCCATCCAAACTCTTGAGAGAG |
| 208 | CAGTGCTTTCATGCACAGGAATTC |
| 209 | ATTCGAAGTTCATCAAAGAATTTT |
| 210 | ATCGAGTTCCTTGATGTAGTTCAT |
| 211 | GCACTTGCACAGAGATGATCTCTG |
| 212 | AATAGATGGGCTTGACTTTCCCAG |

TABLE A-continued

| SEQ ID NO: | Sequence |
| --- | --- |
| 213 | ATAACAGGCAGAAGACATCTGAAA |
| 214 | ATTCCCCAAGGCACTGCAGAGGAG |
| 215 | ATGGGCTGACATTCATAGCCTTCA |
| 216 | CTGTGAAGAGAGTG |
| 217 | TGTGAAGAGAGT |
| 218 | TTGACACAAGTGGG |
| 219 | TGACACAAGTGG |
| 220 | TGACACCCAGAAGC |
| 221 | GACACCCAGAAG |
| 222 | CCAAGTTTCTTCAG |
| 223 | CAAGTTTCTTCA |
| 224 | ACTGGCTGTACATC |
| 225 | CTGGCTGTACAT |
| 226 | GTTCCTTGATGTAG |
| 227 | TTCCTTGATGTA |
| 228 | ATGGGCTTGACTTT |
| 229 | TGGGCTTGACTT |
| 230 | CCAAGGCACTGCAG |
| 231 | CAAGGCACTGCA |

In certain embodiments a method of ameliorating or treating Kennedy's Disease in a subject comprises administering to the subject a compound comprising a modified oligonucleotide consisting of 12 to 30 linked nucleosides and having a nucleobase sequence comprising a nucleobase sequence recited in any of SEQ ID NOs: 12-170 and 174-175. In certain aspects, the antisense compound is capable of inhibiting AR to a greater extent than an antisense compound having a nucleobase sequence consisting of any of SEQ ID NOs: 174-231, described in U.S. Pat. No. 7,737,125 as SEQ ID NOs: 2-80 & 86-106 (herein incorporated by reference) and identified in Table A above.

In certain embodiments a method of ameliorating or treating Kennedy's Disease in a subject comprises administering to the subject a compound comprising a modified oligonucleotide consisting of 12 to 30 linked nucleosides and having a nucleobase sequence consisting of a nucleobase sequence recited in any of SEQ ID NOs: 12-170 and 174-175. In certain aspects, the antisense compound is capable of inhibiting AR to a greater extent than an antisense compound having a nucleobase sequence consisting of any of SEQ ID NOs: 174-231, described in U.S. Pat. No. 7,737,125 as SEQ ID NOs: 2-80 & 86-106 (herein incorporated by reference) and identified in Table A above.

In certain embodiments a method of ameliorating or treating Kennedy's Disease in a subject comprises administering to the subject an antisense compound or modified oligonucleotide targeted to a region of an Androgen Receptor nucleic acid. In certain embodiments, such compounds or oligonucleotides targeted to a region of an Androgen Receptor nucleic acid have a contiguous nucleobase portion that is complementary to an equal length nucleobase portion of the region. For example, the portion can be at least an 8, 9, 10, 11, 12, 13, 14, 15, or 16 contiguous nucleobases portion complementary to an equal length portion of a region recited herein. In certain embodiments, such compounds or oligonucleotide target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments a method of ameliorating or treating Kennedy's Disease in a subject comprises administering to the subject an antisense compound or modified oligonucleotide targeted to a Androgen Receptor nucleic acid, wherein the antisense compound or modified oligonucleotide is at least 90% complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58723-58738, 58724-58739, 58725-58740, 58752-58767, 58753-58768, 58754-58769, 58755-58770, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments a method of ameliorating or treating Kennedy's Disease in a subject comprises administering to the subject an antisense compound or modified oligonucleotide targeted to a Androgen Receptor nucleic acid, wherein the antisense compound or modified oligonucleotide is 100% complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58722-58737, 58723-58738, 58724-58739, 58725-58740, 58752-58767, 58753-58768, 58754-58769, 58755-58770, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

Certain embodiments provide the use of a compound as described herein in the manufacture of a medicament for ameliorating or treating Kennedy's Disease in a subject. Certain embodiments provide the use of a compound as described herein in the manufacture of a medicament for increasing muscle strength, improving muscle atrophy, and/or inhibiting muscle denervation in a subject having Kennedy's Disease. Certain embodiments relate to use of a compound described herein for ameliorating or treating Kennedy's Disease in a subject. Certain embodiments relate to use of a compound described herein for increasing muscle strength, improving muscle atrophy, and/or inhibiting muscle denervation in a subject having Kennedy's Disease. In several aspects, the muscle is a proximal limb muscle (e.g. arms and legs) or bulbar muscle (e.g. mouth, tongue, and throat).

Preventing Kennedy's Disease

Certain embodiments provided herein relate to preventing Kennedy's Disease in a subject having an AR gene mutation associated with Kennedy's Disease by administering an antisense compound targeted to Androgen Receptor. Although Kennedy's Disease typically develops in middle adult life, several embodiments are drawn to preventing the onset or severity of Kennedy's Disease in males who carry an AR gene mutation for Kennedy's Disease but are presently in the presymptomatic stage. Several embodiments are drawn to administering an antisense compound targeted to Androgen Receptor to a subject carrying an AR gene mutation for Kennedy's Disease prior to onset of the disease or its associated symptoms, thereby preventing Kennedy's Disease in the subject. These subjects can have a family history of Kennedy's Disease and can be confirmed as carriers of the Kennedy's Disease AR gene mutation by molecular diagnostic techniques available in the art, such as PCR-based assays for detecting CAG repeat expansions in the androgen receptor gene from a blood sample. Several embodiments are drawn to preventing muscle strength loss, preventing muscle atrophy, and/or preventing muscle denervation in a subject in a subject having an Androgen Receptor (AR) gene mutation associated with Kennedy's Disease by administering an antisense compound targeted to Androgen Receptor. In certain embodiments, the muscle is a proximal limb muscle (e.g. arms and legs) or bulbar muscle (e.g. mouth, tongue, and throat). In several aspects, the subject has an AR gene mutation characterized by an expansion of a CAG trinucleotide repeat known to be genetically associated with Kennedy's Disease. The subject can have, for example, an expansion of about 36-62 trinucleotide repeats.

In certain embodiments, a method of preventing Kennedy's Disease in a subject carrying an Androgen Receptor (AR) gene mutation associated with Kennedy's Disease, such as a CAG trinucleotide repeat expansion, comprises administering to the subject an antisense compound or modified oligonucleotide targeted to human androgen receptor, thereby preventing Kennedy's Disease or at least one symptom of Kennedy's Disease in the subject. In several aspects, the subject carries a mutation in the AR gene associated with Kennedy's Disease but is in the presymptomatic or early symptomatic stage.

In certain embodiments, a method of preventing muscle strength loss in a subject carrying an Androgen Receptor (AR) gene mutation associated with Kennedy's Disease, such as a CAG trinucleotide repeat expansion, comprises administering to the subject an antisense compound or modified oligonucleotide targeted to human androgen receptor (AR), thereby preventing muscle strength loss in the subject. In several aspects, the muscle is a proximal limb muscle (e.g. arms and legs) or bulbar muscle (e.g. mouth, tongue, and throat). In several aspects, the subject carries a mutation in the AR gene associated with Kennedy's Disease but is in the presymptomatic or early symptomatic stage.

In certain embodiments, a method of preventing muscle atrophy in a subject carrying an Androgen Receptor (AR) gene mutation associated with Kennedy's Disease, such as a CAG trinucleotide repeat expansion, comprises administering to the subject an antisense compound or modified oligonucleotide targeted to human androgen receptor (AR), thereby preventing muscle atrophy in the subject. In several aspects, preventing muscle atrophy prevents reduction of muscle cell size. In several aspects, the muscle is a proximal limb muscle (e.g. arms and legs) or bulbar muscle (e.g. mouth, tongue, and throat). In several aspects, the subject carries a mutation in the AR gene associated with Kennedy's Disease but is in the presymptomatic or early symptomatic stage.

In certain embodiments, a method of preventing muscle denervation in a subject carrying an Androgen Receptor (AR) gene mutation associated with Kennedy's Disease, such as a CAG trinucleotide repeat expansion, comprises administering to the subject an antisense compound or modified oligonucleotide targeted to human androgen receptor (AR), thereby preventing muscle denervation in the subject. In several aspects, the muscle is a proximal limb muscle (e.g. arms and legs) or bulbar muscle (e.g. mouth, tongue, and throat). In several aspects, the subject carries a mutation in the AR gene associated with Kennedy's Disease but is in the presymptomatic or early symptomatic stage.

In certain embodiments, a method of inhibiting AR expression in a subject carrying an Androgen Receptor (AR) gene mutation associated with Kennedy's Disease, such as a CAG trinucleotide repeat expansion, comprises administering to the subject an antisense compound or modified oligonucleotide targeted to human androgen receptor (AR), thereby inhibiting AR expression in the subject and preventing Kennedy's Disease or at least one symptom of Kennedy's Disease in the subject. In several aspects, the subject carries a mutation in the AR gene associated with Kennedy's Disease but is in the presymptomatic or early symptomatic stage.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 21 linked nucleosides. In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 16 linked nucleosides, a gap segment consisting of 10 linked deoxynucleosides, a 5' wing segment consisting of three linked nucleosides, a 3' wing segment consisting of three linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 16 linked nucleosides, a gap segment consisting of 9 linked deoxynucleosides, a 5' wing segment consisting of three linked nucleosides, a 3' wing segment consisting of four linked nucleosides; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are each a constrained ethyl (cEt) sugar; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of four linked nucleosides, a 3' wing segment consisting of four linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of seven linked nucleosides, a 3' wing segment consisting of two linked nucleosides; the seven linked nucleosides of the 5' wing segment are a 2'-O-methoxyethyl sugar, a constrained ethyl (cEt) sugar, a constrained ethyl (cEt) sugar, a 2'-O-methoxyethyl sugar, a 2'-O-methoxyethyl sugar, a constrained ethyl (cEt) sugar, and a constrained ethyl (cEt) sugar in the 5' to 3' direction; the two linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of six linked nucleosides, a 3' wing segment consisting of three linked nucleosides; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

Certain embodiments provide a method of reducing AR expression in a subject carrying an Androgen Receptor (AR) gene mutation associated with Kennedy's Disease, such as a CAG trinucleotide repeat expansion, comprising administering to the subject a compound as described herein. In certain embodiments, the compound comprises a modified oligonucleotide 12 to 30 linked nucleosides in length targeted to AR. In certain embodiments, the compound comprises a modified oligonucleotide 15 to 30 linked nucleosides in length targeted to AR. In certain embodiments, the compound comprises a modified oligonucleotide 18 to 21 linked nucleosides in length targeted to AR. In certain embodiments, the compound comprises a modified oligonucleotide 17 to 35 linked nucleosides in length targeted to AR. In certain embodiments, the compound comprises a modified oligonucleotide 17 to 25 linked nucleosides in length targeted to AR. In certain embodiments, the compound comprises a modified oligonucleotide 17 to 24 linked nucleosides in length targeted to AR. In certain embodiments, the compound comprises a modified oligonucleotide 17 to 23 linked nucleosides in length targeted to AR. In certain embodiments, the compound comprises a modified oligonucleotide 17 to 22 linked nucleosides in length targeted to AR. In certain embodiments, the compound comprises a modified oligonucleotide 17 to 21 linked nucleosides in length targeted to AR. In several aspects, the subject carries a mutation in the AR gene associated with Kennedy's Disease but is in the presymptomatic or early symptomatic stage.

Certain embodiments provide a method for preventing Kennedy's Disease in a subject carrying an Androgen Receptor (AR) gene mutation associated with Kennedy's Disease, such as a CAG trinucleotide repeat expansion, comprising: a) identifying said subject as carrying the AR gene mutation, and b) administering to said subject a therapeutically effective amount of a compound comprising a modified oligonucleotide consisting of 12 to 30 linked nucleosides and having a nucleobase sequence at least 90% complementary to any of SEQ ID NOs: 1-8 as measured over the entirety of said modified oligonucleotide. In certain embodiments, the therapeutically effective amount of the compound administered to the subject prevents Kennedy's Disease, or a symptom thereof, in the subject. In several aspects, the subject carries a mutation in the AR gene associated with Kennedy's Disease but is in the presymptomatic or early symptomatic stage.

Certain embodiments provide a method for preventing Kennedy's Disease in a subject carrying an Androgen Receptor (AR) gene mutation associated with Kennedy's Disease, such as a CAG trinucleotide repeat expansion, comprising: a) identifying said subject as carrying the AR gene mutation, and b) administering to said subject a therapeutically effective amount of a compound comprising a modified oligonucleotide consisting of 12 to 30 linked nucleosides and having a nucleobase sequence 100% complementary to any of SEQ ID NOs: 1-8 as measured over the entirety of said modified oligonucleotide. In certain embodiments, the therapeutically effective amount of the compound administered to the subject prevents Kennedy's Disease, or a symptom thereof, in the subject. In several aspects, the subject carries a mutation in the AR gene associated with Kennedy's Disease but is in the presymptomatic or early symptomatic stage.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) upstream of the 3' end of exon 3 and/or upstream of the ligand binding domain. In certain embodiments, an antisense compound provided herein targets AR within exon 1 encoding the N-terminal domain or exons 2 and 3 encoding the DNA binding domain, but not within exons 4-8 encoding the ligand binding domain. In certain embodiments, an antisense compound provided herein targets AR within exon 1. In certain embodiments, an antisense compound provided herein targets AR within exon 1, for example within nucleotide regions 2863-5593 (exon 1) or 27672-27853 (exon 1B) of SEQ ID NO: 1. In certain aspects, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In several aspects, the compound targeted to human androgen receptor (AR) within exon 1 is capable of inhibiting AR to a greater extent than an antisense compound targeted to the ligand binding domain, such as EZN-4176, which is targeted to exon 4 and corresponds to SEQ ID NO: 58 described in U.S. Pat. No. 7,737,125. In several aspects, the subject carries a mutation in the AR gene associated with Kennedy's Disease but is in the presymptomatic or early symptomatic stage.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within intron 1. In certain embodiments, an antisense compound provided herein targets AR within intron 1, for example within nucleotide regions 5594-27671 or 27854-102086 of SEQ ID NO: 1. In certain aspects, an antisense compound provided herein targeted to intron 1 of AR is complementary within any of the following nucleotide regions of SEQ ID NO: 1: 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58722-58737, 58723-58738, 58724-58739, 58725-58740, 58752-58767, 58753-58768, 58754-58769, 58755-58770, 60902-60917, or 67454-67469.

In several aspects, the compound targeted to human androgen receptor (AR) within intron 1 is capable of inhibiting AR to a greater extent than an antisense compound targeted to the ligand binding domain, such as EZN-4176, which is targeted to exon 4 and corresponds to SEQ ID NO: 58 described in U.S. Pat. No. 7,737,125. In several aspects, the subject carries a mutation in the AR gene associated with Kennedy's Disease but is in the presymptomatic or early symptomatic stage.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within exon 2. In certain embodiments, an antisense compound provided herein targets AR within exon 2, for example within nucleotide regions 102087-102238 (exon 2) or 139551-139834 (exon 2c) of SEQ ID NO: 1. In certain aspects, an antisense compound provided herein targeted to exon 2 of AR is complementary within any of the following nucleotide regions of SEQ ID NO: 1: 102156-102171, 139682-139697, 139762-139777, or 139782-139797.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within intron 2. In certain embodiments, an antisense compound provided herein targets AR within intron 2, for example within nucleotide regions 102239-139550 or 139835-144840 of SEQ ID NO: 1. In certain aspects, an antisense compound provided herein targeted to intron 2 of AR is complementary within any of the following nucleotide regions of SEQ ID NO: 1: 114874-114889, 115365-115380, or 134971-134986.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within exon 3. In certain embodiments, an antisense compound provided herein targets AR within exon 3, for example within nucleotide regions 144841-144957 (exon 3), 148380-148594 (exon 3b), or 153504-154908 (exon 3d) of SEQ ID NO: 1. In certain aspects, an antisense compound provided herein targeted to exon 3 of AR is complementary within any of the following nucleotide regions of SEQ ID NO: 1: 144856-144871, 144938-144953, 148406-148421, 148443-148458, or 148520-148535.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within exon 7. In certain embodiments, an antisense compound provided herein targets AR within exon 7, for example within nucleotide region 181658-181815 of SEQ ID NO: 1. In certain aspects, an antisense compound provided herein targeted to exon 7 of AR is complementary within nucleotide region 181695-181710 of SEQ ID NO: 1.

Certain embodiments are drawn to a method preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within exon 8. In certain embodiments, an antisense compound provided herein targets AR within exon 8, for example within nucleotide region 182517-189455 of SEQ ID NO: 1. In certain aspects, an antisense compound provided herein targeted to exon 8 of AR is complementary within nucleotide regions 182958-182973 or 183049-183064 of SEQ ID NO: 1.

Certain embodiments are drawn to a method of preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within the exon 1 and exon 2 junction. In certain aspects, an antisense compound provided herein targeted to the exon 1 and exon 2 junction of AR is complementary within nucleotide region 2721-2736 of SEQ ID NO: 2.

Certain embodiments are drawn to a method preventing Kennedy's Disease in a subject carrying an Androgen Receptor (AR) gene mutation associated with Kennedy's Disease, such as a CAG trinucleotide repeat expansion, comprising administering to the subject an antisense compound or modified oligonucleotide targeted to human androgen receptor (AR) within the exon 2 and exon 3 junction. In certain aspects, an antisense compound provided herein targeted to the exon 2 and exon 3 junction of AR is complementary within nucleotide regions 2870-2885 or 2721-2736 of SEQ ID NO: 2.

In certain embodiments a method of treating Kennedy's Disease in a subject carrying an Androgen Receptor (AR) gene mutation associated with Kennedy's Disease, such as a CAG trinucleotide repeat expansion, comprises administering to the subject an antisense compound or modified oligonucleotide targeted to AR, with the proviso that the antisense compound does not have a nucleobase sequence consisting of any of SEQ ID NOs: 174-231, described in U.S. Pat. No. 7,737,125 as SEQ ID NOs: 2-80 & 86-106 (herein incorporated by reference) and identified in Table A above. In several aspects, the subject carries a mutation in the AR gene associated with Kennedy's Disease but is in the presymptomatic or early symptomatic stage.

In certain embodiments a method of preventing Kennedy's Disease in a subject carrying an Androgen Receptor (AR) gene mutation associated with Kennedy's Disease, such as a CAG trinucleotide repeat expansion, comprises administering to the subject a compound comprising a modified oligonucleotide consisting of 12 to 30 linked nucleosides and having a nucleobase sequence comprising a nucleobase sequence recited in any of SEQ ID NOs: 12-170 and 174-175. In certain aspects, the antisense compound is capable of inhibiting AR to a greater extent than an antisense compound having a nucleobase sequence consisting of any of SEQ ID NOs: 174-231, described in U.S. Pat. No. 7,737,125 and identified in Table A above. In several aspects, the subject carries a mutation in the AR gene associated with Kennedy's Disease but is in the presymptomatic or early symptomatic stage.

In certain embodiments a method of preventing Kennedy's Disease in a subject carrying an Androgen Receptor (AR) gene mutation associated with Kennedy's Disease, such as a CAG trinucleotide repeat expansion, comprises administering to the subject a compound comprising a modified oligonucleotide consisting of 12 to 30 linked nucleosides and having a nucleobase sequence consisting of a nucleobase sequence recited in any of SEQ ID NOs: 12-170 and 174-175. In certain aspects, the antisense compound is capable of inhibiting AR to a greater extent than an antisense compound having a nucleobase sequence consisting of any of SEQ ID NOs: 174-231, described in U.S. Pat. No. 7,737,125 and identified in Table A above. In several aspects, the subject carries a mutation in the AR gene associated with Kennedy's Disease but is in the presymptomatic or early symptomatic stage.

In certain embodiments a method of preventing Kennedy's Disease in a subject carrying an Androgen Receptor (AR) gene mutation associated with Kennedy's Disease, such as a CAG trinucleotide repeat expansion, comprises administering to the subject an antisense compound or modified oligonucleotide targeted to a region of an Androgen Receptor nucleic acid. In certain embodiments, such compounds or oligonucleotides targeted to a region of an Androgen Receptor nucleic acid have a contiguous nucleobase portion that is complementary to an equal length nucleobase portion of the region. For example, the portion can be at least an 8, 9, 10, 11, 12, 13, 14, 15, or 16 contiguous nucleobases portion complementary to an equal length portion of a region recited herein. In certain embodiments, such compounds or oligonucleotide target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064. In several aspects, the subject carries a mutation in the AR gene associated with Kennedy's Disease but is in the presymptomatic or early symptomatic stage.

In certain embodiments a method of preventing Kennedy's Disease in a subject carrying an Androgen Receptor (AR) gene mutation associated with Kennedy's Disease, such as a CAG trinucleotide repeat expansion, comprises administering to the subject an antisense compound or modified oligonucleotide targeted to a Androgen Receptor nucleic acid, wherein the antisense compound or modified oligonucleotide is at least 90% complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58723-58738, 58724-58739, 58725-58740, 58752-58767, 58753-58768, 58754-58769, 58755-58770, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064. In several aspects, the subject carries a mutation in the AR gene associated with Kennedy's Disease but is in the presymptomatic or early symptomatic stage.

In certain embodiments a method of preventing Kennedy's Disease in a subject carrying an Androgen Receptor (AR) gene mutation associated with Kennedy's Disease, such as a CAG trinucleotide repeat expansion, comprises administering to the subject an antisense compound or modified oligonucleotide targeted to a Androgen Receptor nucleic acid, wherein the antisense compound or modified oligonucleotide is 100% complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 9464-9479, 10217-10232, 10250-10265, 10865-10880, 11855-11870, 13189-13204, 13321-13336, 13346-13361, 13405-13420, 16555-16570, 16793-16808, 16968-16983, 17206-17221, 18865-18880, 29329-29344, 32290-32305, 33315-33330, 39055-39070, 42017-42032, 56050-56065, 58722-58737, 58723-58738, 58724-58739, 58725-58740, 58752-58767, 58753-58768, 58754-58769, 58755-58770, 60902-60917, 67454-67469, 102156-102171, 114874-114889, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064. In several aspects, the subject carries a mutation in the AR gene associated with Kennedy's Disease but is in the presymptomatic or early symptomatic stage.

Certain embodiments provide the use of a compound as described herein in the manufacture of a medicament for preventing Kennedy's Disease in a subject carrying an Androgen Receptor (AR) gene mutation associated with Kennedy's Disease, such as a CAG trinucleotide repeat expansion. Certain embodiments provide the use of a compound as described herein in the manufacture of a medicament for preventing muscle strength loss, preventing muscle atrophy, and/or preventing muscle denervation in a subject carrying an Androgen Receptor (AR) gene mutation associated with Kennedy's Disease, such as a CAG trinucleotide repeat expansion. Certain embodiments relate to use of a compound described herein for preventing Kennedy's Disease in a subject carrying an Androgen Receptor (AR) gene mutation associated with Kennedy's Disease, such as a CAG trinucleotide repeat expansion. Certain embodiments relate to use of a compound described herein for preventing muscle strength loss, preventing muscle atrophy, and/or preventing muscle denervation in a subject carrying an Androgen Receptor (AR) gene mutation associated with Kennedy's Disease, such as a CAG trinucleotide repeat expansion. In several aspects, the subject carries a mutation in the AR gene associated with Kennedy's Disease but is in the presymptomatic or early symptomatic stage. In several aspects, the muscle is a proximal limb muscle (e.g. arms and legs) or bulbar muscle (e.g. mouth, tongue, and throat).

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an Androgen Receptor nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an Androgen Receptor nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows:

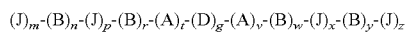

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIe:

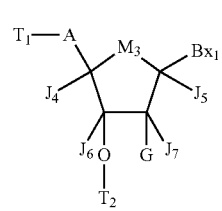

wherein:
T₁ is an optionally protected phosphorus moiety;
T₂ is an internucleoside linking group linking the compound of Formula IIc to the oligomeric compound;
A has one of the formulas:

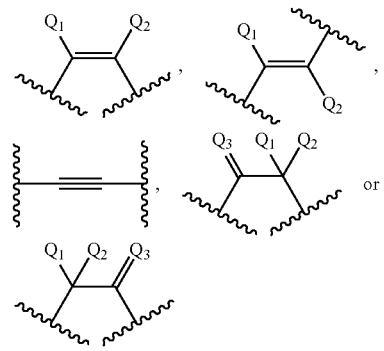

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$Bx_1$ is a heterocyclic base moiety;
or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

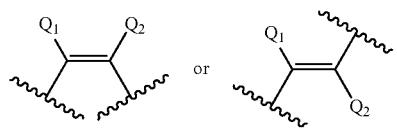

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

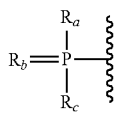

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

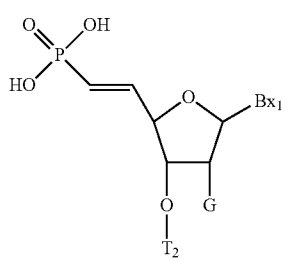

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:
AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and 13 is a nucleoside of a second type. In certain embodiments, A and 13 are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

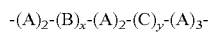

wherein:
A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:

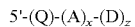

wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is Androgen Receptor. In certain embodiment, the degradation of the targeted Androgen Receptor is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target Androgen Receptor by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group.

In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode human Androgen Receptor include, without limitation, the following: GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), and GENBANK Accession No. FJ235920.1 (incorporated herein as SEQ ID NO: 8). It will be understood that in several embodiments, the nucleobase sequence of any one of SEQ ID NOs: 1-8 can have additional CAG trinucleotide repeats in exon 1. In certain embodiments, compounds provided herein target SEQ ID NOs: 1-8 having about 36-62 CAG trinucleotide repeats in exon 1. For example, in certain embodiments, compounds provided herein target Androgen Receptor having about 36-62 CAG trinucleotide repeats beginning at nucleobase position 1287 (within exon 1) of SEQ ID NO: 2. One can readily determine similar Androgen Receptor sequences having about 36-62 CAG trinucleotide repeats beginning at the corresponding nucleobase position within exon 1 relative to any of SEQ ID NOs: 1 and 3-9, and compounds provided herein can target such Androgen Receptor sequences in several embodiments.

Compounds provided herein targeted to Androgen Receptor, such as any of SEQ ID NOs: 1-8 or an Androgen Receptor sequence having about 36-62 CAG trinucleotide repeats beginning at a nucleobase position corresponding to nucleobase position 1287 (within exon 1) of SEQ ID NO: 2, can be used to ameliorate, treat, or prevent Kennedy's Disease in a subject. In certain embodiments, compounds provided herein target Androgen Receptor pre-mRNA, such as a pre-mRNA having a nucleobase sequence represented by GENBANK Accession No. NT_011669.17_TRUNC_5079000_5270000 (incorporated herein as SEQ ID NO: 1), within intron 1. In certain embodiments, compounds provided herein target Androgen Receptor upstream of the ligand binding domain, which is encoded by exons 4-8. In certain aspects, compounds targeted to Androgen Receptor upstream of the ligand binding domain is targeted to a region of AR upstream of the 3' end of exon 3. In certain embodiments, compounds targeted to Androgen Receptor upstream of the ligand binding domain is targeted within exon 1 encoding the N-terminal domain or exons 2 and 3 encoding the DNA binding domain.

Hybridization

In some embodiments, hybridization occurs between an antisense compound disclosed herein and an Androgen Receptor. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with Androgen Receptor.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Androgen Receptor nucleic acid).

Non-complementary nucleobases between an antisense compound and an Androgen Receptor nucleic acid may be tolerated provided that the antisense compound remains able to specifically hybridize to a target nucleic acid. Moreover, an antisense compound may hybridize over one or more segments of an Androgen Receptor nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Androgen Receptor nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an Androgen Receptor nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Androgen Receptor nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Androgen Receptor nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Androgen Receptor nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein 4'-$(CH_2)$—O-2' (LNA) is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_j)$—$(CH_2)_2$—$N(R_m)(R_n)$, where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2; 4'-$(CH_2)_2$—O-2' (ENA); 4'-$CH(CH_3)$—O-2' (also referred to as constrained ethyl or cEt) and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C—(H)($CH_3$)-2' (see Chattopadhyaya et al., *J. Org. Chem.*, 2009, 74, 118-134); and 4'-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

(A)
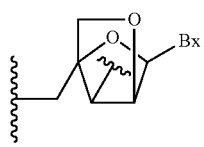

(B)
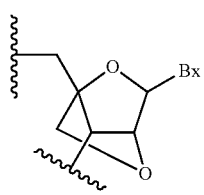

(C)
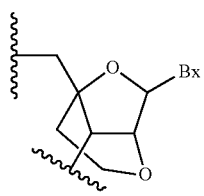

(D)
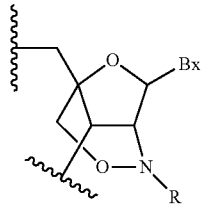

(E)
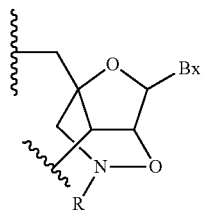

(F)
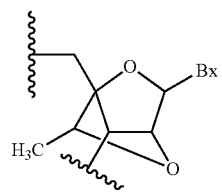

-continued (G)
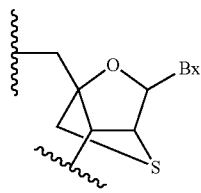

(H)
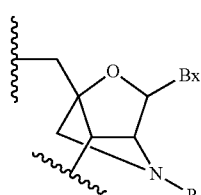

(I)
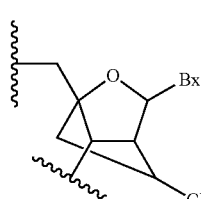

(J)
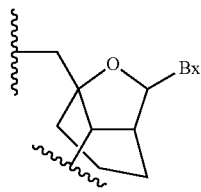

(K)
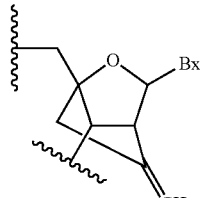

wherein Bx is the base moiety and R is independently H, a protecting group, C$_1$-C$_{12}$ alkyl or C$_1$-C$_{12}$ alkoxy.

In certain embodiments, bicyclic nucleosides are provided having Formula I:

I
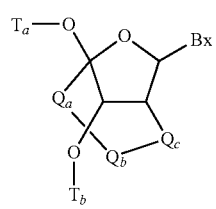

wherein:

Bx is a heterocyclic base moiety;

-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

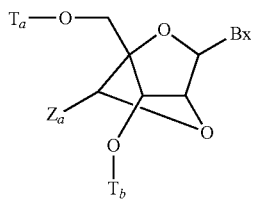

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(\!=\!X)J_c$, and $NJ_eC(\!=\!X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

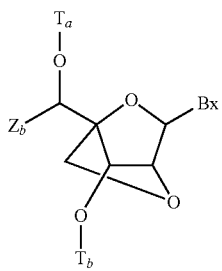

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

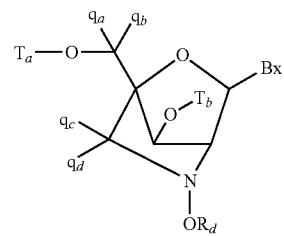

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

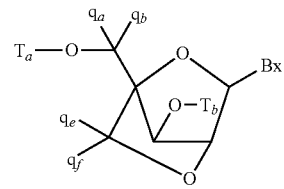

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SO_2J_j$, $SO_2J_j$, $NJ_jJ_k$, $N_3$, CN, $C(\!=\!O)OJ_j$, $C(\!=\!O)NJ_jJ_k$, $C(\!=\!O)J_j$, O—C(=O)—$NJ_jJ_k$, $N(H)C(\!=\!NH)NJ_jJ_k$, $N(H)C(\!=\!O)NJ_jJ_k$ or $N(H)C(\!=\!S)NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

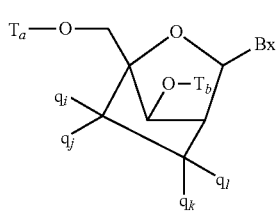

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyran ring system as illustrated below:

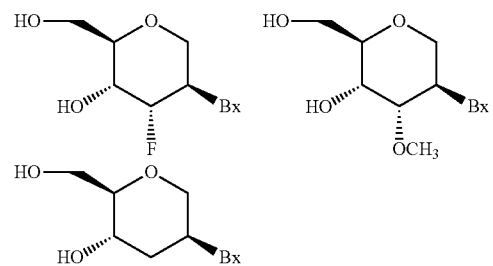

In certain embodiments, sugar surrogates are selected having Formula VII:

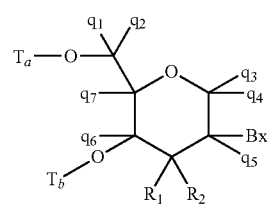

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

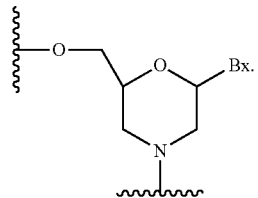

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

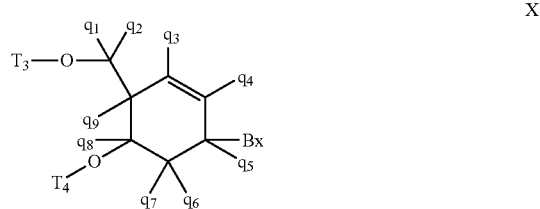

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, Bioorg. Med. Chem., 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an Androgen Receptor nucleic acid comprise one or more modified nucleobases. In certain embodiments, shortened or gap-widened antisense oligonucleotides targeted to an Androgen Receptor nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

For additional conjugates including those useful for ssRNA and their placement within antisense compounds, see e.g., U.S. Application No. 61/583,963.

Certain Indications

In certain embodiments, provided herein are methods of treating an individual comprising administering one or more pharmaceutical compositions as described herein. In certain embodiments, the individual has Kennedy's Disease.

As shown in the examples below, administering compounds targeted to AR, as described herein, have been shown to reduce the severity of physiological symptoms of Kennedy's Disease, including muscle strength loss, muscle atrophy, muscle cell size reduction, and muscle denervation. The ability of the compounds exemplified below to restore muscle strength, muscle cell size, and/or muscle nervation therefore demonstrates that symptoms of Kennedy's Disease may be reversed by treatment with a compound as described herein.

Additionally, administering compounds targeted to AR, as described herein, have been shown to prevent the onset and/or severity of physiological symptoms of Kennedy's Disease, including muscle strength loss, muscle atrophy, muscle cell size reduction, and muscle denervation. The ability of the compounds exemplified below to prevent the onset and/or severity of muscle strength loss, muscle atrophy, muscle cell size reduction, and/or muscle denervation therefore demonstrates that symptoms of Kennedy's Disease may be reversed by treatment with a compound as described herein.

Kennedy's Disease afflicts men who have an inherited AR gene mutation involving expansion of the CAG trinucleotide repeat. Kennedy's Disease is characterized by numerous physical and physiological signs and/or symptoms. Any symptom known to one of skill in the art to be associated with Kennedy's Disease can be ameliorated, treated, or prevented by the methods described above. In certain embodiments, the symptom can include any one or more of muscle fatigue, muscle cramping, muscle weakness, muscle atrophy, muscle twitching or tremoring; and/or bulbar signs such as difficulty with breathing, swallowing, and/or talking.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Compositions and Methods for Formulating Pharmaceutical Compositions

Antisense compounds may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to Androgen Receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to Androgen Receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human AR in HuVEC Cells

Antisense oligonucleotides were designed targeting an AR nucleic acid and were tested for their effects on AR mRNA in vitro. The antisense oligonucleotides were tested in a series of experiments that had similar culture conditions. The results for each experiment are presented in separate tables shown below. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 (forward sequence TCCTTCACCAATGTCAACTCC, designated herein as SEQ ID NO: 9; reverse sequence GAGCCATCCAAACTCTTGAGA, designated herein as SEQ ID NO: 10; probe sequence AGTACCGCATGCACAAGTCCCG, designated herein as SEQ ID NO: 11) was used to measure mRNA levels. AR mRNA levels were adjusted according to total RNA content, as measured by RIBOGREEN®. Results are presented as percent inhibition of AR, relative to untreated control cells. A total of 155 oligonucleotides were tested. Only those oligonucleotides which were selected for further study are shown in Tables 1 and 2.

The newly designed chimeric antisense oligonucleotides in Tables 1 and 2 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 1 or 2 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a' indicates that the oligonucleotide does not target that particular gene sequence.

TABLE 1

| Target Start Site for SEQ ID NO: 1 | Target Start Site for SEQ ID NO: 2 | ISIS No | Seqeunce | % inhibition | SEQ ID NO |
|---|---|---|---|---|---|
| 3799 | 937 | 549332 | GCGCTCTGACAGCCTC | 84 | 9 |
| 3851 | 989 | 549334 | CACCTGCGGGAAGCTC | 83 | 10 |
| 3888 | 1026 | 549338 | GGCTGTGATGATGCGG | 83 | 11 |
| 4059 | 1197 | 549347 | CTTCGCGCACGCTCTG | 84 | 12 |
| 4534 | 1672 | 549358 | ATGGTGCTGGCCTCGC | 91 | 13 |
| 4655 | 1793 | 549360 | GGTCGAAGTGCCCCCT | 89 | 14 |
| 4699 | 1837 | 549361 | GACACCGACACTGCCT | 84 | 15 |
| 4755 | 1893 | 549362 | CCCGAAGCTGTTCCCC | 85 | 16 |
| 4865 | 2003 | 549366 | CTTGCCTGCGCTGTCG | 84 | 17 |
| 5060 | 2198 | 549371 | GTTGTAGTAGTCGCGA | 93 | 18 |
| 5062 | 2200 | 549372 | AAGTTGTAGTAGTCGC | 92 | 19 |
| 5155 | 2293 | 549374 | GCGCTGCCGTAGTCCA | 93 | 20 |
| 5265 | 2403 | 549377 | AGGATGAGGAAGCGGC | 90 | 21 |
| 5392 | 2530 | 549379 | GCTCCCGCCTCGCCGC | 86 | 22 |
| 5448 | 2586 | 549380 | CGCTTTCCTGGCCCGC | 94 | 23 |
| 5483 | 2621 | 549381 | GCCGCCAGGGTACCAC | 89 | 24 |
| n/a | 2721 | 549383 | CCAAACGCATGTCCCC | 88 | 25 |
| 102156 | 2801 | 549387 | AGCTTCATCTCCACAG | 84 | 26 |
| n/a | 2871 | 549388 | TCCCTTCAGCGGCTCT | 88 | 27 |
| 144856 | 2801 | 549390 | TTTCTGCTGGCGCACA | 89 | 28 |

TABLE 2

| Target Start Site for SEQ ID NO: 1 | Target Start Site for SEQ ID NO: 2 | ISIS No | Sequence | % inhibition | SEQ ID NO |
|---|---|---|---|---|---|
| 181695 | 3602 | 549414 | GTTCATTCGAAGTTCA | 81 | 32 |
| 182958 | 4164 | 549432 | GAGGATCATCACAGAT | 90 | 33 |

TABLE 2-continued

| Target Start Site for SEQ ID NO: 1 | Target Start Site for SEQ ID NO: 2 | ISIS No | Sequence | % inhibition | SEQ ID NO |
|---|---|---|---|---|---|
| 183049 | 4255 | 549434 | CTAAACTTCCCGTGGC | 96 | 34 |
| 58722 58752 | n/a | 549458 | GTTGATTTAATGGTTG | 95 | 35 |
| 58725 58755 | n/a | 549459 | ATGGTTGATTTAATGG | 96 | 36 |

Example 2

Dose-Dependent Antisense Inhibition of Human AR in HuVEC Cells

Gapmers from the study described above exhibiting significant in vitro inhibition of AR mRNA were selected and tested at various doses in HuVEC cells. Cells were plated at a density of 20,000 cells per well and transfected using electroporation with 18.5 nM, 55.6 nM, 166.7 nM, 500.0 nM and 1500.0 nM concentrations of antisense oligonucleotide, as specified in Tables 3 and 4. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 3 and 4. As illustrated, AR mRNA levels were reduced in a dose-dependent manner in the antisense oligonucleotide treated cells.

TABLE 3

| ISIS No | 18.5 nM | 55.6 nM | 166.7 nM | 500.0 nM | 1500.0 nM | $IC_{50}$ (nM) |
|---|---|---|---|---|---|---|
| 549358 | 0 | 29 | 63 | 85 | 95 | 141 |
| 549360 | 2 | 44 | 58 | 79 | 83 | 116 |
| 549361 | 0 | 12 | 30 | 52 | 66 | 525 |
| 549362 | 0 | 10 | 23 | 57 | 74 | 447 |
| 549371 | 0 | 30 | 52 | 83 | 88 | 148 |
| 549372 | 0 | 22 | 51 | 85 | 89 | 150 |
| 549374 | 15 | 40 | 59 | 83 | 92 | 108 |
| 549377 | 0 | 13 | 52 | 72 | 93 | 216 |
| 549379 | 9 | 11 | 51 | 68 | 88 | 237 |
| 549380 | 14 | 50 | 87 | 94 | 98 | 62 |
| 549381 | 4 | 14 | 33 | 71 | 91 | 261 |
| 549383 | 2 | 10 | 34 | 75 | 88 | 270 |
| 549388 | 0 | 15 | 42 | 36 | 86 | 428 |
| 549390 | 12 | 0 | 35 | 55 | 91 | 369 |

TABLE 4

| ISIS No | 18.5 nM | 55.6 nM | 166.7 nM | 500.0 nM | 1500.0 nM | $IC_{50}$ (nM) |
|---|---|---|---|---|---|---|
| 549332 | 24 | 35 | 57 | 79 | 79 | 104 |
| 549334 | 9 | 29 | 46 | 63 | 72 | 253 |
| 549338 | 30 | 32 | 47 | 67 | 78 | 154 |

TABLE 4-continued

| ISIS No | 18.5 nM | 55.6 nM | 166.7 nM | 500.0 nM | 1500.0 nM | $IC_{50}$ (nM) |
|---|---|---|---|---|---|---|
| 549347 | 5 | 15 | 37 | 62 | 71 | 357 |
| 549366 | 8 | 44 | 58 | 72 | 91 | 129 |
| 549387 | 2 | 9 | 41 | 68 | 92 | 261 |
| 549414 | 0 | 21 | 35 | 53 | 76 | 366 |
| 549432 | 10 | 15 | 46 | 80 | 92 | 179 |
| 549434 | 27 | 38 | 60 | 86 | 96 | 85 |
| 549458 | 22 | 48 | 84 | 97 | 98 | 57 |
| 549459 | 51 | 61 | 90 | 94 | 97 | 18 |

Example 3

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 82 oligonucleotides were tested. Only those oligonucleotides which were selected for further study are shown in Table 5.

The newly designed chimeric antisense oligonucleotides in Table 5 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 5 is targeted to the human AR genomic sequence, designated herein as SEQ ID NO: 1 (GENBANK Accession No. NT_011669.17 truncated from nucleotides 5079000 to 5270000)

TABLE 5

| Target Start Site | Target Stop Site | ISIS No | ISIS No | % inhibition | SEQ ID NO |
|---|---|---|---|---|---|
| 58722 58752 | 58737 58767 | 549458 | GTTGATTTAATGGTTG | 94 | 35 |
| 58725 58755 | 58740 58770 | 549459 | ATGGTTGATTTAATGG | 92 | 36 |
| 58723 58753 | 58738 58768 | 560099 | GGTTGATTTAATGGTT | 95 | 37 |
| 58724 58754 | 58739 58769 | 560100 | TGGTTGATTTAATGGT | 91 | 38 |

Example 4

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 6. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 6. As illustrated, sequences and were tested at various doses in HuVEC cells. The oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 7 is targeted to the human AR genomic sequence, designated herein as SEQ ID NO: 1 (GENBANK Accession No. NT_011669.17 truncated from nucleotides 5079000 to 5270000)

TABLE 7

| Target Start Site | Target Stop Site | Sequence | ISIS No | Chemistry | SEQ ID NO |
|---|---|---|---|---|---|
| 58722 58752 | 58737 58767 | GTTGATTTAATGGTTG | 549458 | kkk-10-kkk | 35 |
| 58722 58752 | 58737 58767 | GTTGATTTAATGGTTG | 579668 | ekkeekk-7-kk | 35 |
| 58723 58753 | 58738 58768 | GGTTGATTTAATGGTT | 579669 | ekkeekk-7-kk | 37 |
| 58722 58752 | 58737 58767 | GTTGATTTAATGGTTG | 579672 | ekkekk-7-kkk | 35 |
| 58722 58752 | 58737 58767 | GTTGATTTAATGGTTG | 569217 | ekkk-8-kkke | 35 |
| 58723 58753 | 58738 58768 | GGTTGATTTAATGGTT | 569214 | kkk-9-kkke | 37 |
| 58723 58753 | 58738 58768 | GGTTGATTTAATGGTT | 560099 | kkk-10-kkk | 37 |

AR mRNA levels were reduced in a dose-dependent manner in the antisense oligonucleotide treated cells.

TABLE 6

| ISIS No | 31.25 nM | 62.5 nM | 125.0 nM | 250.0 nM | 500.0 nM | 1000.0 nM | $IC_{50}$ (µM) |
|---|---|---|---|---|---|---|---|
| 549458 | 15 | 25 | 47 | 70 | 88 | 93 | 0.10 |
| 549459 | 16 | 23 | 50 | 71 | 85 | 92 | 0.10 |
| 560099 | 13 | 29 | 58 | 72 | 89 | 94 | 0.10 |
| 560100 | 16 | 24 | 53 | 69 | 81 | 93 | 0.10 |

Example 5

Dose-Dependent Antisense Inhibition of Human AR in HuVEC Cells

Additional antisense oligonucleotides were designed as deoxy, MOE and (S)-cEt oligonucleotides targeting AR gene Cells were plated at a density of 20,000 cells per well and transfected using electroporation with 62.5 nM, 125.0 nM, 250.0 nM, 500.0 nM, and 1000.0 nM concentrations of antisense oligonucleotide, as specified in Tables 8-10. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 8-10. As illustrated, AR mRNA levels were reduced in a dose-dependent manner in some of the antisense oligonucleotide treated cells.

TABLE 8

| ISIS No | 62.5 nM | 125.0 nM | 250.0 nM | 500.0 nM | 1000.0 nM | IC$_{50}$ (nM) |
|---|---|---|---|---|---|---|
| 549458 | 25 | 46 | 55 | 64 | 78 | 203 |
| 579668 | 22 | 24 | 13 | 36 | 58 | >1000 |

TABLE 9

| ISIS No | 62.5 nM | 125.0 nM | 250.0 nM | 500.0 nM | 1000.0 nM | IC$_{50}$ (nM) |
|---|---|---|---|---|---|---|
| 549458 | 16 | 22 | 44 | 64 | 74 | 324 |
| 579669 | 24 | 39 | 45 | 74 | 91 | 207 |
| 579672 | 9 | 30 | 50 | 72 | 86 | 258 |

TABLE 10

| ISIS No | 62.5 nM | 125.0 nM | 250.0 nM | 500.0 nM | 1000.0 nM | IC$_{50}$ (nM) |
|---|---|---|---|---|---|---|
| 549458 | 19 | 22 | 45 | 38 | 71 | 470 |
| 560099 | 18 | 33 | 41 | 50 | 71 | 381 |
| 569214 | 20 | 26 | 61 | 62 | 76 | 265 |
| 569217 | 34 | 39 | 49 | 64 | 64 | 247 |

Example 6

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 75 oligonucleotides were tested. Only those oligonucleotides which were selected for further study are shown in Table 11.

The newly designed chimeric antisense oligonucleotides in Table 11 were designed as 3-10-3 (S)-cET gapmers, 3-9-4 (S)-cEt gapmers, 4-8-4 (S)-cEt gapmers, 4-9-3 (S)-cEt gapmers, 5-7-4 (S)-cEt gapmers, 5-8-3 (S)-cEt gapmers, 6-7-3 (S)-cEt gapmers, or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. The 3-9-4 (S)-cEt gapmers are 16 nucleosides in length, wherein the central gap segment comprises of nine 2'-deoxynucleosides and is flanked by a wing segment on the 5' direction comprising three nucleotides and on the 3' direction comprising four nucleosides. The 4-8-4 (S)-cEt gapmers are 16 nucleosides in length, wherein the central gap segment comprises of eight 2'-deoxynucleosides and is flanked by wing segments on both the 5' direction and on the 3' direction comprising four nucleosides. The 4-9-3 (S)-cEt gapmers are 16 nucleosides in length, wherein the central gap segment comprises of nine 2'-deoxynucleosides and is flanked by a wing segment on the 5' direction comprising four nucleotides and on the 3' direction comprising three nucleosides. The 5-7-4 (S)-cEt gapmers are 16 nucleosides in length, wherein the central gap segment comprises of seven 2'-deoxynucleosides and is flanked by a wing segment on the 5' direction comprising five nucleotides and on the 3' direction comprising three four nucleotides. The 5-8-3 (S)-cEt gapmers are 16 nucleosides in length, wherein the central gap segment comprises of eight 2'-deoxynucleosides and is flanked by a wing segment on the 5' direction comprising five nucleotides and on the 3' direction comprising three nucleosides. The 6-7-3 (S)-cEt gapmers are 16 nucleosides in length, wherein the central gap segment comprises of seven 2'-deoxynucleosides and is flanked by a wing segment on the 5' direction comprising six nucleotides and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 11 is targeted to the human AR genomic sequence, designated herein as SEQ ID NO: 1 (GENBANK Accession No. NT_011669.17 truncated from nucleotides 5079000 to 5270000).

TABLE 11

| Target Start Site | Target Stop Site | Sequence | ISIS No | Chemistry | % inhibition | SEQ ID NO |
|---|---|---|---|---|---|---|
| 5062 | 5077 | AAGTTGTAGTAGTCGC | 549372 | kkk-10-kkk | 64 | 22 |
| 5061 | 5076 | AGTTGTAGTAGTCGCG | 585233 | kkk-8-keeee | 69 | 121 |
| 5062 | 5077 | AAGTTGTAGTAGTCGC | 585259 | ekkk-9-kkk | 71 | 22 |
| 5062 | 5077 | AAGTTGTAGTAGTCGC | 585262 | kkk-9-kkke | 77 | 22 |
| 5062 | 5077 | AAGTTGTAGTAGTCGC | 585263 | kkk-8-kkkee | 69 | 22 |

TABLE 11-continued

| Target Start Site | Target Stop Site | Sequence | ISIS No | Chemistry | % inhibition | SEQ ID NO |
|---|---|---|---|---|---|---|
| 5062 | 5077 | AAGTTGTAGTAGTCGC | 585264 | kkk-7-kkkeee | 62 | 22 |
| 5062 | 5077 | AAGTTGTAGTAGTCGC | 585265 | eekk-8-kkee | 69 | 22 |
| 5062 | 5077 | AAGTTGTAGTAGTCGC | 585268 | keke-8-ekek | 72 | 22 |
| 5062 | 5077 | AAGTTGTAGTAGTCGC | 585269 | ekek-8-ekek | 73 | 22 |
| 5062 | 5077 | AAGTTGTAGTAGTCGC | 585271 | ekk-10-kke | 57 | 22 |
| 5062 | 5077 | AAGTTGTAGTAGTCGC | 585274 | kkk-10-kke | 65 | 22 |
| 58722 58752 | 58737 58767 | GTTGATTTAATGGTTG | 560132 | kkk-9-kkke | 58 | 35 |
| 58722 58752 | 58737 58767 | GTTGATTTAATGGTTG | 549458 | kkk-10-kkk | 87 | 35 |
| 58722 58752 | 58737 58767 | GTTGATTTAATGGTTG | 569223 | eekkk-8-kkk | 59 | 35 |
| 58722 58752 | 58737 58767 | GTTGATTTAATGGTTG | 569229 | eekkk-7-kkke | 57 | 35 |
| 58722 58752 | 58737 58767 | GTTGATTTAATGGTTG | 569238 | ekkk-7-kkkee | 51 | 35 |
| 58724 58754 | 58739 58769 | TGGTTGATTTAATGGT | 569215 | kkk-9-kkke | 59 | 38 |
| 58725 58755 | 58740 58770 | ATGGTTGATTTAATGG | 560133 | kkk-9-kkke | 53 | 36 |
| 58725 58755 | 58740 58770 | ATGGTTGATTTAATGG | 569220 | ekkk-8-kkke | 58 | 36 |
| 58722 58752 | 58737 58767 | GTTGATTTAATGGTTG | 586225 | kkkkk-8-kkk | 88 | 35 |

Example 7

Dose-Dependent Antisense Inhibition of Human AR in HuVEC Cells

Antisense oligonucleotides from the studies described above exhibiting significant in vitro inhibition of AR mRNA were selected and tested at various doses in HuVEC cells. Cells were plated at a density of 20,000 cells per well and transfected using electroporation with 31.25 nM, 62.5 nM, 125.0 nM, 250.0 nM, 500.0 nM, and 1000.0 nM concentrations of antisense oligonucleotide, as specified in Table 12. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The half maximal inhibitory concentration (IC$_{50}$) of each oligonucleotide is also presented in Table 12. As illustrated, AR mRNA levels were reduced in a dose-dependent manner in the antisense oligonucleotide treated cells.

TABLE 12

| ISIS No | 31.25 nM | 62.5 nM | 125.0 nM | 250.0 nM | 500.0 nM | 1000.0 nM | IC$_{50}$ μM |
|---|---|---|---|---|---|---|---|
| 549372 | 2 | 17 | 31 | 51 | 61 | 80 | 271 |
| 549458 | 0 | 19 | 40 | 63 | 74 | 90 | 196 |

TABLE 12-continued

| ISIS No | 31.25 nM | 62.5 nM | 125.0 nM | 250.0 nM | 500.0 nM | 1000.0 nM | IC$_{50}$ μM |
|---|---|---|---|---|---|---|---|
| 549459 | 7 | 19 | 31 | 50 | 69 | 82 | 241 |
| 560100 | 20 | 21 | 28 | 49 | 68 | 81 | 236 |
| 560132 | 8 | 19 | 21 | 53 | 65 | 85 | 252 |
| 560133 | 17 | 15 | 24 | 35 | 58 | 79 | 336 |
| 569215 | 12 | 2 | 26 | 55 | 71 | 90 | 234 |
| 569220 | 11 | 29 | 34 | 43 | 59 | 78 | 275 |
| 569223 | 21 | 20 | 30 | 59 | 73 | 87 | 191 |
| 569229 | 16 | 14 | 36 | 47 | 74 | 84 | 220 |
| 569238 | 4 | 32 | 33 | 54 | 71 | 88 | 202 |

Example 8

Dose-Dependent Antisense Inhibition of Human AR in HuVEC Cells

Antisense oligonucleotides from the studies described above exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Table 13. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The half maximal inhibitory concentration (IC$_{50}$) of each oligonucleotide is also presented in Table 13. As illustrated, AR mRNA levels were reduced in a dose-dependent manner in the antisense oligonucleotide treated cells.

TABLE 13

| ISIS No | 46.875 nM | 187.5 nM | 750.0 nM | 3000.0 nM | IC$_{50}$ (µM) |
|---|---|---|---|---|---|
| 549372 | 9 | 41 | 66 | 87 | 0.29 |
| 549458 | 15 | 50 | 85 | 96 | 0.19 |
| 586225 | 17 | 61 | 89 | 97 | 0.13 |

Example 9

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 616 oligonucleotides were tested. Only those oligonucleotides which were selected for further study are shown in Tables 14-21.

The newly designed chimeric antisense oligonucleotides in Tables 14-21 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 14-21 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a' indicates that the oligonucleotide does not target that particular gene sequence.

TABLE 14

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 47 | 22 |
| 58722 58752 | 58737 58767 | GTTGATTTAATGGTTG | 549458 | 60 | 35 |
| 2957 | 2972 | ACAGCACTGGAGCGGC | 583542 | 45 | 39 |
| 3079 | 3094 | AACTTCACCGAAGAGG | 583556 | 43 | 40 |
| 3099 | 3114 | AGTCTTTAGCAGCTTT | 583559 | 52 | 41 |
| 3109 | 3124 | GCTTCCTCCGAGTCTT | 583564 | 45 | 42 |
| 3113 | 3128 | CCTTGCTTCCTCCGAG | 583566 | 47 | 43 |
| 3120 | 3135 | GCACTTTCCTTGCTTC | 583567 | 52 | 44 |
| 3133 | 3148 | TCAGTCCTACCAGGCA | 583571 | 43 | 45 |
| 3224 | 3239 | GACTGAGGCAGCTGCG | 583583 | 45 | 46 |
| 3226 | 3241 | CCGACTGAGGCAGCTG | 583584 | 44 | 47 |

TABLE 15

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 40 | 22 |
| 58722 58752 | 58737 58767 | GTTGATTTAATGGTTG | 549458 | 46 | 35 |

TABLE 15-continued

| Target Start Site on SEQ ID NO: 1 | Target Stop Site on SEQ ID NO: 1 | Sequence | ISIS No | % inhibition | SEQ ID NO |
|---|---|---|---|---|---|
| 3351 | 3366 | GCTAGCTCGCCCGCTC | 583608 | 51 | 48 |
| 3353 | 3368 | CAGCTAGCTCGCCCGC | 583609 | 51 | 49 |
| 3361 | 3376 | GCAATGTGCAGCTAGC | 583613 | 51 | 50 |
| 3388 | 3403 | GTCGCCTGGCTCCTAA | 583620 | 41 | 51 |
| 3513 | 3528 | CTGGCTCCGCACTCGG | 583635 | 50 | 52 |
| 3517 | 3532 | ATCTCTGGCTCCGCAC | 583637 | 43 | 53 |
| 3519 | 3534 | TGATCTCTGGCTCCGC | 583638 | 51 | 54 |
| 3641 | 3656 | AGTGTCCACTGAAGTA | 583642 | 42 | 55 |
| 3735 | 3750 | AGGCTCACAGTCTGTC | 583649 | 46 | 56 |
| 3764 | 3779 | GACACACGGTGGACAA | 583660 | 44 | 57 |
| 3768 | 3783 | AGAAGACACACGGTGG | 583662 | 51 | 58 |
| 3798 | 3813 | CGCTCTGACAGCCTCA | 583667 | 42 | 59 |

TABLE 16

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 26 | 22 |
| 58722 58752 | 58737 58767 | GTTGATTTAATGGTTG | 549458 | 48 | 35 |
| 3870 | 3885 | GTCGCTGCAGCTAGCT | 583685 | 47 | 60 |
| 3874 | 3889 | GGTAGTCGCTGCAGCT | 583687 | 41 | 61 |
| 3876 | 3891 | GCGGTAGTCGCTGCAG | 583688 | 38 | 62 |
| 3878 | 3893 | ATGCGGTAGTCGCTGC | 583689 | 39 | 63 |
| 3884 | 3899 | GTGATGATGCGGTAGT | 583692 | 41 | 64 |
| 3886 | 3901 | CTGTGATGATGCGGTA | 583693 | 36 | 65 |
| 3901 | 3916 | GAAGAGTTCAACAGGC | 583700 | 36 | 66 |
| 3956 | 3971 | GCTTGGCTGAATCTTC | 583709 | 39 | 67 |
| 3962 | 3977 | CCTTGAGCTTGGCTGA | 583712 | 37 | 68 |
| 3964 | 3979 | ATCCTTGAGCTTGGCT | 583713 | 36 | 69 |
| 3967 | 3982 | TCCATCCTTGAGCTTG | 583714 | 36 | 70 |
| 4019 | 4034 | GTAGGTCTTGGACGGC | 583719 | 36 | 71 |
| 4038 | 4053 | GATTCTGGAAAGCTCC | 583727 | 40 | 72 |
| 4049 | 4064 | GCTCTGGAACAGATTC | 583728 | 45 | 73 |
| 4056 | 4071 | CGCGCACGCTCTGGAA | 583731 | 34 | 74 |
| 4062 | 4077 | TCACTTCGCGCACGCT | 583734 | 46 | 75 |
| 4066 | 4081 | TGGATCACTTCGCGCA | 583736 | 47 | 76 |
| 4070 | 4085 | GTTCTGGATCACTTCG | 583738 | 36 | 77 |
| 4101 | 4116 | CGCTCGCGGCCTCTGG | 583745 | 40 | 78 |

TABLE 16-continued

| Target Start Site on SEQ ID NO: 1 | Target Stop Site on SEQ ID NO: 1 | Sequence | ISIS No | % inhibition | SEQ ID NO |
|---|---|---|---|---|---|
| 4103 | 4118 | TGCGCTCGCGGCCTCT | 583746 | 32 | 79 |
| 4105 | 4120 | GCTGCGCTCGCGGCCT | 583747 | 35 | 80 |

TABLE 17

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 39 | 22 |
| 58722 58752 | 58737 58767 | GTTGATTTAATGGTTG | 549458 | 50 | 35 |
| 4109 | 4124 | AGGTGCTGCGCTCGCG | 583749 | 36 | 81 |
| 4305 | 4320 | GCTGTTCCTCATCCAG | 583759 | 38 | 82 |
| 4405 | 4420 | TGCTGCGGCAGCCCCT | 583771 | 40 | 83 |
| 4532 | 4547 | GGTGCTGGCCTCGCTC | 583787 | 37 | 84 |
| 4537 | 4552 | TGCATGGTGCTGGCCT | 583789 | 39 | 85 |
| 4539 | 4554 | GTTGCATGGTGCTGGC | 583790 | 39 | 86 |
| 4555 | 4570 | TGCTGTTGCTGAAGGA | 583795 | 63 | 87 |
| 4571 | 4586 | GGATACTGCTTCCTGC | 583796 | 65 | 88 |
| 4573 | 4588 | TCGGATACTGCTTCCT | 583797 | 35 | 89 |
| 4578 | 4593 | TGCCTTCGGATACTGC | 583799 | 65 | 90 |
| 4597 | 4612 | CTCGCTCTCCCGCTGC | 583802 | 37 | 91 |
| 4632 | 4647 | TGTCCTTGGAGGAAGT | 583809 | 45 | 92 |
| 4656 | 4671 | TGGTCGAAGTGCCCCC | 583818 | 42 | 93 |
| 4662 | 4677 | CAGAAATGGTCGAAGT | 583821 | 42 | 94 |

TABLE 18

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 23 | 22 |
| 58722 58752 | 58737 58767 | GTTGATTTAATGGTTG | 549458 | 54 | 35 |
| 4747 | 4762 | TGTTCCCCTGGACTCA | 583833 | 37 | 95 |
| 4750 | 4765 | AGCTGTTCCCCTGGAC | 583834 | 52 | 96 |
| 4752 | 4767 | GAAGCTGTTCCCCTGG | 583835 | 44 | 97 |
| 4754 | 4769 | CCGAAGCTGTTCCCCT | 583836 | 37 | 98 |
| 4769 | 4784 | GTACATGCAATCCCCC | 583843 | 35 | 99 |
| 4798 | 4813 | ACAGCGGGTGGAACTC | 583847 | 34 | 100 |
| 4804 | 4819 | GGACGCACAGCGGGTG | 583850 | 38 | 101 |
| 4807 | 4822 | GTGGGACGCACAGCGG | 583851 | 33 | 102 |
| 4833 | 4848 | TGCATTCGGCCAATGG | 583853 | 33 | 103 |

TABLE 18-continued

| Target Start Site on SEQ ID NO: 1 | Target Stop Site on SEQ ID NO: 1 | Sequence | ISIS No | % inhibition | SEQ ID NO |
|---|---|---|---|---|---|
| 4837 | 4852 | CCTTTGCATTCGGCCA | 583855 | 44 | 104 |
| 4839 | 4854 | AACCTTTGCATTCGGC | 583856 | 45 | 105 |
| 4868 | 4883 | GCTCTTGCCTGCGCTG | 583862 | 32 | 106 |
| 4872 | 4887 | CAGTGCTCTTGCCTGC | 583864 | 46 | 107 |
| 4874 | 4889 | TTCAGTGCTCTTGCCT | 583865 | 45 | 108 |
| 4876 | 4891 | TCTTCAGTGCTCTTGC | 583866 | 32 | 109 |
| 4887 | 4902 | ACTCAGCAGTATCTTC | 583868 | 34 | 110 |
| 4889 | 4904 | ATACTCAGCAGTATCT | 583871 | 47 | 111 |
| 4916 | 4931 | TTTGGTGTAACCTCCC | 583880 | 39 | 112 |
| 4918 | 4933 | CCTTTGGTGTAACCTC | 583881 | 47 | 113 |
| 4938 | 4953 | CTAGGCTCTCGCCTTC | 583890 | 32 | 114 |
| 4942 | 4957 | CAGCCTAGGCTCTCGC | 583892 | 35 | 115 |
| 4944 | 4959 | AGCAGCCTAGGCTCTC | 583893 | 34 | 116 |
| 4951 | 4966 | CTGCCAGAGCAGCCTA | 583896 | 37 | 117 |

TABLE 19

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 37 | 22 |
| 58722 58752 | 58737 58767 | GTTGATTTAATGGTTG | 549458 | 47 | 35 |
| 5050 | 5065 | TCGCGACTCTGGTACG | 583917 | 37 | 118 |
| 5054 | 5069 | GTAGTCGCGACTCTGG | 583919 | 55 | 119 |
| 5056 | 5071 | TAGTAGTCGCGACTCT | 583920 | 42 | 120 |
| 5061 | 5076 | AGTTGTAGTAGTCGCG | 583922 | 37 | 121 |
| 5133 | 5148 | TCTCCAGCTTGATGCG | 583932 | 39 | 122 |
| 5141 | 5156 | CAGCGGGTTCTCCAGC | 583933 | 38 | 123 |
| 5293 | 5308 | CCTTCTTCGGCTGTGA | 583969 | 44 | 124 |
| 5308 | 5323 | GGTCCATACAACTGGC | 583975 | 42 | 125 |

TABLE 20

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 2200 | AAGTTGTAGTAGTCGC | 549372 | 46 | 22 |
| 58722 58752 | n/a n/a | GTTGATTTAATGGTTG | 549458 | 39 | 35 |
| 5469 | 2607 | ACACATCAGGTGCGGT | 583990 | 30 | 126 |
| 5481 | 2619 | CGCCAGGGTACCACAC | 583996 | 33 | 127 |
| 5486 | 2624 | CATGCCGCCAGGGTAC | 583998 | 45 | 128 |

TABLE 20-continued

| Target Start Site on SEQ ID NO: 1 | Target Stop Site on SEQ ID NO: 1 | Sequence | ISIS No | % inhibition | SEQ ID NO |
|---|---|---|---|---|---|
| 5488 | 2626 | ACCATGCCGCCAGGGT | 583999 | 29 | 129 |
| 5494 | 2632 | CTGCTCACCATGCCGC | 584002 | 30 | 130 |
| 5521 | 2659 | ACACAAGTGGGACTGG | 584006 | 33 | 131 |
| n/a | 2870 | CCCTTCAGCGGCTCTT | 584044 | 29 | 132 |

TABLE 21

| Target Start Site on SEQ ID NO: 1 | Target Stop Site on SEQ ID NO: 1 | Sequence | ISIS No | % inhibition | SEQ ID NO |
|---|---|---|---|---|---|
| 5062 | 5077 | AAGTTGTAGTAGTCGC | 549372 | 25 | 22 |
| 58722<br>58752 | 58737<br>58767 | GTTGATTTAATGGTTG | 549458 | 51 | 35 |
| 144938 | 144953 | CAGAGTCATCCCTGCT | 584069 | 36 | 133 |
| 148406 | 148421 | CACCCTCAAGATTCTT | 584100 | 36 | 134 |
| 148443 | 148458 | AAGGTAGTCTTTAAGG | 584106 | 30 | 135 |
| 148520 | 148535 | GTTTTCAAATGCAGCC | 584111 | 33 | 136 |
| 139682 | 139697 | GCCATGAGACAGCTTT | 584125 | 35 | 137 |
| 139762 | 139777 | ATTCTTGACTGTCTGA | 584128 | 38 | 138 |
| 139782 | 139797 | GCATGCCAGCTGGCTC | 584130 | 29 | 139 |
| 5666 | 5681 | CGCGCAGGTAGGAGCC | 584138 | 35 | 140 |
| 6222 | 6237 | TCTAAACATGACGGTT | 584139 | 37 | 141 |
| 6701 | 6716 | ATGCAATTGCCTGCCA | 584141 | 39 | 142 |

Example 10

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 385 oligonucleotides were tested. Only those oligonucleotides which were selected for further study are shown in Tables 22-26.

The newly designed chimeric antisense oligonucleotides in Tables 22-26 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 22-26 is targeted to the human AR genomic sequence, designated herein as SEQ ID NO: 1 (GENBANK Accession No. NT_011669.17 truncated from nucleotides 5079000 to 5270000)

TABLE 22

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 63 | 22 |
| 58722 | 58737 | GTTGATTTAATGGTTG | 549458 | 88 | 35 |

TABLE 22-continued

| Target Start Site | Target Stop Site | Sequence | ISIS No | % inhibition | SEQ ID NO |
|---|---|---|---|---|---|
| 58752 | 58767 | | | | |
| 7543 | 7558 | ATGGGAGTAACTTTTG | 584145 | 76 | 143 |
| 8471 | 8486 | CATATTATTGTGCTGC | 584148 | 85 | 144 |
| 9464 | 9479 | GAGTTGTGATTTCAGG | 584152 | 88 | 145 |
| 10217 | 10232 | TTGATGGAATGCTGAT | 584157 | 69 | 146 |
| 10250 | 10265 | GGTTAACTTTCTCTGA | 584158 | 69 | 147 |
| 10865 | 10880 | TGGATTGTAAATTACG | 584162 | 82 | 148 |
| 11855 | 11870 | TCAATCTAGATACCAT | 584165 | 70 | 149 |
| 13189 | 13204 | CACATCAGAAGGAGTA | 584166 | 89 | 150 |
| 13321 | 13336 | GAGTGTTAATGAAGAC | 584167 | 78 | 151 |
| 13346 | 13361 | CTGATTAGCTATGACC | 584168 | 70 | 152 |
| 13405 | 13420 | AAACCTTTTGCTGGGT | 584169 | 36 | 153 |
| 16555 | 16570 | ATGAGTCCTCAGAATC | 584179 | 74 | 154 |
| 16793 | 16808 | GTAGATTCTAGCTTTG | 584180 | 81 | 155 |
| 16968 | 16983 | ACAGGCTCTGACTAGG | 584183 | 76 | 156 |
| 17206 | 17221 | TGTGTGACCCTTGGAC | 584184 | 78 | 157 |
| 18865 | 18880 | AAGTATGAGCATGGTT | 584192 | 73 | 158 |

TABLE 23

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 59 | 22 |
| 58722 58752 | 58737 58767 | GTTGATTTAATGGTTG | 549458 | 76 | 35 |
| 29329 | 29344 | GGATTCTCTACACACA | 584233 | 62 | 159 |
| 32290 | 32305 | CCATTTGTGCCAAACC | 584242 | 62 | 160 |
| 33315 | 33330 | AGGTTAGGGAGTAGGC | 584245 | 70 | 161 |
| 39055 | 39070 | TAGGGTTTGGTCAGAA | 584263 | 56 | 162 |
| 42017 | 42032 | GTTATCTTACTCTCCC | 584274 | 70 | 163 |

TABLE 24

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 58 | 22 |
| 58722 58752 | 58737 58767 | GTTGATTTAATGGTTG | 549458 | 79 | 35 |
| 56050 | 56065 | GATTGTGTATAGCTGC | 584312 | 65 | 164 |
| 60902 | 60917 | GGTTATGGTTCTGTCT | 584329 | 58 | 165 |
| 67454 | 67469 | CTTCATTGCAGGTCTG | 584361 | 61 | 166 |

TABLE 25

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 70 | 22 |
| 58722 58752 | 58737 58767 | GTTGATTTAATGGTTG | 549458 | 76 | 35 |
| 114874 | 114889 | TAGCCAACTTTCTTTA | 584465 | 58 | 167 |
| 115365 | 115380 | TTTGGTAACATTAGGC | 584469 | 74 | 168 |
| 134971 | 134986 | ATGGTTGTCCTGTACA | 584495 | 58 | 169 |

TABLE 26

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 54 | 22 |
| 58722 58752 | 58737 58767 | GTTGATTTAATGGTTG | 549458 | 65 | 35 |
| 114874 | 114889 | TAGCCAACTTTCTTTA | 584465 | 54 | 167 |
| 115365 | 115380 | TTTGGTAACATTAGGC | 584469 | 63 | 168 |
| 134971 | 134986 | ATGGTTGTCCTGTACA | 584495 | 53 | 169 |

Example 11

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Tables 27-35. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration (IC$_{50}$) of each oligonucleotide is also presented in Tables 27-35. As illustrated, AR mRNA levels were reduced in a dose-dependent manner in some of the antisense oligonucleotide treated cells.

TABLE 27

| ISIS No | 46.9 nM | 187.5 nM | 750.0 nM | 3000.0 nM | IC$_{50}$ (μM) |
|---|---|---|---|---|---|
| 549372 | 7 | 41 | 70 | 91 | 0.32 |
| 549458 | 21 | 72 | 91 | 97 | 0.11 |
| 583542 | 9 | 28 | 47 | 66 | 0.90 |
| 583556 | 19 | 47 | 68 | 66 | 0.34 |
| 583559 | 30 | 49 | 63 | 80 | 0.22 |
| 583564 | 16 | 33 | 55 | 74 | 0.52 |
| 583566 | 0 | 28 | 50 | 74 | 0.73 |
| 583567 | 17 | 34 | 60 | 79 | 0.43 |
| 583571 | 18 | 36 | 53 | 59 | 0.80 |

TABLE 27-continued

| ISIS No | 46.9 nM | 187.5 nM | 750.0 nM | 3000.0 nM | IC$_{50}$ (μM) |
|---|---|---|---|---|---|
| 583583 | 21 | 31 | 49 | 64 | 0.79 |
| 583584 | 24 | 44 | 52 | 73 | 0.41 |
| 583608 | 12 | 46 | 67 | 76 | 0.35 |
| 583609 | 16 | 48 | 63 | 73 | 0.36 |
| 583613 | 24 | 60 | 70 | 75 | 0.19 |
| 583635 | 35 | 56 | 69 | 78 | 0.13 |
| 583638 | 33 | 64 | 79 | 85 | 0.11 |
| 583649 | 28 | 50 | 68 | 84 | 0.20 |
| 583660 | 21 | 39 | 61 | 72 | 0.42 |
| 583662 | 27 | 59 | 75 | 75 | 0.15 |

TABLE 28

| ISIS No | 46.9 nM | 187.5 nM | 750.0 nM | 3000.0 nM | IC$_{50}$ (μM) |
|---|---|---|---|---|---|
| 549372 | 13 | 29 | 69 | 90 | 0.37 |
| 549458 | 22 | 62 | 92 | 97 | 0.13 |
| 583620 | 0 | 17 | 44 | 54 | 1.85 |
| 583637 | 22 | 32 | 59 | 75 | 0.45 |
| 583642 | 18 | 35 | 67 | 74 | 0.46 |
| 583667 | 35 | 55 | 73 | 82 | 0.14 |
| 583685 | 32 | 53 | 73 | 81 | 0.16 |
| 583687 | 34 | 67 | 83 | 81 | 0.08 |
| 583688 | 3 | 26 | 50 | 60 | 1.05 |
| 583689 | 20 | 34 | 62 | 74 | 0.44 |
| 583692 | 8 | 47 | 61 | 71 | 0.44 |
| 583709 | 8 | 50 | 70 | 84 | 0.29 |
| 583712 | 15 | 47 | 72 | 78 | 0.29 |
| 583727 | 18 | 49 | 70 | 76 | 0.29 |
| 583728 | 9 | 48 | 67 | 70 | 0.40 |
| 583734 | 29 | 60 | 74 | 75 | 0.12 |
| 583736 | 21 | 38 | 60 | 63 | 0.51 |
| 583738 | 16 | 40 | 56 | 71 | 0.51 |
| 583745 | 19 | 51 | 68 | 77 | 0.27 |

TABLE 29

| ISIS No | 46.9 nM | 187.5 nM | 750.0 nM | 3000.0 nM | IC$_{50}$ (μM) |
|---|---|---|---|---|---|
| 549372 | 5 | 36 | 69 | 88 | 0.36 |
| 549458 | 24 | 59 | 92 | 98 | 0.13 |
| 583693 | 12 | 39 | 64 | 80 | 0.38 |
| 583700 | 14 | 34 | 57 | 71 | 0.55 |
| 583713 | 29 | 51 | 67 | 74 | 0.22 |
| 583714 | 22 | 34 | 59 | 79 | 0.40 |
| 583719 | 22 | 46 | 65 | 72 | 0.32 |
| 583731 | 18 | 24 | 47 | 58 | 1.31 |
| 583746 | 24 | 44 | 65 | 67 | 0.35 |
| 583747 | 13 | 38 | 50 | 69 | 0.64 |
| 583771 | 17 | 27 | 47 | 69 | 0.77 |
| 583789 | 30 | 49 | 71 | 85 | 0.19 |
| 583790 | 17 | 42 | 65 | 81 | 0.32 |
| 583795 | 37 | 61 | 83 | 90 | 0.09 |
| 583796 | 38 | 69 | 83 | 90 | 0.07 |
| 583799 | 29 | 60 | 76 | 85 | 0.14 |
| 583809 | 13 | 37 | 68 | 81 | 0.36 |
| 583818 | 9 | 46 | 71 | 84 | 0.31 |
| 583821 | 11 | 35 | 61 | 77 | 0.46 |

TABLE 30

| ISIS No | 46.9 nM | 187.5 nM | 750.0 nM | 3000.0 nM | IC$_{50}$ (μM) |
|---|---|---|---|---|---|
| 549372 | 15 | 39 | 70 | 86 | 0.30 |
| 549458 | 19 | 58 | 89 | 96 | 0.15 |
| 583749 | 34 | 40 | 75 | 87 | 0.17 |
| 583759 | 5 | 28 | 61 | 67 | 0.63 |
| 583787 | 15 | 31 | 66 | 74 | 0.43 |
| 583797 | 21 | 50 | 74 | 82 | 0.22 |
| 583802 | 17 | 25 | 47 | 60 | 1.07 |
| 583834 | 34 | 54 | 73 | 84 | 0.13 |
| 583835 | 20 | 55 | 74 | 88 | 0.19 |
| 583836 | 11 | 27 | 67 | 86 | 0.39 |
| 583850 | 9 | 21 | 54 | 78 | 0.60 |
| 583855 | 22 | 50 | 81 | 91 | 0.18 |
| 583856 | 31 | 55 | 74 | 89 | 0.14 |
| 583864 | 30 | 49 | 72 | 85 | 0.17 |
| 583864 | 0 | 47 | 62 | 85 | 0.37 |
| 583865 | 33 | 42 | 68 | 85 | 0.19 |
| 583871 | 28 | 30 | 68 | 87 | 0.28 |
| 583880 | 13 | 52 | 78 | 92 | 0.22 |
| 583881 | 28 | 50 | 85 | 91 | 0.15 |

TABLE 31

| ISIS No | 46.9 nM | 187.5 nM | 750.0 nM | 3000.0 nM | IC$_{50}$ (μm) |
|---|---|---|---|---|---|
| 549372 | 14 | 33 | 64 | 90 | 0.34 |
| 549458 | 21 | 61 | 90 | 96 | 0.13 |
| 583833 | 26 | 43 | 70 | 74 | 0.26 |
| 583843 | 22 | 40 | 67 | 85 | 0.30 |
| 583847 | 8 | 30 | 60 | 84 | 0.46 |
| 583851 | 8 | 24 | 54 | 76 | 0.61 |
| 583853 | 24 | 51 | 70 | 80 | 0.21 |
| 583862 | 15 | 37 | 64 | 79 | 0.41 |
| 583866 | 17 | 48 | 71 | 91 | 0.24 |
| 583868 | 19 | 31 | 59 | 81 | 0.41 |
| 583890 | 0 | 0 | 17 | 33 | >30 |
| 583892 | 22 | 38 | 68 | 83 | 0.27 |
| 583893 | 15 | 35 | 62 | 79 | 0.42 |
| 583896 | 13 | 17 | 49 | 69 | 0.86 |
| 583919 | 27 | 60 | 85 | 91 | 0.14 |
| 583920 | 11 | 16 | 50 | 72 | 0.76 |
| 583969 | 12 | 26 | 66 | 86 | 0.44 |
| 583975 | 19 | 49 | 55 | 88 | 0.36 |

TABLE 32

| ISIS No | 46.9 nM | 187.5 nM | 750.0 nM | 3000.0 nM | IC$_{50}$ (μM) |
|---|---|---|---|---|---|
| 549372 | 14 | 36 | 64 | 88 | 0.32 |
| 549458 | 14 | 53 | 84 | 95 | 0.18 |
| 583917 | 6 | 30 | 50 | 70 | 0.64 |
| 583922 | 16 | 43 | 76 | 92 | 0.23 |
| 583932 | 9 | 35 | 64 | 81 | 0.38 |
| 583933 | 22 | 25 | 56 | 81 | 0.41 |
| 583990 | 0 | 9 | 33 | 56 | 1.92 |
| 583996 | 26 | 12 | 50 | 70 | 0.71 |
| 583998 | 4 | 25 | 38 | 70 | 0.89 |
| 583999 | 13 | 12 | 30 | 64 | 1.53 |
| 584002 | 12 | 46 | 70 | 92 | 0.25 |
| 584006 | 21 | 26 | 59 | 88 | 0.35 |
| 584044 | 23 | 30 | 51 | 78 | 0.44 |
| 584069 | 18 | 40 | 63 | 82 | 0.30 |
| 584100 | 6 | 5 | 20 | 44 | 7.79 |
| 584125 | 12 | 12 | 47 | 76 | 0.72 |
| 584128 | 20 | 22 | 41 | 72 | 0.74 |
| 584139 | 13 | 33 | 56 | 85 | 0.4 |
| 584141 | 22 | 37 | 61 | 85 | 0.29 |

TABLE 33

| ISIS No | 46.9 nM | 187.5 nM | 750.0 nM | 3000.0 nM | IC$_{50}$ (μM) |
|---|---|---|---|---|---|
| 549372 | 0 | 28 | 64 | 88 | 0.42 |
| 549458 | 13 | 49 | 84 | 91 | 0.19 |
| 584106 | 3 | 13 | 12 | 32 | >30 |
| 584111 | 22 | 30 | 59 | 84 | 0.33 |
| 584130 | 0 | 10 | 11 | 37 | >30 |
| 584138 | 2 | 40 | 62 | 89 | 0.37 |
| 584145 | 6 | 32 | 63 | 88 | 0.36 |
| 584148 | 16 | 48 | 79 | 95 | 0.20 |
| 584152 | 28 | 59 | 87 | 95 | 0.11 |
| 584162 | 24 | 45 | 80 | 92 | 0.18 |
| 584166 | 34 | 52 | 84 | 92 | 0.10 |
| 584167 | 13 | 45 | 76 | 93 | 0.21 |
| 584179 | 1 | 25 | 62 | 87 | 0.44 |
| 584180 | 26 | 56 | 84 | 96 | 0.12 |
| 584183 | 3 | 41 | 64 | 87 | 0.31 |
| 584184 | 9 | 42 | 76 | 93 | 0.23 |
| 584192 | 1 | 34 | 73 | 95 | 0.30 |

TABLE 34

| ISIS No | 46.9 nM | 187.5 nM | 750.0 nM | 3000.0 nM | IC$_{50}$ (μM) |
|---|---|---|---|---|---|
| 549372 | 2 | 26 | 61 | 85 | 0.42 |
| 549458 | 1 | 51 | 83 | 96 | 0.23 |
| 584157 | 6 | 6 | 52 | 82 | 0.59 |
| 584158 | 14 | 37 | 70 | 89 | 0.26 |
| 584165 | 12 | 34 | 66 | 89 | 0.30 |
| 584168 | 5 | 32 | 70 | 91 | 0.32 |
| 584233 | 0 | 30 | 66 | 86 | 0.39 |
| 584242 | 12 | 38 | 66 | 93 | 0.27 |
| 584245 | 4 | 33 | 69 | 90 | 0.32 |
| 584263 | 9 | 24 | 67 | 90 | 0.34 |
| 584274 | 17 | 36 | 74 | 93 | 0.23 |
| 584312 | 17 | 37 | 65 | 93 | 0.26 |
| 584329 | 0 | 17 | 67 | 86 | 0.46 |
| 584361 | 0 | 18 | 71 | 87 | 0.41 |
| 584465 | 0 | 0 | 32 | 51 | 2.5 |
| 584469 | 13 | 46 | 73 | 89 | 0.22 |
| 584495 | 0 | 14 | 55 | 74 | 0.65 |

TABLE 35

| ISIS No | 46.9 nM | 187.5 nM | 750.0 nM | 3000.0 nM | IC$_{50}$ (μM) |
|---|---|---|---|---|---|
| 549372 | 9 | 41 | 66 | 87 | 0.29 |
| 549458 | 15 | 50 | 85 | 96 | 0.19 |
| 586195 | 41 | 62 | 90 | 95 | 0.07 |
| 586197 | 27 | 47 | 77 | 94 | 0.14 |
| 586198 | 39 | 62 | 89 | 96 | 0.07 |
| 586199 | 25 | 56 | 89 | 97 | 0.13 |
| 586200 | 23 | 44 | 85 | 95 | 0.15 |
| 586205 | 34 | 67 | 89 | 95 | 0.07 |
| 586207 | 0 | 39 | 79 | 93 | 0.3 |
| 586208 | 32 | 70 | 88 | 93 | 0.08 |
| 586212 | 20 | 60 | 86 | 94 | 0.13 |
| 586221 | 39 | 72 | 94 | 98 | 0.04 |
| 586224 | 39 | 75 | 93 | 98 | 0.05 |
| 586225 | 17 | 61 | 89 | 97 | 0.13 |
| 586232 | 24 | 45 | 82 | 91 | 0.17 |
| 586240 | 14 | 49 | 83 | 93 | 0.18 |
| 586570 | 16 | 44 | 81 | 91 | 0.21 |

Example 12

Efficacy of Antisense Oligonucleotides Targeting Human Androgen Receptor (AR) in a Transgenic Mouse Model ISIS oligonucleotides targeting AR were evaluated for efficacy in the BAC human AR transgenic mouse model, FxAR121. These mice have acute urinary tract obstruction, onset of grip strength weakening at 10 weeks, and onset of premature death starting on the 16$^{th}$ week. The survival of the mice after treatment with ISIS oligonucleotide was assessed.

Treatment

Groups of 10 mice each were systemically injected with 100 mg/kg/week of ISIS 549372 or ISIS 549458. A control group of mice was systemically injected with phosphate buffered saline (PBS). After 4 weeks of dosing, the dose of antisense oligonucleotide was reduced to 50 mg/kg/week for 8 wks.

Survival Analysis

The mice were monitored daily and deaths were recorded. The data of the survival of the mice in the treatment and control groups are presented in Table 36. The results indicate that treatment of the mice with antisense oligonucleotides targeting AR significantly improved the survival rate of the mice.

TABLE 36

Survival (% of original number) of AR transgenic mice

| | Week 12 | Week 17 | Week 18 | Week 19 | Week 20 | Week 23 | Week 38 |
|---|---|---|---|---|---|---|---|
| PBS | 100 | 80 | 60 | 50 | 10 | 0 | 0 |
| ISIS 549458 | 100 | 100 | 100 | 100 | 100 | 100 | 100 |
| ISIS 549372 | 100 | 90 | 80 | 80 | 80 | 80 | 70 |

Example 13

Efficacy of ISIS 549458 in the AR Transgenic Mouse Model

ISIS 549458 was evaluated for efficacy in the BAC human AR transgenic (Tg) mouse model, FxAR121. Body weight, survival and grip strength was assessed.

Treatment

The treatment was started when the mice were 12 weeks of age and was carried out until they were 19 weeks old. A group of seven Tg mice was systemically injected with 50 mg/kg/week of ISIS 549458 for 8 weeks. A control group of five Tg mice was systemically injected with phosphate buffered saline (PBS) for 8 weeks. Another group of four wild-type mice was systemically injected with 50 mg/kg/week of ISIS 549458 for 8 weeks.

Survival Analysis

The mice were monitored daily and deaths were recorded. The data of the survival of the mice in the treatment and control groups are presented in Table 37. The results indicate that treatment of the mice with antisense oligonucleotides targeting AR significantly improved the survival rate of the Tg mice. The weeks noted in the table indicate the age of the mice.

TABLE 37

Survival (% of original number)

| | Week 12 | Week 17 | Week 20 | Week 21 | Week 22 | Week 32 |
|---|---|---|---|---|---|---|
| PBS (Tg mice) | 100 | 80 | 60 | 40 | 20 | 0 |
| ISIS 549458 (Tg mice) | 100 | 100 | 100 | 100 | 100 | 100 |
| ISIS 549458 (WT mice) | 100 | 100 | 100 | 100 | 100 | 100 |

Body Weight Analysis

The mice were weighed regularly and changes in weights were recorded. The data is presented in Table 38. The results indicate that treatment of the mice with antisense oligonucleotides targeting AR significantly stabilizes the weights of the Tg mice compared to that of the control, and is comparable to the weights of the WT mice. The weeks noted in the table indicate the age of the mice.

TABLE 38

Weights (grams)

| | Week 12 | Week 17 | Week 20 | Week 21 | Week 22 | Week 24 |
|---|---|---|---|---|---|---|
| PBS (Tg mice) | 23.4 | 22.8 | 22.4 | 22.1 | 21.1 | 20.1 |
| ISIS 549458 (Tg mice) | 23.8 | 23.7 | 23.1 | 23.4 | 22.8 | 23.1 |
| ISIS 549458 (WT mice) | 23.5 | 24.5 | 25.0 | 24.8 | 24.4 | 24.3 |

Muscle Grip Strength Analysis

Grip tests were performed with a grip-strength meter (model 1027csx) purchased from Columbus instruments (Columbus, Ohio). Untrained mice were tested five times in succession without rest and the highest number from the five tests was recorded for each mouse. The data is presented in Table 39. The results indicate that treatment of the mice with antisense oligonucleotides targeting AR significantly stabilizes the muscle grip strength of the Tg mice compared to that of the control, and is comparable to that of the WT mice. 'n.d.' indicates no data because of there were no surviving mice in that group at that time point.

TABLE 39

Grip Strength (g)

| | Week 9 | Week 13 | Week 15 | Week 19 | Week 27 | Week 30 | Week 32 |
|---|---|---|---|---|---|---|---|
| PBS (Tg mice) | 116 | 100 | 81 | 66 | n.d. | n.d. | n.d. |
| ISIS 549458 (Tg mice) | 121 | 115 | 85 | 87 | 104 | 119 | 97 |

TABLE 39-continued

| | Grip Strength (g) | | | | | | |
|---|---|---|---|---|---|---|---|
| | Week 9 | Week 13 | Week 15 | Week 19 | Week 27 | Week 30 | Week 32 |
| ISIS 549458 (WT mice) | 117 | 137 | 125 | 119 | 147 | 135 | 128 |

RNA Analysis

RNA was isolated from the liver of WT mice and Tg mice treated with PBS or ISIS 549458. Mouse and human AR mRNA expressions were analyzed by RT-PCR. The data is presented in Table 40. The results indicate that compared to the AR expression in 32-week old WT mice, treatment of either WT mice or Tg mice with antisense oligonucleotides targeting AR inhibited the expression of human AR mRNA expression.

TABLE 40

% expression of muscle AR mRNA levels in treated mice compared to a 32-week old WT PBS control

| Mouse strain | Murine AR (liver) | Murine AR (muscle) | Human AR (liver) | Human AR (muscle) |
|---|---|---|---|---|
| WT | 57 | 86 | 0 | 0 |
| Tg | 72 | 106 | 29 | 10 |

Muscle Atrophy Analysis

Muscle atrophy of external urethral sphincter muscle (EUS) was assessed by measuring the minimal diameter of the EUC muscle fibre microscopically using Aperio-Indica imaging system. The data is presented in Table 41. The results indicate that treatment of the mice with antisense oligonucleotides targeting AR improves EUS muscle atrophy of the Tg mice in a dose dependent manner when compared to that of the control, and is comparable to that of the WT mice.

TABLE 41

Muscle minimal diameter (μm) in 24-week mice

| | Treatment time (weeks) | Diameter |
|---|---|---|
| WT mice (24 wks old) | — | 9.6 |
| Tg mice (23 wks old- end stage) | — | 3.7 |
| Tg mice treated with ISIS 549458 | 2 | 4.5 |
| | 4 | 5.6 |
| | 8 | 6.3 |
| WT mice (28 wks old) | — | 9.4 |

Example 14

Effect of Dose-Dependent Inhibition of AR in the AR Transgenic Mouse Model

The effect of dose-dependent inhibition of AR mRNA expression in the AR Tg mice after treatment with ISIS 549458 was evaluated. Body weight, survival, grip strength and external urethral sphincter (EUS) muscle minimal diameter was assessed Treatment The treatment was started when the mice were 11 weeks of age. Groups of 5-8 Tg mice were systemically injected with 25 mg/kg/week of ISIS 549458 for 2 weeks, 4 weeks, or 8 weeks. A control group of five Tg mice was systemically injected with phosphate buffered saline (PBS) for 8 weeks. A groups of six wild-type mice was systemically injected with PBS for 8 weeks.

Body Weight Analysis

The mice were weighed regularly and changes in weights were recorded. The data is presented in Table 42. The results indicate that treatment of the mice with antisense oligonucleotides targeting AR significantly stabilizes the weights of the Tg mice compared to that of the control Tg mice group. 'n.d.' indicates no data because of there were no surviving mice in that group at that time point.

TABLE 42

| | Weights (grams) | | | | | | |
|---|---|---|---|---|---|---|---|
| | Dose (weeks) | Week 11 | Week 15 | Week 18 | Week 20 | Week 22 | Week 24 |
| PBS (WT mice) | 8 | 27.4 | 27.4 | 29.3 | 29.3 | 28.8 | 30.2 |
| PBS (Tg mice) | 8 | 25.8 | 24.0 | 23.3 | 22.7 | 18.4 | n.d. |
| ISIS 549458 (Tg mice) | 2 | 23.3 | 22.4 | 22.4 | 22.1 | 22.0 | n.d. |
| | 4 | 24.3 | 23.1 | 23.7 | 23.4 | 23.6 | n.d. |
| | 8 | 23.8 | 23.3 | 23.4 | 22.6 | 22.7 | 23.1 |

Muscle Grip Strength Analysis

Grip tests were performed with a grip-strength meter (model 1027csx) purchased from Columbus Instruments (Columbus, Ohio). Untrained mice were tested five times in succession without rest and the highest number from the five tests was recorded for each mouse. The data is presented in Table 43. The results indicate that treatment of the mice with antisense oligonucleotides targeting AR significantly stabilizes the muscle grip strength of the Tg mice compared to that of the control, and is comparable to that of the WT mice. 'n.d.' indicates no data because of there were no surviving mice in that group at that time point.

TABLE 43

| | Grip Strength (g) | | | | |
|---|---|---|---|---|---|
| | Dose (weeks) | Week 14 | Week 18 | Week 22 | Week 24 |
| PBS (WT mice) | 8 | 170 | 174 | 164 | 134 |
| PBS (Tg mice) | 8 | 90 | 56 | 64 | n.d. |
| ISIS 549458 (Tg mice) | 2 | 83 | 88 | 79 | n.d. |
| | 4 | 87 | 109 | 91 | n.d. |
| | 8 | 120 | 92 | 119 | 117 |

Survival Analysis

The mice were monitored daily and deaths were recorded. The data of the survival of the mice in the treatment and control groups are presented in Table 44. The results indicate that treatment of the mice with antisense oligonucleotides targeting AR significantly improved the survival rate of the Tg mice. 'n.d.' indicates no data because of there were no surviving mice in that group at that time point.

TABLE 44

| | Survival (% of original number) | | | | | | |
|---|---|---|---|---|---|---|---|
| | Dose (weeks) | Week 11 | Week 14 | Week 18 | Week 20 | Week 22 | Week 24 | Week 28 |
| PBS (WT mice) | 8 | 100 | 100 | 100 | 100 | 100 | 100 | 100 |
| PBS (Tg mice) | 8 | 100 | 100 | 90 | 60 | 10 | n.d. | n.d. |
| ISIS | 2 | 100 | 100 | 87 | 50 | 37 | 37 | n.d. |

TABLE 44-continued

Survival (% of original number)

|  | Dose (weeks) | Week 11 | Week 14 | Week 18 | Week 20 | Week 22 | Week 24 | Week 28 |
|---|---|---|---|---|---|---|---|---|
| 549458 (Tg mice) | 4 | 100 | 100 | 100 | 86 | 57 | 57 | n.d. |
|  | 8 | 98 | 98 | 98 | 98 | 98 | 98 | 80 |

RNA Analysis

RNA was isolated from the liver and muscle of 14-week old Tg mice treated with PBS, WT mice treated with ISIS 549458 for 8 weeks, and Tg mice treated with ISIS 549458 for 2 weeks, 4 weeks or 8 weeks. The mice undergoing treatment were sacrificed 10-11 weeks post-dose. Human AR mRNA expression was analyzed by RT-PCR. The data is presented in Tables 45 and 46. The results indicate that treatment of the mice with antisense oligonucleotides targeting human AR specifically inhibited the expression of human AR mRNA compared to the Tg control.

TABLE 45

% expression of mRNA in muscle compared to WT control mice

| Mice strain | Mice age (weeks) | Treatment | Dose (weeks) | % mouse AR | % human AR |
|---|---|---|---|---|---|
| Tg | 28 | ISIS 549458 | 8 | 150 | 43 |
| WT | 24 | PBS | 4 | 100 | 0 |
| Tg | 24 | ISIS 549458 | 4 | 89 | 62 |
| WT | 23 | PBS | 2 | 100 | 0 |
| Tg | 23 | ISIS 549458 | 2 | 164 | 197 |

TABLE 46

% expression of mRNA in liver compared to WT control mice

| Mice strain | Mice age (weeks) | Treatment | Dose (weeks) | % mouse AR | % human AR |
|---|---|---|---|---|---|
| Tg | 28 | ISIS 549458 | 8 | 91 | 39 |
| WT | 24 | PBS | 4 | 100 | 0 |
| Tg | 24 | ISIS 549458 | 4 | 103 | 48 |
| WT | 23 | PBS | 2 | 100 | 0 |
| Tg | 23 | ISIS 549458 | 2 | 101 | 79 |

Muscle Atrophy Analysis

Muscle atrophy of external urethral sphincter muscle (EUS) was assessed by measuring the minimal diameter of the EUC muscle fibre microscopically using Aperio-Indica imaging system. The data is presented in Table 47. The results indicate that treatment of the mice with antisense oligonucleotides targeting AR improves EUS muscle atrophy of the Tg mice in a dose dependent manner when compared to that of the control, and is comparable to that of the WT mice.

TABLE 47

Muscle minimal diameter (μm) in 24-week mice

|  | Dose (weeks) | Diameter |
|---|---|---|
| PBS (WT mice) | 8 | 9.6 |
| PBS (Tg mice) | 8 | 3.7 |
| ISIS 549458 (Tg mice) | 2 | 4.5 |
|  | 4 | 5.6 |
|  | 8 | 6.3 |

Example 15

Efficacy of ISIS 549458 in a Non-Symptomatic AR Transgenic Mouse Model

ISIS 549458 was evaluated for efficacy in the AR (Tg) mouse model at 6 weeks of age, when disease symptoms are not manifested. Body weight, survival, grip strength, muscle gene expression and EUS muscle fiber minimal diameter were assessed.

Treatment

The treatment was started when the mice were 6 weeks of age. A group of ten Tg mice was systemically injected with 50 mg/kg/week of ISIS 549458 for 4 weeks. A control group of nine Tg mice was systemically injected with PBS for 4 weeks. Two groups of wild-type mice were systemically injected with 50 mg/kg/week of ISIS 549458 or PBS for 4 weeks.

Body Weight Analysis

The mice were weighed regularly and changes in weights were recorded. The data is presented in Table 48. The results indicate that treatment of the mice with antisense oligonucleotides targeting AR significantly stabilizes the weights of the Tg mice compared to that of the control, and is comparable to the weights of the WT mice.

TABLE 48

Weights (grams)

|  | Week 6 | Week 8 | Week 10 | Week 12 | Week 15 |
|---|---|---|---|---|---|
| PBS (Tg mice) | 20.4 | 23.2 | 24.5 | 24.8 | 24.7 |
| ISIS 549458 (Tg mice) | 19.8 | 22.7 | 23.8 | 25.5 | 26.3 |
| ISIS 549458 (WT mice) | 19.4 | 22.5 | 23.4 | 25.4 | 26.8 |

Muscle Grip Strength Analysis

Grip tests were performed with a grip-strength meter (model 1027csx) purchased from Columbus instruments (Columbus, Ohio). Untrained mice were tested five times in succession without rest and the results of the five tests were averaged for each mouse. The data is presented in Table 49. The results indicate that treatment of the mice with antisense oligonucleotides targeting AR significantly stabilizes the muscle grip strength of the Tg mice compared to that of the control, and is comparable to that of the WT mice.

TABLE 49

Grip Strength (g)

|  | Week 10 | Week 13 | Week 16 | 18 |
|---|---|---|---|---|
| PBS (Tg mice) | 150 | 106 | 91 | nd |
| ISIS 549458 (Tg mice) | 124 | 158 | 123 | 152 |
| ISIS 549458 (WT mice) | 133 | 143 | 134 | 151 |

Muscle Atrophy Analysis

Muscle atrophy was assessed in both external urethral sphincter muscle (EUS) and quadriceps muscle by imaging analysis. The data is presented in Table 50. The effect of antisense inhibition of total lean body mass was also measured with an Echo MRI system (Echo Medical System, Houston, Tex.) when the mice were 16 weeks of age. The data is presented in Table 51. The results indicate that treatment of the mice with antisense oligonucleotides targeting AR significantly improves EUS muscle atrophy and prevents total lean body mass loss of the Tg mice compared to that of the control, and is comparable to that of the WT mice.

TABLE 50

Muscle minimal diameter (μm) in 10 and 16-week old mice

|  | 10 week EUS diameter | 16 week EUS diameter | 10 week Quad diameter | 16 week Quad diameter |
| --- | --- | --- | --- | --- |
| WT mice | 9.1 | 11.7 | 25.5 | 29.4 |
| PBS Tg mice | 6.5 | 7.2 | 28.8 | 25.1 |
| ISIS 549458 Tg mice | 8.1 | 10.7 | 29.8 | 30.3 |

TABLE 51

Lean body mass content of 16-week mice

|  | % |
| --- | --- |
| WT mice | 74 |
| PBS Tg mice | 71 |
| ISIS 549458 Tg mice | 75 |

RNA Analysis

RNA was isolated from the quadriceps muscle of 10-week old and 16-week old mice, and mouse and human AR mRNA expressions were analyzed by RT-PCR. The data is presented in Table 52. The results indicate that treatment of the mice with antisense oligonucleotides targeting human AR specifically inhibited the expression of human AR mRNA compared to the age matched PBS control. The expression of muscle denervation markers, cholinergic receptor (nicotinic alpha) mRNA, calcium channel, voltage dependent, L type, alpha 1S subunit mRNA, myogenin mRNA, and MyoD1 mRNA in the mice was also measured. The data is presented in Tables 53-56. The results indicate that treatment with ISIS 549458 inhibited cholinergic receptor, calcium channel, and myogenin expressions in the mice compared to the PBS Tg control.

TABLE 52

% expression of AR mRNA

| Mice age (weeks) | Treatment | Murine AR | Human AR |
| --- | --- | --- | --- |
| 10 | PBS | 100 | 100 |
| 10 | ISIS 549458 | 100 | 1 |
| 16 | PBS | 100 | 100 |
| 16 | ISIS 549458 | 63 | 1 |
| 22 | ISIS 549458 | 100 | 6 |

TABLE 53

% expression of cholinergic receptor mRNA

| Mice age (weeks) | Treatment | % |
| --- | --- | --- |
| 10 | PBS | 100 |
| 10 | ISIS 549458 | 21 |
| 16 | PBS | 100 |
| 16 | ISIS 549458 | 6 |
| 22 | ISIS 549458 | 18 |

TABLE 54

% change of calcium channel, voltage mRNA compared to 7-week old Tg control

| Mice age (weeks) | Treatment | % |
| --- | --- | --- |
| 10 | PBS | 100 |
| 10 | ISIS 549458 | 309 |
| 16 | PBS | 100 |
| 16 | ISIS 549458 | 64 |
| 22 | ISIS 549458 | 83 |

TABLE 55

% expression of muscle myogenin mRNA

| Mice age (weeks) | Treatment | % |
| --- | --- | --- |
| 10 | PBS | 100 |
| 10 | ISIS 549458 | 33 |
| 16 | PBS | 100 |
| 16 | ISIS 549458 | 18 |
| 22 | ISIS 549458 | 16 |

TABLE 56

% expression of muscle MyoD-1 mRNA

| Mice age (weeks) | Treatment | % |
| --- | --- | --- |
| 10 | PBS | 100 |
| 10 | ISIS 549458 | 172 |
| 16 | PBS | 100 |
| 16 | ISIS 549458 | 78 |
| 22 | ISIS 549458 | 95 |

Since Kennedy's patients experience difficulty in speech and in swallowing, tongue tissue in these mice was assessed.

RNA was isolated from the tongue tissue of the ISIS 549458-treated and control-treated 16-week old mice, and human AR mRNA expression was analyzed by RT-PCR. The results indicate that treatment of the mice with ISIS 549458 decreased AR expression by 77% compared to untreated 10-week old mice. The results also showed that human AR expression in the PBS-treated control group was increased by 21% compared to the untreated 10-week old mice. Hence, human AR expression in ISIS 549458-treated 16-week old mice was reduced by over 90% compared to the control 16-week old mice.

Mouse AR expression was also analyzed by RT-PCR. The results indicate that treatment of the mice with ISIS 549458 decreased AR expression by 18% compared to untreated 10-week old mice. The results also showed that human AR expression in the PBS-treated control group was increased by 32% compared to the untreated 10-week old mice. Hence, mouse AR expression in ISIS 549458-treated 16-week old mice was reduced by 50% compared to the control 16-week old mice.

Example 16

Antisense Inhibition of Human Androgen Receptor (AR) mRNA in C4-2B Cells

C4-2B cells are androgen-independent human prostate adenocarcinoma cells commonly used in the field of oncology and have been established as clinically relevant cultured cells (Thalmann, G. N. et al., Cancer Res. 1994. 54: 2577). MDV3100 or Enzalutamide is an experimental androgen receptor antagonist drug developed by Medivation for the treatment of castration-resistant prostate cancer. The effect of ISIS 549372, ISIS 549458, ISIS 554221, and ISIS 549434 on AR mRNA levels was tested in MDV3100-resistant C4-2B MR cells.

Cells were plated at a density of 40,000/ml cells per well and cultured in RPMI1640 medium with 10% fetal bovine serum. The cells were cultured in the presence of 5 µM concentration of MDV3100 over the course of 2 months to induce MDV3100 resistance. ISIS 549372, ISIS 549458, ISIS 549434, and ISIS 554221 were each added at 0.04 µM, 0.20 µM, 1.00 µM, and 5.00 µM concentrations of antisense oligonucleotide to culture media for free uptake by the cells. A control oligonucleotide, ISIS 347526 (sequence TCTTAT-GTTTCCGAACCGTT (SEQ ID NO: 170) 5-10-5 MOE gapmer) with no known target region in human gene sequences, was included as a negative control. After a treatment period of 2 days, total AR mRNA levels were measured by quantitative real-time PCR. Human AR primer probe set hAR_LTS00943 (forward sequence GCCCCTG-GATGGATAGCTACT, designated herein as SEQ ID NO: 171; reverse sequence CCACAGATCAGGCAGGTCTTC, designated herein as SEQ ID NO: 172; probe sequence ACTGCCAGGGACCATGTTTTGCCC, designated herein as SEQ ID NO: 173) was used to measure mRNA levels. AR mRNA levels were adjusted according to total RNA content, as measured by RIBOGREEN®. Results are presented in Table 57 as percent inhibition of total AR, relative to untreated control cells. Treatment of the cells with ISIS 549372, ISIS 549458, and ISIS 549434 reduced full-length AR mRNA in a dose dependent manner more extensively than treatment with ISIS 554221.

TABLE 57

Percent inhibition of full-length AR mRNA in C4-2B MR cells

| ISIS No | 0.04 µM | 0.20 µM | 1.00 µM | 5.00 µM |
|---------|---------|---------|---------|---------|
| 549372  | 35      | 47      | 88      | 91      |
| 549434  | 9       | 36      | 66      | 88      |
| 549458  | 41      | 78      | 94      | 97      |
| 554221  | 0       | 0       | 0       | 23      |
| 347526  | 28      | 35      | 31      | 17      |

Example 17

Antisense Inhibition of Human Androgen Receptor (AR) mRNA in CWR22-RV1 Cells

The effect of ISIS 549372, ISIS 549434, ISIS 549458, and ISIS 554221 AR mRNA levels was tested in CWR22-RV1 cells. CWR22-RV1 cells were plated and the ISIS oligonucleotides were individually added to the culture media at 1.7 nM, 5.0 nM, 16.7 nM, or 50 nM concentrations. ISIS 347526 was included as a negative control. After a treatment period of 6 days, the target reduction and proliferative capacity of the cancer cells was measured.

Antisense inhibition of AR full-length mRNA was measured with the RTS3559 primer probe set. The results are presented in Table 58 as percent inhibition relative to non-treated cells.

TABLE 58

Percent inhibition of AR full-length mRNA

| Dose (nM) | ISIS 549372 | ISIS 549434 | ISIS 549458 | ISIS 554221 | ISIS 347526 |
|-----------|-------------|-------------|-------------|-------------|-------------|
| 1.7       | 24          | 27          | 28          | 24          | 0           |
| 5.0       | 53          | 46          | 41          | 41          | 3           |
| 16.7      | 64          | 69          | 61          | 67          | 4           |
| 50.0      | 78          | 86          | 78          | 72          | 0           |

Example 18

Effect of Antisense Inhibition of Human Androgen Receptor (AR) mRNA by Free Uptake of Antisense Oligonucleotide by C4-2B Cells The effect of free uptake of antisense oligonucleotides on AR mRNA levels was investigated. ISIS 549372, ISIS 549434, ISIS 549458, and ISIS 554221 were tested.

Cells were plated at a concentration of 1,000 cells/well to measure cell proliferation and at 4,000 cells/well to measure target reduction. ISIS 549458, ISIS 549372, ISIS 549434, and ISIS 554221 were added individually at 0.04 µM, 0.20 µM, 1.00 µM, or 5.00 µM. After an incubation period of 24 hrs, mRNA levels were measured. The data is presented in Table 59. The results indicate that ISIS 549458, ISIS 549372, and ISIS 549434 inhibited AR mRNA expression more potently than ISIS 554221.

TABLE 59

Percent inhibition of AR full-length mRNA

| Dose (µM) | ISIS 549372 | ISIS 549434 | ISIS 549458 | ISIS 554221 |
|-----------|-------------|-------------|-------------|-------------|
| 0.04      | 10          | 10          | 16          | 0           |
| 0.20      | 36          | 35          | 48          | 0           |
| 1.00      | 73          | 52          | 80          | 0           |
| 5.00      | 80          | 55          | 86          | 0           |

What is claimed:

1. A method of treating Kennedy's Disease in a subject comprising administering to the subject a modified oligonucleotide 12 to 30 linked nucleosides in length and having a 12 contiguous nucleobase portion complementary within nucleotides 58722-58737 or 58752-58767 of SEQ ID NO: 1, thereby treating Kennedy's disease in the subject.

2. The method of claim 1, wherein administering the modified oligonucleotide increases muscle strength in the subject.

3. The method of claim 1, wherein administering the modified oligonucleotide improves muscle atrophy in the subject.

4. The method of claim 3, wherein improving muscle atrophy increases the size of a muscle cell.

5. The method of claim 1, wherein administering the modified oligonucleotide inhibits muscle denervation in the subject.

6. The method of claim 1, wherein the subject carries an Androgen Receptor (AR) gene mutation associated with Kennedy's Disease.

7. The method of claim 1, wherein the modified oligonucleotide comprises at least one modified sugar, at least one modified internucleoside linkage, and at least one modified nucleobase.

8. The method of claim 2, wherein muscle strength is increased by 15% compared to the control.

9. The method of claim 1, wherein the modified oligonucleotide is administered to a subject at risk of having Kennedy's disease, thereby preventing Kennedy's disease in the subject.

10. The method of claim 7, wherein the at least one modified sugar comprises a 2'-O-methoxyethyl group.

11. The method of claim 7, wherein the at least one modified sugar is a bicyclic sugar.

12. The method of claim 11, wherein the bicyclic sugar comprises a 4'-CH(CH$_3$)—O-2' group, 4'-CH$_2$-O-2' or 4'-(CH$_2$)$_2$-O-2' group.

13. The method of claim 7, wherein the at least one modified internucleoside linkage is a phosphorothioate linkage.

14. The method of claim 7, wherein the at least one modified nucleobase is 5-methylcytosine.

* * * * *